(12) United States Patent
Swayze

(10) Patent No.: US 10,385,341 B2
(45) Date of Patent: Aug. 20, 2019

(54) COMPOSITIONS FOR MODULATING SOD-1 EXPRESSION

(71) Applicant: Biogen MA Inc., Cambridge, MA (US)

(72) Inventor: Eric E. Swayze, Encinitas, CA (US)

(73) Assignee: Biogen MA Inc., Cambridge, MA (US)

(*) Notice: Subject to any disclaimer, the term of this patent is extended or adjusted under 35 U.S.C. 154(b) by 0 days.

(21) Appl. No.: 15/301,004

(22) PCT Filed: Apr. 1, 2015

(86) PCT No.: PCT/US2015/023934
§ 371 (c)(1),
(2) Date: Sep. 30, 2016

(87) PCT Pub. No.: WO2015/153800
PCT Pub. Date: Oct. 8, 2015

(65) Prior Publication Data
US 2017/0037410 A1    Feb. 9, 2017

Related U.S. Application Data

(60) Provisional application No. 61/973,803, filed on Apr. 1, 2014.

(51) Int. Cl.
C07H 21/04    (2006.01)
C12N 15/113   (2010.01)

(52) U.S. Cl.
CPC .. *C12N 15/1137* (2013.01); *C12Y 115/01001* (2013.01); *C12N 2310/11* (2013.01); *C12N 2310/315* (2013.01); *C12N 2310/321* (2013.01); *C12N 2310/3231* (2013.01); *C12N 2310/3341* (2013.01); *C12N 2310/341* (2013.01); *C12N 2310/346* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |

(Continued)

FOREIGN PATENT DOCUMENTS

| | | |
|---|---|---|
| CA | 2451643 | 11/2012 |
| CN | 103582648 | 2/2014 |

(Continued)

OTHER PUBLICATIONS

Miyagishi et al. (Antisense and Nucleic Acid Drug Development, 2003, 13:1-7).*
Vickers et al. (The Journal of Biological Chemistry, 2003, 278:7108-7118).*
Dean et al. (Oncogene, 2003, 22:9087-9096).*
Agrawal, S., et al., "Antisense therapeutics: is it as simple as complementary base recognition?," Mol. Medicine Today (2000) 6:72-81.
Al-Chalabi, A. et al., "Recent advances in amyotrophic lateral sclerosis," Curr Opin Neurol. (2000) 13(4):397-405.
Alisky, J.M. et al., "Gene therapy for amyotrophic lateral sclerosis and other motor neuron diseases," Hum Gene Ther. (2000) 11(17):2315-29.

(Continued)

*Primary Examiner* — Kimberly Chong
(74) *Attorney, Agent, or Firm* — Fish & Richardson P.C.

(57) ABSTRACT

Disclosed herein are antisense compounds and methods for decreasing SOD-1 mRNA and protein expression. Such methods, compounds, and compositions are useful to treat, prevent, or ameliorate SOD-1 associated diseases, disorders, and conditions. Such SOD-1 associated diseases include amyotrophic sclerosis (ALS).

24 Claims, No Drawings
Specification includes a Sequence Listing.

(56) References Cited

U.S. PATENT DOCUMENTS

| | | |
|---|---|---|
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,638 A | 7/1996 | Rossau et al. |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,843,641 A | 12/1998 | Brown et al. |
| 5,849,290 A | 12/1998 | Brown et al. |
| 5,859,221 A | 1/1999 | Cook et al. |
| 5,948,903 A | 9/1999 | Cook et al. |
| 5,994,076 A | 11/1999 | Chenchik et al. |
| 5,994,517 A | 11/1999 | Ts'O |
| 5,998,148 A | 12/1999 | Bennett et al. |
| 6,005,087 A | 12/1999 | Cook et al. |
| 6,005,096 A | 12/1999 | Matteucci et al. |
| 6,077,833 A | 6/2000 | Bennett et al. |
| 6,166,199 A | 12/2000 | Cook et al. |
| 6,194,150 B1 | 2/2001 | Stinchcomb et al. |
| 6,300,319 B1 | 10/2001 | Manoharan |
| 6,303,374 B1 | 10/2001 | Zhang et al. |
| 6,352,829 B1 | 3/2002 | Chenchik et al. |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,784,290 B1 | 8/2004 | Monia et al. |
| 7,015,315 B1 | 3/2006 | Cook et al. |
| 7,053,199 B2 | 5/2006 | Imanishi et al. |
| 7,053,207 B2 | 5/2006 | Wengel et al. |
| 7,060,809 B2 | 6/2006 | Wengel et al. |
| 7,054,125 B2 | 8/2006 | Wengel |
| 7,101,993 B1 | 9/2006 | Cook et al. |
| 7,132,530 B2 | 11/2006 | Bennett et al. |
| 7,217,805 B2 | 5/2007 | Imanishi et al. |
| 7,262,177 B2 | 8/2007 | Ts'o et al. |
| 7,314,923 B2 | 1/2008 | Kaneko et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,622,455 B2 | 11/2009 | Bennett et al. |
| 7,632,938 B2 | 12/2009 | Khvorova et al. |
| 7,655,785 B1 | 2/2010 | Bentwich |
| 7,666,854 B2 | 2/2010 | Seth et al. |
| 7,678,895 B2 | 3/2010 | Bennett et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,875,733 B2 | 1/2011 | Bhat et al. |
| 7,888,497 B2 | 2/2011 | Bentwich et al. |
| 7,902,163 B2 | 3/2011 | Bennett et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,039,610 B2 | 10/2011 | Khvorova et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| 8,575,123 B2 | 11/2013 | Manoharan et al. |
| RE44,779 E | 2/2014 | Imanishi et al. |
| 8,828,956 B2 | 9/2014 | Manoharan et al. |
| 8,921,331 B2 | 12/2014 | Bennett et al. |
| 8,993,529 B2 | 3/2015 | Bennett et al. |
| 9,005,906 B2 | 4/2015 | Swayze et al. |
| 9,012,421 B2 | 4/2015 | Migawa et al. |

(56) References Cited

U.S. PATENT DOCUMENTS

| | | | |
|---|---|---|---|
| 9,102,938 | B2 | 8/2015 | Rajeev et al. |
| 9,127,276 | B2 | 8/2015 | Prakash et al. |
| 9,290,760 | B2 | 3/2016 | Rajeev et al. |
| 9,476,051 | B2 | 10/2016 | Bennett et al. |
| 2001/0053519 | A1 | 12/2001 | Fodor et al. |
| 2002/0156040 | A1 | 10/2002 | Oberley et al. |
| 2003/0158403 | A1 | 8/2003 | Manoharan et al. |
| 2003/0175906 | A1 | 9/2003 | Manoharan et al. |
| 2003/0228597 | A1 | 12/2003 | Cowsert et al. |
| 2004/0091919 | A1 | 5/2004 | Bennett et al. |
| 2004/0171570 | A1 | 9/2004 | Allerson et al. |
| 2004/0192629 | A1* | 9/2004 | Xu .................. C12N 15/1137 514/44 A |
| 2004/0241651 | A1 | 12/2004 | Olek et al. |
| 2005/0019915 | A1 | 1/2005 | Bennett et al. |
| 2005/0118625 | A1 | 6/2005 | Mounts |
| 2005/0130923 | A1 | 6/2005 | Bhat et al. |
| 2005/0244851 | A1 | 11/2005 | Blume et al. |
| 2005/0261218 | A1* | 11/2005 | Esau .................. C12N 15/111 514/44 A |
| 2006/0148740 | A1 | 7/2006 | Platenburg |
| 2006/0229268 | A1 | 10/2006 | Benjamin et al. |
| 2006/0293269 | A1 | 12/2006 | Bennett et al. |
| 2007/0031844 | A1 | 2/2007 | Khvorova et al. |
| 2007/0054869 | A1 | 3/2007 | Bennett et al. |
| 2007/0117772 | A1 | 5/2007 | Bennett et al. |
| 2008/0039618 | A1 | 2/2008 | Allerson et al. |
| 2009/0130195 | A1 | 5/2009 | Acevedo-Duncan et al. |
| 2010/0081705 | A1 | 4/2010 | Bennett et al. |
| 2010/0190837 | A1 | 7/2010 | Migawa et al. |
| 2010/0197762 | A1 | 8/2010 | Swayze et al. |
| 2011/0039914 | A1* | 2/2011 | Pavco .................. C12N 15/111 514/44 A |
| 2011/0191912 | A1 | 8/2011 | Alexandrov et al. |
| 2012/0029049 | A1 | 2/2012 | Bennett et al. |
| 2012/0214865 | A1 | 8/2012 | Bennett et al. |
| 2013/0130378 | A1 | 5/2013 | Manoharan et al. |
| 2013/0053430 | A1 | 8/2013 | Bell et al. |
| 2013/0323836 | A1 | 12/2013 | Manoharan et al. |
| 2014/0107330 | A1 | 4/2014 | Freier et al. |
| 2015/0018540 | A1 | 1/2015 | Prakash et al. |
| 2015/0167008 | A1 | 6/2015 | Bennett et al. |
| 2015/0184153 | A1 | 7/2015 | Freier et al. |
| 2015/0191727 | A1 | 7/2015 | Migawa et al. |
| 2015/0267195 | A1 | 9/2015 | Seth et al. |
| 2015/0275212 | A1 | 10/2015 | Albaek et al. |

FOREIGN PATENT DOCUMENTS

| | | |
|---|---|---|
| EP | 2221376 | 11/2012 |
| EP | 2270024 | 10/2018 |
| WO | WO 16/016449 A1 | 2/1916 |
| WO | WO 90/05181 A1 | 5/1990 |
| WO | WO 94/19493 A1 | 9/1994 |
| WO | WO 97/26270 A2 | 7/1997 |
| WO | WO 97/31012 A1 | 8/1997 |
| WO | WO 02/03979 A2 | 1/2002 |
| WO | WO 02/44321 A2 | 6/2002 |
| WO | WO 02/057414 A2 | 7/2002 |
| WO | WO 03/000707 A3 | 1/2003 |
| WO | WO 03/004602 A2 | 1/2003 |
| WO | WO 05/040180 A3 | 6/2005 |
| WO | WO 06/066203 A2 | 6/2006 |
| WO | WO 07/092182 A2 | 6/2007 |
| WO | WO 09/102427 A2 | 8/2009 |
| WO | WO 2013/173637 | 11/2013 |
| WO | WO 2015/031392 | 3/2015 |
| WO | WO 15/153800 A2 | 10/2015 |
| WO | WO 2016/077687 | 5/2016 |
| WO | WO 2017/007813 | 1/2017 |
| WO | WO 2017/007825 | 1/2017 |
| WO | WO 2018/204786 | 11/2018 |

OTHER PUBLICATIONS

Amorfix Life Sciences Ltd. "Amorfix Life Sciences Discovers Common Link Between ALS and Alzheimer's Disease" Press Release, Nov. 27, 2007.

Berger, M. et al., "Universal bases for hybridization, replication and chain termination" Nucleic Acids Research (2000) 28(15): 2911-2914.

Berger, I., et al., "Crystal structures of B-DNA with incorporated 2'-deoxy-2'-fluoro-arabino-furanosyl thymines: implications of conformational peorganization for duplex stability," Nucleic Acids Res. (1998) 26(10):2473-80.

Braasch et al., "Novel Antisense and Peptide Nucleic Acid Strategies for Controlling Gene Expression" Biochemistry (2002) 41(14):4503-4510.

Branch, A. D., "A good antisense molecule is hard to find," TIBS (1998)23:45-50.

Brooks, B.R. et al., "El Escorial revisited: Revisited criteria for the diagnosis of amyotrophic lateral sclerosis," ALS and Other Motor Neuron Disorders (2000) 1:293-299.

Bruijn, L. I., et al., "Aggregation and motor neuron toxicity of an ALS-linked SOD1 mutant independent from wild-type SOD1," Science (1998) 281(5384):1851-4.

Chin, Andrew "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Cleveland, D. W., al., "Oxidation versus aggregation—how do SOD1 mutants cause ALS?" Nat Med. (2000) 6(12):1320-1.

Condon, T. et al., "Altered mRNA splicing and inhibition of human E-selectin expression by an antisense oligonucleotide in human umbilical vein endothelial cells." (1996) J. Biol. Chem. 271(48):30398-403.

Crooke, ST., et al., "Antisense Drug Technology" Second Edition, CRC Press (2008) Chapters 1-28.

Crooke, S.T., "Basic Principles of Antisense Therapeutics," (1998), Chapter 1, Springer-Verlag, New York.

Dean et al., "Antisense Oligonucleotide-based Therapeutics for Cancer," Oncogene (2003) 22:9087-9096.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

Fridovich, I., "Superoxide radical and superoxide dismutases," Annu. Rev. Biochem. (1995) 64:97-112.

Gautschi et al., "Activity of a novel bcl-2/bcl-xL bispecific antisense oligonucleotide against tumors of diverse histologic origins" J. Natl. Cancer Inst. (2001) 93:463-471.

Green, D. W., et al, "Antisense Oligonucleotides: An Evolving Technology for the Modulation of Gene Expression in Human Disease," J Am Coll Surg. (2000) 191(1):93-105.

Grzanna, R., et al, "Intrastriatal and intraventricular injections of oligodeoxynucleotides in the rat brain tissue penetration, intracellular distribution and c-fos antisense effects," Mol Brain Res. (1998) 63(1):35-52.

Gulesserian, T., et al., "Superoxide Dimutase SOD 1, Encoded on Chromosome 21, but Not SOD2 Is Overexpressed in Brains of Patients With Down Syndrome," J. Investig Med. (2001) 49(1):41-6.

Haidet-Phillips et al., "Astrocytes from familial and sporadic ALS patients are toxic to motor neurons" Nature Biotech. (2011) 29(9): 824-830.

Hanze J., et al., "Monitoring of antisense effects of oligonucleotides targeted to the neuropeptide Y Y1 receptor gene." Eur J Pharmacol (1997) 330(1):87-92.

Hammond, S.M. et al., "Post-Transcriptional Gene Silencing by Double-Stranded RNA," Nature (2001) 2:110-119.

Ho, Y. et al, "cDNA and deduced amine acid sequence of rat coper-zinc-containing superoxide dismutase" Nuclic Acid Research (1987) 15(16):6746.

(56) References Cited

OTHER PUBLICATIONS

Hottinger, A. F., "The copper chelator d-penicillamine delays onset of disease and extends survival in a transgenic mouse model of familial amyotrophic lateral sclerosis," Eur J Neurosci. (1997) 9(7):1548-51.
Huang, P. et al., "Superoxide dismutase as a target for the selective killing of cancer cells," Nature. (2000) 407(6802):390-5.
Jen, K.Y., et al., "Suppression of Gene Expression by Targeted Disruption of Messenger RNA: Available Options and Current Strategies," Stem Cells (2000) 18:307-19.
Kagiyama et al., "Antisense inhibition of angiotensinogen attenuates vasopressin release in the paraventricular hypothalamic nucleus of spontaneously hypertensive rats" Brain Research (1999) 829:120-124.
Kawata, A., et al., "Aberrant splicing of human Cu/Zn superoxide dimutase (SOD1) RNA transcripts," Neuroreport. (2000) 11(12):2649-53.
Klivenyi, P., et al., "Neuroprotective effects of creatine in a transgenic animal model of amyotrophic lateral sclerosis," Nat Med. (1999) 5(3):347-50.
Klug et al. European Journal of Physiology. (2001) 441(6): R205. Abstract No. P20-7.
Lee, W. G., et al., "Molecular Cloning and High-Level Expression of Human Cytoplasmic Superoxide Dismutase Gene in *Escherichia coli*," Kor. Jour. Microbiol. (1990) 28(2): 91-7.
Levanon, D., et al., "Architecture and anatomy of the chromosomal locus in human chromosome 21 encoding the Cu/Zn superoxide dismutase." EMBO (1985) 4(1):77-84.
Maher at al., "Comparative hybrid arrest by tandem antisense oligodeoxyribonucleotides or oligodeoxyribonucleoside methylpbosphonates in a cell-free system" Nucl. Acid. Res. (1998) 16(8):3341-3358.
Milner, N., et al., "Selecting effective antisense reagents on combinatorial oligonucleotide arrays," Nature Biotechnology (1997) 15:537-41.
Misra, A., et al, "Drug delivery to the central nervous system: a review," J Pharm Pharmaceut Sci (2003) 6(2):252-273.
Muramatsu, H., et al., "Superoxide Dismutase in SAS Human Tongue Carcinoma Cell Line Is a Factor Defining Invasiveness and Cell Motility," Cancer Research (1995) 55:6210-4.
New England Biolabs 1998/99 Catalog (cover page and pp. 121 and 284).
Reynolds et al., "Rational siRNA design for RNA interference" Nature Biotechnology (2004) 22:326-330.
Rosen et al. "Mutations in Cu/Zn superoxide dismutase gene are associated with familial amyotrophic lateral sclerosis" Nature (1993) 362: 59-62.
Rothstein, J. D., et al, "Chronic inhibition of superoxide dismutase produces apoptotic death of spinal Neurons" Proc Natl Acad Sci U S A (1994) 91(10):4155-9.
Rowland, L. P., "Six important themes in amyotrophic lateral sclerosis (ALS) research, 1999," J. Neurol. Sci. (2000) 180:2-6.
Rowland et al. "Amyotrophic Lateral Sclerosis" N. Engl. J. Med. (2001) 334: 1688-1700.
Sanghvi, Y.S., "Heterocyclic Base Modifications in Nucleic Acids and Their Applications in Antisense Oligonucleotides," Antisense Research and Applications (1993) CRC Press, Boca Raton, pp. 276-278.
Sau et al. "Mutation of SOD1 in ALS: a gain of a loss of function" Hum. Mol. Genet. (2007) 16: 1604-1618.
Scanlon, "Anti-Genes: siRNA, Ribozymes and Antisense" Current Pharmaceutical Biotechnology (2004) 5:415-420.
Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.
Sinnayah et al., "Effects of angiotensinogen antisense oligonucleotides on fluid intake in response to different dipsogenic stimuli in the rat" Molecular Brain Research (1997) 50:43-50.
Skerra, A., "Phosphorothioate primers improve the amplification of DNA sequences by DNA polymerases with proofreading activity," Nucleic Acids Research (1992) 20(14):3551-4.
Smith et al., "Antisense oligonucleotide therapy for neurodegenerative disease" Journal of Clinical Investigation (2006) 116(8):2290-2296.
Tasheva E.S., et al., "Regulation of human RPS14 transcription by intronic antisense RNAs and ribosomal protein S14." Genes Dev (1995) 9(3):304-316.
Trotti, D., et al., "SOD1 mutants linked to amyotrophic lateral sclerosis selectively inactivate a glial glutamate transporter," Nat Neurosci. (1999) 2(5):427-33.
Troy, C. M., et al., "Down-regulation of Cu/Zn superoxide dismutase leads to cell death via the nitric oxide-peroxynitrite pathway," J Neurosci. (1996) 16(1):253-61.
Troy, C. M., et al., "Down-regulation of copper/zinc superoxide dismutase causes apoptotic death in PC12 neuronal cells," Proc Natl Acad Sci U S A. (1994) 91(14):6384-7.
Turrens "Mitochondrial formation of reactive oxygen species" J. Physiol. (2003) 552: 335-344.
Wang, S., et al., "Delivery of antisense oligodeoxyribonucleotides against the human epidermal growth factor receptor into cultured KB cells with liposomes conjugated to folate via polyethylene glycol." Proc Natl Acad Sci USA (1995) 92(8):3318-3322.
Woolf et al., "Specificity of antisense oligonucleotides in vivo" PNAS (1992) 89: 7305-7309.
PCT International Search Report for PCT/US2004/031673 dated Aug. 22, 2005.
PCT International Search Report for PCT/US2002/19664 dated Jan. 14, 2003.
PCT International Search Report for PCT/US15/23934 dated Sep. 30, 2015.
Partial European Search Report for Application EP 02742241 dated Nov. 8, 2004.
Burel, S.A., et al., "Hepatotocixity of high affinity gapmer antisense oligonucleotides is mediated by RNase H1 dependent promiscuous reduction of very long pre-mRNA transcripts." Nucleic Acids Research (2015) 44(5):2093-2109.
Hoye, M. et al., "microRNA profiling reveals marker of motor neuron disease in ALS models" J Neuroscience (2017) 37(22):5574-5586 (online Apr. 17, 2017).
Miller, T.M., et al., "An Antisense oligonucleotide against SOD1 deliverd intrathecally for patients with SOD1 familial amyotrophic lateral sclerosis: a phase 1, randomized, first-in-man study." Lancet Neural (2013) 12(5):435-42.
Vickers, T.A., et al., "The rates of the major steps in the molecular mechanism of RNase H1-dependent antisense oligonucleotide induced degradation of RNA." Nucleic Acids Research (2015) 43(18):8955-8963.
Vickers, T.A., et al., "Antisense Oligonucleotides Capable of Promoting Specific Target mRNA Reduction via Comopeting Rnase H1-Dependent and Independent Mechanisms." PLOS One (2014) 9(10):1-12.
Winer, L. et al., "SOD1 in Cerebral Spincal Fluid as a Pharmacodynamic Marker for Antisense Oliognueleolide Therapy" Arch Neruol (2013) 70(2);201-207 (online Nov. 12, 2012).
GenBank Accession No. X02312 (PRI 1-28-1995), 2 pages.
Sherman et al., "Nucleotide Sequence and Expression of Human Chromosome 21-encoded Superoxide Dismutase mRNA," Proc. Natl. Acad. Sci., 1983, 80:5465-5469.
Bosco et al., "Wild-Type and Mutant SOD1 Share an Aberrant Conformation and a Common Pathogenic Pathway in ALS," Nat Neurosci, 2010, 13(11):1396-1403.
Lima et al., "Defining the Factors that Contribute to On-Target Specificity of Antisense Oligonucleotides," PloS One, 2014, 9(7): e101752, 19 pages.
Ward et al., "Nonsense-Mediated Decay as a Terminating Mechanism for Antisense Oligonucleotides," Nucleic Acids Res, 2014, 42(9): 5871-5879.
European Extended Search Report in European Application No. 15773965.7, dated Oct. 6, 2017, 9 pages.

(56) References Cited

OTHER PUBLICATIONS

International Preliminary Report on Patentability in International Application No. PCT/US2015/023934, dated Oct. 4, 2016, 9 pages.

* cited by examiner

COMPOSITIONS FOR MODULATING SOD-1 EXPRESSION

SEQUENCE LISTING

The present application is being filed along with a Sequence Listing in electronic format. The Sequence Listing is provided as a file entitled BIOL0240USASEQ_ST25.pdf created Sep. 28, 2016, which is 320 Kb in size. The information in the electronic format of the sequence listing is incorporated herein by reference in its entirety.

FIELD

Provided are compositions and methods for reducing expression of superoxide dismutase 1, soluble (SOD-1) mRNA and protein in an animal. Such methods are useful to treat, prevent, or ameliorate neurodegenerative diseases, including amyotrophic lateral sclerosis (ALS) by inhibiting expression of SOD-1 in an animal.

BACKGROUND

The soluble SOD-1 enzyme (also known as Cu/Zn superoxide dismutase) is one of the superoxide dismutases that provide defense against oxidative damage of biomolecules by catalyzing the dismutation of superoxide to hydrogen peroxide ($H_2O_2$) (Fridovich, Annu. Rev. Biochem., 1995, 64, 97-112). The superoxide anion ($O_2$-) is a potentially harmful cellular by-product produced primarily by errors of oxidative phosphorylation in mitochondria (Turrens, J. Physiol. 2003, 552, 335-344)

Mutations in the SOD-1 gene are associated with a dominantly-inherited form of amyotrophic lateral sclerosis (ALS, also known as Lou Gehrig's disease) a disorder characterized by a selective degeneration of upper and lower motor neurons (Rowland, N. Engl. J. Med. 2001, 344, 1688-1700). There is a tight genetic linkage between familial ALS and missense mutations in the SOD1 gene (Rosen, Nature, 1993, 362, 59-62). The toxicity of mutant SOD1 is believed to arise from an initial misfolding (gain of function) reducing nuclear protection from the active enzyme (loss of function in the nuclei), a process that may be involved in ALS pathogenesis (Sau, Hum. Mol. Genet. 2007, 16, 1604-1618).

ALS is a devastating progressive neurodegenerative disease affecting as many as 30,000 Americans at any given time. The progressive degeneration of the motor neurons in ALS eventually leads to their death. When the motor neurons die, the ability of the brain to initiate and control muscle movement is lost. With voluntary muscle action progressively affected, patients in the later stages of the disease may become totally paralyzed.

Currently lacking are acceptable options for treating such neurodegenerative diseases. It is therefore an object herein to provide methods for the treatment of such diseases.

SUMMARY

Provided herein are methods, compounds, and compositions for modulating expression of superoxide dismutase 1, soluble (SOD-1) mRNA and protein. In certain embodiments, compounds useful for modulating expression of SOD-1 mRNA and protein are antisense compounds. In certain embodiments, the antisense compounds are modified oligonucleotides.

In certain embodiments, modulation can occur in a cell or tissue. In certain embodiments, the cell or tissue is in an animal. In certain embodiments, the animal is a human. In certain embodiments, SOD-1 mRNA levels are reduced. In certain embodiments, SOD-1 protein levels are reduced. Such reduction can occur in a time-dependent manner or in a dose-dependent manner.

Also provided are methods, compounds, and compositions useful for preventing, treating, and ameliorating diseases, disorders, and conditions. In certain embodiments, such SOD-1 related diseases, disorders, and conditions are neurodegenerative diseases. In certain embodiments, such neurodegenerative diseases, disorders, and conditions include amyotrophic lateral sclerosis (ALS).

Such diseases, disorders, and conditions can have one or more risk factors, causes, or outcomes in common. Certain risk factors and causes for development of ALS include growing older, having a personal or family history, or genetic predisposition. However, the majority of ALS cases are sporadic and no known risk factors are known. Certain symptoms and outcomes associated with development of ALS include but are not limited to: fasciculations, cramps, tight and stiff muscles (spasticity), muscle weakness affecting an arm or a leg, slurred and nasal speech, difficulty walking, difficulty chewing or swallowing (dysphagia), difficulty speaking or forming words (dysarthria), weakness or atrophy, spasticity, exaggerated reflexes (hyperreflexia), and presence of Babinski's sign. As ALS progresses, symptoms and outcomes by include weakening of other limbs, perhaps accompanied by twitching, muscle cramping, and exaggerated, faster reflexes; problems with chewing, swallowing, and breathing; drooling may occur; eventual paralysis; and death.

In certain embodiments, methods of treatment include administering an SOD-1 antisense compound to an individual in need thereof. In certain embodiments, methods of treatment include administering an SOD-1 modified oligonucleotide to an individual in need thereof.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise. Also, all sequences described herein are listed 5' to 3', unless otherwise stated.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorpo- Definitions Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-deoxynucleoside" (also 2'-deoxyribonucleoside) means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

"2'-deoxyribose sugar" means a 2'-H furanosyl sugar moiety, as found in naturally occurring deoxyribonucleic acids (DNA).

"2'-O-methoxyethyl" (also 2'-MOE and 2'-OCH$_2$CH$_2$—OCH$_3$ and MOE and 2'-O-methoxyethylribose) refers to an O-methoxy-ethyl modification of the 2' position of a furanose ring. A 2'-O-methoxyethylribose modified sugar is a modified sugar.

"2'-O-methoxyethylribose modified nucleoside" (also 2'-MOE nucleoside) means a nucleoside comprising a 2'-MOE modified sugar moiety.

"2'-substituted nucleoside" means a nucleoside comprising a substituent at the 2'-position of the furanose ring other than H or OH. In certain embodiments, 2' substituted nucleosides include nucleosides with bicyclic sugar modifications.

"5-methylcytosine" means a cytosine modified with a methyl group attached to the 5 position. A 5-methylcytosine is a modified nucleobase.

"About" means within ±10% of a value. For example, if it is stated, "the compounds affected at least about 50% inhibition of SOD-1", it is implied that the SOD-1 levels are inhibited within a range of 45% and 55%. "Administered concomitantly" refers to the co-administration of two pharmaceutical agents in any manner in which the pharmacological effects of both are manifest in the patient at the same time. Concomitant administration does not require that both pharmaceutical agents be administered in a single pharmaceutical composition, in the same dosage form, or by the same route of administration. The effects of both pharmaceutical agents need not manifest themselves at the same time. The effects need only be overlapping for a period of time and need not be coextensive.

"Administering" means providing a pharmaceutical agent to an animal, and includes, but is not limited to administering by a medical professional and self-administering.

"Amelioration" refers to a lessening, slowing, stopping, or reversing of at least one indicator of the severity of a condition or disease. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels or in the absence of the antisense compound.

"Antisense mechanisms" are all those mechanisms involving hybridization of a compound with a target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding segment of a target nucleic acid.

"Base complementarity" refers to the capacity for the precise base pairing of nucleobases of an oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar" means a furanose ring modified by the bridging of two atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Cap structure" or "terminal cap moiety" means chemical modifications, which have been incorporated at either terminus of an antisense compound.

"cEt" or "constrained ethyl" or "cEt modified sugar" means a bicyclic nucleoside having a sugar moiety comprising a bridge connecting the 4'-carbon and the 2'-carbon, wherein the bridge has the formula: 4'-CH(CH$_3$)—O-2'. A cEt modified sugar is a modified sugar.

"cEt modified nucleoside" means a bicyclic nucleoside having a sugar moiety comprising a bridge connecting the 4'-carbon and the 2'-carbon, wherein the bridge has the formula: 4'-CH(CH$_3$)—O-2'. A cEt modified sugar is a modified sugar.

"Chemically distinct region" refers to a region of an antisense compound that is in some way chemically different than another region of the same antisense compound. For example, a region having 2'-O-methoxyethyl nucleosides is chemically distinct from a region having nucleosides without 2'-O-methoxyethyl modifications.

"Chimeric antisense compound" means an antisense compound that has at least two chemically distinct regions, each position having a plurality of subunits.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Comprise," "comprises," and "comprising" will be understood to imply the inclusion of a stated step or element or group of steps or elements but not the exclusion of any other step or element or group of steps or elements.

"Contiguous nucleobases" means nucleobases immediately adjacent to each other.

"Designing" or "designed to" refer to the process of designing an oligomeric compound that specifically hybridizes with a selected nucleic acid molecule.

"Diluent" means an ingredient in a composition that lacks pharmacological activity, but is pharmaceutically necessary or desirable. For example, in drugs that are injected, the diluent may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" in the context of modulating an activity or of treating or preventing a condition means the administration of that amount of pharmaceutical agent to a subject in need of such modulation, treatment, or prophylaxis, either in a single dose or as part of a series, that is effective for modulation of that effect, or for treatment or prophylaxis or improvement of that condition. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Gap-narrowed" means a chimeric antisense compound having a gap segment of 9 or fewer contiguous 2'-deoxyribonucleosides positioned between and immediately adjacent to 5' and 3' wing segments having from 1 to 6 nucleosides.

"Gap-widened" means a chimeric antisense compound having a gap segment of 12 or more contiguous 2'-deoxyribonucleosides positioned between and immediately adjacent to 5' and 3' wing segments having from 1 to 6 nucleosides.

"Hybridization" means the annealing of complementary nucleic acid molecules. In certain embodiments, complementary nucleic acid molecules include, but are not limited to, an antisense compound and a target nucleic acid. In certain embodiments, complementary nucleic acid molecules include, but are not limited to, an oligonucleotide and a nucleic acid target.

"Identifying an animal having a SOD-1 associated disease" means identifying an animal having been diagnosed with a SOD-1 associated disease or predisposed to develop a SOD-1 associated disease. Individuals predisposed to develop a SOD-1 associated disease include those having one or more risk factors for developing a SOD-1 associated disease, including, growing older, having a personal or family history, or genetic predisposition of one or more SOD-1 associated diseases. Such identification may be accomplished by any method including evaluating an individual's medical history and standard clinical tests or assessments, such as genetic testing.

"Immediately adjacent" means there are no intervening elements between the immediately adjacent elements.

"Individual" means a human or non-human animal selected for treatment or therapy.

"Inhibiting SOD-1" means reducing the level or expression of a SOD-1 mRNA and/or protein. In certain embodiments, SOD-1 mRNA and/or protein levels are inhibited in the presence of an antisense compound targeting SOD-1, including a modified oligonucleotide targeting SOD-1, as compared to expression of SOD-1 mRNA and/or protein levels in the absence of a SOD-1 antisense compound, such as a modified oligonucleotide.

"Inhibiting the expression or activity" refers to a reduction or blockade of the expression or activity and does not necessarily indicate a total elimination of expression or activity.

"Internucleoside linkage" refers to the chemical bond between nucleosides.

"Linked nucleosides" means adjacent nucleosides linked together by an internucleoside linkage.

"Mismatch" or "non-complementary nucleobase" refers to the case when a nucleobase of a first nucleic acid is not capable of pairing with the corresponding nucleobase of a second or target nucleic acid.

"Mixed backbone" means a pattern of internucleoside linkages including at least two different internucleoside linkages. For example, an oligonucleotide with a mixed backbone may include at least one phosphodiester linkage and at least one phosphorothioate linkage.

"Modified internucleoside linkage" refers to a substitution or any change from a naturally occurring internucleoside bond (i.e., a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

A "modified nucleoside" means a nucleoside having, independently, a modified sugar moiety and/or modified nucleobase.

"Modified nucleotide" means a nucleotide having, independently, a modified sugar moiety, modified internucleoside linkage, and/or modified nucleobase.

"Modified oligonucleotide" means an oligonucleotide comprising at least one modified internucleoside linkage, modified sugar, and/or modified nucleobase.

"Modified sugar" means substitution and/or any change from a natural sugar moiety.

"Monomer" means a single unit of an oligomer. Monomers include, but are not limited to, nucleosides and nucleotides, whether naturally occurring or modified.

"Motif" means the pattern of unmodified and modified nucleosides in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Off-target effect" refers to an unwanted or deleterious biological effect associated with modulation of RNA or protein expression of a gene other than the intended target nucleic acid.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection (e.g., bolus injection) or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Without limitation, as used herein, peptide refers to polypeptides and proteins.

"Pharmaceutical agent" means a substance that provides a therapeutic benefit when administered to an individual. For example, in certain embodiments, a modified oligonucleotide targeted to SOD-1 is a pharmaceutical agent.

"Pharmaceutical composition" means a mixture of substances suitable for administering to a subject. For example, a pharmaceutical composition may comprise a modified oligonucleotide and a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to days, weeks to months, or indefinitely.

"Prodrug" means a therapeutic agent that is prepared in an inactive form that is converted to an active form (i.e., drug) within the body or cells thereof by the action of endogenous enzymes or other chemicals and/or conditions.

"Prophylactically effective amount" refers to an amount of a pharmaceutical agent that provides a prophylactic or preventative benefit to an animal.

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Salts" mean a physiologically and pharmaceutically acceptable salts of antisense compounds, i.e., salts that retain the desired biological activity of the parent oligonucleotide and do not impart undesired toxicological effects thereto.

"Segments" are defined as smaller or sub-portions of regions within a target nucleic acid.

"Shortened" or "truncated" versions of oligonucleotides SOD-1ght herein have one, two or more nucleosides deleted.

"Side effects" means physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies.

"Single-stranded oligonucleotide" means an oligonucleotide which is not hybridized to a complementary strand.

"Sites," as used herein, are defined as unique nucleobase positions within a target nucleic acid.

"Slows progression" means decrease in the development of the disease.

"SOD-1" means the mammalian gene superoxide dismutase 1, soluble (SOD-1), including the human gene superoxide dismutase 1, soluble (SOD-1).

"SOD-1 associated disease" means any disease associated with any SOD-1 nucleic acid or expression product thereof. Such diseases may include a neurodegenerative disease. Such neurodegenerative diseases may include amyotrophic lateral sclerosis (ALS).

"SOD-1 mRNA" means any messenger RNA expression product of a DNA sequence encoding SOD-1.

"SOD-1 nucleic acid" means any nucleic acid encoding SOD-1. For example, in certain embodiments, a SOD-1 nucleic acid includes a DNA sequence encoding SOD-1, an RNA sequence transcribed from DNA encoding SOD-1 (including genomic DNA comprising introns and exons), and a mRNA sequence encoding SOD-1. "SOD-1 mRNA" means a mRNA encoding a SOD-1 protein.

"SOD-1 protein" means the polypeptide expression product of a SOD-1 nucleic acid.

"Specifically hybridizable" refers to an antisense compound having a sufficient degree of complementarity between an oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Stringent hybridization conditions" or "stringent conditions" refer to conditions under which an oligomeric compound will hybridize to its target sequence, but to a minimal number of other sequences.

"Subject" means a human or non-human animal selected for treatment or therapy.

"Sugar chemistry motif" means a pattern of sugar modifications including at least two different sugar modifications. For example, an oligonucleotide with a mixed backbone may include at least one 2'-O-methoxyethyl modified nucleoside, and/or one cEt modified nucleoside, and/or one 2'-deoxynucleoside.

"Target" refers to a protein, the modulation of which is desired.

"Target gene" refers to a gene encoding a target.

"Targeting" or "targeted" means the process of design and selection of an antisense compound that will specifically hybridize to a target nucleic acid and induce a desired effect.

"Target nucleic acid," "target RNA," and "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" or "treating" or "treatment" refers administering a composition to effect an alteration or improvement of the disease or condition.

"Unmodified nucleobases" mean the purine bases adenine (A) and guanine (G), and the pyrimidine bases thymine (T), cytosine (C) and uracil (U).

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Wing segment" means a plurality of nucleosides modified to impart to an oligonucleotide properties such as enhanced inhibitory activity, increased binding affinity for a target nucleic acid, or resistance to degradation by in vivo nucleases.

CERTAIN EMBODIMENTS

Certain embodiments provide methods, compounds, and compositions for inhibiting SOD-1 mRNA and protein expression. Certain embodiments provide methods, compounds, and composition for decreasing SOD-1 mRNA and protein levels.

Certain embodiments provide antisense compounds targeted to a SOD-1 nucleic acid. In certain embodiments, the SOD-1 nucleic acid is the sequence set forth in GENBANK Accession No. NM_000454.4 (incorporated herein as SEQ ID NO: 1), GENBANK Accession No. NT_011512.10 truncated from nucleotides 18693000 to Ser. No. 18/704,000 (incorporated herein as SEQ ID NO: 2), and the complement of GENBANK Accession No. NW_001114168.1 truncated from nucleotides 2258000 to U.S. Pat. No. 2,271,000 (incorporated herein as SEQ ID NO: 3).

Certain embodiments provide methods for the treatment, prevention, or amelioration of diseases, disorders, and conditions associated with SOD-1 in an individual in need thereof. Also contemplated are methods for the preparation of a medicament for the treatment, prevention, or amelioration of a disease, disorder, or condition associated with SOD-1. SOD-1 associated diseases, disorders, and conditions include neurodegenerative diseases. In certain embodiments, SOD-1 associated diseases include amyotrophic lateral sclerosis (ALS).

Embodiment 1

A compound, comprising a modified oligonucleotide consisting of 12 to 30 linked nucleosides and having a nucleobase sequence comprising at least 8, at least 9, at least 10, at least 11, at least 12, at least 13, at least 14, at least 15, at least 16, at least 17, at least 18, at least 19, or at least 20 consecutive nucleobases of any of the nucleobase sequences of SEQ ID NOs: 118-1461.

Embodiment 2

A compound, comprising a modified oligonucleotide consisting of 12 to 30 linked nucleosides and having a nucleobase sequence comprising at least 8, at least 9, at least 10, at least 11, at least 12, at least 13, at least 14, at least 15, at least 16, at least 17, at least 18, at least 19, or at least 20 consecutive nucleobases of any of the nucleobase sequences of SEQ ID NOs:15, 21, 23, 47, 54, and 67, wherein at least one internucleoside linkage is a phosphodiester linkage.

Embodiment 3

The compound of any preceding embodiment, wherein the modified oligonucleotide has a mixed backbone.

Embodiment 4

The compound of embodiment 3, wherein the mixed backbone motif is any of the following:

```
sosssssssooss,
sooossssssssoss,
sooossssssssoss,
sooosssssssooss,
sooossssssooss,
sooossssssssooss,
sooossssssssssooss,
sooossssssssssooos,
soooossssssssssooss,
sooossssssssssooss,
sosossssssssssosos,
and
sooossssssssssoooss,
wherein
s = a phosphorothioate internucleoside linkage,
and
o = a phosphodiester internucleoside linkage.
```

Embodiment 5

The compound of any preceding embodiment, wherein the modified oligonucleotide has a sugar chemistry motif of any of the following:

```
ekdddddddddekekee,
kekeddddddddekek,
eeeedddddddddkkee,
eeeedddddddddekeke,
eeeeddddddddkekee,
```

```
eeeedddddddddkkeee,
eeeeeddddddddkkee,
eeeekddddddddkeee,
eeeekddddddddkeeee,
eeekddddddddkeeee,
eeekkddddddddkkeee,
eekkddddddddkkee,
eekkdddddddeeeee,
eekkdddddddkkeee,
ekekdddddddeeeee,
ekekddddddddkekee,
and
kekeddddddddeeeee,
wherein
e = a 2'-O-methoxyethylribose modified sugar,
k = a cEt modified sugar,
d = a 2'-deoxyribose sugar,
```

Embodiment 6

The compound of any preceding embodiment, wherein the nucleobase sequence of the modified oligonucleotide is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% complementary to SEQ ID NO: 1 or SEQ ID NO: 2.

Embodiment 7

The compound of any preceding embodiment, consisting of a single-stranded modified oligonucleotide.

Embodiment 8

The compound of any preceding embodiment, wherein at least one internucleoside linkage is a modified internucleoside linkage.

Embodiment 9

The compound of embodiment 8, wherein at least one modified internucleoside linkage is a phosphorothioate internucleoside linkage.

Embodiment 10

The compound of embodiment 9, wherein each modified internucleoside linkage is a phosphorothioate internucleoside linkage.

Embodiment 11

The compound of any preceding embodiment, wherein at least one internucleoside linkage is a phosphodiester internucleoside linkage.

Embodiment 12

The compound of any preceding embodiment, wherein at least one internucleoside linkage is a phosphorothioate linkage and at least one internucleoside linkage is a phosphodiester linkage.

Embodiment 13

The compound of any preceding embodiment, wherein at least one nucleoside comprises a modified nucleobase.

Embodiment 14

The compound of embodiment 13, wherein the modified nucleobase is a 5-methylcytosine.

Embodiment 15

The compound of any preceding embodiment, wherein at least one nucleoside of the modified oligonucleotide comprises a modified sugar.

Embodiment 16

The compound of embodiment 15, wherein the at least one modified sugar is a bicyclic sugar.

Embodiment 17

The compound of embodiment 16, wherein the bicyclic sugar comprises a chemical link between the 2' and 4' position of the sugar 4'-CH$_2$—N(R)—O-2' bridge wherein R is, independently, H, C$_1$-C$_{12}$ alkyl, or a protecting group.

Embodiment 18

The compound of embodiment 17, wherein the bicyclic sugar comprises a 4'-CH$_2$—N(R)—O-2' bridge wherein R is, independently, H, C$_1$-C$_{12}$ alkyl, or a protecting group.

Embodiment 19

The compound of embodiment 15, wherein at least one modified sugar comprises a 2'-O-methoxyethyl group.

Embodiment 20

The compound of embodiment 15, wherein the modified sugar comprises a 2'-O(CH$_2$)$_2$—OCH$_3$ group.

Embodiment 21

The compound of any preceding embodiment, wherein the modified oligonucleotide comprises:
  a gap segment consisting of 10 linked deoxynucleosides;
  a 5' wing segment consisting of 5 linked nucleosides; and
  a 3' wing segment consisting of 5 linked nucleosides;
  wherein the gap segment is positioned between the 5' wing segment and the 3' wing segment and wherein each nucleoside of each wing segment comprises a modified sugar.

Embodiment 22

The compound of any preceding embodiment, wherein the modified oligonucleotide comprises:
  a gap segment consisting of 9 linked deoxynucleosides;
  a 5' wing segment consisting of 5 linked nucleosides; and
  a 3' wing segment consisting of 5 linked nucleosides;
  wherein the gap segment is positioned between the 5' wing segment and the 3' wing segment and wherein each nucleoside of each wing segment comprises a modified sugar.

Embodiment 23

The compound of any preceding embodiment, wherein the modified oligonucleotide comprises:
  a gap segment consisting of 8 linked deoxynucleosides;
  a 5' wing segment consisting of 5 linked nucleosides; and
  a 3' wing segment consisting of 5 linked nucleosides;
  wherein the gap segment is positioned between the 5' wing segment and the 3' wing segment and wherein each nucleoside of each wing segment comprises a modified sugar.

Embodiment 24

The compound of any preceding embodiment, wherein the modified oligonucleotide comprises:
  a gap segment consisting of 8 linked deoxynucleosides;
  a 5' wing segment consisting of 4 linked nucleosides; and
  a 3' wing segment consisting of 5 linked nucleosides;
  wherein the gap segment is positioned between the 5' wing segment and the 3' wing segment and wherein each nucleoside of each wing segment comprises a modified sugar.

Embodiment 25

The compound of any preceding embodiment, wherein the modified oligonucleotide comprises:
  a gap segment consisting of 8 linked deoxynucleosides;
  a 5' wing segment consisting of 5 linked nucleosides; and
  a 3' wing segment consisting of 7 linked nucleosides;
  wherein the gap segment is positioned between the 5' wing segment and the 3' wing segment and wherein each nucleoside of each wing segment comprises a modified sugar.

Embodiment 26

The compound of any preceding embodiment, wherein the modified oligonucleotide comprises:
  a gap segment consisting of 8 linked deoxynucleosides;
  a 5' wing segment consisting of 6 linked nucleosides; and
  a 3' wing segment consisting of 6 linked nucleosides;
  wherein the gap segment is positioned between the 5' wing segment and the 3' wing segment and wherein each nucleoside of each wing segment comprises a modified sugar.

Embodiment 27

The compound of any preceding embodiment, wherein the modified oligonucleotide comprises:
  a gap segment consisting of 9 linked deoxynucleosides;
  a 5' wing segment consisting of 6 linked nucleosides; and
  a 3' wing segment consisting of 5 linked nucleosides;
  wherein the gap segment is positioned between the 5' wing segment and the 3' wing segment and wherein each nucleoside of each wing segment comprises a modified sugar.

Embodiment 28
The compound of any preceding embodiment, wherein the modified oligonucleotide consists of 12, 13, 14, 15, 16, 17, 18, 19, or 20 linked nucleosides.
Embodiment 29
A compound consisting of a modified oligonucleotide according to the following formula:
(SEQ ID NO: 725)
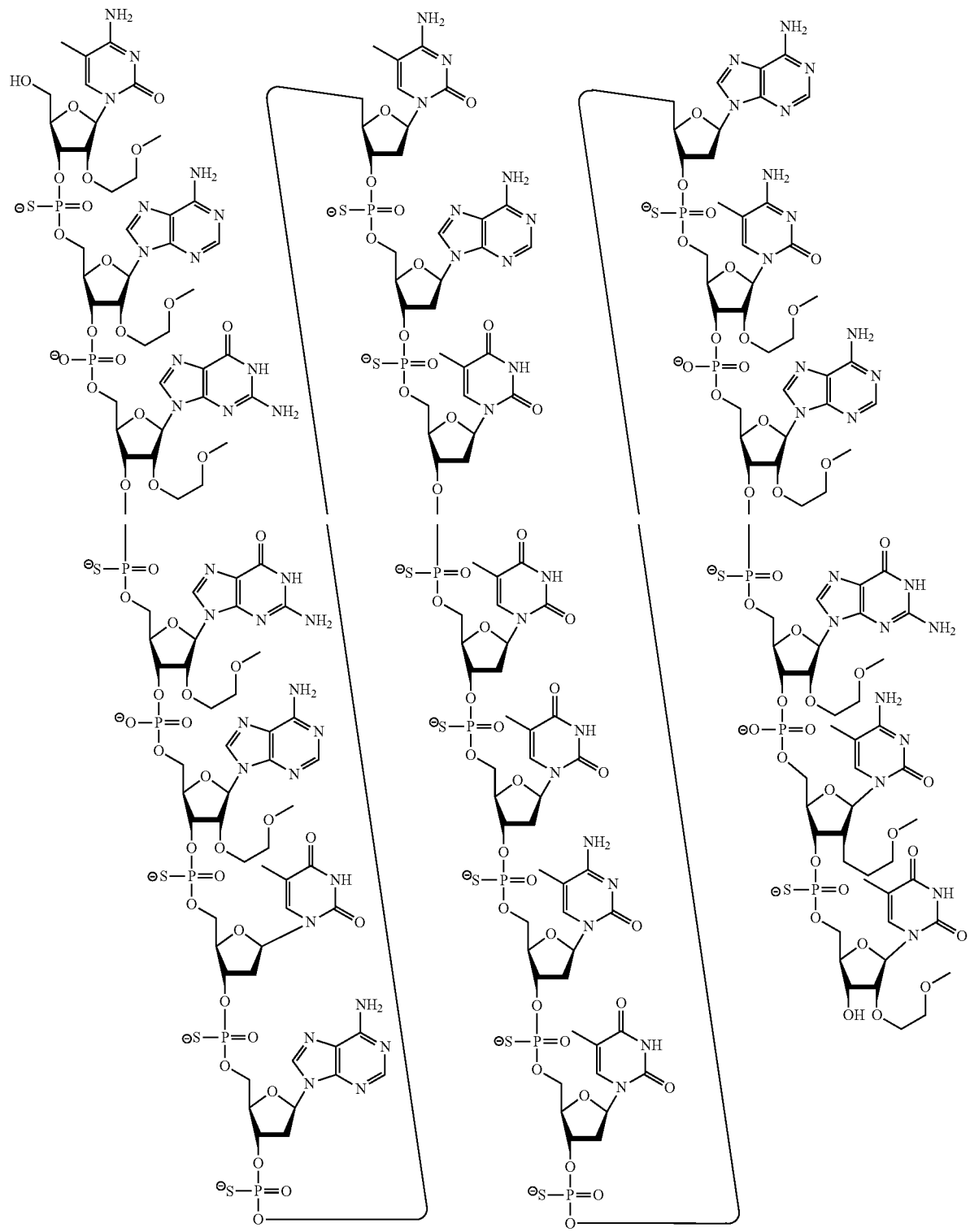

Embodiment 30
A compound consisting of a modified oligonucleotide according to the following formula:
(SEQ ID NO: 1351)
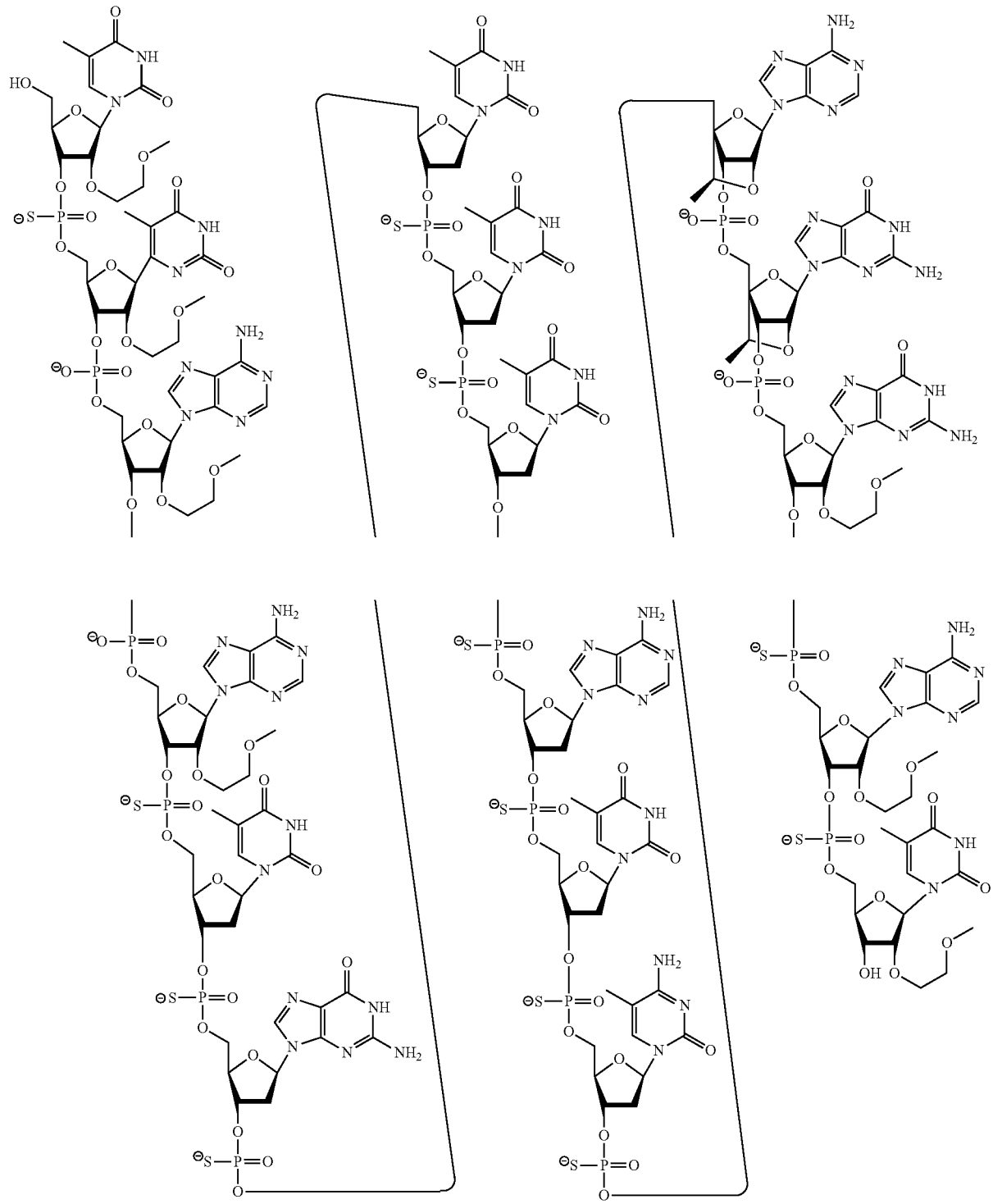

Embodiment 31
A compound consisting of a modified oligonucleotide according to the following formula:
(SEQ ID NO: 1342)
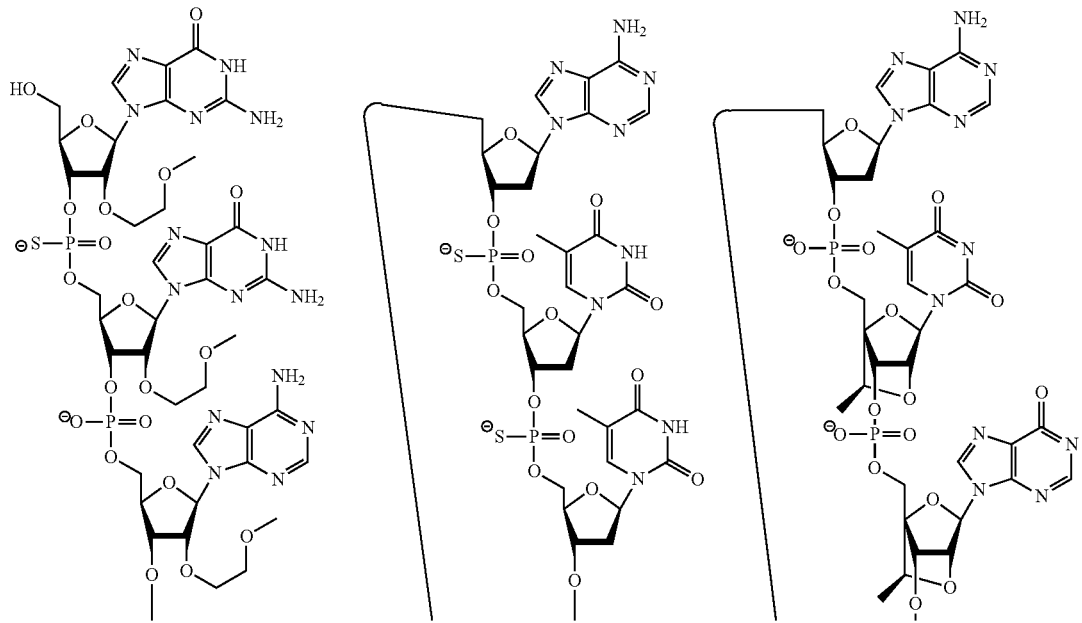
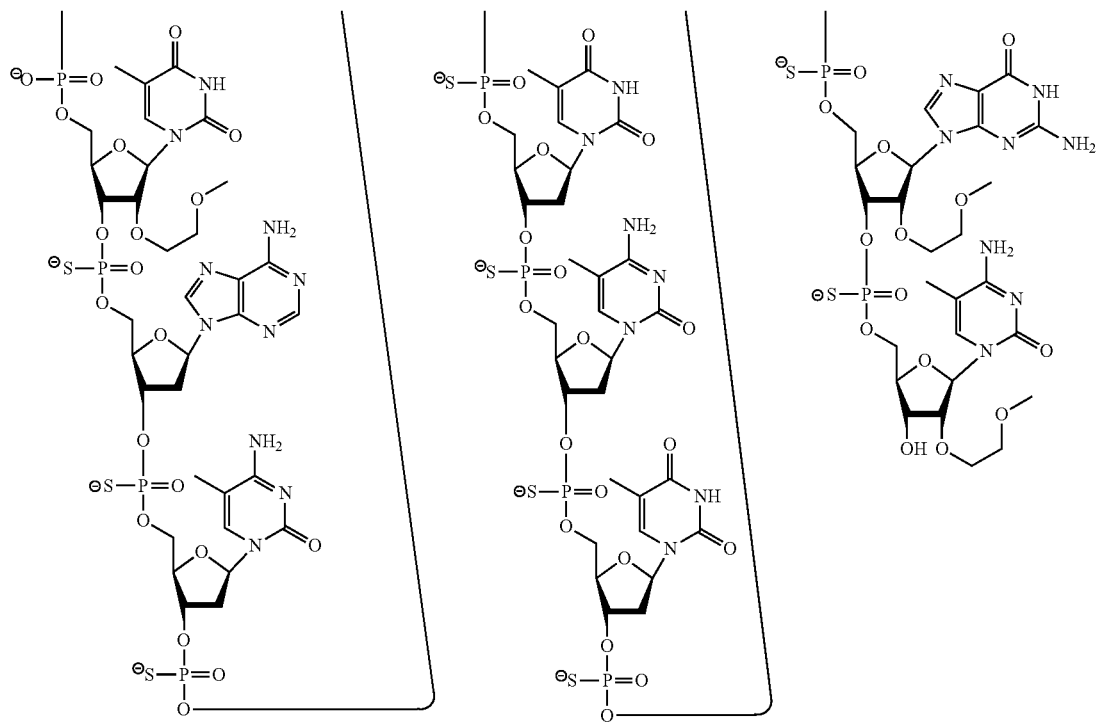

Embodiment 32
A compound consisting of a modified oligonucleotide according to the following formula:
(SEQ ID NO: 1342)
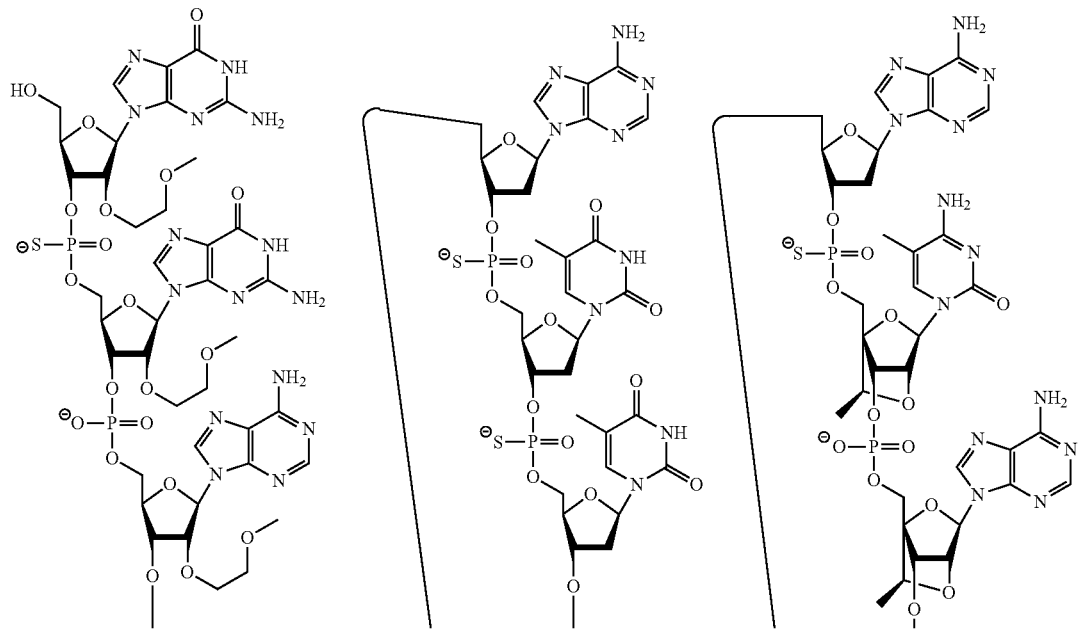
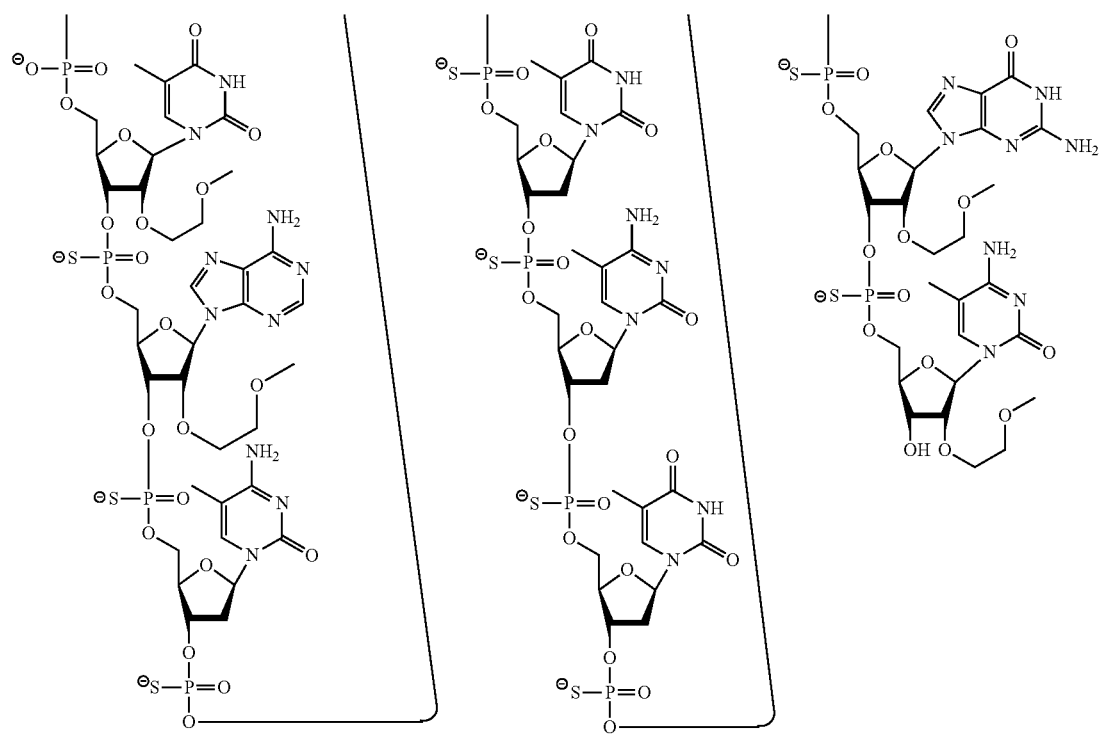

Embodiment 33
A compound consisting of a modified oligonucleotide according to the following formula:
(SEQ ID NO: 1342)
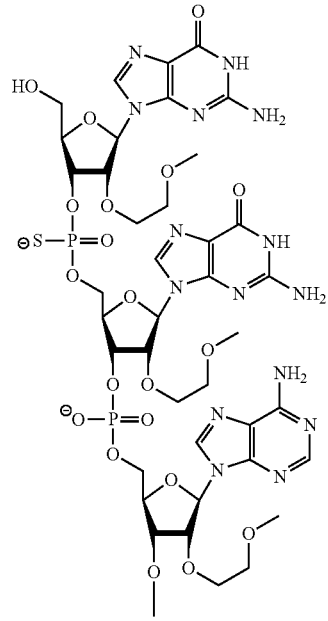
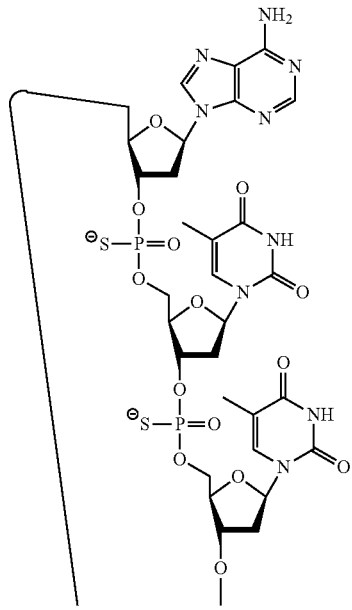
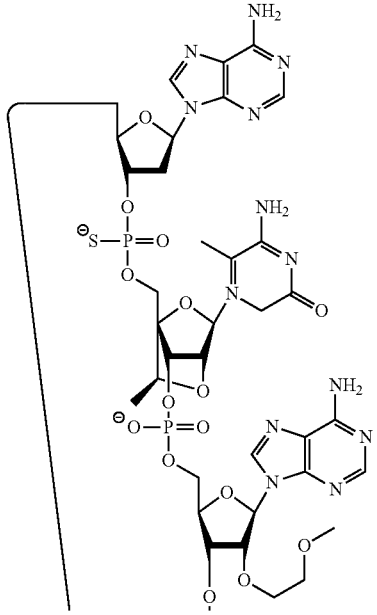
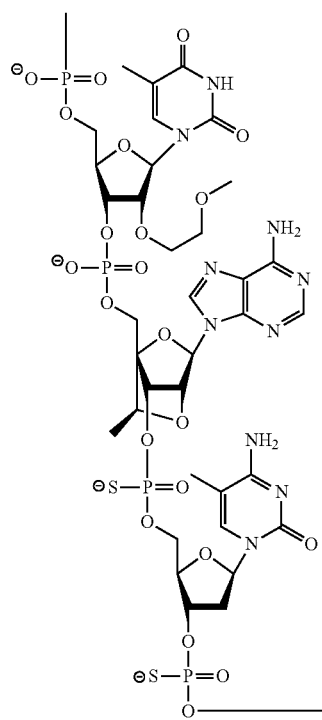
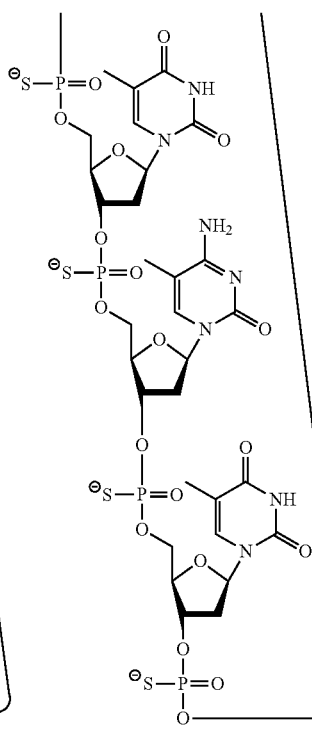
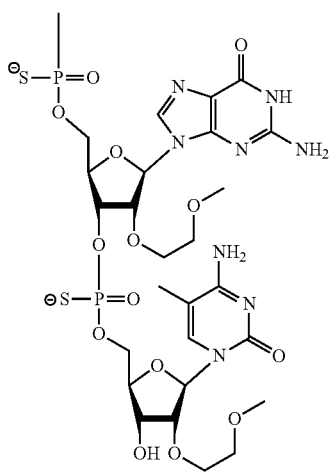

Embodiment 34
A compound consisting of a modified oligonucleotide according to the following formula:
(SEQ ID NO: 1173)
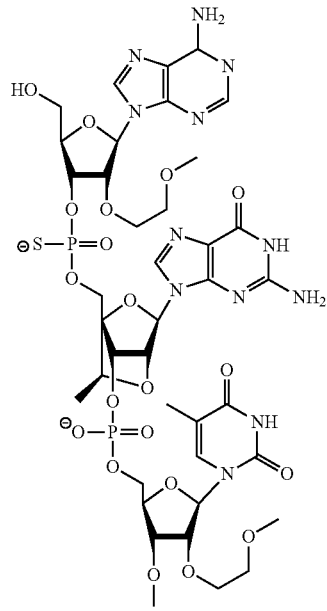
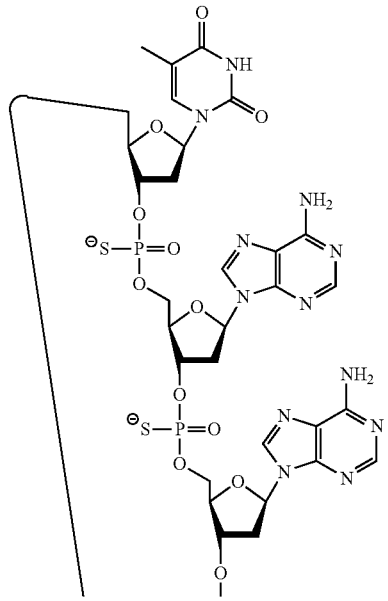
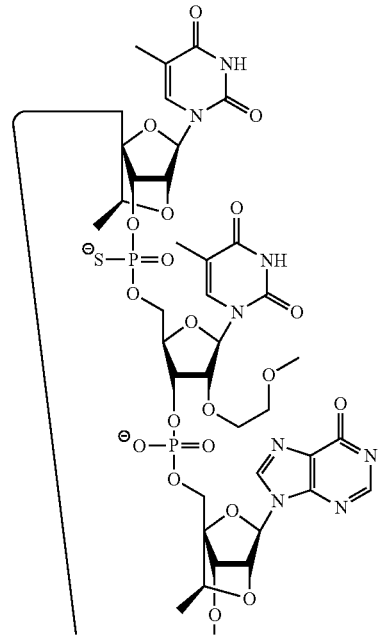
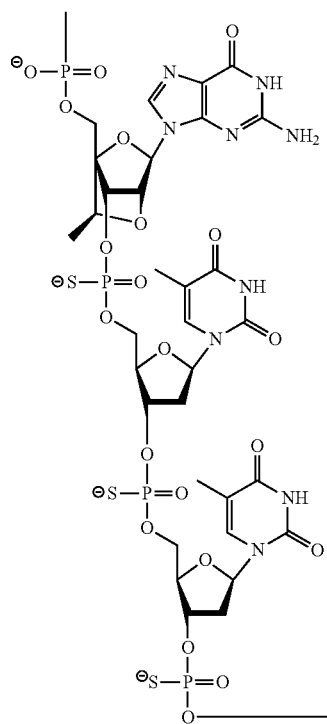
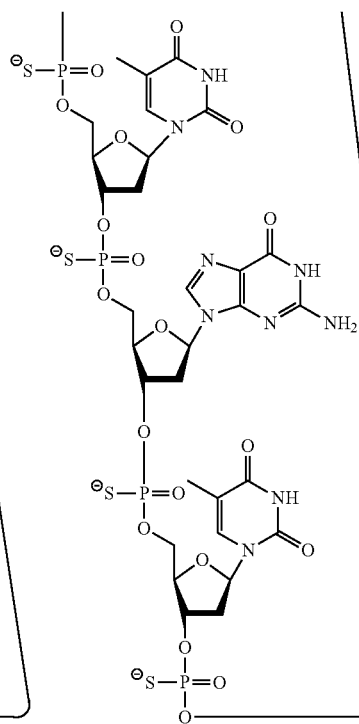
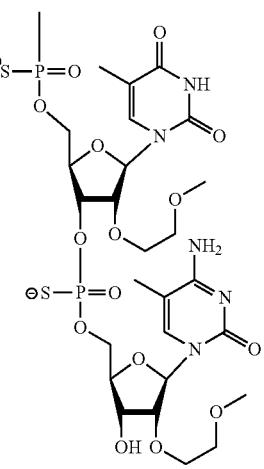

Embodiment 35
A compound consisting of a modified oligonucleotide according to the following formula:
(SEQ ID NO: 1173)
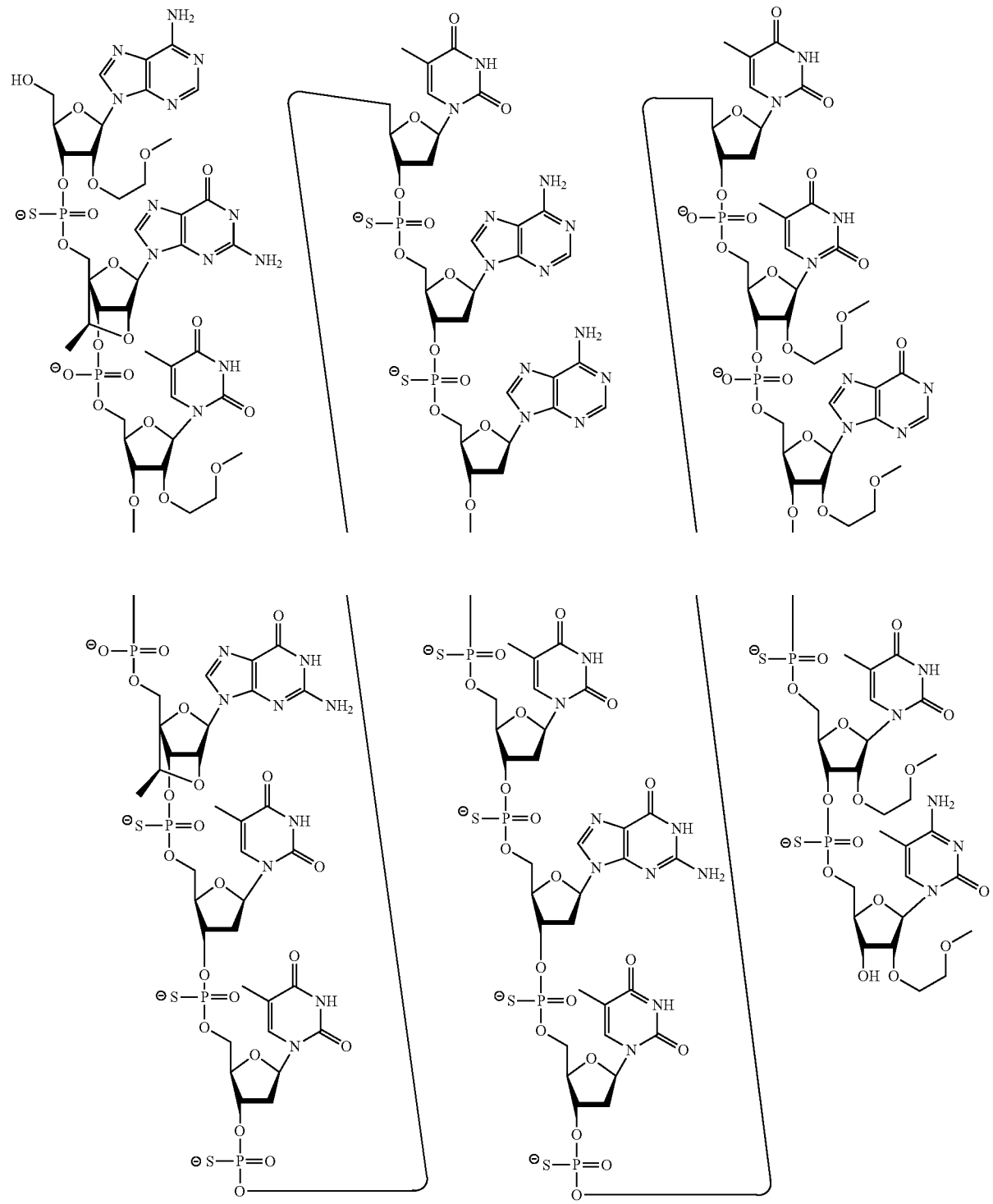

Embodiment 36
A compound consisting of a modified oligonucleotide according to the following formula:
(SEQ ID NO: 1173)
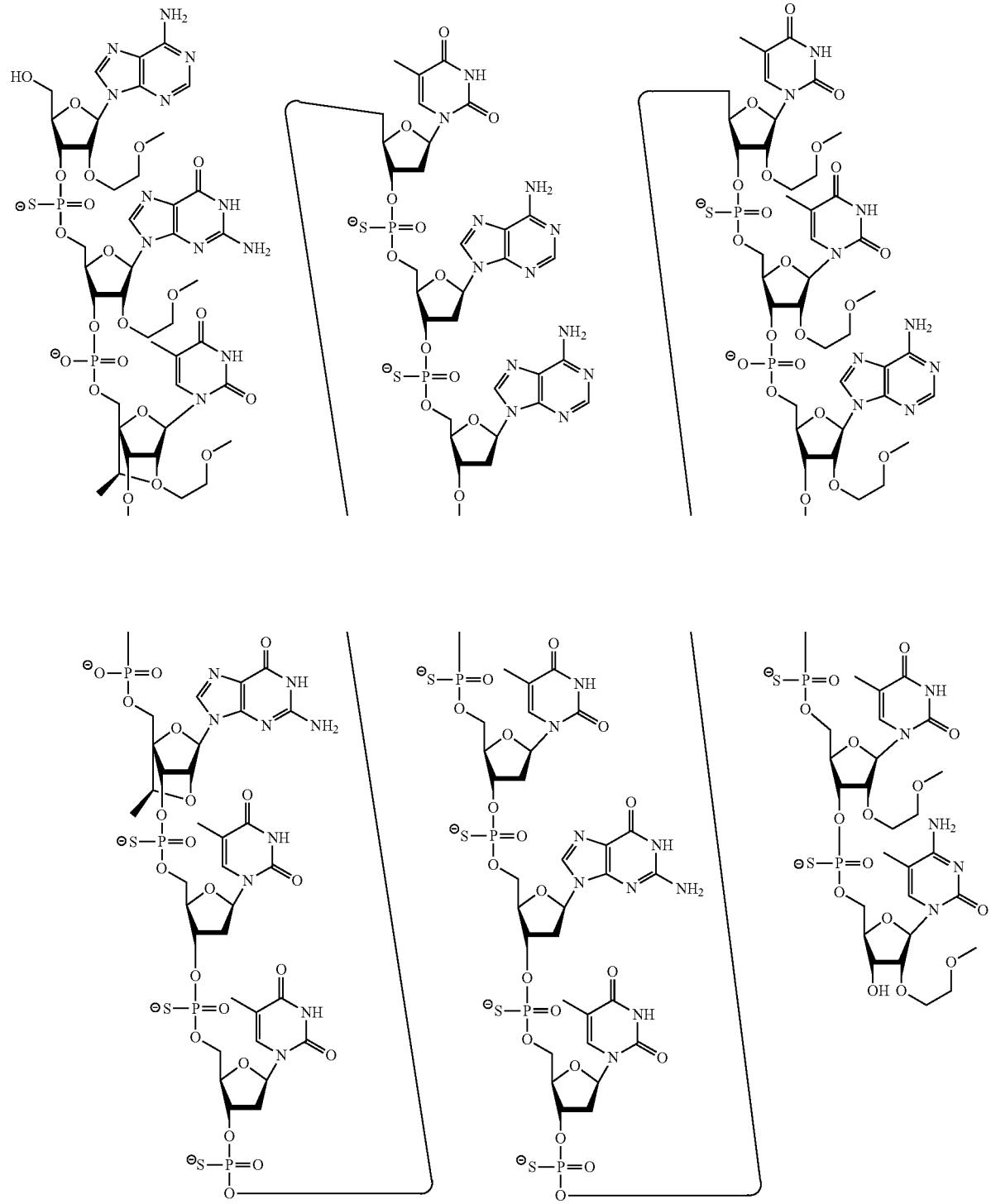

Embodiment 37

A compound consisting of a modified oligonucleotide according to the following formula: mCes Aeo Ges Geo Aes Tds Ads mCds Ads Tds Tds Tds mCds Tds Ads mCeo Aes Geo mCes Te; wherein,
A=an adenine,
mC=a 5'-methylcytosine
G=a guanine,
T=a thymine,
e=a 2'-O-methoxyethylribose modified sugar,
d=a 2'-deoxyribose sugar,
s=a phosphorothioate internucleoside linkage, and
o=a phosphodiester internucleoside linkage.

Embodiment 38

A compound consisting of a modified oligonucleotide according to the following formula: Tes Teo Aeo Aes Tds Gds Tds Tds Tds Ads Tds mCds Ako Gko Ges Aes Te; wherein,
A=an adenine,
mC=a 5'-methylcytosine
G=a guanine,
T=a thymine,
e=a 2'-O-methoxyethylribose modified sugar,
k=a cEt modified sugar,
d=a 2'-deoxyribose sugar,
s=a phosphorothioate internucleoside linkage, and
o=a phosphodiester internucleoside linkage.

Embodiment 39

A compound consisting of a modified oligonucleotide according to the following formula: Ges Geo Aeo Teo Ads mCds Ads Tds Tds Tds mCds Tds Ads mCko Aks Ges mCe; wherein,
A=an adenine,
mC=a 5'-methylcytosine
G=a guanine,
T=a thymine,
e=a 2'-O-methoxyethylribose modified sugar,
k=a cEt modified sugar,
d=a 2'-deoxyribose sugar,
s=a phosphorothioate internucleoside linkage, and
o=a phosphodiester internucleoside linkage.

Embodiment 40

A compound consisting of a modified oligonucleotide according to the following formula: Ges Geo Aeo Teo Aes mCds Ads Tds Tds Tds mCds Tds Ads mCko Aks Ges mCe; wherein,
A=an adenine,
mC=a 5'-methylcytosine
G=a guanine,
T=a thymine,
e=a 2'-O-methoxyethylribose modified sugar,
k=a cEt modified sugar,
d=a 2'-deoxyribose sugar,
s=a phosphorothioate internucleoside linkage, and
o=a phosphodiester internucleoside linkage.

Embodiment 41

A compound consisting of a modified oligonucleotide according to the following formula: Ges Geo Aeo Teo Aks mCds Ads Tds Tds Tds mCds Tds Ads mCko Aes Ges mCe; wherein,
A=an adenine,
mC=a 5'-methylcytosine
G=a guanine,
T=a thymine,
e=a 2'-O-methoxyethylribose modified sugar,
k=a cEt modified sugar,
d=a 2'-deoxyribose sugar,
s=a phosphorothioate internucleoside linkage, and
o=a phosphodiester internucleoside linkage.

Embodiment 42

A compound consisting of a modified oligonucleotide according to the following formula: Aes Gko Teo Gks Tds Tds Tds Ads Ads Tds Gds Tds Tko Teo Aks Tes mCe; wherein,
A=an adenine,
mC=a 5'-methylcytosine
G=a guanine,
T=a thymine,
e=a 2'-O-methoxyethylribose modified sugar,
k=a cEt modified sugar,
d=a 2'-deoxyribose sugar,
s=a phosphorothioate internucleoside linkage, and
o=a phosphodiester internucleoside linkage.

Embodiment 43

A compound consisting of a modified oligonucleotide according to the following formula: Aes Gko Teo Gks Tds Tds Tds Ads Ads Tds Gds Tds Teo Teo Aes Tes mCe; wherein,
A=an adenine,
mC=a 5'-methylcytosine
G=a guanine,
T=a thymine,
e=a 2'-O-methoxyethylribose modified sugar,
k=a cEt modified sugar,
d=a 2'-deoxyribose sugar,
s=a phosphorothioate internucleoside linkage, and
o=a phosphodiester internucleoside linkage.

Embodiment 44

A compound consisting of a modified oligonucleotide according to the following formula: Aes Geo Tko Gks Tds Tds Tds Ads Ads Tds Gds Tds Teo Teo Aes Tes mCe; wherein,
A=an adenine,
mC=a 5'-methylcytosine
G=a guanine,
T=a thymine,
e=a 2'-O-methoxyethylribose modified sugar,
k=a cEt modified sugar,
d=a 2'-deoxyribose sugar,
s=a phosphorothioate internucleoside linkage, and
o=a phosphodiester internucleoside linkage.

Embodiment 45

A compound consisting of a modified oligonucleotide according to the following formula: mCes mCeo Geo Teo mCeo Gds mCds mCds mCds Tds Tds mCds Ads Gds mCds Aeo mCeo Ges mCes Ae, wherein,
A=an adenine,
mC=a 5'-methylcytosine
G=a guanine, T=a thymine,
e=a 2'-O-methoxyethylribose modified sugar,
d=a 2'-deoxyribose sugar,
s=a phosphorothioate internucleoside linkage, and
o=a phosphodiester internucleoside linkage.

Embodiment 46

A compound consisting of a modified oligonucleotide according to the following formula: mCes mCeo Geo Teo mCes Gds mCds mCds mCds Tds Tds mCds Ads Ges mCeo Aeo mCeo Ges mCes Ae, wherein,
A=an adenine,
mC=a 5'-methylcytosine
G=a guanine,
T=a thymine,
e=a 2'-O-methoxyethylribose modified sugar,
d=a 2'-deoxyribose sugar,
s=a phosphorothioate internucleoside linkage, and
o=a phosphodiester internucleoside linkage.

Embodiment 47

A compound consisting of a modified oligonucleotide according to the following formula: mCes mCeo Geo Teo mCes Gds mCds mCds mCds Tds Tds mCds Ads Gds mCds Aeo mCeo Geo mCes Ae, wherein,
A=an adenine,
mC=a 5'-methylcytosine
G=a guanine,
T=a thymine,
e=a 2'-O-methoxyethylribose modified sugar,
d=a 2'-deoxyribose sugar,
s=a phosphorothioate internucleoside linkage, and
o=a phosphodiester internucleoside linkage.

Embodiment 48

A compound consisting of a modified oligonucleotide according to the following formula: Aes mCeo Aeo mCeo mCes Tds Tds mCds Ads mCds Tds Gds Gds Tds mCds mCeo Aeo Teo Tes Ae, wherein,
A=an adenine,
mC=a 5'-methylcytosine
G=a guanine,
T=a thymine,
e=a 2'-O-methoxyethylribose modified sugar,
d=a 2'-deoxyribose sugar,
s=a phosphorothioate internucleoside linkage, and
o=a phosphodiester internucleoside linkage.

Embodiment 49

A compound consisting of a modified oligonucleotide according to the following formula: Ges Geo mCeo Geo Aes Tds mCds mCds mCds Ads Ads Tds Tds Ads mCds Aeo mCeo mCeo Aes mCe, wherein,
A=an adenine,
mC=a 5'-methylcytosine
G=a guanine,
T=a thymine,
e=a 2'-O-methoxyethylribose modified sugar,
d=a 2'-deoxyribose sugar,
s=a phosphorothioate internucleoside linkage, and
o=a phosphodiester internucleoside linkage.

Embodiment 50

A compound consisting of a modified oligonucleotide according to the following formula: Ges Geo mCeo Geo Aes Tes mCds mCds mCds Ads Ads Tds Tds Ads mCeo Aeo mCeo mCes Aes mCe, wherein,
A=an adenine,
mC=a 5'-methylcytosine
G=a guanine,
T=a thymine,
e=a 2'-O-methoxyethylribose modified sugar,
d=a 2'-deoxyribose sugar,
s=a phosphorothioate internucleoside linkage, and
o=a phosphodiester internucleoside linkage.

Embodiment 51

A compound consisting of a modified oligonucleotide according to the following formula: Ges Geo mCeo Geo Aes Tds mCds mCds mCds Ads Ads Tds Tds Aes mCeo Aeo mCeo mCes Aes mCe, wherein,
A=an adenine,
mC=a 5'-methylcytosine
G=a guanine,
T=a thymine,
e=a 2'-O-methoxyethylribose modified sugar,
d=a 2'-deoxyribose sugar,
s=a phosphorothioate internucleoside linkage, and
o=a phosphodiester internucleoside linkage.

Embodiment 52

A compound consisting of a modified oligonucleotide according to the following formula: Ges Geo mCeo Geo Aeo Tes mCds mCds mCds Ads Ads Tds Tds Ads mCds Aeo mCeo mCes Aes mCe, wherein,
A=an adenine,
mC=a 5'-methylcytosine
G=a guanine,
T=a thymine,
e=a 2'-O-methoxyethylribose modified sugar,
d=a 2'-deoxyribose sugar,
s=a phosphorothioate internucleoside linkage, and
o=a phosphodiester internucleoside linkage.

Embodiment 53

A compound consisting of a modified oligonucleotide according to the following formula: Ges Teo mCeo Geo mCes mCds mCds Tds Tds mCds Ads Gds mCds Ads mCds Geo mCeo Aeo mCes Ae, wherein,
A=an adenine,
mC=a 5'-methylcytosine
G=a guanine,
T=a thymine,
e=a 2'-O-methoxyethylribose modified sugar,
d=a 2'-deoxyribose sugar,
s=a phosphorothioate internucleoside linkage, and
o=a phosphodiester internucleoside linkage.

Embodiment 54

A compound consisting of a modified oligonucleotide according to the following formula: Tes mCeo Geo mCeo mCes mCds Tds Tds mCds Ads Gds mCds Ads mCds Gds mCeo Aeo mCeo Aes mCe, wherein,
A=an adenine,
mC=a 5'-methylcytosine
G=a guanine,
T=a thymine,
e=a 2'-O-methoxyethylribose modified sugar, d=a 2'-deoxyribose sugar,
s=a phosphorothioate internucleoside linkage, and
o=a phosphodiester internucleoside linkage.

Embodiment 55

A compound consisting of a modified oligonucleotide according to the following formula: Ges Aes Aes Aes Tes Tds Gds Ads Tds Gds Ads Tds Gds mCds mCds mCes Tes Ges mCes Ae, wherein,
A=an adenine,
mC=a 5'-methylcytosine
G=a guanine,
T=a thymine,
e=a 2'-O-methoxyethylribose modified sugar,
d=a 2'-deoxyribose sugar, and
s=a phosphorothioate internucleoside linkage.

Embodiment 56

A composition comprising the compound of any preceding embodiment or salt thereof and at least one of a pharmaceutically acceptable carrier or diluent.

Embodiment 57

A method comprising administering to an animal the compound or composition of any preceding embodiment.

Embodiment 58

The method of embodiment 57, wherein the animal is a human.

Embodiment 59

The method of embodiment 57, wherein administering the compound prevents, treats, ameliorates, or slows progression of a SOD-1 associated disease.

Embodiment 60

The method of embodiment 59, wherein the SOD-1 associated disease is a neurodegenerative disease.

Embodiment 61

The method of embodiment 60, wherein the SOD-1 associated disease is ALS.

Embodiment 62

Use of the compound or composition of any preceding embodiment for the manufacture of a medicament for treating a neurodegenerative disorder.

Embodiment 63

Use of the compound or composition of any preceding embodiment for the manufacture of a medicament for treating ALS.

Embodiment 64

The compound or composition of any preceding embodiment wherein the modified oligonucleotide does not have the nucleobase sequence of SEQ ID NO: 21.

Embodiment 65

The compound or composition of any preceding embodiment wherein the modified oligonucleotide does not have the nucleobase sequence of any of SEQ ID NOs: 21-118.

Embodiment 66

A compound comprising a modified oligonucleotide consisting of 12 to 30 linked nucleosides and having a nucleobase sequence, wherein the nucleobase sequence comprises an at least 12 consecutive nucleobase portion complementary to an equal number of nucleobases of nucleotides 665 to 684 of SEQ ID NO: 1, wherein the modified oligonucleotide is at least 80% complementary to SEQ ID NO: 1.

Embodiment 67

The compound of embodiment 66, wherein the modified oligonucleotide is 100% complementary to SEQ ID NO: 1.

Embodiment 68

The compound of embodiment 66, wherein the modified oligonucleotide is a single-stranded modified oligonucleotide.

Embodiment 69

The compound of embodiments 66-68 wherein at least one internucleoside linkage is a modified internucleoside linkage.

Embodiment 70

The compound of embodiment 69, wherein at least one modified internucleoside linkage is a phosphorothioate internucleoside linkage.

Embodiment 71

The compound of embodiment 70, wherein each modified internucleoside linkage is a phosphorothioate internucleoside linkage.

Embodiment 72

The compound of embodiments 66-69, wherein at least one internucleoside linkage is a phosphodiester internucleoside linkage.

Embodiment 73

The compound of embodiments 66-71 and 72-73, wherein at least one internucleoside linkage is a phosphorothioate linkage and at least one internucleoside linkage is a phosphodiester linkage.

Embodiment 74

The compound of embodiments 66-73, wherein at least one nucleoside comprises a modified nucleobase.

Embodiment 75

The compound of embodiment 74, wherein the modified nucleobase is a 5-methylcytosine.

Embodiment 76

The compound of embodiments 66-75, wherein at least one nucleoside of the modified oligonucleotide comprises a modified sugar.

Embodiment 77

The compound of embodiment 76, wherein the at least one modified sugar is a bicyclic sugar.

Embodiment 78

The compound of embodiment 77, wherein the bicyclic sugar comprises a 4'-CH(R)—O-2' bridge wherein R is, independently, H, $C_1$-$C_{12}$ alkyl, or a protecting group.

Embodiment 79

The compound of embodiment 78, wherein R is methyl.

Embodiment 80

The compound of embodiment 78, wherein R is H.

Embodiment 81

The compound of embodiment 76, wherein the at least one modified sugar comprises a 2'-O-methoxyethyl group.

Antisense Compounds

Oligomeric compounds include, but are not limited to, oligonucleotides, oligonucleosides, oligonucleotide analogs, oligonucleotide mimetics, antisense compounds, antisense oligonucleotides, modified oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an oligonucleotide has a nucleobase sequence that, when written in the 5' to 3' direction, comprises the reverse complement of the target segment of a target nucleic acid to which it is targeted.

In certain embodiments, an antisense compound targeted to a SOD-1 nucleic acid is 12 to 30 subunits in length. In certain embodiments, an antisense compound targeted to a SOD-1 nucleic acid is 12 to 25 subunits in length. In certain embodiments, an antisense compound targeted to a SOD-1 nucleic acid is 12 to 22 subunits in length. In certain embodiments, an antisense compound targeted to a SOD-1 nucleic acid is 14 to 20 subunits in length. In certain embodiments, an antisense compound targeted to a SOD-1 nucleic acid is 15 to 25 subunits in length. In certain embodiments, an antisense compound targeted to a SOD-1 nucleic acid is 18 to 22 subunits in length. In certain embodiments, an antisense compound targeted to a SOD-1 nucleic acid is 19 to 21 subunits in length. In certain embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 30, 18 to 50, 19 to 30, 19 to 50, or 20 to 30 linked subunits in length.

In certain embodiments, an antisense compound targeted to a SOD-1 nucleic acid is 12 subunits in length. In certain embodiments, an antisense compound targeted to a SOD-1 nucleic acid is 13 subunits in length. In certain embodiments, an antisense compound targeted to a SOD-1 nucleic acid is 14 subunits in length. In certain embodiments, an antisense compound targeted to a SOD-1 nucleic acid is 15 subunits in length. In certain embodiments, an antisense compound targeted to a SOD-1 nucleic acid is 16 subunits in length. In certain embodiments, an antisense compound targeted to a SOD-1 nucleic acid is 17 subunits in length. In certain embodiments, an antisense compound targeted to a SOD-1 nucleic acid is 18 subunits in length. In certain embodiments, an antisense compound targeted to a SOD-1 nucleic acid is 19 subunits in length. In certain embodiments, an antisense compound targeted to a SOD-1 nucleic acid is 20 subunits in length. In certain embodiments, an antisense compound targeted to a SOD-1 nucleic acid is 21 subunits in length. In certain embodiments, an antisense compound targeted to a SOD-1 nucleic acid is 22 subunits in length. In certain embodiments, an antisense compound targeted to a SOD-1 nucleic acid is 23 subunits in length. In certain embodiments, an antisense compound targeted to a SOD-1 nucleic acid is 24 subunits in length. In certain embodiments, an antisense compound targeted to a SOD-1 nucleic acid is 25 subunits in length. In certain embodiments, an antisense compound targeted to a SOD-1 nucleic acid is 26 subunits in length. In certain embodiments, an antisense compound targeted to a SOD-1 nucleic acid is 27 subunits in length. In certain embodiments, an antisense compound targeted to a SOD-1 nucleic acid is 28 subunits in length. In certain embodiments, an antisense compound targeted to a SOD-1 nucleic acid is 29 subunits in length. In certain embodiments, an antisense compound targeted to a SOD-1 nucleic acid is 30 subunits in length. In certain embodiments, the antisense compound targeted to a SOD-1 nucleic acid is 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In certain embodiments the antisense compound is a modified oligonucleotide, and the linked subunits are nucleosides.

In certain embodiments, oligonucleotides targeted to a SOD-1 nucleic acid may be shortened or truncated. For example, a single subunit may be deleted from the 5' end (5' truncation), or alternatively from the 3' end (3' truncation). A shortened or truncated antisense compound targeted to a SOD-1 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as a modified oligonucleotide, and/or introduce mismatch bases without eliminating activity. For example, in Woolf et al. (Proc. Natl. Acad. Sci. USA 89:7305-7309, 1992), a series of oligonucleotides 13-25 nucleobases in length were tested for their ability to induce cleavage of a target RNA in an oocyte injection model. Oligonucleotides 25 nucleobases in length with 8 or 11 mismatch bases near the ends of the oligonucleotides were able to direct specific cleavage of the target mRNA, albeit to a lesser extent than oligonucleotides that contained no mismatches. Similarly, target specific cleavage was achieved using 13 nucleobase oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase oligonucleotides, and a 28 and 42 nucleobase oligonucleotides comprised of the sequence of two or three of the tandem oligonucleotides, respectively, for their ability to arrest translation of human DHFR in a rabbit reticulocyte assay. Each of the three 14 nucleobase oligonucleotides alone was able to inhibit translation, albeit at a more modest level than the 28 or 42 nucleobase oligonucleotides.

Antisense Compound Motifs

In certain embodiments, antisense compounds targeted to a SOD-1 nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH$_2$) n-O-2' bridge, where n=1 or n=2 and 4'-CH$_2$—O—CH$_2$-2'). In certain embodiments, wings may include several modified sugar moieties, including, for example 2'-MOE. In certain embodiments, wings may include several modified and unmodified sugar moieties. In certain embodiments, wings may include various combinations of 2'-MOE nucleosides and 2'-deoxynucleosides.

Each distinct region may comprise uniform sugar moieties, variant, or alternating sugar moieties. The wing-gap-wing motif is frequently described as "X—Y—Z", where "X" represents the length of the 5' wing, "Y" represents the length of the gap, and "Z" represents the length of the 3' wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X—Y—Z" has a configuration such that the gap is positioned immediately adjacent to each of the 5' wing and the 3' wing. Thus, no intervening nucleotides exist between the 5' wing and gap, or the gap and the 3' wing. Any of the antisense compounds described herein can have a gapmer motif. In certain embodiments, "X" and "Z" are the same; in other embodiments they are different.

In certain embodiments, gapmers provided herein include, for example 20-mers having a motif of 5-10-5.

In certain embodiments, gapmers provided herein include, for example 19-mers having a motif of 5-9-5.

In certain embodiments, gapmers provided herein include, for example 18-mers having a motif of 5-8-5.

In certain embodiments, gapmers provided herein include, for example 18-mers having a motif of 4-8-5.

In certain embodiments, gapmers provided herein include, for example 18-mers having a motif of 5-8-7.

In certain embodiments, gapmers provided herein include, for example 18-mers having a motif of 6-8-6.

In certain embodiments, gapmers provided herein include, for example 18-mers having a motif of 6-8-5.

In certain embodiments, the modified oligonucleotide contains at least one 2'-O-methoxyethyl modified nucleoside, at least one cEt modified nucleoside, and at least one 2'-deoxynucleoside. In certain embodiments, the modified oligonucleotide has a sugar chemistry motif of any of the following:

```
ekdddddddddekekee kekedddddddddekek eeeedddddddddkkee eeeedddddddddekeke eeeedddddddddkekee eeeedddddddddkkeee eeeeedddddddddkkee eeeekdddddddddkeee eeeekdddddddddkeeee eeekdddddddddkeeee eeekkdddddddddkkeee eekkdddddddddkkee eekkdddddddddeeeee eekkdddddddddkkeee ekekdddddddddeeeee ekekdddddddddkekee kekedddddddddeeeee,
```

-continued
```
wherein
    e = a 2'-O-methoxyethylribose modified sugar,
    k = a cEt modified sugar,
    d = a 2'-deoxyribose sugar,
```

Target Nucleic Acids, Target Regions and Nucleotide Sequences

Nucleotide sequences that encode SOD-1 include, without limitation, the following: GENBANK Accession No. NM_000454.4 (incorporated herein as SEQ ID NO: 1), GENBANK Accession No. NT_011512.10 truncated from nucleotides 18693000 to Ser. No. 18/704,000 (incorporated herein as SEQ ID NO: 2), and the complement of GENBANK Accession No. NW_001114168.1 truncated from nucleotides 2258000 to U.S. Pat. No. 2,271,000 (incorporated herein as SEQ ID NO: 3).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for SOD-1 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in SOD-1 mRNA levels are indicative of inhibition of SOD-1 expression. Reductions in levels of a SOD-1 protein are also indicative of inhibition of target mRNA expression. Phenotypic changes are indicative of inhibition of SOD-1 expression. Improvement in neurological function is indicative of inhibition of SOD-1 expression. Improved motor function is indicative of inhibition of SOD-1 expression.

Hybridization

In some embodiments, hybridization occurs between an antisense compound disclosed herein and a SOD-1 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a SOD-1 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a SOD-1 nucleic acid).

Non-complementary nucleobases between an antisense compound and a SOD-1 nucleic acid may be tolerated provided that the antisense compound remains able to specifically hybridize to a target nucleic acid. Moreover, an antisense compound may hybridize over one or more segments of a SOD-1 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a SOD-1 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to a SOD-1 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer oligonucleotide.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a SOD-1 nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a SOD-1 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds, are complementary to at least an 11 nucleobase portion of a target segment. In certain embodiments, the antisense compounds, are complementary to at least a 12 nucleobase portion of a target segment. In certain embodiments, the antisense compounds, are complementary to at least a 13 nucleobase portion of a target segment. In certain embodiments, the antisense compounds, are complementary to at least a 14 nucleobase portion of a target segment. In certain embodiments, the antisense compounds, are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, modified oligonucleotides targeted to a SOD-1 nucleic acid comprise one or more modified internucleoside linkages. In certain embodiments, the modified internucleoside linkages are interspersed throughout the antisense compound. In certain embodiments, the modified internucleoside linkages are phosphorothioate linkages. In certain embodiments, each internucleoside linkage of a modified oligonucleotide is a phosphorothioate internucleoside linkage.

In certain embodiments, the modified oligonucleotides targeted to a SOD-1 nucleic acid comprise one or more phosphodiester internucleoside linkages. In certain embodiments, modified oligonucleotides targeted to a SOD-1 nucleic acid comprise at least one phosphorothioate internucleoside linkage and at least one phosphodiester internucleoside linkage. In certain embodiments, the modified oligonucleotide has a mixed backbone motif of the following:

```
sosssssssooss,
sooossssssssoss,
sooossssssssoss,
soossssssssooss,
sooossssssssooss,
sooossssssssooss,
sooossssssssooss,
sooossssssssooss,
sooossssssssooos,
soooossssssssooss,
sooossssssssooss,
sosossssssssosos,
and
sooossssssssooss,
```
wherein s = a phosphorothioate internucleoside linkage, and
o = a phosphodiester internucleoside linkage.

Modified Sugar Moieties

Antisense compounds of the invention can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$, 2'-OCH$_2$CH$_3$, 2'-OCH$_2$CH$_2$F and 2'-O(CH$_2$)$_2$OCH$_3$ substituent groups. The substituent at the 2' position can also be selected from allyl, amino, azido, thio, O-allyl, O—$C_1$-$C_{10}$ alkyl, OCF$_3$, OCH$_2$F, O(CH$_2$)$_2$SCH$_3$, O(CH$_2$)$_2$—O—N($R_m$)($R_n$), O—CH$_2$—C(=O)—N($R_m$)($R_n$), and O—CH$_2$—C(=O)—N($R_l$)—(CH$_2$)$_2$—N($R_m$)($R_n$), where each $R_l$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-(CH$_2$)—O-2' (LNA); 4'-(CH$_2$)—S-2; 4'-(CH$_2$)$_2$—O-2' (ENA); 4'-CH(CH$_3$)—O-2' and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see PCT/US2008/068922 published as WO/2009/006478, published Jan. 8, 2009); 4'-CH$_2$—N(OCH$_3$)-2' (and analogs thereof see PCT/US2008/064591 published as WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya et al., *J. Org. Chem.*, 2009, 74, 118-134); and 4'-CH$_2$—C(=CH$_2$)-2' (and analogs thereof see PCT/US2008/066154 published as WO 2008/154401, published on Dec. 8, 2008).

Further bicyclic nucleosides have been reported in published literature (see for example: Srivastava et al., *J. Am. Chem. Soc.*, 2007, 129(26) 8362-8379; Frieden et al., *Nucleic Acids Research*, 2003, 21, 6365-6372; Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; Wahlestedt et al., *Proc. Natl. Acad. Sci. U.S.A*, 2000, 97, 5633-5638; Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; U.S. Pat. Nos. 7,399,845; 7,053,207; 7,034,133; 6,794,499; 6,770,748; 6,670,461; 6,525,191; 6,268,490; U.S. Patent Publication Nos.: US2008-0039618; US2007-0287831; US2004-0171570; U.S. patent application Ser. Nos. 12/129,154; 61/099,844; 61/097,787; 61/086,231; 61/056,564; 61/026,998; 61/026,995; 60/989,574; International applications WO 2007/134181; WO 2005/021570; WO 2004/106356; WO 94/14226; and PCT International Applications Nos.: PCT/US2008/068922; PCT/US2008/066154; and PCT/US2008/064591). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

In certain embodiments, bicyclic sugar moieties of BNA nucleosides include, but are not limited to, compounds having at least one bridge between the 4' and the 2' carbon atoms of the pentofuranosyl sugar moiety including without limitation, bridges comprising 1 or from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—; wherein: x is 0, 1, or 2; n is 1, 2, 3, or 4; each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In certain embodiments, the bridge of a bicyclic sugar moiety is, —[C(R$_a$)(R$_b$)]$_n$—, —[C(R$_a$)(R$_b$)]$_n$—O—, —C(R$_a$R$_b$)—N(R)—O— or —C(R$_a$R$_b$)—O—N(R)—. In certain embodiments, the bridge is 4'-CH$_2$—2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or C$_1$-C$_{12}$ alkyl.

In certain embodiments, bicyclic nucleosides are further defined by isomeric configuration. For example, a nucleoside comprising a 4'-(CH$_2$)—O-2' bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include those having a 4' to 2' bridge wherein such bridges include without limitation, α-L-4'-(CH$_2$)—O-2', β-D-4'-CH$_2$—O-2', 4'-(CH$_2$)$_2$—O-2', 4'-CH$_2$—O—N(R)-2'4'-CH$_2$—N(R)—O-2', 4'-CH(CH$_3$)—O-2', 4'-CH$_2$—S-2', 4'-CH$_2$—N(R)-2', 4'-CH$_2$—CH(CH$_3$)-2', and 4'-(CH$_2$)$_3$-2', wherein R is H, a protecting group or C$_1$-C$_{12}$ alkyl.

In certain embodiment, bicyclic nucleosides have the formula:

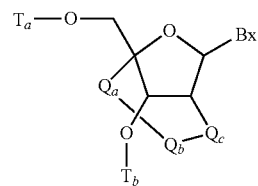

wherein:

Bx is a heterocyclic base moiety;

-Q$_a$-Q$_b$-Q$_c$- is —CH$_2$—N(R$_c$)—CH$_2$—, —C(=O)—N(R$_c$)—CH$_2$—, —CH$_2$—O—N(R$_c$)—, —CH$_2$—N(R$_c$)—O— or —N(R$_c$)—O—CH$_2$;

R$_c$ is C$_1$-C$_{12}$ alkyl or an amino protecting group; and

T$_a$ and T$_b$ are each, independently H, a hydroxyl protecting group, a conjugate group, a reactive phosphorus group, a phosphorus moiety or a covalent attachment to a support medium.

In certain embodiments, bicyclic nucleosides have the formula:

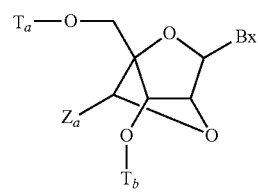

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thiol.

In one embodiment, each of the substituted groups, is, independently, mono or poly substituted with substituent groups independently selected from halogen, oxo, hydroxyl, $OJ_c$, $SJ_c$, $N_3$, $OC(=X)J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides have the formula:

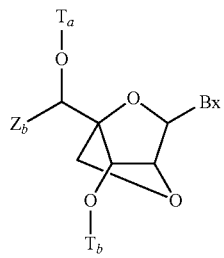

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides have the formula:

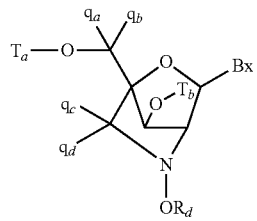

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides have the formula:

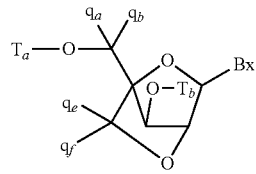

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)NJ$_j$J$_k$, C(=O)J$_j$, O—C(=O)NJ$_j$J$_k$, N(H)C(=NH)NJ$_j$J$_k$, N(H)C(=O)NJ$_j$J$_k$ or N(H)C(=S)NJ$_j$J$_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of adenine, cytosine, guanine, 5-methyl-cytosine, thymine and uracil bicyclic nucleosides having a 4'-CH$_2$—O-2' bridge, along with their oligomerization, and nucleic acid recognition properties have been described (Koshkin et al., *Tetrahedron*, 1998, 54, 3607-3630). The synthesis of bicyclic nucleosides has also been described in WO 98/39352 and WO 99/14226.

Analogs of various bicyclic nucleosides that have 4' to 2' bridging groups such as 4'-CH$_2$—O-2' and 4'-CH$_2$—S-2', have also been prepared (Kumar et al., *Bioorg. Med. Chem. Lett.*, 1998, 8, 2219-2222). Preparation of oligodeoxyribonucleotide duplexes comprising bicyclic nucleosides for use as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides have the formula:

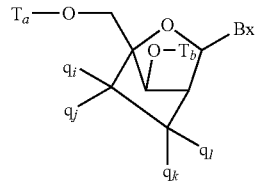

wherein:

Bx is a heterocyclic base moiety;

$T_a$ and $T_b$ are each, independently, H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_i$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-(CH$_2$)$_3$-2' bridge and the alkenyl analog bridge 4'-CH=CH—CH$_2$-2' have been described (Frier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.* 2007, 129(26), 8362-8379).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, (F) methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, (J) propylene carbocyclic (4'-(CH$_2$)$_3$-2') BNA, and (K) vinyl BNA as depicted below.

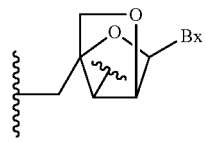

(A)

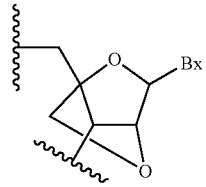

(B)

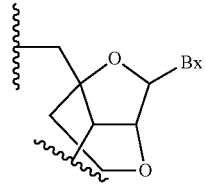

(C)

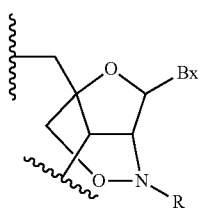

(D)

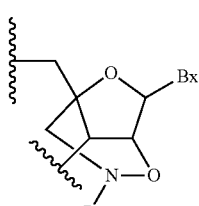

(E)

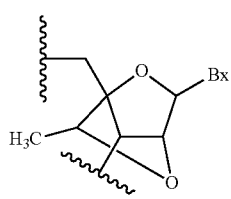

(F)

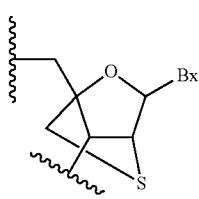

(G)

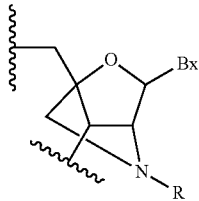

(H)

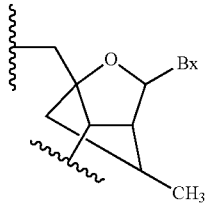

(I)

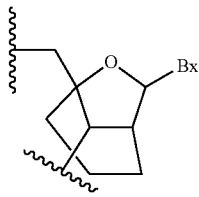

(J)

(K)

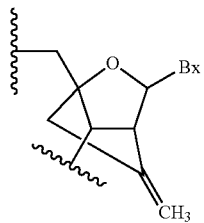

wherein Bx is the base moiety and R is, independently, H, a protecting group, $C_1$-$C_6$ alkyl or $C_1$-$C_6$ alkoxy.

As used herein, the term "modified tetrahydropyran nucleoside" or "modified THP nucleoside" means a nucleoside having a six-membered tetrahydropyran "sugar" substituted for the pentofuranosyl residue in normal nucleosides and can be referred to as a sugar surrogate. Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854) or fluoro HNA (F-HNA) having a tetrahydropyranyl ring system as illustrated below.

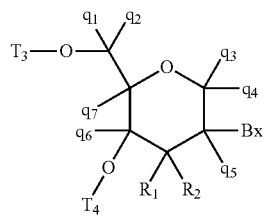

In certain embodiment, sugar surrogates are selected having the formula:

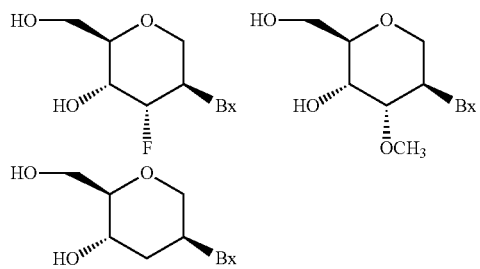

wherein:
Bx is a heterocyclic base moiety;
$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to an oligomeric compound or oligonucleotide and the other of $T_3$ and $T_4$ is H, a hydroxyl protecting group, a linked conjugate group or a 5' or 3'-terminal group;
$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and
one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides are provided wherein one of $R_1$ and $R_2$ is F. In certain embodiments, $R_1$ is fluoro and $R_2$ is H; $R_1$ is methoxy and $R_2$ is H, and $R_1$ is methoxyethoxy and $R_2$ is H.

In certain embodiments, sugar surrogates comprise rings having more than 5 atoms and more than one heteroatom. For example nucleosides comprising morpholino sugar moieties and their use in oligomeric compounds has been reported (see for example: Braasch et al., *Biochemistry*, 2002, 41, 4503-4510; and U.S. Pat. Nos. 5,698,685; 5,166,315; 5,185,444; and 5,034,506). As used here, the term "morpholino" means a sugar surrogate having the following formula:

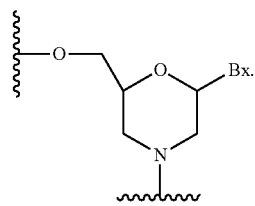

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horvath et al., *Tetrahedron Letters*, 2007, 48, 3621-3623; Nauwelaerts et al., *J. Am. Chem. Soc.*, 2007, 129(30), 9340-9348; Gu et al., *Nucleosides, Nucleotides & Nucleic Acids*, 2005, 24(5-7), 993-998; Nauwelaerts et al., *Nucleic Acids Research*, 2005, 33(8), 2452-2463; Robeyns et al., *Acta Crystallographica, Section F: Structural Biology and Crystallization Communications*, 2005, F61(6), 585-586; Gu et al., *Tetrahedron,*

2004, 60(9), 2111-2123; Gu et al., *Oligonucleotides*, 2003, 13(6), 479-489; Wang et al., *J. Org. Chem.*, 2003, 68, 4499-4505; Verbeure et al., *Nucleic Acids Research*, 2001, 29(24), 4941-4947; Wang et al., *J. Org. Chem.*, 2001, 66, 8478-82; Wang et al., *Nucleosides, Nucleotides & Nucleic Acids*, 2001, 20(4-7), 785-788; Wang et al., *J. Am. Chem.*, 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

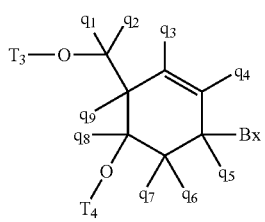

wherein independently for each of said at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

Many other monocyclic, bicyclic and tricyclic ring systems are known in the art and are suitable as sugar surrogates that can be used to modify nucleosides for incorporation into oligomeric compounds as provided herein (see for example review article: Leumann, Christian J. *Bioorg. & Med. Chem.*, 2002, 10, 841-854). Such ring systems can undergo various additional substitutions to further enhance their activity.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nF$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2'substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—$N(R_m)(R_n)$, or O—$CH_2$—C(=O)—$N(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position of the sugar ring.

As used herein, "2'-OMe" or "2'-$OCH_3$", "2'-O-methyl" or "2'-methoxy" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

Methods for the preparations of modified sugars are well known to those skilled in the art. Some representative U.S. patents that teach the preparation of such modified sugars include without limitation, U.S.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH(CH₃)—O-2') bridging group. In certain embodiments, the (4'-CH(CH₃)—O-2') modified nucleosides are arranged throughout the wings of a gapmer motif.

Compositions and Methods for Formulating Pharmaceutical Compositions

Oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to a SOD-1 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a SOD-1 nucleic acid and a pharmaceutically acceptable diluent. In certain embodiments, the pharmaceutically acceptable diluent is PBS. In certain embodiments, the antisense compound is a modified oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of SOD-1 nucleic acids can be tested in vitro in a variety of cell types. Cell types used for such analyses are available from commerical vendors (e.g. American Type Culture Collection, Manassas, Va.; Zen-Bio, Inc., Research Triangle Park, N.C.; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, HepG2 cells, Hep3B cells, primary hepatocytes, A431 cells, and SH-SY5Y cells.

In Vitro Testing of Oligonucleotides

Described herein are methods for treatment of cells with oligonucleotides, which can be modified appropriately for treatment with other antisense compounds.

Cells may be treated with oligonucleotides when the cells reach approximately 60-80% confluency in culture.

One reagent commonly used to introduce oligonucleotides into cultured cells includes the cationic lipid transfection reagent LIPOFECTIN (Invitrogen, Carlsbad, Calif.). Oligonucleotides may be mixed with LIPOFECTIN in OPTI-MEM 1 (Invitrogen, Carlsbad, Calif.) to achieve the desired final concentration of oligonucleotide and a LIPOFECTIN concentration that may range from 2 to 12 ug/mL per 100 nM oligonucleotide.

Another reagent used to introduce oligonucleotides into cultured cells includes LIPOFECTAMINE (Invitrogen, Carlsbad, Calif.). Oligonucleotide is mixed with LIPOFECTAMINE in OPTI-MEM 1 reduced serum medium (Invitrogen, Carlsbad, Calif.) to achieve the desired concentration of oligonucleotide and a LIPOFECTAMINE concentration that may range from 2 to 12 ug/mL per 100 nM oligonucleotide.

Another technique used to introduce oligonucleotides into cultured cells includes electroporation.

Cells are treated with oligonucleotides by routine methods. Cells may be harvested 16-24 hours after oligonucleotide treatment, at which time RNA or protein levels of target nucleic acids are measured by methods known in the art and described herein. In general, when treatments are performed in multiple replicates, the data are presented as the average of the replicate treatments.

The concentration of oligonucleotide used varies from cell line to cell line. Methods to determine the optimal oligonucleotide concentration for a particular cell line are well known in the art. Oligonucleotides are typically used at concentrations ranging from 1 nM to 300 nM when transfected with LIPOFECTAMINE. Oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Inhibition of levels or expression of a SOD-1 nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900

Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents may be obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invetrogen, Inc. Eugene, Oreg.). Methods of RNA quantification by RIBOGREEN are SOD-1ght in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a SOD-1 nucleic acid. Methods for designing real-time PCR probes and primers are well known in the art, and may include the use of software such as PRIMER EXPRESS Software (Applied Biosystems, Foster City, Calif.).

Analysis of Protein Levels

Antisense inhibition of SOD-1 nucleic acids can be assessed by measuring SOD-1 protein levels. Protein levels of SOD-1 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. In certain embodiments, the compounds herein provide improved reduction in protein levels.

In Vivo Testing of Antisense Compounds

Antisense compounds, for example, modified oligonucleotides, are tested in animals to assess their ability to inhibit expression of SOD-1 and produce phenotypic changes, such as, improved motor function. In certain embodiments, motor function is measured by walking initiation analysis, rotarod, grip strength, pole climb, open field performance, balance beam, hindpaw footprint testing in the animal. Testing may be performed in normal animals, or in experimental disease models. For administration to animals, oligonucleotides are formulated in a pharmaceutically acceptable diluent, such as phosphate-buffered saline. Administration includes parenteral routes of administration, such as intraperitoneal, intravenous, and subcutaneous. Oligonucleotide dosage and dosing frequency depends upon multiple factors such as, but not limited to, route of administration and animal body weight. Following a period of treatment with oligonucleotides, RNA is isolated from CNS tissue or CSF and changes in SOD-1 nucleic acid expression are measured.

Certain Indications

In certain embodiments, provided herein are methods, compounds, and compositions of treating an individual comprising administering one or more pharmaceutical compositions described herein. In certain embodiments, the individual has a neurodegenerative disease. In certain embodiments, the individual is at risk for developing a neurodegenerative disease, including, but not limited to, amyotrophic lateral sclerosis (ALS). In certain embodiments, the individual has been identified as having a SOD-1 associated disease. In certain embodiments, provided herein are methods for prophylactically reducing SOD-1 expression in an individual. Certain embodiments include treating an individual in need thereof by administering to an individual a therapeutically effective amount of an antisense compound targeted to a SOD-1 nucleic acid.

In one embodiment, administration of a therapeutically effective amount of an antisense compound targeted to a SOD-1 nucleic acid is accompanied by monitoring of SOD-1 levels in an individual, to determine an individual's response to administration of the antisense compound. An individual's response to administration of the antisense compound may be used by a physician to determine the amount and duration of therapeutic intervention.

In certain embodiments, administration of an antisense compound targeted to a SOD-1 nucleic acid results in reduction of SOD-1 expression by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values. In certain embodiments, administration of an antisense compound targeted to a SOD-1 nucleic acid results in improved motor function in an animal. In certain embodiments, administration of a SOD-1 antisense compound improves motor function by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values.

In certain embodiments, pharmaceutical compositions comprising an antisense compound targeted to SOD-1 are used for the preparation of a medicament for treating a patient suffering or susceptible to a neurodegenerative disease including amyotrophic lateral sclerosis (ALS).

Certain Comparator Compositions

Antisense oligonucleotides targeting human SOD-1 were described in an earlier publication (see WO 2005/040180, incorporated by reference herein, in its entirety). Several oligonucleotides (ISIS 333611, ISIS 146144, ISIS 146145, ISIS 150437, ISIS 150441, ISIS 150443, ISIS 150444, ISIS 150445, ISIS 150446, ISIS 150447, ISIS 150448, ISIS 150449, ISIS 150452, ISIS 150454, ISIS 150458, ISIS 150460, ISIS 150462-150467, ISIS 150470, ISIS 150472, ISIS 150474, ISIS 150475, ISIS 150476, ISIS 150479-150483, ISIS 150488, ISIS 150489, ISIS 150490, ISIS 150491-150493, ISIS 150495-150498, ISIS 150511, ISIS 333605, ISIS 333606, ISIS 333609-333617, ISIS 333619, ISIS 333620-333636, ISIS 333638, and ISIS 333640)

described therein, were used as comparator compounds throughout select screens for new antisense compounds described herein.

In certain embodiments, ISIS 333611, a 5-10-5 MOE gapmer, having a sequence of (from 5' to 3') CCGTCGC-CCTTCAGCACGCA (incorporated herein as SEQ ID NO: 21), wherein each internucleoside linkage is a phosphorothioate linkage, each cytosine is a 5-methylcytosine, and each of nucleosides 1-5 and 16-20 (from 5' to 3') comprise a 2'-O-methoxyethyl moiety was used as a comparator compound. ISIS 333611 was selected as a comparator compound because it exhibited high levels of dose-dependent inhibition in various studies as described in WO 2005/040180. Additionally, phase 1 human clinical trials were completed using ISIS 333611. See, MILLER et al., "An antisense oligonucleotide against SOD1 delivered intrathecally for patients with SOD1 familial amyotrophic lateral sclerosis: a phase 1, randomised, first-in-man study" Lancet Neurol. (2013) 12(5): 435-442. Thus, ISIS 333611 was deemed a highly efficacious and potent compound with an acceptable safety profile (such that it was tested in human patients).

In certain embodiments, the compounds described herein benefit from one or more improved properties relative to the antisense compounds described in WO 2005/040180. Some of the improved properties are demonstrated in the examples provided herein. In certain embodiments, compounds described herein are more efficacious, potent, and/or tolerable in various in vitro and in vivo studies than comparator compounds described herein, including ISIS 333611. In certain embodiments, ISIS 666853, ISIS 666859, ISIS 666919, ISIS 666921, ISIS 666922, ISIS 666869, ISIS 666870, and ISIS 666867 are more efficacious and/or potent in various in vitro and in vivo studies than comparator compounds described herein, including ISIS 333611. In certain embodiments, ISIS 666853, ISIS 666859, ISIS 666919, ISIS 666921, ISIS 666922, ISIS 666869, ISIS 666870, and ISIS 666867 are more tolerable in one or more tolerability assays in animals than comparator compounds described herein, including ISIS 333611. This is despite 333611 being sufficiently well tolerated to progress to human clinical trials.

In certain embodiments, certain compounds described herein are more efficacious than comparator compounds by virtue of an in vitro IC50 of less than 2 µM, less than 1.9 µM, less than 1.8 µM, less than 1.7 µM, less than 1.6 µM, less than 1.5 µM, less than 1.4 µM, less than 1.3 µM, less than 1.2 µM, less than 1.1 µM, less than 1 µM, less than 0.9 µM, less than 0.8 µM, less than 0.7 µM, less than 0.6 µM, or less than 0.5 µM less than 0.4 µM, less than 0.3 µM, less than 0.2 µM, less than 0.1 µM, when tested in human cells, for example, in the HepG2 A431 or SH-SY5Y cell lines (For example, see Examples 6-11).

In certain embodiments, certain compounds described herein are more efficacious than comparator compounds by virtue of their ability to inhibit SOD-1 expression in vivo. In certain embodiments, the compounds inhibit SOD-1 in lumbar spinal cord and cervical spinal cord by at least 60%, at least 65%, at least 70%, at least 75%, at least 80%, at least 85%, at least 90% or at least 95% in, for example, a transgenic animal model.

In certain embodiments, certain compounds described herein are more tolerable than comparator compounds on the basis of reduced microglial marker levels (e.g., IBA1), reduced astrocytic marker levels (e.g., GFAP), and/or FOB scores in rats, mice, and/or monkeys. See, for example, Examples 14, 15, 18, and 19.

ISIS 666853

For example, as provided in Example 12 (hereinbelow), ISIS 666853 achieved 81% inhibition in lumbar spinal cord and 74% in cervical spinal cord of an SOD-1 transgenic rat model when dosed with 30 µL of 16.67 mg/ml solution of oligonucleotide diluted in PBS (500 µg final dose), whereas ISIS 333611 achieved 51% inhibition in lumbar spinal cord and 47% inhibition in cervical spinal cord.

For example, as provided in Example 14 (hereinbelow), ISIS 666853 achieved a FOB score of 0 whereas ISIS 333611 achieved a FOB score of 4 in Sprague-Dawley rats after 3 hours when treated with 3 mg of oligonucleotide. Microglial marker (IBA1) levels and astrocytic marker (GFAP) levels were also reduced in ISIS 666853 treated rats as compared to ISIS 333611 treated rats.

For example, as provided in Example 15 (hereinbelow), ISIS 666853 achieved an $ED_{50}$ of 81.3 and 242.6 in lumbar tissue and cervical tissue (respectively) in SOD-1 transgenic rats when treated intrathecally with 10, 30, 100, 300, or 3000 µg of oligonucleotide. $ED_{50}$ in lumbar and cervical tissues could not be calculated in ISIS 333611 treated transgenic rats because the highest concentration tested (3000 µg) filed to inhibit human SOD-1 mRNA greater than 55-65%.

For example, as provided in Example 16 (hereinbelow), at doses of 1 mg and 3 mg ISIS 666853 achieved 3 hour FOB scores of 0.0 and 0.5 (respectively) whereas ISIS 333611 achieved FOB scores of 3.0 and 4.9 (respectively). At doses of 1 mg and 3 mg ISIS 666853 achieved 8 week FOB scores of 0.0 and 0.0 (respectively) whereas ISIS 333611 achieved FOB scores of 0.0 and 1.2 (respectively).

For example, as provided in Example 17 (hereinbelow), ISIS 666853 achieved an $ED_{50}$ of 136 and 188 in lumbar tissue and cortex tissue (respectively) whereas ISIS 333611 achieved an $ED_{50}$ of 401 and 786 in lumbar tissue and cortex tissue (respectively) in SOD-1 transgenic mice when treated with an intracerebral ventricular bolus of 10, 30, 100, 300, or 700 µg of oligonucleotide.

For example, as provided in Example 18 (hereinbelow), ISIS 666853 achieved a FOB score of 1.25 whereas ISIS 333611 achieved a FOB score of 6.5 in C57bl6 mice after 3 hours when treated with 700 µg of oligonucleotide. Microglial marker (IBA1) levels and astrocytic marker (GFAP) levels were also reduced in ISIS 666853 treated mice as compared to ISIS 333611 treated mice.

ISIS 666859

For example, as provided in Example 12 (hereinbelow), ISIS 666859 achieved 79% inhibition in lumbar spinal cord and 64% inhibition in cervical spinal cord of an SOD-1 transgenic rat model when dosed with 30 µL of 16.67 mg/ml solution of oligonucleotide diluted in PBS (500 µg final dose), whereas ISIS 333611 achieved 51% inhibition in lumbar spinal cord and 47% inhibition in cervical spinal cord.

For example, as provided in Example 14 (hereinbelow), ISIS 666859 achieved a FOB score of 1 whereas ISIS 333611 achieved a FOB score of 4 in Sprague-Dawley rats after 3 hours when treated with 3 mg of oligonucleotide. Microglial marker (IBA1) levels and astrocytic marker (GFAP) levels were also reduced in ISIS 666859 treated rats as compared to ISIS 333611 treated rats.

For example, as provided in Example 15 (hereinbelow), ISIS 666859 achieved an $ED_{50}$ of 74.0 and 358.8 in lumbar tissue and cervical tissue (respectively) in SOD-1 transgenic rats when treated intrathecally with 10, 30, 100, 300, or 3000 μg of oligonucleotide. $ED_{50}$ in lumbar and cervical tissues could not be calculated in ISIS 333611 treated transgenic rats because the highest concentration tested (3000 μg) filed to inhibit human SOD-1 mRNA greater than 55-65%.

For example, as provided in Example 16 (hereinbelow), at doses of 1 mg and 3 mg ISIS 666859 achieved 3 hour FOB scores of 0.0 and 2.1 (respectively) whereas ISIS 333611 achieved FOB scores of 3.0 and 4.9 (respectively). At doses of 1 mg and 3 mg ISIS 666859 achieved 8 week FOB scores of 0.0 and 0.3 (respectively) whereas ISIS 333611 achieved FOB scores of 0.0 and 1.2 (respectively).

For example, as provided in Example 17 (hereinbelow), ISIS 666859 achieved an $ED_{50}$ of 106 and 206 in lumbar tissue and cortex tissue (respectively) whereas ISIS 333611 achieved an $ED_{50}$ of 401 and 786 in lumbar tissue and cortex tissue (respectively) in SOD-1 transgenic mice when treated with an intracerebral ventricular bolus of 10, 30, 100, 300, or 700 μg of oligonucleotide.

For example, as provided in Example 18 (hereinbelow), ISIS 666859 achieved a FOB score of 1.75 whereas ISIS 333611 achieved a FOB score of 6.5 in C57bl6 mice after 3 hours when treated with 700 μg of oligonucleotide. Microglial marker (IBA1) levels and astrocytic marker (GFAP) levels were also reduced in ISIS 666859 treated mice as compared to ISIS 333611 treated mice.

ISIS 666919

For example, as provided in Example 12 (hereinbelow), ISIS 666919 achieved 76% inhibition in lumbar spinal cord and 68% in cervical spinal cord of an SOD-1 transgenic rat model when dosed with 30 μL of 16.67 mg/ml solution of oligonucleotide diluted in PBS (500 μg final dose), whereas ISIS 333611 achieved 51% inhibition in lumbar spinal cord and 47% inhibition in cervical spinal cord.

For example, as provided in Example 14 (hereinbelow), ISIS 666919 achieved a FOB score of 2 whereas ISIS 333611 achieved a FOB score of 4 in Sprague-Dawley rats after 3 hours when treated with 3 mg of oligonucleotide. Microglial marker (IBA1) levels and astrocytic marker (GFAP) levels were also reduced in ISIS 666919 treated rats as compared to ISIS 333611 treated rats.

For example, as provided in Example 15 (hereinbelow), ISIS 666919 achieved an $ED_{50}$ of 104.1 and 613.5 in lumbar tissue and cervical tissue (respectively) in SOD-1 transgenic rats when treated intrathecally with 10, 30, 100, 300, or 3000 μg of oligonucleotide. $ED_{50}$ in lumbar and cervical tissues could not be calculated in ISIS 333611 treated transgenic rats because the highest concentration tested (3000 μg) filed to inhibit human SOD-1 mRNA greater than 55-65%.

For example, as provided in Example 16 (hereinbelow), at doses of 1 mg and 3 mg ISIS 666919 achieved 3 hour FOB scores of 1.3 and 3.5 (respectively) whereas ISIS 333611 achieved FOB scores of 3.0 and 4.9 (respectively). At doses of 1 mg and 3 mg ISIS 666919 achieved 8 week FOB scores of 0.0 and 0.1 (respectively) whereas ISIS 333611 achieved FOB scores of 0.0 and 1.2 (respectively).

For example, as provided in Example 17 (hereinbelow), ISIS 666919 achieved an $ED_{50}$ of 168 in lumbar tissue whereas ISIS 333611 achieved an $ED_{50}$ of 401 in lumbar tissue in SOD-1 transgenic mice when treated with an intracerebral ventricular bolus of 10, 30, 100, 300, or 700 of oligonucleotide.

For example, as provided in Example 18 (hereinbelow), ISIS 666919 achieved a FOB score of 0.0 whereas ISIS 333611 achieved a FOB score of 6.5 in C57bl6 mice after 3 hours when treated with 700 μg of oligonucleotide. Microglial marker (IBA1) levels and astrocytic marker (GFAP) levels were also reduced in ISIS 666919 treated mice as compared to ISIS 333611 treated mice.

ISIS 666921

For example, as provided in Example 12 (hereinbelow), ISIS 66621 achieved 71% inhibition in lumbar spinal cord and 65% in cervical spinal cord of an SOD-1 transgenic rat model when dosed with 30 μL of 16.67 mg/ml solution of oligonucleotide diluted in PBS (500 μg final dose), whereas ISIS 333611 achieved 51% inhibition in lumbar spinal cord and 47% inhibition in cervical spinal cord.

For example, as provided in Example 14 (hereinbelow), ISIS 666921 achieved a FOB score of 2 whereas ISIS 333611 achieved a FOB score of 4 in Sprague-Dawley rats after 3 hours when treated with 3 mg of oligonucleotide. Microglial marker (IBA1) levels and astrocytic marker (GFAP) levels were also reduced in ISIS 666919 treated rats as compared to ISIS 333611 treated rats.

ISIS 666922

For example, as provided in Example 12 (hereinbelow), ISIS 666922 achieved 67% inhibition in lumbar spinal cord and 62% in cervical spinal cord of an SOD-1 transgenic rat model when dosed with 30 μL of 16.67 mg/ml solution of oligonucleotide diluted in PBS (500 μg final dose), whereas ISIS 333611 achieved 51% inhibition in lumbar spinal cord and 47% inhibition in cervical spinal cord.

For example, as provided in Example 14 (hereinbelow), ISIS 666922 achieved a FOB score of 3 whereas ISIS 333611 achieved a FOB score of 4 in Sprague-Dawley rats after 3 hours when treated with 3 mg of oligonucleotide. Microglial marker (IBA1) levels and astrocytic marker (GFAP) levels were also reduced in ISIS 666919 treated rats as compared to ISIS 333611 treated rats.

ISIS 666869

For example, as provided in Example 12 (hereinbelow), ISIS 666869 achieved 82% inhibition in lumbar spinal cord and 81% in cervical spinal cord of an SOD-1 transgenic rat model when dosed with 30 μL of 16.67 mg/ml solution of oligonucleotide diluted in PBS (500 μg final dose), whereas ISIS 333611 achieved 51% inhibition in lumbar spinal cord and 47% inhibition in cervical spinal cord.

ISIS 666870

For example, as provided in Example 12 (hereinbelow), ISIS 666870 achieved 76% inhibition in lumbar spinal cord and 68% in cervical spinal cord of an SOD-1 transgenic rat model when dosed with 30 μL of 16.67 mg/ml solution of oligonucleotide diluted in PBS (500 μg final dose), whereas ISIS 333611 achieved 51% inhibition in lumbar spinal cord and 47% inhibition in cervical spinal cord.

For example, as provided in Example 15 (hereinbelow), ISIS 666870 achieved an $ED_{50}$ of 139.4 and 1111 in lumbar tissue and cervical tissue (respectively) in SOD-1 transgenic rats when treated intrathecally with 10, 30, 100, 300, or 3000 μg of oligonucleotide. $ED_{50}$ in lumbar and cervical tissues could not be calculated in ISIS 333611 treated transgenic rats because the highest concentration tested (3000 μg) filed to inhibit human SOD-1 mRNA greater than 55-65%.

For example, as provided in Example 17 (hereinbelow), ISIS 666870 achieved an $ED_{50}$ of 148 and 409 in lumbar tissue and cortex tissue (respectively) whereas ISIS 333611 achieved an $ED_{50}$ of 401 and 786 in lumbar tissue and cortex tissue (respectively) in SOD-1 transgenic mice when treated with an intracerebral ventricular bolus of 10, 30, 100, 300, or 700 μg of oligonucleotide.

For example, as provided in Example 18 (hereinbelow), ISIS 666870 achieved a FOB score of 4.75 whereas ISIS 333611 achieved a FOB score of 6.5 in C57bl6 mice after 3 hours when treated with 700 μg of oligonucleotide.
ISIS 666867

For example, as provided in Example 12 (hereinbelow), ISIS 666867 achieved 59% inhibition in lumbar spinal cord and 48% in cervical spinal cord of an SOD-1 transgenic rat model when dosed with 30 μL of 16.67 mg/ml solution of oligonucleotide diluted in PBS (500 μg final dose), whereas ISIS 333611 achieved 51% inhibition in lumbar spinal cord and 47% inhibition in cervical spinal cord.

Certain Compositions
1. ISIS 666853

In certain embodiments, ISIS 666853 is characterized as a 5-10-5 MOE gapmer, having a sequence of (from 5' to 3') CAGGATACATTTCTACAGCT (incorporated herein as SEQ ID NO: 725), wherein each of nucleosides 1-5 and 16-20 are 2'-O-methoxyethylribose modified nucleosides, and each of nucleosides 6-15 are 2'-deoxynucleosides, wherein the internucleoside linkages between nucleosides 2 to 3, 4 to 5, 16 to 17, and 18 to 19 are phosphodiester linkages and the internucleoside linkages between nucleosides 1 to 2, 3 to 4, 5 to 6, 6 to 7, 7 to 8, 8 to 9, 9 to 10, 10 to 11, 11 to 12, 12 to 13, 13 to 14, 14 to 15, 15 to 16, 17 to 18, and 19 to 20 are phosphorothioate linkages, and wherein each cytosine is a 5'-methylcytosine.

In certain embodiments, ISIS 666853 is described by the following chemical notation: mCes Aeo Ges Geo Aes Tds Ads mCds Ads Tds Tds Tds mCds Tds Ads mCeo Aes Geo mCes Te; wherein,
A=an adenine,
mC=a 5'-methylcytosine
G=a guanine,
T=a thymine,
e=a 2'-O-methoxyethylribose modified sugar,
d=a 2'-deoxyribose sugar,
s=a phosphorothioate internucleoside linkage, and
o=a phosphodiester internucleoside linkage.

In certain embodiments, ISIS 666853 is described by the following chemical structure:

Structure 1. ISIS 666853

(SEQ ID NO: 725)

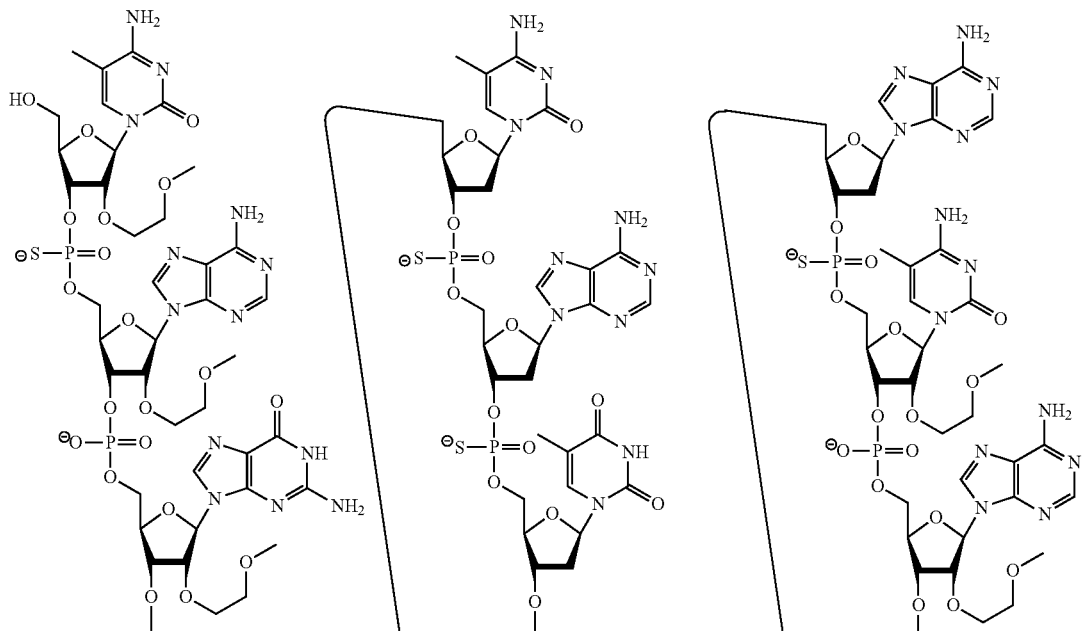

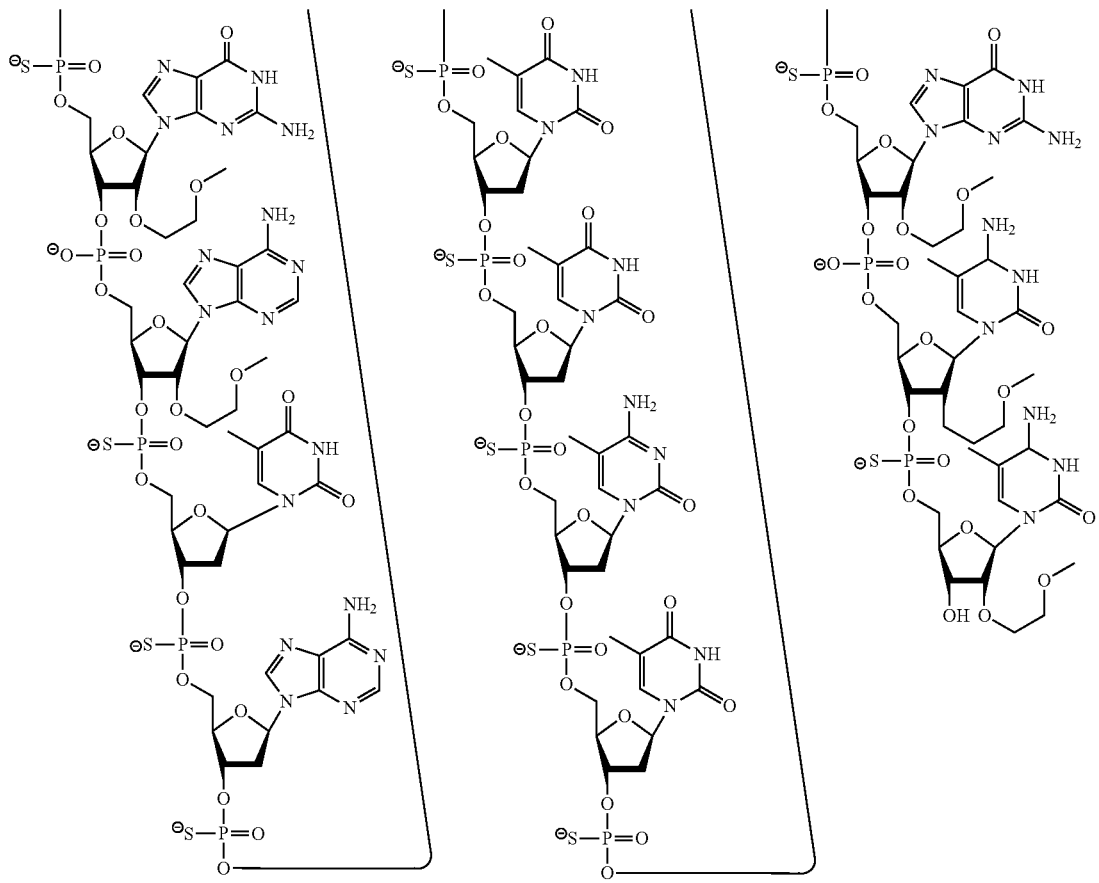

2. ISIS 666859

In certain embodiments, ISIS 666859 is characterized as a modified oligonucleotide having the nucleobase sequence (from 5' to 3') TTAATGTTTATCAGGAT (incorporated herein as SEQ ID NO: 1351), consisting of seventeen nucleosides, wherein each of nucleosides 1-4 and 15-17 are 2'-O-methoxyethylribose nucleosides, wherein each of nucleosides 13 and 14 are cEt modified nucleosides, wherein each of nucleosides 5-12 are 2'-deoxyribonucleosides, wherein the internucleoside linkages between nucleosides 2 to 3, 3 to 4, 13 to 14, 14 to 15 are phosphodiester linkages and the internucleoside linkages between nucleosides 1 to 2, 4 to 5, 5 to 6, 6 to 7, 7 to 8, 8 to 9, 9 to 10, 10 to 11, 11 to 12, 12 to 13, 15 to 16, and 16 to 17 are phosphorothioate linkages, and wherein each cytosine is a 5'-methylcytosine.

In certain embodiments, ISIS 666859 is described by the following chemical notation: Tes Teo Aeo Aes Tds Gds Tds Tds Tds Ads Tds mCds Ako Gko Ges Aes Te; wherein, A=an adenine,
mC=a 5'-methylcytosine
G=a guanine,
T=a thymine,
e=a 2'-O-methoxyethylribose modified sugar,
k=a cEt modified sugar,
d=a 2'-deoxyribose sugar,
s=a phosphorothioate internucleoside linkage, and
o=a phosphodiester internucleoside linkage.

In certain embodiments, ISIS 666859 is described by the following chemical structure:

Structure 2. ISIS 666859

(SEQ ID NO: 1351)

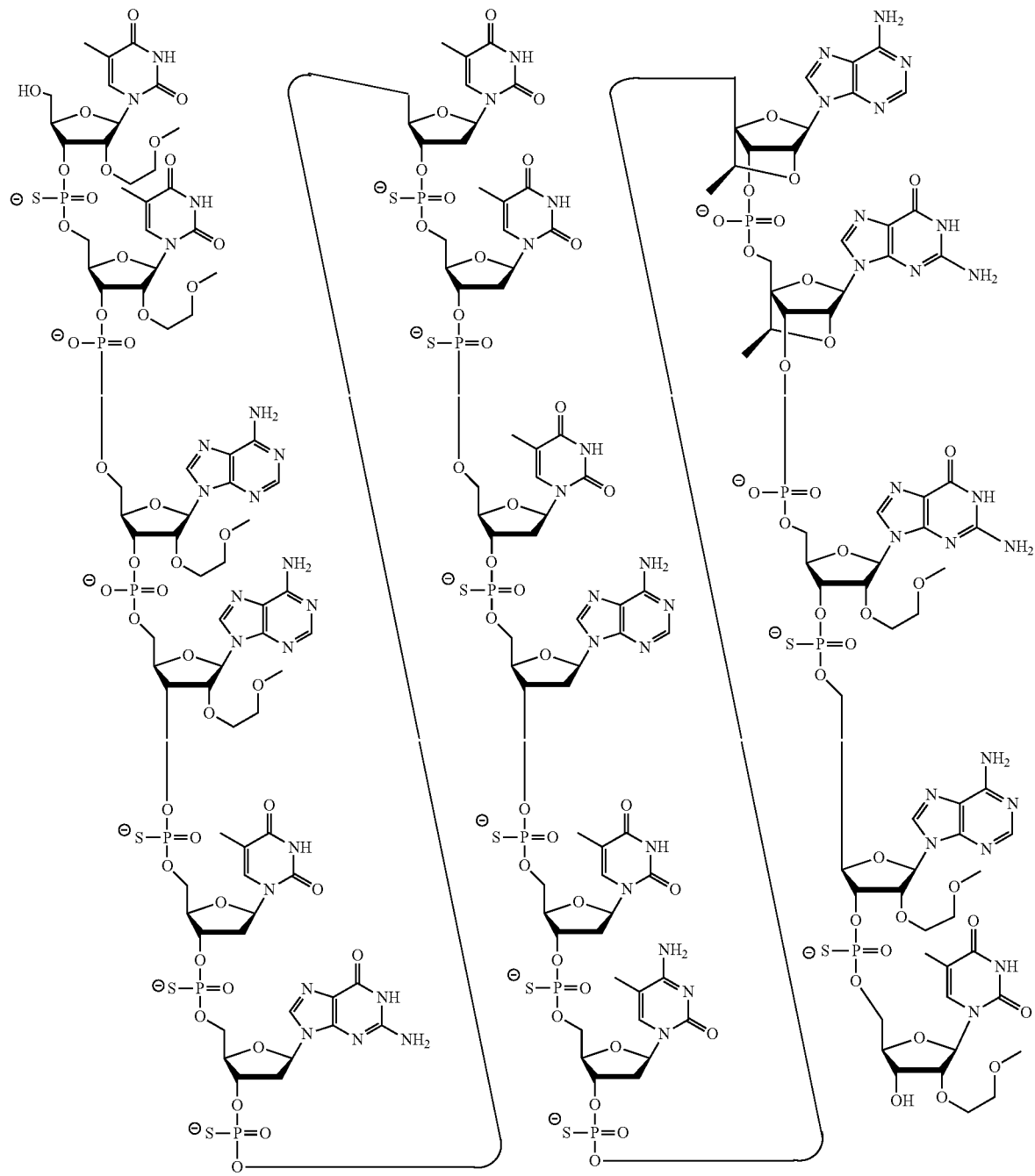

3. ISIS 666919

In certain embodiments, ISIS 666919 is characterized as a modified oligonucleotide having the nucleobase sequence (from 5' to 3') GGATACATTTCTACAGC (incorporated herein as SEQ ID NO: 1342), consisting of seventeen nucleosides, wherein each of nucleosides 1-4 and 16-17 are 2'-O-methoxyethylribose modified nucleosides, wherein each of nucleosides 14 and 15 are cEt modified nucleosides, wherein each of nucleosides 5-13 are 2'-deoxyribonucleosides, wherein the internucleoside linkages between nucleosides 2 to 3, 3 to 4, 4 to 5, and 14 to 15 are phosphodiester linkages and the internucleoside linkages between nucleosides 1 to 2, 5 to 6, 6 to 7, 7 to 8, 8 to 9, 9 to 10, 10 to 11, 11 to 12, 12 to 13, 13 to 14, 15 to 16, and 16 to 17 are phosphorothioate linkages, and wherein each cytosine is a 5'-methylcytosine.

In certain embodiments, ISIS 666919 is described by the following chemical notation: Ges Geo Aeo Teo Ads mCds Ads Tds Tds Tds mCds Tds Ads mCko Aks Ges mCe; wherein, A=an adenine,
mC=a 5'-methylcytosine
G=a guanine,
T=a thymine,
e=a 2'-O-methoxyethylribose modified sugar,
k=a cEt modified sugar,
d=a 2'-deoxyribose sugar,
s=a phosphorothioate internucleoside linkage, and
o=a phosphodiester internucleoside linkage.
In certain embodiments, ISIS 666919 is described by the following chemical structure:
Structure 3. ISIS 666919
(SEQ ID NO: 1342)
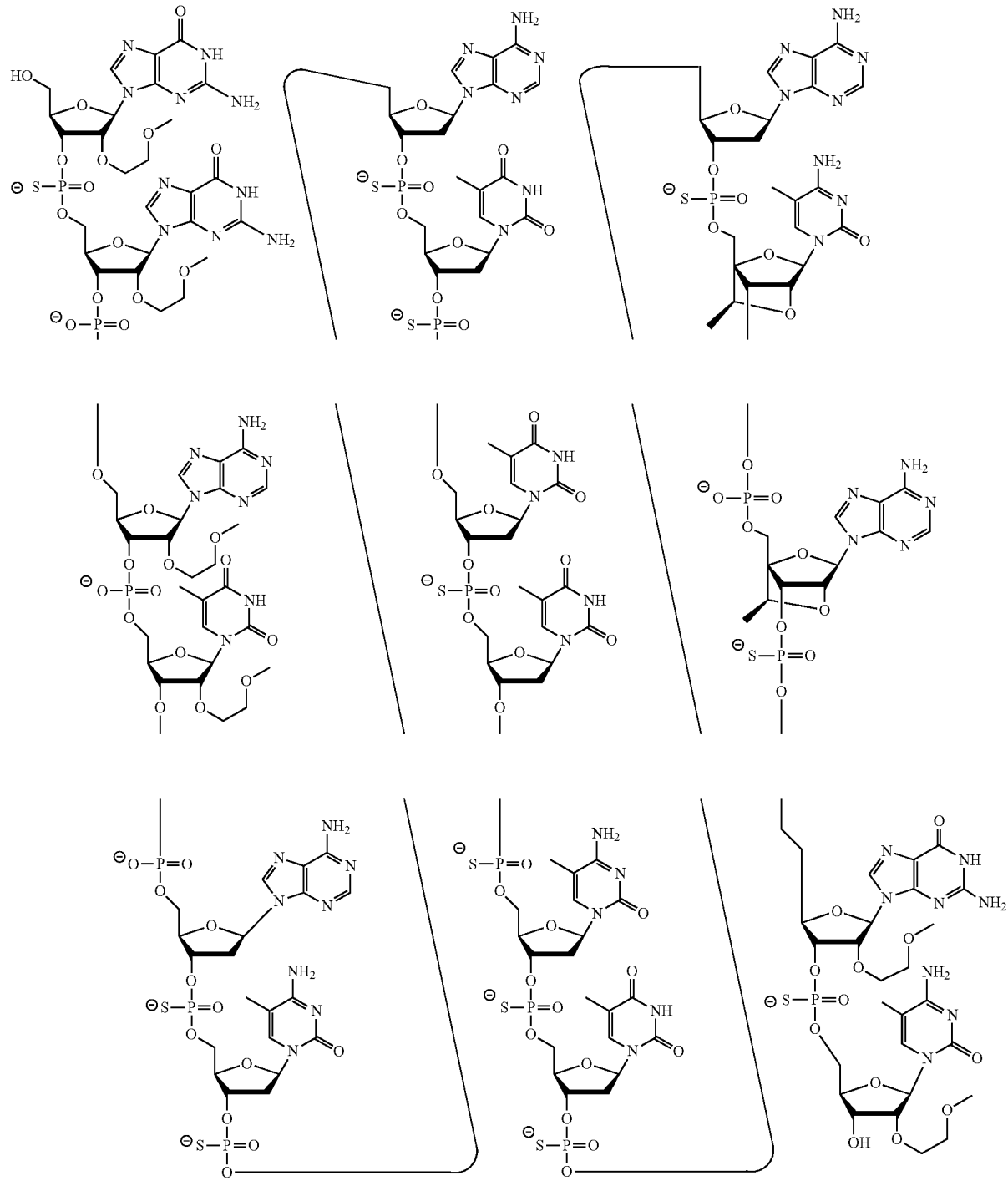

4. ISIS 666921

In certain embodiments, ISIS 666921 is characterized as a modified oligonucleotide having the nucleobase sequence (from 5' to 3') GGATACATTTCTACAGC (incorporated herein as SEQ ID NO: 1342), consisting of seventeen nucleosides, wherein each of nucleosides 1-5 and 16-17 are 2'-O-methoxyethylribose modified nucleosides, wherein each of nucleosides 14-15 are cEt modified nucleosides, wherein each of nucleosides 6-13 are 2'-deoxyribonucleosides, wherein the internucleoside linkages between nucleosides 2 to 3, 3 to 4, 4 to 5, and 14 to 15 are phosphodiester linkages and the internucleoside linkages between nucleosides 1 to 2, 5 to 6, 6 to 7, 7 to 8, 8 to 9, 9 to 10, 10 to 11, 11 to 12, 12 to 13, 13 to 14, 15 to 16, and 16 to 17 are phosphorothioate linkages, and wherein each cytosine is a 5'-methylcytosine.

In certain embodiments, ISIS 666921 is described by the following chemical notation: Ges Geo Aeo Teo Aes mCds Ads Tds Tds Tds mCds Tds Ads mCko Aks Ges mCe; wherein, A=an adenine,
mC=a 5'-methylcytosine
G=a guanine,
T=a thymine,
e=a 2'-O-methoxyethylribose modified sugar,
k=a cEt modified sugar,
d=a 2'-deoxyribose sugar,
s=a phosphorothioate internucleoside linkage, and
o=a phosphodiester internucleoside linkage.

In certain embodiments, ISIS 666921 is described by the following chemical structure:

Structure 4. ISIS 666921

(SEQ ID NO: 1342)

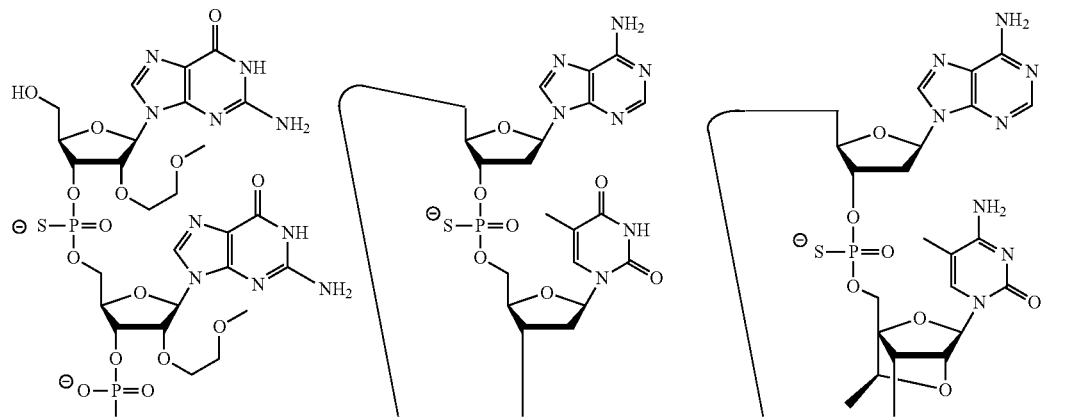

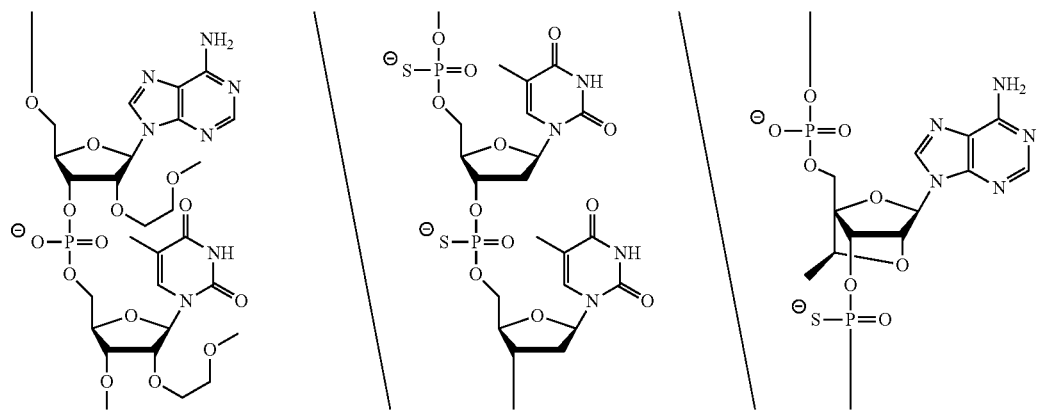

-continued

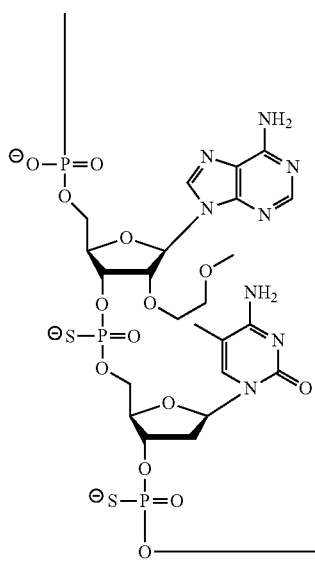
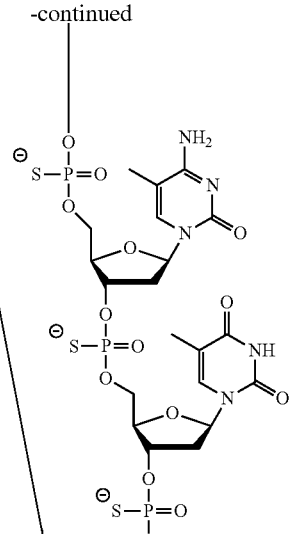
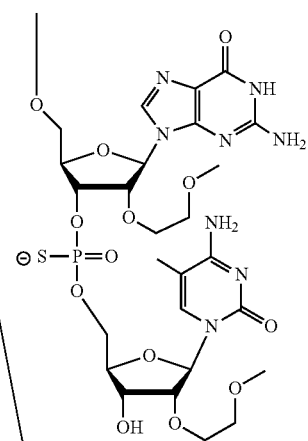

5. ISIS 666922

In certain embodiments, ISIS 666922 is characterized as a modified oligonucleotide having the nucleobase sequence (from 5' to 3') GGATACATTTCTACAGC (incorporated herein as SEQ ID NO: 1342), consisting of seventeen nucleosides, wherein each of nucleosides 1-4 and 15-17 are 2'-O-methoxyethylribose modified nucleosides, wherein each of nucleosides 5 and 14 are cEt modified nucleosides, wherein each of nucleosides 6-13 are 2'-deoxyribonucleosides, wherein the internucleoside linkages between nucleosides 2 to 3, 3 to 4, 4 to 5, and 14 to 15 are phosphodiester linkages and the internucleoside linkages between nucleosides 1 to 2, 5 to 6, 6 to 7, 7 to 8, 8 to 9, 9 to 10, 10 to 11, 11 to 12, 12 to 13, 13 to 14, 15 to 16, and 16 to 17 are phosphorothioate linkages, and wherein each cytosine is a 5'-methylcytosine.

In certain embodiments, ISIS 666922 is described by the following chemical notation: Ges Geo Aeo Teo Aks mCds Ads Tds Tds Tds mCds Tds Ads mCko Aes Ges mCe; wherein, A=an adenine,
mC=a 5'-methylcytosine
G=a guanine,
T=a thymine,
e=a 2'-O-methoxyethylribose modified sugar,
k=a cEt modified sugar,
d=a 2'-deoxyribose sugar,
s=a phosphorothioate internucleoside linkage, and
o=a phosphodiester internucleoside linkage.

In certain embodiments, ISIS 666922 is described by the following chemical structure:

Structure 5. ISIS 666922

(SEQ ID NO: 1342)

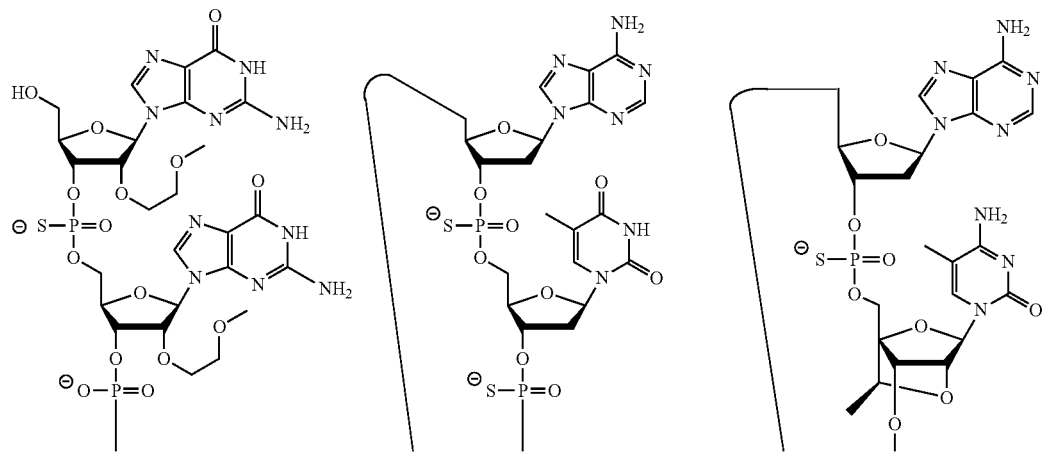

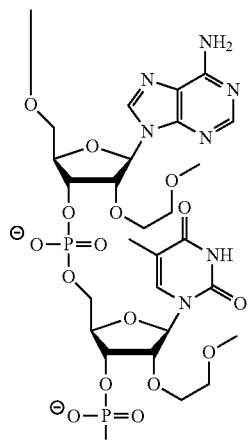
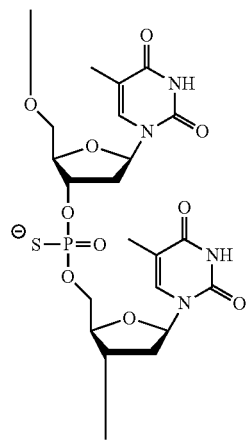
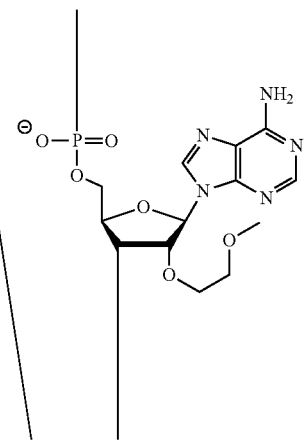
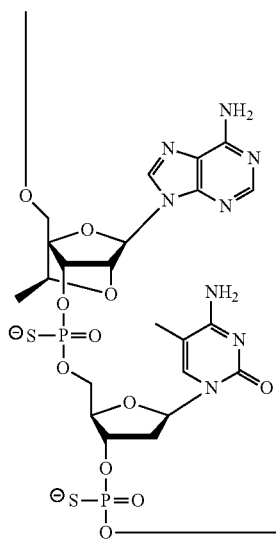
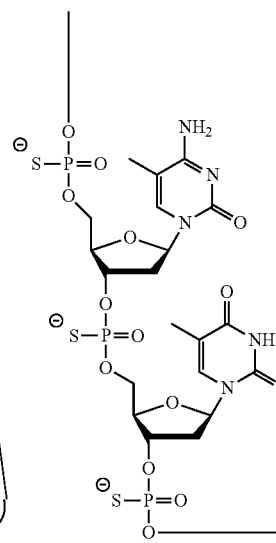
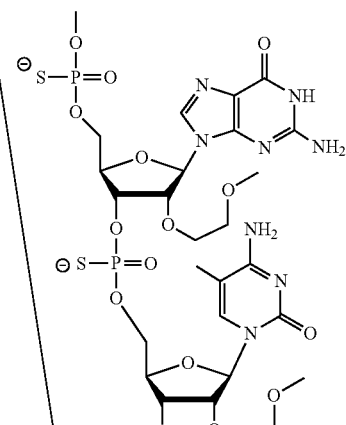

6. ISIS 666869

In certain embodiments, ISIS 666869 is characterized as a modified oligonucleotide having the nucleobase sequence (from 5' to 3') AGTGTTTAATGTTTATC (incorporated herein as SEQ ID NO: 1173), consisting of seventeen nucleosides, wherein each of nucleosides 1, 3, 14, and 16-17 are 2'-O-methoxyethylribose modified nucleosides, wherein each of nucleosides 2, 4, 13, and 15 are cEt modified nucleosides, wherein each of nucleosides 5-12 are 2'-deoxyribonucleosides, wherein the internucleoside linkages between nucleosides 2 to 3, 3 to 4, 13 to 14, and 14 to 15 are phosphodiester linkages and the internucleoside linkages between nucleosides 1 to 2, 4 to 5, 5 to 6, 6 to 7, 7 to 8, 8 to 9, 9 to 10, 10 to 11, 11 to 12, 12 to 13, 15 to 16, and 16 to 17 are phosphorothioate linkages, and wherein each cytosine is a 5'-methylcytosine.

In certain embodiments, ISIS 666869 is described by the following chemical notation: Aes Gko Teo Gks Tds Tds Tds Ads Ads Tds Gds Tds Tko Teo Aks Tes mCe; wherein, A=an adenine,
mC=a 5'-methylcytosine
G=a guanine,
T=a thymine,
e=a 2'-O-methoxyethylribose modified sugar,
k=a cEt modified sugar,
d=a 2'-deoxyribose sugar,
s=a phosphorothioate internucleoside linkage, and
o=a phosphodiester internucleoside linkage.

In certain embodiments, ISIS 666869 is described by the following chemical structure:

Structure 6. ISIS 666869

(SEQ ID NO: 1173)

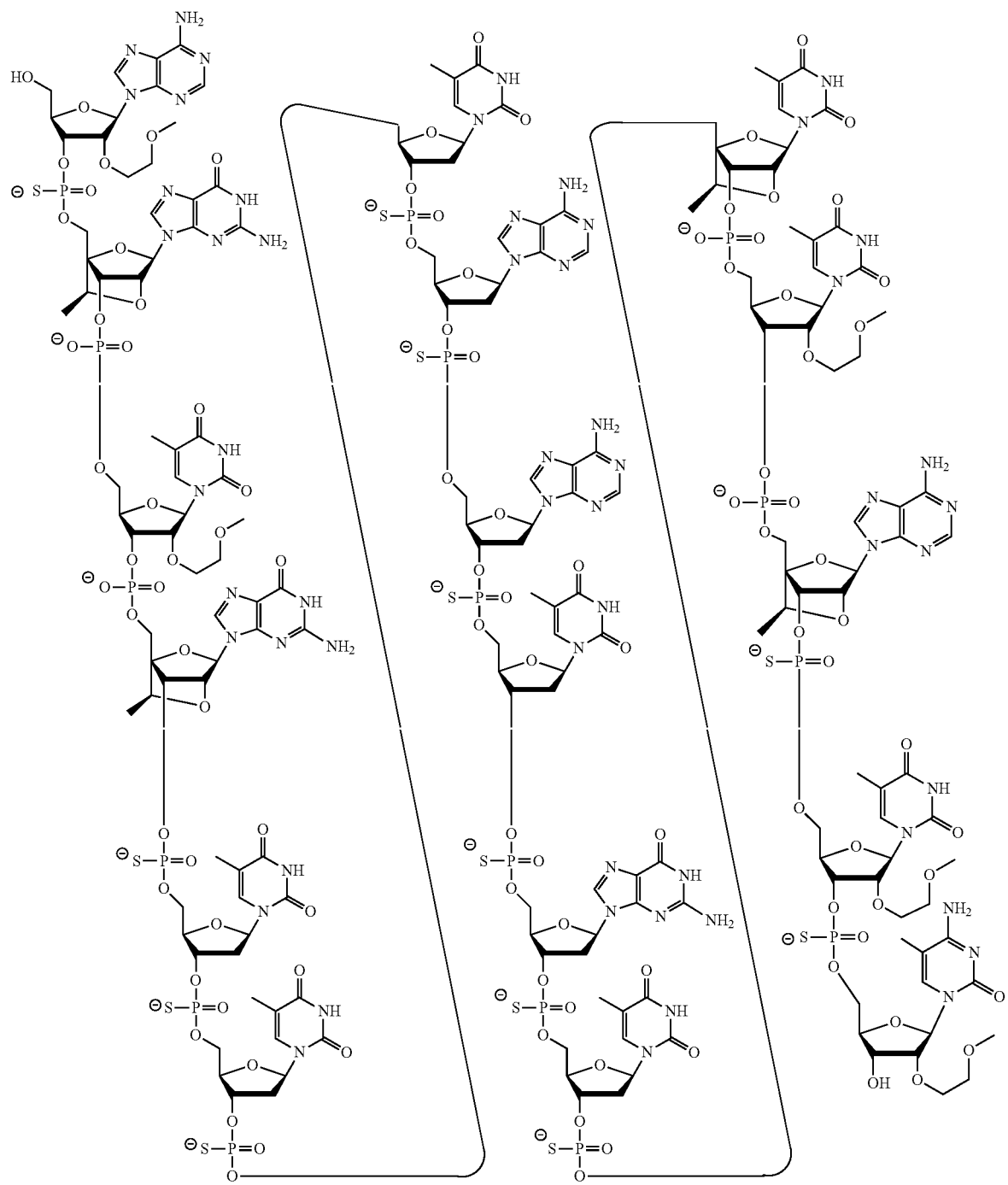

7. ISIS 666870

In certain embodiments, ISIS 666870 is characterized as a modified oligonucleotide having the nucleobase sequence (from 5' to 3') AGTGTTTAATGTTTATC (incorporated herein as SEQ ID NO: 1173), consisting of seventeen nucleosides, wherein each of nucleosides 1, 3, 13-17 are 2'-O-methoxyethylribose modified nucleosides, wherein each of nucleosides 2 and 4 are cEt modified nucleosides, wherein each of nucleosides 5-12 are 2'-deoxyribonucleosides, wherein the internucleoside linkages between nucleosides 2 to 3, 3 to 4, 13 to 14, and 14 to 15 are phosphodiester linkages and the internucleoside linkages between nucleosides 1 to 2, 4 to 5, 5 to 6, 6 to 7, 7 to 8, 8 to 9, 9 to 10, 10 to 11, 11 to 12, 12 to 13, 15 to 16, and 16 to 17 are phosphorothioate linkages, and wherein each cytosine is a 5'-methylcytosine.

In certain embodiments, ISIS 666870 is described by the following chemical notation: Aes Gko Teo Gks Tds Tds Tds Ads Ads Tds Gds Tds Teo Teo Aes Tes mCe; wherein,
A=an adenine,
mC=a 5'-methylcytosine
G=a guanine,
T=a thymine,
e=a 2'-O-methoxyethylribose modified sugar,
k=a cEt modified sugar,
d=a 2'-deoxyribose sugar,
s=a phosphorothioate internucleoside linkage, and
o=a phosphodiester internucleoside linkage.

In certain embodiments, ISIS 666870 is described by the following chemical structure:

Structure 7. ISIS 666870

(SEQ ID NO: 1173)

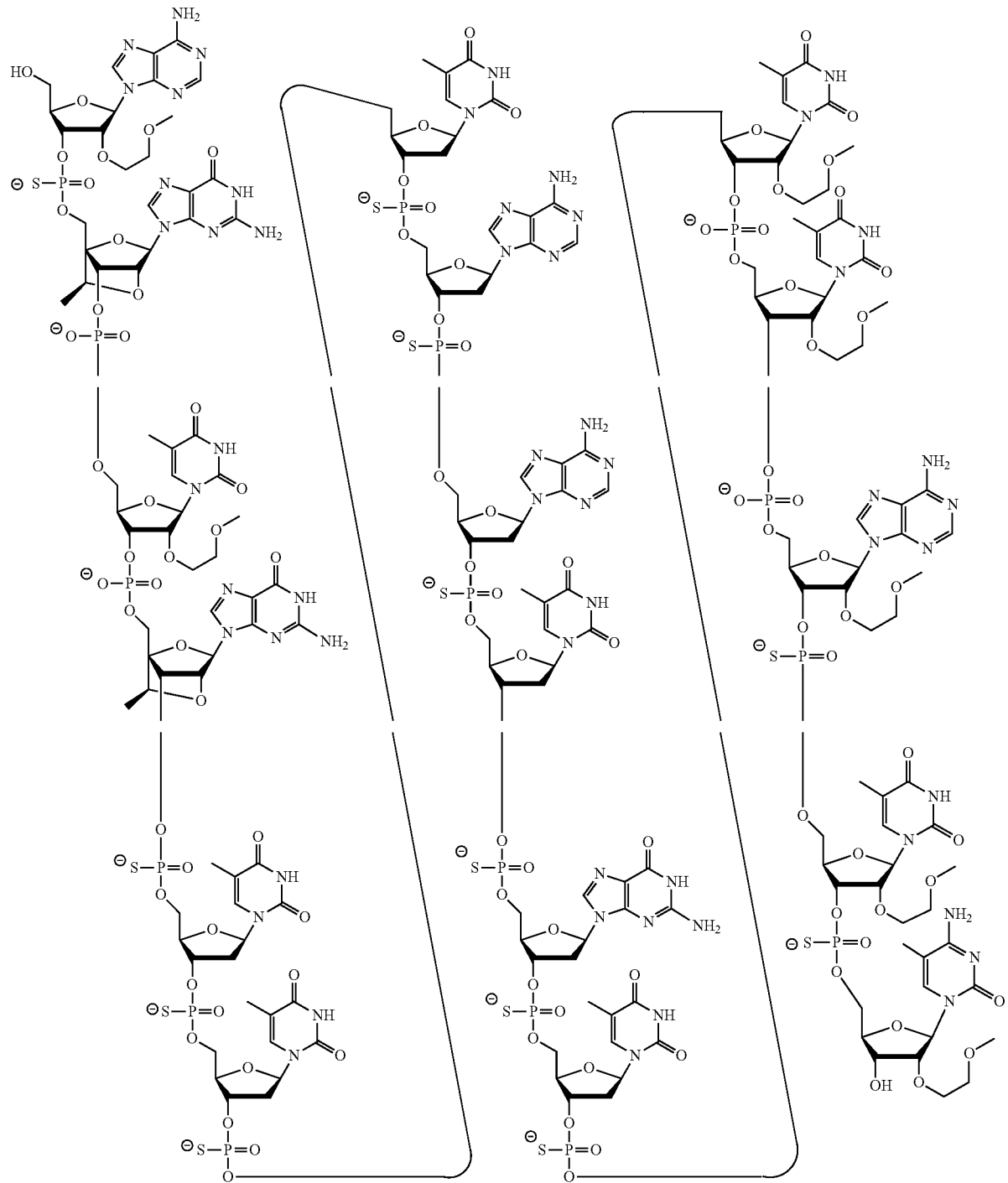

8. ISIS 666867

In certain embodiments, ISIS 666867 is characterized as a modified oligonucleotide having the nucleobase sequence (from 5' to 3') AGTGTTTAATGTTTATC (incorporated herein as SEQ ID NO: 1173), consisting of seventeen nucleosides, wherein each of nucleosides 1-2 and 13-17 are 2'-O-methoxyethylribose modified nucleosides, wherein each of nucleosides 3 and 4 are cEt modified nucleosides, wherein each of nucleosides 5-12 are 2'-deoxyribonucleosides, wherein the internucleoside linkages between nucleosides 2 to 3, 3 to 4, 13 to 14, and 14 to 15 are phosphodiester linkages and the internucleoside linkages between nucleosides 1 to 2, 4 to 5, 5 to 6, 6 to 7, 7 to 8, 8 to 9, 9 to 10, 10 to 11, 11 to 12, 12 to 13, 15 to 16, and 16 to 17 are phosphorothioate linkages, and wherein each cytosine is a 5'-methylcytosine.

In certain embodiments, ISIS 666867 is described by the following chemical notation: Aes Geo Tko Gks Tds Tds Tds Ads Ads Tds Gds Tds Teo Teo Aes Tes mCe; wherein, A=an adenine,
mC=a 5'-methylcytosine
G=a guanine,
T=a thymine,
e=a 2'-O-methoxyethylribose modified sugar,
k=a cEt modified sugar,
d=a 2'-deoxyribose sugar,
s=a phosphorothioate internucleoside linkage, and
o=a phosphodiester internucleoside linkage.

In certain embodiments, ISIS 666867 is described by the following chemical structure:

Structure 8. ISIS 666867

(SEQ ID NO: 1173)

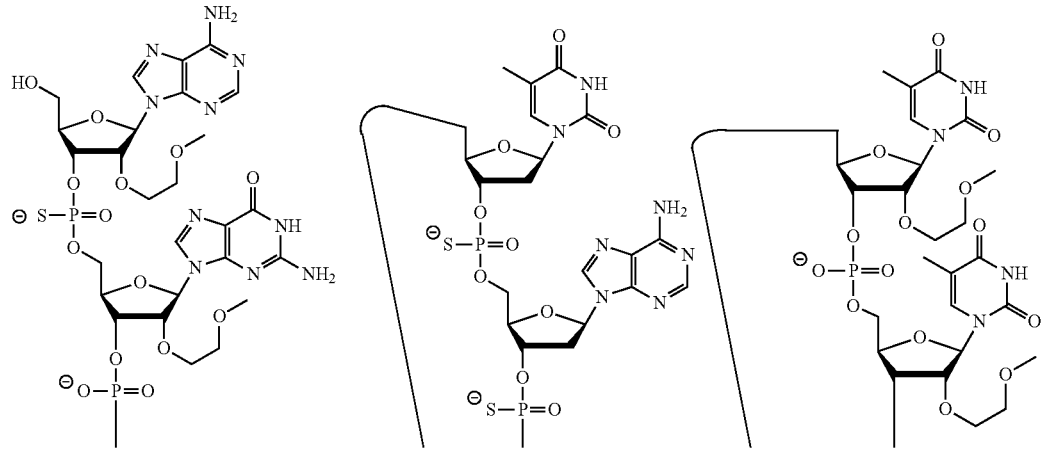

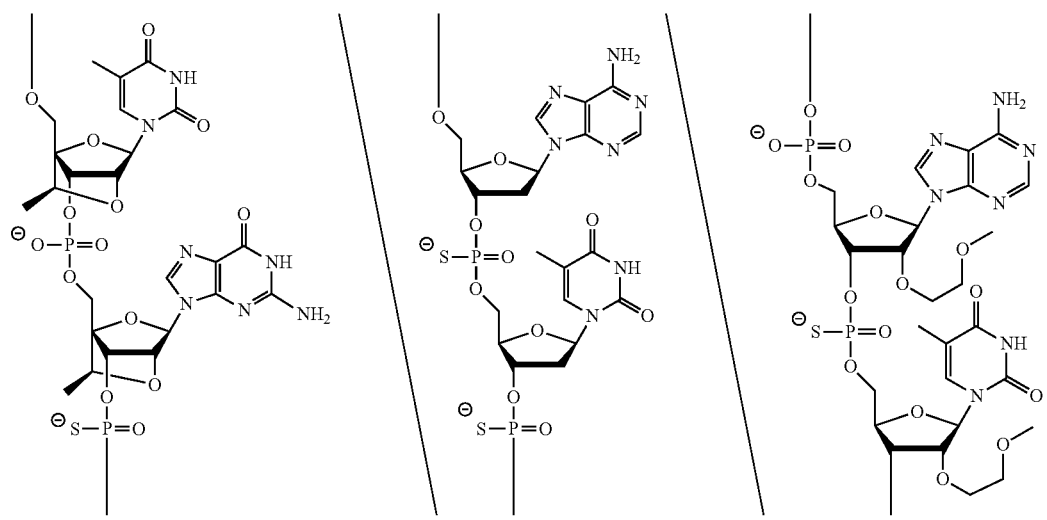

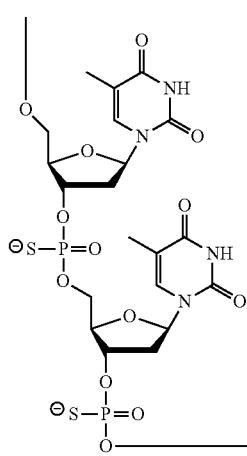
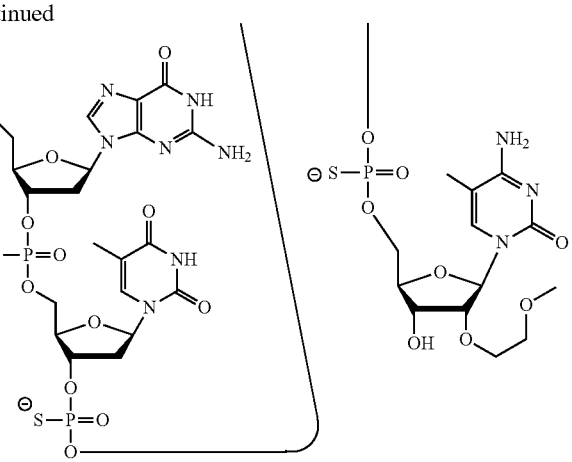

EXAMPLES

Non-Limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1: Inhibition of Human Superoxide Dismutase 1, Soluble (SOD-1) in HepG2 Cells by MOE Gapmers Modified oligonucleotides were designed targeting a superoxide dismutase 1, soluble (SOD-1) nucleic acid and were tested for their effects on SOD-1 mRNA in vitro. ISIS 146144, ISIS 146145, ISIS 150437, ISIS 150441, ISIS 150443, ISIS 150444, ISIS 150445, ISIS 150446, ISIS 150447, ISIS 150448, ISIS 150449, ISIS 150452, ISIS 150454, ISIS 150458, ISIS 150460, ISIS 150462-150467, ISIS 150470, ISIS 150472, ISIS 150474, ISIS 150475, ISIS 150476, ISIS 150479-150483, ISIS 150488, ISIS 150489, ISIS 150490, ISIS 150491-150493, ISIS 150495-150498, ISIS 150511, ISIS 333605, ISIS 333606, ISIS 333609-333617, ISIS 333619, ISIS 333620-333636, ISIS 333638, and ISIS 333640, previously disclosed in WO 2005/040180, were also included in this assay. ISIS 333611, previously disclosed in WO 2005/040180, was also designated as a benchmark or comparator oligonucleotide. ISIS 333611 was recently tested in human clinical trials. See, MILLER et al., "An antisense oligonucleotide against SOD1 delivered intrathecally for patients with SOD1 familial amyotrophic lateral sclerosis: a phase 1, randomised, first-in-man study" Lancet Neurol. (2013) 12(5): 435-442.

The modified oligonucleotides were tested in a series of experiments that had similar culture conditions. The results for each experiment are presented in separate tables shown below. Cultured HepG2 cells at a density of 20,000 cells per well were transfected using electroporation with 7,000 nM modified oligonucleotide. After a treatment period of approximately 24 hours, RNA was isolated from the cells and SOD-1 mRNA levels were measured by quantitative real-time PCR.

Human primer probe set RTS3898 (forward sequence CTCTCAGGAGACCATTGCATCA, designated herein as SEQ ID NO: 11; reverse sequence TCCTGTCTTTG-TACTTTCTTCATTTCC; designated herein as SEQ ID NO: 12; probe sequence CCGCACACTGGTGGTCCAT-GAAAA, designated herein as SEQ ID NO: 13) was used to measure mRNA levels. In cases where the oligonucleotide overlapped the amplicon of the primer probe set, an alternative primer probe set, HTS90 (forward sequence CGTG-GCCTAGCGAGTTATGG, designated herein as SEQ ID NO: 14; reverse sequence GAAATTGATGATGCCCTGCA; designated herein as SEQ ID NO: 15; probe sequence ACGAAGGCCGTGTGCGTGCTGX, designated herein as SEQ ID NO: 16), was used to measure mRNA levels. SOD-1 mRNA levels were adjusted according to total RNA content, as measured by RIBOGREEN®. Results are presented as percent inhibition of SOD-1, relative to untreated control cells. 'n.d.' indicates that inhibition levels were not measured using the particular primer probe set.

The newly designed modified oligonucleotides in the Tables below were designed as 5-10-5 MOE gapmers. The 5-10-5 MOE gapmers are 20 nucleosides in length, wherein the central gap segment is comprised of ten 2'-deoxyribo-nucleosides and is flanked by wing segments on the 5' direction and the 3' directions comprising five nucleosides each. Each nucleoside in the 5' wing segment and each nucleoside in the 3' wing segment has a 2'-MOE modification. The internucleoside linkages throughout each gapmer are phosphorothioate linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human SOD-1 mRNA, designated herein as SEQ ID NO: 1 (GENBANK Accession No. NM_000454.4) or the human SOD-1 genomic sequence, designated herein as SEQ ID NO: 2 (GENBANK Accession No. NT_011512.10 truncated from nucleotides 18693000 to Ser. No. 18/704,000). 'n/a' indicates that the modified oligonucleotide does not target that particular gene sequence with 100% complementarity.

TABLE 1

Percent Inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 590065 | 1 | 20 | CGCCCACTCTGGCCCCAAAC | 7 | 807 | 826 | 118 |
| 590066 | 35 | 54 | CCGCGACTACTTTATAGGCC | 5 | 841 | 860 | 119 |
| 333611 | 167 | 186 | CCGTCGCCCTTCAGCACGCA | 85 | 973 | 992 | 21 |
| 590067 | 202 | 221 | CCTTCTGCTCGAAATTGATG | 74 | 1008 | 1027 | 120 |
| 590068 | 203 | 222 | TCCTTCTGCTCGAAATTGAT | 58 | n/a | n/a | 121 |
| 590069 | 204 | 223 | TTCCTTCTGCTCGAAATTGA | 50 | n/a | n/a | 122 |
| 590070 | 205 | 224 | TTTCCTTCTGCTCGAAATTG | 47 | n/a | n/a | 123 |
| 590071 | 206 | 225 | CTTTCCTTCTGCTCGAAATT | 31 | n/a | n/a | 124 |
| 590072 | 207 | 226 | ACTTTCCTTCTGCTCGAAAT | 42 | n/a | n/a | 125 |
| 590073 | 208 | 227 | TACTTTCCTTCTGCTCGAAA | 38 | n/a | n/a | 126 |
| 590074 | 209 | 228 | TTACTTTCCTTCTGCTCGAA | 33 | n/a | n/a | 127 |
| 590075 | 210 | 229 | ATTACTTTCCTTCTGCTCGA | 39 | n/a | n/a | 128 |
| 590076 | 211 | 230 | CATTACTTTCCTTCTGCTCG | 28 | n/a | n/a | 129 |
| 590077 | 212 | 231 | CCATTACTTTCCTTCTGCTC | 58 | n/a | n/a | 130 |
| 590078 | 213 | 232 | TCCATTACTTTCCTTCTGCT | 58 | n/a | n/a | 131 |
| 590079 | 214 | 233 | GTCCATTACTTTCCTTCTGC | 69 | n/a | n/a | 132 |
| 590080 | 215 | 234 | GGTCCATTACTTTCCTTCTG | 68 | n/a | n/a | 133 |
| 590081 | 216 | 235 | TGGTCCATTACTTTCCTTCT | 61 | n/a | n/a | 134 |
| 590082 | 217 | 236 | CTGGTCCATTACTTTCCTTC | 69 | n/a | n/a | 135 |
| 590083 | 218 | 237 | ACTGGTCCATTACTTTCCTT | 54 | 4972 | 4991 | 136 |
| 150445 | 219 | 238 | CACTGGTCCATTACTTTCCT | 84 | 4973 | 4992 | 22 |
| 590084 | 220 | 239 | TCACTGGTCCATTACTTTCC | 65 | 4974 | 4993 | 137 |
| 590085 | 221 | 240 | TTCACTGGTCCATTACTTTC | 45 | 4975 | 4994 | 138 |
| 590086 | 222 | 241 | CTTCACTGGTCCATTACTTT | 43 | 4976 | 4995 | 139 |
| 590087 | 223 | 242 | CCTTCACTGGTCCATTACTT | 67 | 4977 | 4996 | 140 |
| 590088 | 224 | 243 | ACCTTCACTGGTCCATTACT | 59 | 4978 | 4997 | 141 |
| 436841 | 225 | 244 | CACCTTCACTGGTCCATTAC | 65 | 4979 | 4998 | 142 |
| 150446 | 226 | 245 | ACACCTTCACTGGTCCATTA | 83 | 4980 | 4999 | 23 |
| 393336 | 227 | 246 | CACACCTTCACTGGTCCATT | 81 | 4981 | 5000 | 143 |
| 150447 | 228 | 247 | CCACACCTTCACTGGTCCAT | 89 | 4982 | 5001 | 24 |
| 590089 | 229 | 248 | CCCACACCTTCACTGGTCCA | 82 | 4983 | 5002 | 144 |
| 590090 | 230 | 249 | CCCCACACCTTCACTGGTCC | 89 | 4984 | 5003 | 145 |
| 590091 | 231 | 250 | TCCCCACACCTTCACTGGTC | 84 | 4985 | 5004 | 146 |
| 590092 | 232 | 251 | TTCCCCACACCTTCACTGGT | 61 | 4986 | 5005 | 147 |
| 590093 | 233 | 252 | CTTCCCCACACCTTCACTGG | 60 | 4987 | 5006 | 148 |
| 590094 | 234 | 253 | GCTTCCCCACACCTTCACTG | 78 | 4988 | 5007 | 149 |

TABLE 1-continued

Percent Inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 590095 | 235 | 254 | TGCTTCCCCACACCTTCACT | 72 | 4989 | 5008 | 150 |
| 590096 | 236 | 255 | ATGCTTCCCCACACCTTCAC | 76 | 4990 | 5009 | 151 |
| 393337 | 237 | 256 | AATGCTTCCCCACACCTTCA | 76 | 4991 | 5010 | 152 |
| 590097 | 238 | 257 | TAATGCTTCCCCACACCTTC | 68 | 4992 | 5011 | 153 |
| 590098 | 264 | 283 | TCCATGCAGGCCTTCAGTCA | 63 | 5018 | 5037 | 154 |
| 590099 | 265 | 284 | ATCCATGCAGGCCTTCAGTC | 64 | 5019 | 5038 | 155 |
| 590100 | 266 | 285 | AATCCATGCAGGCCTTCAGT | 52 | 5020 | 5039 | 156 |
| 590101 | 267 | 286 | GAATCCATGCAGGCCTTCAG | 53 | 5021 | 5040 | 157 |
| 590102 | 268 | 287 | GGAATCCATGCAGGCCTTCA | 65 | 5022 | 5041 | 158 |
| 393339 | 269 | 288 | TGGAATCCATGCAGGCCTTC | 43 | 5023 | 5042 | 159 |
| 590103 | 270 | 289 | ATGGAATCCATGCAGGCCTT | 56 | 5024 | 5043 | 160 |
| 590104 | 271 | 290 | CATGGAATCCATGCAGGCCT | 57 | 5025 | 5044 | 161 |
| 590105 | 272 | 291 | ACATGGAATCCATGCAGGCC | 52 | 5026 | 5045 | 162 |
| 590106 | 273 | 292 | AACATGGAATCCATGCAGGC | 54 | 5027 | 5046 | 163 |
| 590107 | 274 | 293 | GAACATGGAATCCATGCAGG | 51 | 5028 | 5047 | 164 |
| 590108 | 275 | 294 | TGAACATGGAATCCATGCAG | 58 | 5029 | 5048 | 165 |
| 393340 | 276 | 295 | ATGAACATGGAATCCATGCA | 62 | 5030 | 5049 | 166 |
| 590109 | 316 | 335 | GACCTGCACTGGTACAGCCT | 69 | 7632 | 7651 | 167 |
| 436847 | 317 | 336 | GGACCTGCACTGGTACAGCC | 74 | 7633 | 7652 | 168 |
| 590110 | 318 | 337 | AGGACCTGCACTGGTACAGC | 70 | 7634 | 7653 | 169 |
| 590111 | 319 | 338 | GAGGACCTGCACTGGTACAG | 74 | 7635 | 7654 | 170 |
| 590112 | 320 | 339 | TGAGGACCTGCACTGGTACA | 68 | 7636 | 7655 | 171 |
| 590113 | 321 | 340 | GTGAGGACCTGCACTGGTAC | 80 | 7637 | 7656 | 172 |
| 393343 | 322 | 341 | AGTGAGGACCTGCACTGGTA | 79 | 7638 | 7657 | 173 |
| 590114 | 323 | 342 | AAGTGAGGACCTGCACTGGT | 65 | 7639 | 7658 | 174 |
| 590115 | 324 | 343 | AAAGTGAGGACCTGCACTGG | 48 | 7640 | 7659 | 175 |
| 590116 | 325 | 344 | TAAAGTGAGGACCTGCACTG | 51 | 7641 | 7660 | 176 |
| 436848 | 326 | 345 | TTAAAGTGAGGACCTGCACT | 59 | 7642 | 7661 | 177 |
| 590117 | 327 | 346 | ATTAAAGTGAGGACCTGCAC | 43 | 7643 | 7662 | 178 |
| 590118 | 328 | 347 | GATTAAAGTGAGGACCTGCA | 43 | 7644 | 7663 | 179 |
| 590119 | 329 | 348 | GGATTAAAGTGAGGACCTGC | 67 | 7645 | 7664 | 180 |
| 590120 | 330 | 349 | AGGATTAAAGTGAGGACCTG | 63 | 7646 | 7665 | 181 |
| 436849 | 331 | 350 | GAGGATTAAAGTGAGGACCT | 64 | 7647 | 7666 | 182 |
| 393344 | 332 | 351 | AGAGGATTAAAGTGAGGACC | 59 | 7648 | 7667 | 183 |
| 590121 | 333 | 352 | TAGAGGATTAAAGTGAGGAC | 52 | 7649 | 7668 | 184 |

TABLE 1-continued

Percent Inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 590122 | 334 | 353 | ATAGAGGATTAAAGTGAGGA | 36 | 7650 | 7669 | 185 |
| 590123 | 335 | 354 | GATAGAGGATTAAAGTGAGG | 25 | 7651 | 7670 | 186 |
| 590124 | 336 | 355 | GGATAGAGGATTAAAGTGAG | 34 | 7652 | 7671 | 187 |
| 590125 | 337 | 356 | TGGATAGAGGATTAAAGTGA | 49 | 7653 | 7672 | 188 |
| 590126 | 338 | 357 | CTGGATAGAGGATTAAAGTG | 34 | 7654 | 7673 | 189 |
| 590127 | 339 | 358 | TCTGGATAGAGGATTAAAGT | 39 | 7655 | 7674 | 190 |
| 590128 | 360 | 379 | ATCCTTTGGCCCACCGTGTT | 60 | 7676 | 7695 | 191 |

TABLE 2

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | % inhibition with HTS90 | SEQ ID NO: 2 Start Site | SEQ ID NO: 2 Stop Site | SEQ ID NO |
|---|---|---|---|---|---|---|---|---|
| 333611 | 167 | 186 | CCGTCGCCCTTCAGCACGCA | 76 | 95 | 973 | 992 | 21 |
| 393347 | 361 | 380 | CATCCTTTGGCCCACCGTGT | 70 | 72 | 7677 | 7696 | 192 |
| 590129 | 362 | 381 | TCATCCTTTGGCCCACCGTG | 66 | 68 | 7678 | 7697 | 193 |
| 590130 | 363 | 382 | TTCATCCTTTGGCCCACCGT | 53 | 55 | 7679 | 7698 | 194 |
| 590131 | 364 | 383 | CTTCATCCTTTGGCCCACCG | 52 | 50 | 7680 | 7699 | 195 |
| 590132 | 365 | 384 | TCTTCATCCTTTGGCCCACC | 61 | 64 | 7681 | 7700 | 196 |
| 590133 | 366 | 385 | CTCTTCATCCTTTGGCCCAC | 45 | 54 | 7682 | 7701 | 197 |
| 590134 | 367 | 386 | TCTCTTCATCCTTTGGCCCA | 44 | 34 | 7683 | 7702 | 198 |
| 590135 | 368 | 387 | CTCTCTTCATCCTTTGGCCC | 52 | 49 | 7684 | 7703 | 199 |
| 590136 | 369 | 388 | CCTCTCTTCATCCTTTGGCC | 48 | 47 | 7685 | 7704 | 200 |
| 590137 | 370 | 389 | GCCTCTCTTCATCCTTTGGC | 35 | 44 | n/a | n/a | 201 |
| 590138 | 371 | 390 | TGCCTCTCTTCATCCTTTGG | 52 | 45 | n/a | n/a | 202 |
| 590139 | 372 | 391 | ATGCCTCTCTTCATCCTTTG | 50 | 45 | n/a | n/a | 203 |
| 590140 | 373 | 392 | CATGCCTCTCTTCATCCTTT | 49 | 27 | n/a | n/a | 204 |
| 590141 | 374 | 393 | ACATGCCTCTCTTCATCCTT | 34 | 18 | n/a | n/a | 205 |
| 590142 | 375 | 394 | AACATGCCTCTCTTCATCCT | 38 | 35 | n/a | n/a | 206 |
| 333612 | 376 | 395 | CAACATGCCTCTCTTCATCC | 34 | 33 | n/a | n/a | 25 |
| 333613 | 377 | 396 | CCAACATGCCTCTCTTCATC | 46 | 55 | n/a | n/a | 26 |
| 333614 | 378 | 397 | TCCAACATGCCTCTCTTCAT | 42 | 48 | n/a | n/a | 27 |
| 333615 | 379 | 398 | CTCCAACATGCCTCTCTTCA | 42 | 15 | n/a | n/a | 28 |
| 333616 | 380 | 399 | TCTCCAACATGCCTCTCTT | 35 | 44 | n/a | n/a | 29 |
| 333617 | 381 | 400 | GTCTCCAACATGCCTCTCTT | 42 | 47 | n/a | n/a | 30 |

TABLE 2-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | % inhibition with HTS90 | SEQ ID NO: 2 Start Site | SEQ ID NO: 2 Stop Site | SEQ ID NO |
|---|---|---|---|---|---|---|---|---|
| 590143 | 501 | 520 | TGCTTTTTCATGGACCACCA | n.d. | 65 | n/a | n/a | 207 |
| 590144 | 502 | 521 | CTGCTTTTTCATGGACCACC | n.d. | 70 | n/a | n/a | 208 |
| 590145 | 503 | 522 | TCTGCTTTTTCATGGACCAC | n.d. | 64 | n/a | n/a | 209 |
| 436860 | 504 | 523 | ATCTGCTTTTTCATGGACCA | n.d. | 65 | n/a | n/a | 210 |
| 590146 | 505 | 524 | CATCTGCTTTTTCATGGACC | n.d. | 68 | 9655 | 9674 | 211 |
| 590147 | 506 | 525 | TCATCTGCTTTTTCATGGAC | n.d. | 59 | 9656 | 9675 | 212 |
| 393359 | 507 | 526 | GTCATCTGCTTTTTCATGGA | n.d. | 56 | 9657 | 9676 | 213 |
| 590148 | 508 | 527 | AGTCATCTGCTTTTTCATGG | n.d. | 45 | 9658 | 9677 | 214 |
| 590149 | 509 | 528 | AAGTCATCTGCTTTTTCATG | n.d. | 23 | 9659 | 9678 | 215 |
| 590150 | 510 | 529 | CAAGTCATCTGCTTTTTCAT | n.d. | 43 | 9660 | 9679 | 216 |
| 590151 | 511 | 530 | CCAAGTCATCTGCTTTTTCA | n.d. | 72 | 9661 | 9680 | 217 |
| 489513 | 512 | 531 | CCCAAGTCATCTGCTTTTTC | n.d. | 73 | 9662 | 9681 | 218 |
| 590152 | 513 | 532 | GCCCAAGTCATCTGCTTTTT | n.d. | 74 | 9663 | 9682 | 219 |
| 436861 | 514 | 533 | TGCCCAAGTCATCTGCTTTT | n.d. | 75 | 9664 | 9683 | 220 |
| 590153 | 515 | 534 | TTGCCCAAGTCATCTGCTTT | n.d. | 47 | 9665 | 9684 | 221 |
| 393360 | 516 | 535 | TTTGCCCAAGTCATCTGCTT | n.d. | 57 | 9666 | 9685 | 222 |
| 590154 | 517 | 536 | CTTTGCCCAAGTCATCTGCT | n.d. | 79 | 9667 | 9686 | 223 |
| 590155 | 518 | 537 | CCTTTGCCCAAGTCATCTGC | n.d. | 67 | 9668 | 9687 | 224 |
| 590156 | 519 | 538 | ACCTTTGCCCAAGTCATCTG | n.d. | 57 | 9669 | 9688 | 225 |
| 333620 | 520 | 539 | CACCTTTGCCCAAGTCATCT | n.d. | 68 | 9670 | 9689 | 31 |
| 333621 | 521 | 540 | CCACCTTTGCCCAAGTCATC | n.d. | 72 | 9671 | 9690 | 32 |
| 333622 | 522 | 541 | TCCACCTTTGCCCAAGTCAT | n.d. | 77 | 9672 | 9691 | 33 |
| 333623 | 523 | 542 | TTCCACCTTTGCCCAAGTCA | n.d. | 73 | 9673 | 9692 | 34 |
| 333624 | 524 | 543 | TTTCCACCTTTGCCCAAGTC | n.d. | 77 | 9674 | 9693 | 35 |
| 333625 | 525 | 544 | ATTTCCACCTTTGCCCAAGT | n.d. | 79 | 9675 | 9694 | 36 |
| 333626 | 526 | 545 | CATTTCCACCTTTGCCCAAG | n.d. | 72 | 9676 | 9695 | 37 |
| 333627 | 527 | 546 | TCATTTCCACCTTTGCCCAA | n.d. | 55 | 9677 | 9696 | 38 |
| 333628 | 528 | 547 | TTCATTTCCACCTTTGCCCA | n.d. | 59 | 9678 | 9697 | 39 |
| 333629 | 529 | 548 | CTTCATTTCCACCTTTGCCC | n.d. | 73 | 9679 | 9698 | 40 |
| 333630 | 530 | 549 | TCTTCATTTCCACCTTTGCC | n.d. | 76 | 9680 | 9699 | 41 |
| 333631 | 531 | 550 | TTCTTCATTTCCACCTTTGC | n.d. | 62 | 9681 | 9700 | 42 |
| 333632 | 532 | 551 | TTTCTTCATTTCCACCTTTG | n.d. | 64 | 9682 | 9701 | 43 |
| 333633 | 533 | 552 | CTTTCTTCATTTCCACCTTT | n.d. | 69 | 9683 | 9702 | 44 |
| 333634 | 534 | 553 | ACTTTCTTCATTTCCACCTT | n.d. | 55 | 9684 | 9703 | 45 |
| 333635 | 535 | 554 | TACTTTCTTCATTTCCACCT | n.d. | 72 | 9685 | 9704 | 46 |

TABLE 2-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | % inhibition with HTS90 | SEQ ID NO: 2 Start Site | SEQ ID NO: 2 Stop Site | SEQ ID NO |
|---|---|---|---|---|---|---|---|---|
| 489517 | 582 | 601 | CCCAATTACACCACAAGCCA | 68 | 72 | 9732 | 9751 | 226 |
| 436863 | 583 | 602 | TCCCAATTACACCACAAGCC | 83 | 86 | 9733 | 9752 | 227 |
| 590157 | 584 | 603 | ATCCCAATTACACCACAAGC | 64 | 62 | 9734 | 9753 | 228 |
| 590158 | 585 | 604 | GATCCCAATTACACCACAAG | 51 | 61 | 9735 | 9754 | 229 |
| 590159 | 586 | 605 | CGATCCCAATTACACCACAA | 60 | 55 | 9736 | 9755 | 230 |
| 590160 | 587 | 606 | GCGATCCCAATTACACCACA | 59 | 63 | 9737 | 9756 | 231 |
| 150463 | 588 | 607 | GGCGATCCCAATTACACCAC | 78 | 79 | 9738 | 9757 | 47 |
| 393363 | 589 | 608 | GGGCGATCCCAATTACACCA | 65 | 65 | 9739 | 9758 | 232 |
| 590161 | 590 | 609 | TGGGCGATCCCAATTACACC | 56 | 60 | 9740 | 9759 | 233 |
| 590162 | 591 | 610 | TTGGGCGATCCCAATTACAC | 48 | 51 | 9741 | 9760 | 234 |
| 489518 | 592 | 611 | ATTGGGCGATCCCAATTACA | 51 | 59 | 9742 | 9761 | 235 |
| 436864 | 593 | 612 | TATTGGGCGATCCCAATTAC | 39 | 41 | 9743 | 9762 | 236 |
| 590163 | 594 | 613 | TTATTGGGCGATCCCAATTA | 35 | 34 | 9744 | 9763 | 237 |
| 590164 | 595 | 614 | TTTATTGGGCGATCCCAATT | 42 | 44 | 9745 | 9764 | 238 |
| 590165 | 596 | 615 | GTTTATTGGGCGATCCCAAT | 58 | 61 | 9746 | 9765 | 239 |
| 393364 | 597 | 616 | TGTTTATTGGGCGATCCCAA | 60 | 69 | 9747 | 9766 | 240 |
| 590166 | 598 | 617 | ATGTTTATTGGGCGATCCCA | 51 | 54 | 9748 | 9767 | 241 |
| 590167 | 599 | 618 | AATGTTTATTGGGCGATCCC | 48 | 45 | 9749 | 9768 | 242 |
| 590168 | 600 | 619 | GAATGTTTATTGGGCGATCC | 60 | 65 | 9750 | 9769 | 243 |
| 150464 | 601 | 620 | GGAATGTTTATTGGGCGATC | 58 | 63 | 9751 | 9770 | 48 |
| 393365 | 607 | 626 | TCCAAGGGAATGTTTATTGG | 50 | 58 | 9757 | 9776 | 244 |

TABLE 3

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 333611 | 167 | 186 | CCGTCGCCCTTCAGCACGCA | 80 | 973 | 992 | 21 |
| 590169 | 608 | 627 | ATCCAAGGGAATGTTTATTG | 63 | 9758 | 9777 | 245 |
| 590170 | 609 | 628 | CATCCAAGGGAATGTTTATT | 53 | 9759 | 9778 | 246 |
| 590171 | 610 | 629 | ACATCCAAGGGAATGTTTAT | 49 | 9760 | 9779 | 247 |
| 590172 | 611 | 630 | TACATCCAAGGGAATGTTTA | 56 | 9761 | 9780 | 248 |
| 489519 | 612 | 631 | CTACATCCAAGGGAATGTTT | 60 | 9762 | 9781 | 249 |
| 590173 | 613 | 632 | ACTACATCCAAGGGAATGTT | 61 | 9763 | 9782 | 250 |
| 590174 | 614 | 633 | GACTACATCCAAGGGAATGT | 65 | 9764 | 9783 | 251 |

TABLE 3-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 393366 | 615 | 634 | AGACTACATCCAAGGGAATG | 58 | 9765 | 9784 | 252 |
| 590175 | 616 | 635 | CAGACTACATCCAAGGGAAT | 50 | 9766 | 9785 | 253 |
| 436865 | 617 | 636 | TCAGACTACATCCAAGGGAA | 69 | 9767 | 9786 | 254 |
| 590176 | 618 | 637 | CTCAGACTACATCCAAGGGA | 78 | 9768 | 9787 | 255 |
| 150465 | 619 | 638 | CCTCAGACTACATCCAAGGG | 91 | 9769 | 9788 | 49 |
| 590177 | 620 | 639 | GCCTCAGACTACATCCAAGG | 90 | 9770 | 9789 | 256 |
| 590178 | 621 | 640 | GGCCTCAGACTACATCCAAG | 92 | 9771 | 9790 | 257 |
| 489520 | 622 | 641 | GGGCCTCAGACTACATCCAA | 88 | 9772 | 9791 | 258 |
| 590179 | 643 | 662 | CAGGATAACAGATGAGTTAA | 79 | 9793 | 9812 | 259 |
| 590180 | 644 | 663 | GCAGGATAACAGATGAGTTA | 83 | 9794 | 9813 | 260 |
| 590181 | 645 | 664 | AGCAGGATAACAGATGAGTT | 81 | 9795 | 9814 | 261 |
| 590182 | 646 | 665 | TAGCAGGATAACAGATGAGT | 68 | 9796 | 9815 | 262 |
| 590183 | 647 | 666 | CTAGCAGGATAACAGATGAG | 74 | 9797 | 9816 | 263 |
| 590184 | 648 | 667 | GCTAGCAGGATAACAGATGA | 70 | 9798 | 9817 | 264 |
| 393370 | 649 | 668 | AGCTAGCAGGATAACAGATG | 61 | 9799 | 9818 | 265 |
| 590185 | 650 | 669 | CAGCTAGCAGGATAACAGAT | 78 | 9800 | 9819 | 266 |
| 590186 | 651 | 670 | ACAGCTAGCAGGATAACAGA | 72 | 9801 | 9820 | 267 |
| 489522 | 652 | 671 | TACAGCTAGCAGGATAACAG | 78 | 9802 | 9821 | 268 |
| 590187 | 653 | 672 | CTACAGCTAGCAGGATAACA | 88 | 9803 | 9822 | 269 |
| 378879 | 654 | 673 | TCTACAGCTAGCAGGATAAC | 86 | 9804 | 9823 | 270 |
| 590188 | 655 | 674 | TTCTACAGCTAGCAGGATAA | 85 | 9805 | 9824 | 271 |
| 393371 | 656 | 675 | TTTCTACAGCTAGCAGGATA | 84 | 9806 | 9825 | 272 |
| 436868 | 657 | 676 | ATTTCTACAGCTAGCAGGAT | 81 | 9807 | 9826 | 273 |
| 590189 | 658 | 677 | CATTTCTACAGCTAGCAGGA | 87 | 9808 | 9827 | 274 |
| 590190 | 659 | 678 | ACATTTCTACAGCTAGCAGG | 92 | 9809 | 9828 | 275 |
| 590191 | 660 | 679 | TACATTTCTACAGCTAGCAG | 88 | 9810 | 9829 | 276 |
| 590192 | 661 | 680 | ATACATTTCTACAGCTAGCA | 88 | 9811 | 9830 | 277 |
| 489523 | 662 | 681 | GATACATTTCTACAGCTAGC | 93 | 9812 | 9831 | 278 |
| 590193 | 683 | 702 | ACAGTGTTTAATGTTTATCA | 74 | 9833 | 9852 | 279 |
| 590194 | 684 | 703 | TACAGTGTTTAATGTTTATC | 64 | 9834 | 9853 | 280 |
| 590195 | 685 | 704 | TTACAGTGTTTAATGTTTAT | 56 | 9835 | 9854 | 281 |
| 590196 | 686 | 705 | ATTACAGTGTTTAATGTTTA | 50 | 9836 | 9855 | 282 |
| 590197 | 687 | 706 | GATTACAGTGTTTAATGTTT | 74 | 9837 | 9856 | 283 |
| 590198 | 688 | 707 | AGATTACAGTGTTTAATGTT | 37 | 9838 | 9857 | 284 |
| 590199 | 689 | 708 | AAGATTACAGTGTTTAATGT | 58 | 9839 | 9858 | 285 |

TABLE 3-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 393375 | 690 | 709 | TAAGATTACAGTGTTTAATG | 58 | 9840 | 9859 | 286 |
| 590200 | 691 | 710 | TTAAGATTACAGTGTTTAAT | 46 | 9841 | 9860 | 287 |
| 436876 | 772 | 791 | CAAATCTTCCAAGTGATCAT | 36 | 9922 | 9941 | 288 |
| 590201 | 773 | 792 | ACAAATCTTCCAAGTGATCA | 33 | 9923 | 9942 | 289 |
| 590202 | 774 | 793 | TACAAATCTTCCAAGTGATC | 34 | 9924 | 9943 | 290 |
| 150474 | 775 | 794 | ATACAAATCTTCCAAGTGAT | 47 | 9925 | 9944 | 50 |
| 590203 | 776 | 795 | TATACAAATCTTCCAAGTGA | 29 | 9926 | 9945 | 291 |
| 393382 | 777 | 796 | CTATACAAATCTTCCAAGTG | 41 | 9927 | 9946 | 292 |
| 436877 | 778 | 797 | ACTATACAAATCTTCCAAGT | 45 | 9928 | 9947 | 293 |
| 590204 | 779 | 798 | AACTATACAAATCTTCCAAG | 27 | 9929 | 9948 | 294 |
| 590205 | 780 | 799 | AAACTATACAAATCTTCCAA | 33 | 9930 | 9949 | 295 |
| 590206 | 781 | 800 | AAAACTATACAAATCTTCCA | 35 | 9931 | 9950 | 296 |
| 489533 | 782 | 801 | TAAAACTATACAAATCTTCC | 26 | 9932 | 9951 | 297 |
| 590207 | 783 | 802 | ATAAAACTATACAAATCTTC | 19 | 9933 | 9952 | 298 |
| 590208 | 784 | 803 | TATAAAACTATACAAATCTT | 2 | 9934 | 9953 | 299 |
| 590209 | 785 | 804 | TTATAAAACTATACAAATCT | 7 | 9935 | 9954 | 300 |
| 590210 | 786 | 805 | TTTATAAAACTATACAAATC | 0 | 9936 | 9955 | 301 |
| 590211 | 787 | 806 | TTTTATAAAACTATACAAAT | 4 | 9937 | 9956 | 302 |
| 590212 | 788 | 807 | GTTTTATAAAACTATACAAA | 5 | 9938 | 9957 | 303 |
| 590213 | 789 | 808 | AGTTTTATAAAACTATACAA | 3 | 9939 | 9958 | 304 |
| 436878 | 790 | 809 | GAGTTTTATAAAACTATACA | 7 | 9940 | 9959 | 305 |
| 150475 | 791 | 810 | TGAGTTTTATAAAACTATAC | 28 | 9941 | 9960 | 51 |
| 489536 | 812 | 831 | CATTGAAACAGACATTTTAA | 28 | 9962 | 9981 | 306 |
| 150479 | 813 | 832 | TCATTGAAACAGACATTTTA | 36 | 9963 | 9982 | 52 |
| 393385 | 814 | 833 | GTCATTGAAACAGACATTTT | 50 | 9964 | 9983 | 307 |
| 590214 | 815 | 834 | GGTCATTGAAACAGACATTT | 45 | 9965 | 9984 | 308 |
| 590215 | 816 | 835 | AGGTCATTGAAACAGACATT | 47 | 9966 | 9985 | 309 |
| 590216 | 817 | 836 | CAGGTCATTGAAACAGACAT | 39 | 9967 | 9986 | 310 |
| 590217 | 818 | 837 | ACAGGTCATTGAAACAGACA | 44 | 9968 | 9987 | 311 |
| 590218 | 819 | 838 | TACAGGTCATTGAAACAGAC | 42 | 9969 | 9988 | 312 |
| 150480 | 820 | 839 | ATACAGGTCATTGAAACAGA | 46 | 9970 | 9989 | 53 |
| 393386 | 821 | 840 | AATACAGGTCATTGAAACAG | 36 | 9971 | 9990 | 313 |
| 489537 | 822 | 841 | AAATACAGGTCATTGAAACA | 12 | 9972 | 9991 | 314 |
| 590219 | 823 | 842 | AAAATACAGGTCATTGAAAC | 16 | 9973 | 9992 | 315 |
| 590220 | 824 | 843 | CAAAATACAGGTCATTGAAA | 21 | 9974 | 9993 | 316 |

TABLE 4

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 590251 | n/a | n/a | CCTTGCCTTCTGCTCGAAAT | 57 | 1013 | 1032 | 317 |
| 590252 | n/a | n/a | AATAAAGTTGACCTCTTTTT | 45 | 5479 | 5498 | 318 |
| 590253 | n/a | n/a | CTCTGATATAAAAATCTTGT | 54 | 8142 | 8161 | 319 |
| 590254 | n/a | n/a | GCCCCGCGGCGGCCTCGGTC | 38 | 1238 | 1257 | 320 |
| 590255 | n/a | n/a | GCTATCGCCATTATTACAAG | 38 | 7722 | 7741 | 321 |
| 590256 | n/a | n/a | CTCAAATGTGAAAGTTGTCC | 57 | 3414 | 3433 | 322 |
| 590257 | n/a | n/a | GTTCTATATTCAATAAATGC | 37 | 7925 | 7944 | 323 |
| 590258 | n/a | n/a | AATTAAAGTTCCCAAATACA | 0 | 7578 | 7597 | 324 |
| 590259 | n/a | n/a | GATCATTACAAAAGTTAAGA | 17 | 6150 | 6169 | 325 |
| 590260 | n/a | n/a | CCTTCTCTGCCCTTGCAGCC | 55 | 1685 | 1704 | 326 |
| 590261 | n/a | n/a | ACCCAAATAACTATGTTGTA | n.d. | 9394 | 9413 | 327 |
| 590262 | n/a | n/a | CCAGGTTTTAAACTTAACAA | n.d. | 8890 | 8909 | 328 |
| 590263 | n/a | n/a | ATCTCAGGACTAAAATAAAC | 44 | 3663 | 3682 | 329 |
| 590264 | n/a | n/a | AAATAACTATGTTGTAGACC | n.d. | 9390 | 9409 | 330 |
| 590265 | n/a | n/a | AAGAACCTTTTCCAGAAAAT | 37 | 2449 | 2468 | 331 |
| 590266 | n/a | n/a | GGAACAGAAACAAGTCTATG | 25 | 7458 | 7477 | 332 |
| 590267 | n/a | n/a | AGAAAGCTATCGCCATTATT | 27 | 7727 | 7746 | 333 |
| 590268 | n/a | n/a | TTCCCAAATACATTCTAAAA | 7 | 7570 | 7589 | 334 |
| 590269 | n/a | n/a | AACTGCTCTAGGCCTGTGTC | 53 | 4787 | 4806 | 335 |
| 590270 | n/a | n/a | AAATGGATCAAATCTGATCA | 31 | 6595 | 6614 | 336 |
| 590271 | n/a | n/a | GTAGGTGCACATCAAAATCA | 58 | 1928 | 1947 | 337 |
| 590272 | n/a | n/a | TCTGATATAAAAATCTTGTC | 28 | 8141 | 8160 | 338 |
| 590273 | n/a | n/a | ACCATATGAACTCCAGAAAG | 45 | 7741 | 7760 | 339 |
| 590274 | n/a | n/a | AACATCAAGGTAGTTCATGA | 10 | 8379 | 8398 | 340 |
| 590275 | n/a | n/a | GCAATTACAGAAATGGATCA | 42 | 6605 | 6624 | 341 |
| 590276 | n/a | n/a | TTTTAAGCATATTCCAAAGT | 45 | 6331 | 6350 | 342 |
| 590277 | n/a | n/a | TCAACCCCAGCTCAAACAC | 26 | 6174 | 6193 | 343 |
| 590278 | n/a | n/a | AGAAAAATAACATTAATCCT | n.d. | 9541 | 9560 | 344 |
| 590279 | n/a | n/a | AAGATTTTAAACACGGAATA | 31 | 3085 | 3104 | 345 |
| 146145 | 165 | 184 | GTCGCCCTTCAGCACGCACA | 82 | 971 | 990 | 54 |
| 333611 | 167 | 186 | CCGTCGCCCTTCAGCACGCA | 81 | 973 | 992 | 21 |
| 590250 | 399 | 418 | AGCAGTCACATTGCCCAAGT | 75 | 8454 | 8473 | 346 |
| 489525 | 682 | 701 | CAGTGTTTAATGTTTATCAG | 69 | 9832 | 9851 | 347 |
| 436879 | 825 | 844 | GCAAATACAGGTCATTGAA | 49 | 9975 | 9994 | 348 |
| 590221 | 826 | 845 | GGCAAATACAGGTCATTGA | 54 | 9976 | 9995 | 349 |
| 590222 | 827 | 846 | TGGCAAATACAGGTCATTG | 52 | 9977 | 9996 | 350 |

TABLE 4-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 393387 | 828 | 847 | CTGGCAAAATACAGGTCATT | 51 | 9978 | 9997 | 351 |
| 590223 | 829 | 848 | TCTGGCAAAATACAGGTCAT | 47 | 9979 | 9998 | 352 |
| 590224 | 830 | 849 | GTCTGGCAAAATACAGGTCA | 44 | 9980 | 9999 | 353 |
| 590225 | 831 | 850 | AGTCTGGCAAAATACAGGTC | 50 | 9981 | 10000 | 354 |
| 489538 | 832 | 851 | AAGTCTGGCAAAATACAGGT | 38 | 9982 | 10001 | 355 |
| 590226 | 833 | 852 | TAAGTCTGGCAAAATACAGG | 33 | 9983 | 10002 | 356 |
| 590227 | 834 | 853 | TTAAGTCTGGCAAAATACAG | 20 | 9984 | 10003 | 357 |
| 150482 | 853 | 872 | TTTAATACCCATCTGTGATT | 29 | 10003 | 10022 | 55 |
| 590228 | 854 | 873 | GTTTAATACCCATCTGTGAT | 33 | 10004 | 10023 | 358 |
| 150483 | 855 | 874 | AGTTTAATACCCATCTGTGA | 44 | 10005 | 10024 | 56 |
| 590229 | 856 | 875 | AAGTTTAATACCCATCTGTG | 51 | 10006 | 10025 | 359 |
| 590230 | 857 | 876 | CAAGTTTAATACCCATCTGT | 42 | 10007 | 10026 | 360 |
| 590231 | 858 | 877 | ACAAGTTTAATACCCATCTG | 38 | 10008 | 10027 | 361 |
| 393389 | 859 | 878 | GACAAGTTTAATACCCATCT | 48 | 10009 | 10028 | 362 |
| 590232 | 860 | 879 | TGACAAGTTTAATACCCATC | 55 | 10010 | 10029 | 363 |
| 590233 | 861 | 880 | CTGACAAGTTTAATACCCAT | 49 | 10011 | 10030 | 364 |
| 489541 | 862 | 881 | TCTGACAAGTTTAATACCCA | 52 | 10012 | 10031 | 365 |
| 590234 | 863 | 882 | TTCTGACAAGTTTAATACCC | 39 | 10013 | 10032 | 366 |
| 590235 | 864 | 883 | ATTCTGACAAGTTTAATACC | 21 | 10014 | 10033 | 367 |
| 590236 | 865 | 884 | AATTCTGACAAGTTTAATAC | 4 | 10015 | 10034 | 368 |
| 393390 | 866 | 885 | AAATTCTGACAAGTTTAATA | 7 | 10016 | 10035 | 369 |
| 590237 | 867 | 886 | GAAATTCTGACAAGTTTAAT | 5 | 10017 | 10036 | 370 |
| 436881 | 868 | 887 | AGAAATTCTGACAAGTTTAA | 33 | 10018 | 10037 | 371 |
| 590238 | 869 | 888 | AAGAAATTCTGACAAGTTTA | 20 | 10019 | 10038 | 372 |
| 590239 | 891 | 910 | TTATTCACAGGCTTGAATGA | 23 | 10041 | 10060 | 373 |
| 489544 | 892 | 911 | TTTATTCACAGGCTTGAATG | 41 | 10042 | 10061 | 374 |
| 590240 | 893 | 912 | TTTTATTCACAGGCTTGAAT | 40 | 10043 | 10062 | 375 |
| 436884 | 894 | 913 | TTTTTATTCACAGGCTTGAA | 31 | 10044 | 10063 | 376 |
| 590241 | 895 | 914 | GTTTTTATTCACAGGCTTGA | 39 | 10045 | 10064 | 377 |
| 150488 | 896 | 915 | GGTTTTTATTCACAGGCTTG | 51 | 10046 | 10065 | 57 |
| 590242 | 897 | 916 | GGGTTTTTATTCACAGGCTT | 46 | 10047 | 10066 | 378 |
| 150489 | 898 | 917 | AGGGTTTTTATTCACAGGCT | 52 | 10048 | 10067 | 58 |
| 590243 | 899 | 918 | CAGGGTTTTTATTCACAGGC | 49 | 10049 | 10068 | 379 |
| 590244 | 900 | 919 | ACAGGGTTTTTATTCACAGG | 38 | 10050 | 10069 | 380 |
| 590245 | 901 | 920 | TACAGGGTTTTTATTCACAG | 34 | 10051 | 10070 | 381 |

TABLE 4-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 150490 | 902 | 921 | ATACAGGGTTTTTATTCACA | 30 | 10052 | 10071 | 59 |
| 590246 | 903 | 922 | CATACAGGGTTTTTATTCAC | 34 | 10053 | 10072 | 382 |
| 150491 | 904 | 923 | CCATACAGGGTTTTTATTCA | 34 | 10054 | 10073 | 60 |
| 590247 | 905 | 924 | GCCATACAGGGTTTTTATTC | 34 | 10055 | 10074 | 383 |
| 590248 | 906 | 925 | TGCCATACAGGGTTTTTATT | 33 | 10056 | 10075 | 384 |
| 393393 | 907 | 926 | GTGCCATACAGGGTTTTTAT | 43 | 10057 | 10076 | 385 |
| 590249 | 908 | 927 | AGTGCCATACAGGGTTTTTA | 12 | 10058 | 10077 | 386 |

TABLE 5

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 333611 | 167 | 186 | CCGTCGCCCTTCAGCACGCA | 86 | 973 | 992 | 21 |
| 590280 | n/a | n/a | TGGAAAAACTCAAATGTGAA | 51 | 3422 | 3441 | 387 |
| 590281 | n/a | n/a | TTTCCCTTTCTTTTCCACAC | 76 | 5738 | 5757 | 388 |
| 590282 | n/a | n/a | TCTTTCCCTTTCTTTTCCAC | 65 | 5740 | 5759 | 389 |
| 590283 | n/a | n/a | TACCTTCTCTGCCCTTGCAG | 74 | 1687 | 1706 | 390 |
| 590284 | n/a | n/a | GCAAGGGCCAAGGCTGCTGC | 75 | 6879 | 6898 | 391 |
| 590285 | n/a | n/a | AAAGCTAAATTATGAATTAA | 12 | 7592 | 7611 | 392 |
| 590286 | n/a | n/a | CTAATGAAGGCTCAGTATGA | 59 | 3193 | 3212 | 393 |
| 590287 | n/a | n/a | GGAGTCAAATGCCAAAGAAC | 60 | 2463 | 2482 | 394 |
| 590288 | n/a | n/a | TGAATTAAAGTTCCCAAATA | 5 | 7580 | 7599 | 395 |
| 590289 | n/a | n/a | ACTTGGTGCAGGCAGAATAT | 63 | 6916 | 6935 | 396 |
| 590290 | n/a | n/a | CCTCTGATATAAAAATCTTG | 67 | 8143 | 8162 | 397 |
| 590291 | n/a | n/a | AAAGTTGGAGAGAGTTTCTG | 8 | 4940 | 4959 | 398 |
| 590292 | n/a | n/a | TCTCTGCCCTTGCAGCCCAA | 80 | 1682 | 1701 | 399 |
| 590293 | n/a | n/a | TTACTTGGTGCAGGCAGAAT | 56 | 6918 | 6937 | 400 |
| 590294 | n/a | n/a | AATGGAGTCAAATGCCAAAG | 66 | 2466 | 2485 | 401 |
| 590295 | n/a | n/a | TATGAATTAAAGTTCCCAAA | 20 | 7582 | 7601 | 402 |
| 590296 | n/a | n/a | AGTTCTATATTCAATAAATG | 21 | 7926 | 7945 | 403 |
| 590297 | n/a | n/a | TACAAGTAGTATACCATATG | 33 | 7753 | 7772 | 404 |
| 590298 | n/a | n/a | TAGCCTTAGAGCTGTACAAA | 70 | 1553 | 1572 | 405 |
| 590299 | n/a | n/a | GTCCCCATTTGTCAATTCCT | 71 | 7882 | 7901 | 406 |
| 590300 | n/a | n/a | AACCTGCCTACTGGCAGAGC | 59 | 2095 | 2114 | 407 |

TABLE 5-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 590301 | n/a | n/a | CTTGTTCCCACACTCAATGC | 56 | 4747 | 4766 | 408 |
| 590302 | n/a | n/a | ACAAGTCATGATAACCTGCA | 61 | 8952 | 8971 | 409 |
| 590303 | n/a | n/a | TGTTTTCCAAACTCAGATCT | 52 | 8796 | 8815 | 410 |
| 590304 | n/a | n/a | AGAACCTCATAATATTAGAA | 9 | 9557 | 9576 | 411 |
| 590305 | n/a | n/a | GGTTTTAAACTTAACAAAAT | 1 | 8887 | 8906 | 412 |
| 590306 | n/a | n/a | CTCTGGTGTATTTTTAGTAA | 65 | 1831 | 1850 | 413 |
| 590307 | n/a | n/a | TATCTCTGCATATCTGGAAA | 71 | 3034 | 3053 | 414 |
| 590308 | n/a | n/a | CAGCCTTTTTAACCCAAAAG | 68 | 4407 | 4426 | 415 |
| 590309 | n/a | n/a | TGGAATGCTCCACTATCCAA | 57 | 3012 | 3031 | 416 |
| 590310 | n/a | n/a | CGTTCAGAAGTTTGTCTCTG | 67 | 2126 | 2145 | 417 |
| 590311 | n/a | n/a | CTGCTCAGGGAAGGTGGAAA | 53 | 2922 | 2941 | 418 |
| 590312 | n/a | n/a | TCAAGAGAAGCTAGGAAAAC | 50 | 3154 | 3173 | 419 |
| 590313 | n/a | n/a | TCCCTTTCTTTTCCACACCT | 74 | 5736 | 5755 | 420 |
| 590314 | n/a | n/a | TTGTTCCCACACTCAATGCA | 56 | 4746 | 4765 | 421 |
| 590315 | n/a | n/a | TCACCAGCACAGCACAACAC | 58 | 5076 | 5095 | 422 |
| 590316 | n/a | n/a | CCTGGGATCATTACAAAAGT | 42 | 6155 | 6174 | 423 |
| 590317 | n/a | n/a | AGTAGTATACCATATGAACT | 35 | 7749 | 7768 | 424 |
| 590318 | n/a | n/a | TCTAATATGGTCAAATGTAA | 27 | 8779 | 8798 | 425 |
| 590319 | n/a | n/a | GGTTGGGCTCTGGTGTATTT | 64 | 1838 | 1857 | 426 |
| 590320 | n/a | n/a | TGCCCTTTACTTGGTGCAGG | 56 | 6924 | 6943 | 427 |
| 590321 | n/a | n/a | AGAGAGTTTCTGAACAAAGA | 24 | 4932 | 4951 | 428 |
| 590322 | n/a | n/a | GAATTTCAGCAATTACAGAA | 33 | 6613 | 6632 | 429 |
| 590323 | n/a | n/a | ACAAGTTAAACAAGTCATGA | 9 | 8961 | 8980 | 430 |
| 590324 | n/a | n/a | TGTGCCCTTTACTTGGTGCA | 47 | 6926 | 6945 | 431 |
| 590325 | n/a | n/a | TTAGGAGGAGGAAAAGGACC | 23 | 1719 | 1738 | 432 |
| 590326 | n/a | n/a | ACTGGCAGAGCAATTTTAAA | 25 | 2086 | 2105 | 433 |
| 590327 | n/a | n/a | AGTCAAATGCCAAAGAACCT | 58 | 2461 | 2480 | 434 |
| 590328 | n/a | n/a | AAGCATCAGATGGATTAGGG | 17 | 8411 | 8430 | 435 |
| 590329 | n/a | n/a | GTCCGCGGGACCCTCAGGAA | 54 | 1414 | 1433 | 436 |
| 590330 | n/a | n/a | CAATTACAGAAATGGATCAA | 42 | 6604 | 6623 | 437 |
| 590331 | n/a | n/a | GCTGTCAAGTAATCACTACC | 27 | 9606 | 9625 | 438 |
| 590332 | n/a | n/a | AGTGCAAAGTTGGAGAGAGT | 33 | 4945 | 4964 | 439 |
| 590333 | n/a | n/a | ACTTGCTTCCAATCCCAAAT | 78 | 6436 | 6455 | 440 |
| 590334 | n/a | n/a | AACTCAAATGTGAAAGTTGT | 51 | 3416 | 3435 | 441 |
| 590335 | n/a | n/a | TTTTAGTAAGATCTTCAAAT | 14 | 1820 | 1839 | 442 |

TABLE 5-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 590336 | n/a | n/a | ATTTCAGCAATTACAGAAAT | 27 | 6611 | 6630 | 443 |
| 590337 | n/a | n/a | TTAAGTGTCCCCATTTGTCA | 56 | 7888 | 7907 | 444 |
| 590338 | n/a | n/a | TTAGCAACCTGCCTACTGGC | 57 | 2100 | 2119 | 445 |
| 590339 | n/a | n/a | TATTACAAGAGTTAAGCATC | 41 | 7711 | 7730 | 446 |
| 590340 | n/a | n/a | ATGTTGAATATACATGTACA | 36 | 4545 | 4564 | 447 |
| 590341 | n/a | n/a | TTTGTCTCTGACCATCTTAG | 74 | 2116 | 2135 | 448 |
| 590342 | n/a | n/a | TTTTCCACCAGTTGGTAACT | 59 | 2253 | 2272 | 449 |
| 590343 | n/a | n/a | CAACAGCTTCCCACAAGTTA | 28 | 8973 | 8992 | 450 |
| 590344 | n/a | n/a | CAAATGTGAAAGTTGTCCCT | 62 | 3412 | 3431 | 451 |
| 590345 | n/a | n/a | GCTACCTTCTCTGCCCTTGC | 73 | 1689 | 1708 | 452 |
| 590346 | n/a | n/a | TCTTAGCAGAACAGTGTTCT | 51 | 8743 | 8762 | 453 |
| 590347 | n/a | n/a | ATACATTCTAAAAAGAAACA | 41 | 7563 | 7582 | 454 |
| 590348 | n/a | n/a | GCACATATTTACAAGTAGTA | 58 | 7762 | 7781 | 455 |
| 590349 | n/a | n/a | GGGTCACCAGCACAGCACAA | 35 | 5079 | 5098 | 456 |
| 590350 | n/a | n/a | GTGCAAGGGCCAAGGCTGCT | 66 | 6881 | 6900 | 457 |
| 590351 | n/a | n/a | ACCTGGGTTCATGCATGGAT | 72 | 2902 | 2921 | 458 |
| 590352 | n/a | n/a | ATCACTATTTGAAACTAAAT | 0 | 6569 | 6588 | 459 |
| 590353 | n/a | n/a | ATACAATAAAGTTGACCTCT | 64 | 5483 | 5502 | 460 |
| 590354 | n/a | n/a | TTTTAAACTTAACAAAATGT | 10 | 8885 | 8904 | 461 |
| 590355 | n/a | n/a | CTCCCCGCGCTCCCGCCACG | 15 | 1268 | 1287 | 462 |
| 590356 | n/a | n/a | GAAGGCTCAGTATGAAGAGA | 65 | 3188 | 3207 | 463 |

TABLE 6

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 333611 | 167 | 186 | CCGTCGCCCTTCAGCACGCA | 87 | 973 | 992 | 21 |
| 590357 | n/a | n/a | AGAAAACAGCTGATTTACCT | 40 | 4915 | 4934 | 464 |
| 590358 | n/a | n/a | CCACAAGTTAAACAAGTCAT | n.d. | 8963 | 8982 | 465 |
| 590359 | n/a | n/a | CAAATTTGCAAACAAGTAGC | 61 | 8331 | 8350 | 466 |
| 590360 | n/a | n/a | CCTAATTTGAACTGCAAGTA | n.d. | 8665 | 8684 | 467 |
| 590361 | n/a | n/a | AAAAAACTCATCTCCCCAGC | 70 | 6969 | 6988 | 468 |
| 590362 | n/a | n/a | AGGCTCAGTATGAAGAGATC | 67 | 3186 | 3205 | 469 |
| 590363 | n/a | n/a | TGTTATCAAGAGCACAGGGC | 58 | 3383 | 3402 | 470 |

TABLE 6-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 590364 | n/a | n/a | CCTCAAAAGGGAGATGGTAA | 41 | 4768 | 4787 | 471 |
| 590365 | n/a | n/a | AGTATGGGTCACCAGCACAG | 71 | 5084 | 5103 | 472 |
| 590366 | n/a | n/a | TCACAATCTAGTGCAGTTAC | 70 | 5584 | 5603 | 473 |
| 590367 | n/a | n/a | CAAGTGAGAAACCCAATCCT | n.d. | 8856 | 8875 | 474 |
| 590368 | n/a | n/a | AGAAAATCTGGCCATTTTAA | n.d. | 8832 | 8851 | 475 |
| 590369 | n/a | n/a | ACAGGTAATGGTGCTCCGTG | 71 | 3716 | 3735 | 476 |
| 590370 | n/a | n/a | TGAAAGGCTTTCAGAAAACA | 44 | 8102 | 8121 | 477 |
| 590371 | n/a | n/a | CAGGCAAGTTACAGGAAGCA | 64 | 6687 | 6706 | 478 |
| 590372 | n/a | n/a | CAGCAAGCTGCTTAACTGCT | 65 | 4800 | 4819 | 479 |
| 590373 | n/a | n/a | TGTTGCAAAGACATTACCTT | n.d. | 9455 | 9474 | 480 |
| 590374 | n/a | n/a | GAAACTAAATTAGCAAGATG | 43 | 6559 | 6578 | 481 |
| 590375 | n/a | n/a | TCAAGAGCACAGGGCCAAAA | 60 | 3378 | 3397 | 482 |
| 590376 | n/a | n/a | AGGAGGAGGAAAAGGACCTC | 53 | 1717 | 1736 | 483 |
| 590377 | n/a | n/a | CCTCAGCCTTTTTAACCCAA | 73 | 4410 | 4429 | 484 |
| 590378 | n/a | n/a | CTATGTTGTAGACCACCACA | n.d. | 9384 | 9403 | 485 |
| 590379 | n/a | n/a | CTCCGTGGCTACATACAGAA | 66 | 3703 | 3722 | 486 |
| 590380 | n/a | n/a | TTTATCTGGATCTTTAGAAA | n.d. | 8642 | 8661 | 487 |
| 590381 | n/a | n/a | AAAAAAAGGAAAGTGAAAGT | n.d. | 9279 | 9298 | 488 |
| 590382 | n/a | n/a | GGTTCATGCATGGATTCTCA | 76 | 2897 | 2916 | 489 |
| 590383 | n/a | n/a | CTGCAAAGTGTCACACAAAC | 76 | 1630 | 1649 | 490 |
| 590384 | n/a | n/a | TTCAGAAGTACCAAAGGGTA | 53 | 8227 | 8246 | 491 |
| 590385 | n/a | n/a | TAAAAGCATTCCAGCATTTG | 44 | 7848 | 7867 | 492 |
| 590386 | n/a | n/a | TAGTATACCATATGAACTCC | 73 | 7747 | 7766 | 493 |
| 590387 | n/a | n/a | TGCATATCTGGAAAGCTGGA | 59 | 3028 | 3047 | 494 |
| 590388 | n/a | n/a | CTTAACTGCTCTAGGCCTGT | 54 | 4790 | 4809 | 495 |
| 590389 | n/a | n/a | AGGCACCGACCGGGCGGCAC | 21 | 1155 | 1174 | 496 |
| 590390 | n/a | n/a | TGCAAAGTTGGAGAGAGTTT | 32 | 4943 | 4962 | 497 |
| 590391 | n/a | n/a | TCCTCAAAAGGGAGATGGTA | 37 | 4769 | 4788 | 498 |
| 590392 | n/a | n/a | AGTATACCATATGAACTCCA | 76 | 7746 | 7765 | 499 |
| 590393 | n/a | n/a | TATTTGTACATGTTGAATAT | 2 | 4554 | 4573 | 500 |
| 590394 | n/a | n/a | ACCCAAAAGGTGTATGTCTC | 71 | 4396 | 4415 | 501 |
| 590395 | n/a | n/a | CTTTGGAAAAAAGGAAAGT | n.d. | 9285 | 9304 | 502 |
| 590396 | n/a | n/a | GGGAGAAAGGCAGGCAAGTT | 20 | 6697 | 6716 | 503 |
| 590397 | n/a | n/a | TTAAGCCCAGGAAGTAAAAG | 9 | 7862 | 7881 | 504 |
| 590398 | n/a | n/a | AGACATTACCTTTAAACATT | n.d. | 9447 | 9466 | 505 |

TABLE 6-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 590399 | n/a | n/a | GTGGCTTAAGAAATGCTCCG | 26 | 2050 | 2069 | 506 |
| 590400 | n/a | n/a | GTGAGAAGGGAACAGAAACA | 48 | 7466 | 7485 | 507 |
| 590401 | n/a | n/a | AAAAGCATCAGATGGATTAG | 21 | 8413 | 8432 | 508 |
| 590402 | n/a | n/a | TTCCACCAGTTGGTAACTTC | 78 | 2251 | 2270 | 509 |
| 590403 | n/a | n/a | TTTTTAGTAAGATCTTCAAA | 15 | 1821 | 1840 | 510 |
| 590404 | n/a | n/a | ATCTGTGTCCAAATCCCAGG | 59 | 4847 | 4866 | 511 |
| 590405 | n/a | n/a | TAAGATCTTCAAATAAGCTA | 33 | 1814 | 1833 | 512 |
| 590406 | n/a | n/a | ATCAACTCTTTCCCTTTCTT | 63 | 5746 | 5765 | 513 |
| 590407 | n/a | n/a | TGTGTCCTCAAAAGGGAGAT | 37 | 4773 | 4792 | 514 |
| 590408 | n/a | n/a | TACCTCCTCCCAACAATACC | n.d. | 9590 | 9609 | 515 |
| 590409 | n/a | n/a | TTCTGCTTTACAACTATGGC | n.d. | 9133 | 9152 | 516 |
| 590410 | n/a | n/a | GTACATGTTGAATATACATG | 35 | 4549 | 4568 | 517 |
| 590411 | n/a | n/a | TTTGTGGCTAATCTTAAGGT | 47 | 5699 | 5718 | 518 |
| 590412 | n/a | n/a | TCCTGCCTCAGCCTTTTTAA | 34 | 4415 | 4434 | 519 |
| 590413 | n/a | n/a | CGGTGTCCGCGGGACCCTCA | 59 | 1418 | 1437 | 520 |
| 590414 | n/a | n/a | GAAATGGATCAAATCTGATC | 50 | 6596 | 6615 | 521 |
| 590415 | n/a | n/a | GGTAGTTCATGAGCTAAATT | 31 | 8371 | 8390 | 522 |
| 590416 | n/a | n/a | AATGGAGTCTCGACTAGTTT | 62 | 8072 | 8091 | 523 |
| 590417 | n/a | n/a | CAAGTATGGGTCACCAGCAC | 57 | 5086 | 5105 | 524 |
| 590418 | n/a | n/a | GGTGTCCGCGGGACCCTCAG | 40 | 1417 | 1436 | 525 |
| 590419 | n/a | n/a | CGCCACGCGCAGGCCCAGCC | 37 | 1255 | 1274 | 526 |
| 590420 | n/a | n/a | TCTAGGCCTGTGTCCTCAAA | 75 | 4781 | 4800 | 527 |
| 590421 | n/a | n/a | ACTGTCCTGGGCTAATGAAG | 36 | 3204 | 3223 | 528 |
| 590422 | n/a | n/a | AAGCATCTTGTTACCTCTCT | 52 | 7698 | 7717 | 529 |
| 590423 | n/a | n/a | GCCCAGGAAGTAAAAGCATT | 38 | 7858 | 7877 | 530 |
| 590424 | n/a | n/a | GTAAGATCTTCAAATAAGCT | 46 | 1815 | 1834 | 531 |
| 590425 | n/a | n/a | AAAGGGAGATGGTAATCTTG | 48 | 4763 | 4782 | 532 |
| 590426 | n/a | n/a | GCCAAGGCTGCTGCCTTACA | 66 | 6873 | 6892 | 533 |
| 590427 | n/a | n/a | CAGACTAACTGTTCCTGTCC | 43 | 2363 | 2382 | 534 |
| 590428 | n/a | n/a | TTTGTCAATTCCTTTAAGCC | 39 | 7875 | 7894 | 535 |
| 590429 | n/a | n/a | ACTACCTCCTCCCAACAATA | n.d. | 9592 | 9611 | 536 |
| 590430 | n/a | n/a | TACCTCTCTTCATCCTTTGG | 50 | 7687 | 7706 | 537 |
| 590431 | n/a | n/a | ACTGCTCTAGGCCTGTGTCC | 59 | 4786 | 4805 | 538 |
| 590432 | n/a | n/a | CCTCCTCCCAACAATACCCA | n.d. | 9588 | 9607 | 539 |
| 590433 | n/a | n/a | GGCAGGCAAGTTACAGGAAG | 42 | 6689 | 6708 | 540 |

TABLE 7

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 592596 | 2 | 21 | TCGCCCACTCTGGCCCCAAA | 86 | 808 | 827 | 541 |
| 592597 | 4 | 23 | CCTCGCCCACTCTGGCCCCA | 89 | 810 | 829 | 542 |
| 592598 | 6 | 25 | CGCCTCGCCCACTCTGGCCC | 56 | 812 | 831 | 543 |
| 592599 | 8 | 27 | CGCGCCTCGCCCACTCTGGC | 68 | 814 | 833 | 544 |
| 592600 | 10 | 29 | TCCGCGCCTCGCCCACTCTG | 64 | 816 | 835 | 545 |
| 592601 | 12 | 31 | CCTCCGCGCCTCGCCCACTC | 83 | 818 | 837 | 546 |
| 592602 | 14 | 33 | GACCTCCGCGCCTCGCCCAC | 89 | 820 | 839 | 547 |
| 592603 | 16 | 35 | CAGACCTCCGCGCCTCGCCC | 88 | 822 | 841 | 548 |
| 592604 | 18 | 37 | GCCAGACCTCCGCGCCTCGC | 79 | 824 | 843 | 549 |
| 592605 | 20 | 39 | AGGCCAGACCTCCGCGCCTC | 89 | 826 | 845 | 550 |
| 592606 | 22 | 41 | ATAGGCCAGACCTCCGCGCC | 88 | 828 | 847 | 551 |
| 592607 | 24 | 43 | TTATAGGCCAGACCTCCGCG | 75 | 830 | 849 | 552 |
| 592608 | 26 | 45 | CTTTATAGGCCAGACCTCCG | 21 | 832 | 851 | 553 |
| 592609 | 28 | 47 | TACTTTATAGGCCAGACCTC | 76 | 834 | 853 | 554 |
| 592610 | 30 | 49 | ACTACTTTATAGGCCAGACC | 60 | 836 | 855 | 555 |
| 592611 | 32 | 51 | CGACTACTTTATAGGCCAGA | 0 | 838 | 857 | 556 |
| 592612 | 34 | 53 | CGCGACTACTTTATAGGCCA | 0 | 840 | 859 | 557 |
| 592613 | 36 | 55 | TCCGCGACTACTTTATAGGC | 0 | 842 | 861 | 558 |
| 592614 | 38 | 57 | TCTCCGCGACTACTTTATAG | 7 | 844 | 863 | 559 |
| 592615 | 40 | 59 | CGTCTCCGCGACTACTTTAT | 0 | 846 | 865 | 560 |
| 592616 | 42 | 61 | CCCGTCTCCGCGACTACTTT | 0 | 848 | 867 | 561 |
| 592617 | 44 | 63 | ACCCGTCTCCGCGACTACT | 0 | 850 | 869 | 562 |
| 592618 | 46 | 65 | GCACCCCGTCTCCGCGACTA | 0 | 852 | 871 | 563 |
| 592619 | 48 | 67 | CAGCACCCCGTCTCCGCGAC | 0 | 854 | 873 | 564 |
| 592620 | 50 | 69 | ACCAGCACCCCGTCTCCGCG | 0 | 856 | 875 | 565 |
| 592621 | 52 | 71 | AAACCAGCACCCCGTCTCCG | 2 | 858 | 877 | 566 |
| 592622 | 54 | 73 | GCAAACCAGCACCCCGTCTC | 4 | 860 | 879 | 567 |
| 592623 | 56 | 75 | ACGCAAACCAGCACCCCGTC | 0 | 862 | 881 | 568 |
| 592624 | 58 | 77 | CGACGCAAACCAGCACCCCG | 0 | 864 | 883 | 569 |
| 592625 | 60 | 79 | TACGACGCAAACCAGCACCC | 0 | 866 | 885 | 570 |
| 592626 | 62 | 81 | ACTACGACGCAAACCAGCAC | 0 | 868 | 887 | 571 |
| 592627 | 64 | 83 | AGACTACGACGCAAACCAGC | 1 | 870 | 889 | 572 |
| 592628 | 66 | 85 | GGAGACTACGACGCAAACCA | 0 | 872 | 891 | 573 |
| 592629 | 68 | 87 | CAGGAGACTACGACGCAAAC | 0 | 874 | 893 | 574 |
| 592630 | 70 | 89 | TGCAGGAGACTACGACGCAA | 0 | 876 | 895 | 575 |
| 592631 | 72 | 91 | GCTGCAGGAGACTACGACGC | 1 | 878 | 897 | 576 |

TABLE 7-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 150511 | 74 | 93 | ACGCTGCAGGAGACTACGAC | 0 | 880 | 899 | 61 |
| 592632 | 90 | 109 | GCAACGGAAACCCCAGACGC | 2 | 896 | 915 | 577 |
| 592633 | 92 | 111 | CTGCAACGGAAACCCCAGAC | 0 | 898 | 917 | 578 |
| 592634 | 94 | 113 | GACTGCAACGGAAACCCCAG | 0 | 900 | 919 | 579 |
| 345715 | 95 | 114 | GGACTGCAACGGAAACCCCA | 0 | 901 | 920 | 580 |
| 592635 | 96 | 115 | AGGACTGCAACGGAAACCCC | 1 | 902 | 921 | 581 |
| 150437 | 98 | 117 | CGAGGACTGCAACGGAAACC | 6 | 904 | 923 | 62 |
| 592636 | 100 | 119 | TCCGAGGACTGCAACGGAAA | 6 | 906 | 925 | 582 |
| 592637 | 102 | 121 | GTTCCGAGGACTGCAACGGA | 12 | 908 | 927 | 583 |
| 592638 | 104 | 123 | TGGTTCCGAGGACTGCAACG | 0 | 910 | 929 | 584 |
| 592639 | 106 | 125 | CCTGGTTCCGAGGACTGCAA | 32 | 912 | 931 | 585 |
| 592640 | 108 | 127 | GTCCTGGTTCCGAGGACTGC | 68 | 914 | 933 | 586 |
| 345717 | 110 | 129 | AGGTCCTGGTTCCGAGGACT | 65 | 916 | 935 | 587 |
| 592641 | 112 | 131 | CGAGGTCCTGGTTCCGAGGA | 84 | 918 | 937 | 588 |
| 592642 | 114 | 133 | GCCGAGGTCCTGGTTCCGAG | 86 | 920 | 939 | 589 |
| 592643 | 116 | 135 | ACGCCGAGGTCCTGGTTCCG | 78 | 922 | 941 | 590 |
| 592644 | 118 | 137 | CCACGCCGAGGTCCTGGTTC | 79 | 924 | 943 | 591 |
| 345719 | 120 | 139 | GGCCACGCCGAGGTCCTGGT | 63 | 926 | 945 | 592 |
| 150441 | 122 | 141 | TAGGCCACGCCGAGGTCCTG | 81 | 928 | 947 | 63 |
| 592645 | 124 | 143 | GCTAGGCCACGCCGAGGTCC | 63 | 930 | 949 | 593 |
| 592646 | 126 | 145 | TCGCTAGGCCACGCCGAGGT | 56 | 932 | 951 | 594 |
| 592647 | 128 | 147 | ACTCGCTAGGCCACGCCGAG | 48 | 934 | 953 | 595 |
| 345721 | 130 | 149 | TAACTCGCTAGGCCACGCCG | 63 | 936 | 955 | 596 |
| 592648 | 132 | 151 | CATAACTCGCTAGGCCACGC | 38 | 938 | 957 | 597 |
| 592649 | 134 | 153 | GCCATAACTCGCTAGGCCAC | 52 | 940 | 959 | 598 |
| 592650 | 136 | 155 | TCGCCATAACTCGCTAGGCC | 59 | 942 | 961 | 599 |
| 592651 | 138 | 157 | CGTCGCCATAACTCGCTAGG | 55 | 944 | 963 | 600 |
| 592652 | 156 | 175 | CAGCACGCACACGGCCTTCG | 56 | 962 | 981 | 601 |
| 333605 | 158 | 177 | TTCAGCACGCACACGGCCTT | 85 | 964 | 983 | 64 |
| 333606 | 160 | 179 | CCTTCAGCACGCACACGGCC | 82 | 966 | 985 | 65 |
| 146144 | 162 | 181 | GCCCTTCAGCACGCACACGG | 58 | 968 | 987 | 66 |
| 333609 | 164 | 183 | TCGCCCTTCAGCACGCACAC | 79 | 970 | 989 | 67 |
| 146145 | 165 | 184 | GTCGCCCTTCAGCACGCACA | 86 | 971 | 990 | 54 |
| 333610 | 166 | 185 | CGTCGCCCTTCAGCACGCAC | 79 | 972 | 991 | 68 |
| 333611 | 167 | 186 | CCGTCGCCCTTCAGCACGCA | 83 | 973 | 992 | 21 |

TABLE 7-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 592653 | 168 | 187 | GCCGTCGCCCTTCAGCACGC | 79 | 974 | 993 | 602 |
| 592654 | 169 | 188 | GGCCGTCGCCCTTCAGCACG | 72 | 975 | 994 | 603 |
| 592655 | 170 | 189 | GGGCCGTCGCCCTTCAGCAC | 51 | 976 | 995 | 604 |
| 592656 | 172 | 191 | CTGGGCCGTCGCCCTTCAGC | 45 | 978 | 997 | 605 |
| 592657 | 174 | 193 | CACTGGGCCGTCGCCCTTCA | 33 | 980 | 999 | 606 |
| 592658 | 176 | 195 | TGCACTGGGCCGTCGCCCTT | 72 | 982 | 1001 | 607 |
| 592659 | 178 | 197 | CCTGCACTGGGCCGTCGCCC | 76 | 984 | 1003 | 608 |

TABLE 8

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 333611 | 167 | 186 | CCGTCGCCCTTCAGCACGCA | 87 | 973 | 992 | 21 |
| 150443 | 180 | 199 | GCCCTGCACTGGGCCGTCGC | 65 | 986 | 1005 | 69 |
| 592660 | 182 | 201 | ATGCCCTGCACTGGGCCGTC | 52 | 988 | 1007 | 609 |
| 592661 | 184 | 203 | TGATGCCCTGCACTGGGCCG | 30 | 990 | 1009 | 610 |
| 592662 | 186 | 205 | GATGATGCCCTGCACTGGGC | 38 | 992 | 1011 | 611 |
| 592663 | 188 | 207 | TTGATGATGCCCTGCACTGG | 36 | 994 | 1013 | 612 |
| 150444 | 190 | 209 | AATTGATGATGCCCTGCACT | 48 | 996 | 1015 | 70 |
| 592664 | 192 | 211 | GAAATTGATGATGCCCTGCA | 35 | 998 | 1017 | 15 |
| 592665 | 194 | 213 | TCGAAATTGATGATGCCCTG | 40 | 1000 | 1019 | 614 |
| 592666 | 196 | 215 | GCTCGAAATTGATGATGCCC | 68 | 1002 | 1021 | 615 |
| 592667 | 198 | 217 | CTGCTCGAAATTGATGATGC | 63 | 1004 | 1023 | 616 |
| 592668 | 200 | 219 | TTCTGCTCGAAATTGATGAT | 47 | 1006 | 1025 | 617 |
| 592669 | 239 | 258 | TTAATGCTTCCCCACACCTT | 68 | 4993 | 5012 | 618 |
| 592670 | 241 | 260 | CTTTAATGCTTCCCCACACC | 71 | 4995 | 5014 | 619 |
| 592671 | 243 | 262 | TCCTTTAATGCTTCCCCACA | 69 | 4997 | 5016 | 620 |
| 150448 | 245 | 264 | AGTCCTTTAATGCTTCCCCA | 76 | 4999 | 5018 | 71 |
| 592672 | 247 | 266 | TCAGTCCTTTAATGCTTCCC | 75 | 5001 | 5020 | 621 |
| 592673 | 249 | 268 | AGTCAGTCCTTTAATGCTTC | 58 | 5003 | 5022 | 622 |
| 592674 | 251 | 270 | TCAGTCAGTCCTTTAATGCT | 46 | 5005 | 5024 | 623 |
| 592675 | 253 | 272 | CTTCAGTCAGTCCTTTAATG | 41 | 5007 | 5026 | 624 |
| 592676 | 255 | 274 | GCCTTCAGTCAGTCCTTTAA | 62 | 5009 | 5028 | 625 |
| 150449 | 257 | 276 | AGGCCTTCAGTCAGTCCTTT | 65 | 5011 | 5030 | 72 |

TABLE 8-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 592677 | 259 | 278 | GCAGGCCTTCAGTCAGTCCT | 69 | 5013 | 5032 | 626 |
| 592678 | 261 | 280 | ATGCAGGCCTTCAGTCAGTC | 65 | 5015 | 5034 | 627 |
| 592679 | 263 | 282 | CCATGCAGGCCTTCAGTCAG | 53 | 5017 | 5036 | 628 |
| 592680 | 277 | 296 | CATGAACATGGAATCCATGC | 63 | 5031 | 5050 | 629 |
| 592681 | 279 | 298 | CTCATGAACATGGAATCCAT | 60 | 5033 | 5052 | 630 |
| 592682 | 281 | 300 | AACTCATGAACATGGAATCC | 56 | 5035 | 5054 | 631 |
| 592683 | 284 | 303 | CCAAACTCATGAACATGGAA | 60 | 5038 | 5057 | 632 |
| 592684 | 286 | 305 | CTCCAAACTCATGAACATGG | 69 | 5040 | 5059 | 633 |
| 592685 | 288 | 307 | ATCTCCAAACTCATGAACAT | 40 | 5042 | 5061 | 634 |
| 592686 | 290 | 309 | TTATCTCCAAACTCATGAAC | 35 | 5044 | 5063 | 635 |
| 592687 | 292 | 311 | TATTATCTCCAAACTCATGA | 26 | 5046 | 5065 | 636 |
| 592688 | 294 | 313 | TGTATTATCTCCAAACTCAT | 41 | 5048 | 5067 | 637 |
| 150452 | 296 | 315 | GCTGTATTATCTCCAAACTC | 51 | 5050 | 5069 | 73 |
| 592689 | 298 | 317 | CTGCTGTATTATCTCCAAAC | 43 | 5052 | 5071 | 638 |
| 592690 | 300 | 319 | GCCTGCTGTATTATCTCCAA | 37 | n/a | n/a | 639 |
| 592691 | 302 | 321 | CAGCCTGCTGTATTATCTCC | 33 | n/a | n/a | 640 |
| 592692 | 304 | 323 | TACAGCCTGCTGTATTATCT | 27 | n/a | n/a | 641 |
| 592693 | 306 | 325 | GGTACAGCCTGCTGTATTAT | 21 | n/a | n/a | 642 |
| 592694 | 308 | 327 | CTGGTACAGCCTGCTGTATT | 23 | n/a | n/a | 643 |
| 592695 | 310 | 329 | CACTGGTACAGCCTGCTGTA | 46 | n/a | n/a | 644 |
| 592696 | 312 | 331 | TGCACTGGTACAGCCTGCTG | 40 | n/a | n/a | 645 |
| 592697 | 314 | 333 | CCTGCACTGGTACAGCCTGC | 62 | n/a | n/a | 646 |
| 592698 | 340 | 359 | TTCTGGATAGAGGATTAAAG | 41 | 7656 | 7675 | 647 |
| 592699 | 342 | 361 | TTTTCTGGATAGAGGATTAA | 29 | 7658 | 7677 | 648 |
| 592700 | 344 | 363 | TGTTTTCTGGATAGAGGATT | 51 | 7660 | 7679 | 649 |
| 592701 | 346 | 365 | CGTGTTTTCTGGATAGAGGA | 64 | 7662 | 7681 | 650 |
| 592702 | 348 | 367 | ACCGTGTTTTCTGGATAGAG | 44 | 7664 | 7683 | 651 |
| 592703 | 350 | 369 | CCACCGTGTTTTCTGGATAG | 62 | 7666 | 7685 | 652 |
| 592704 | 352 | 371 | GCCCACCGTGTTTTCTGGAT | 60 | 7668 | 7687 | 653 |
| 592705 | 354 | 373 | TGGCCCACCGTGTTTTCTGG | 62 | 7670 | 7689 | 654 |
| 592706 | 356 | 375 | TTTGGCCCACCGTGTTTTCT | 49 | 7672 | 7691 | 655 |
| 592707 | 358 | 377 | CCTTTGGCCCACCGTGTTTT | 52 | 7674 | 7693 | 656 |
| 592708 | 382 | 401 | AGTCTCCAACATGCCTCTCT | 53 | n/a | n/a | 657 |
| 592709 | 384 | 403 | CAAGTCTCCAACATGCCTCT | 39 | n/a | n/a | 658 |
| 489501 | 386 | 405 | CCCAAGTCTCCAACATGCCT | 75 | 8441 | 8460 | 659 |

TABLE 8-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 150454 | 388 | 407 | TGCCCAAGTCTCCAACATGC | 86 | 8443 | 8462 | 74 |
| 592710 | 390 | 409 | ATTGCCCAAGTCTCCAACAT | 71 | 8445 | 8464 | 660 |
| 592711 | 392 | 411 | ACATTGCCCAAGTCTCCAAC | 64 | 8447 | 8466 | 661 |
| 592712 | 394 | 413 | TCACATTGCCCAAGTCTCCA | 59 | 8449 | 8468 | 662 |
| 489502 | 396 | 415 | AGTCACATTGCCCAAGTCTC | 70 | 8451 | 8470 | 663 |
| 592713 | 398 | 417 | GCAGTCACATTGCCCAAGTC | 70 | 8453 | 8472 | 664 |
| 592714 | 400 | 419 | CAGCAGTCACATTGCCCAAG | 84 | 8455 | 8474 | 665 |
| 592715 | 402 | 421 | GTCAGCAGTCACATTGCCCA | 83 | 8457 | 8476 | 666 |
| 592716 | 404 | 423 | TTGTCAGCAGTCACATTGCC | 59 | 8459 | 8478 | 667 |
| 489503 | 406 | 425 | CTTTGTCAGCAGTCACATTG | 47 | 8461 | 8480 | 668 |
| 592717 | 408 | 427 | ATCTTTGTCAGCAGTCACAT | 54 | 8463 | 8482 | 669 |
| 592718 | 410 | 429 | CCATCTTTGTCAGCAGTCAC | 76 | 8465 | 8484 | 670 |
| 592719 | 412 | 431 | CACCATCTTTGTCAGCAGTC | 75 | 8467 | 8486 | 671 |
| 592720 | 414 | 433 | CACACCATCTTTGTCAGCAG | 66 | 8469 | 8488 | 672 |
| 489504 | 416 | 435 | GCCACACCATCTTTGTCAGC | 60 | 8471 | 8490 | 673 |
| 592721 | 418 | 437 | CGGCCACACCATCTTTGTCA | 62 | 8473 | 8492 | 674 |
| 592722 | 420 | 439 | ATCGGCCACACCATCTTTGT | 57 | 8475 | 8494 | 675 |
| 592723 | 422 | 441 | ACATCGGCCACACCATCTTT | 54 | 8477 | 8496 | 676 |
| 150458 | 424 | 443 | ACACATCGGCCACACCATCT | 77 | 8479 | 8498 | 75 |
| 489505 | 426 | 445 | AGACACATCGGCCACACCAT | 84 | 8481 | 8500 | 677 |
| 592724 | 428 | 447 | ATAGACACATCGGCCACACC | 66 | 8483 | 8502 | 678 |

TABLE 9

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | % inhibition with HTS90 | SEQ ID NO: 2 Start Site | SEQ ID NO: 2 Stop Site | SEQ ID NO |
|---|---|---|---|---|---|---|---|---|
| 333611 | 167 | 186 | CCGTCGCCCTTCAGCACGCA | 87 | n.d. | 973 | 992 | 21 |
| 592725 | 430 | 449 | CAATAGACACATCGGCCACA | 67 | 65 | 8485 | 8504 | 679 |
| 592726 | 432 | 451 | TTCAATAGACACATCGGCCA | 62 | 66 | 8487 | 8506 | 680 |
| 592727 | 434 | 453 | TCTTCAATAGACACATCGGC | 56 | 49 | 8489 | 8508 | 681 |
| 489506 | 436 | 455 | AATCTTCAATAGACACATCG | 25 | 28 | 8491 | 8510 | 682 |
| 592728 | 438 | 457 | AGAATCTTCAATAGACACAT | 12 | 0 | 8493 | 8512 | 683 |
| 592729 | 440 | 459 | ACAGAATCTTCAATAGACAC | 24 | 16 | 8495 | 8514 | 684 |
| 592730 | 442 | 461 | TCACAGAATCTTCAATAGAC | 34 | 24 | 8497 | 8516 | 685 |

TABLE 9-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | % inhibition with HTS90 | SEQ ID NO: 2 Start Site | SEQ ID NO: 2 Stop Site | SEQ ID NO |
|---|---|---|---|---|---|---|---|---|
| 592731 | 444 | 463 | GATCACAGAATCTTCAATAG | 15 | 14 | 8499 | 8518 | 686 |
| 489507 | 446 | 465 | GAGATCACAGAATCTTCAAT | 42 | 46 | 8501 | 8520 | 687 |
| 592732 | 448 | 467 | GTGAGATCACAGAATCTTCA | n.d. | 58 | 8503 | 8522 | 688 |
| 592733 | 450 | 469 | GAGTGAGATCACAGAATCTT | n.d. | 45 | 8505 | 8524 | 689 |
| 592734 | 452 | 471 | GAGAGTGAGATCACAGAATC | n.d. | 48 | 8507 | 8526 | 690 |
| 592735 | 454 | 473 | CTGAGAGTGAGATCACAGAA | n.d. | 66 | 8509 | 8528 | 691 |
| 489508 | 456 | 475 | TCCTGAGAGTGAGATCACAG | n.d. | 60 | 8511 | 8530 | 692 |
| 333619 | 458 | 477 | TCTCCTGAGAGTGAGATCAC | n.d. | 65 | 8513 | 8532 | 76 |
| 592736 | 460 | 479 | GGTCTCCTGAGAGTGAGATC | n.d. | 40 | 8515 | 8534 | 693 |
| 592737 | 462 | 481 | ATGGTCTCCTGAGAGTGAGA | n.d. | 37 | 8517 | 8536 | 694 |
| 592738 | 464 | 483 | CAATGGTCTCCTGAGAGTGA | n.d. | 41 | 8519 | 8538 | 695 |
| 489509 | 466 | 485 | TGCAATGGTCTCCTGAGAGT | n.d. | 43 | 8521 | 8540 | 696 |
| 592739 | 468 | 487 | GATGCAATGGTCTCCTGAGA | n.d. | 16 | 8523 | 8542 | 697 |
| 592740 | 470 | 489 | ATGATGCAATGGTCTCCTGA | n.d. | 6 | 8525 | 8544 | 698 |
| 592741 | 472 | 491 | CAATGATGCAATGGTCTCCT | n.d. | 0 | 8527 | 8546 | 699 |
| 592742 | 474 | 493 | GCCAATGATGCAATGGTCTC | n.d. | 25 | 8529 | 8548 | 700 |
| 489510 | 476 | 495 | CGGCCAATGATGCAATGGTC | n.d. | 32 | 8531 | 8550 | 701 |
| 592743 | 478 | 497 | TGCGGCCAATGATGCAATGG | n.d. | 14 | 8533 | 8552 | 702 |
| 592744 | 480 | 499 | TGTGCGGCCAATGATGCAAT | n.d. | 0 | 8535 | 8554 | 703 |
| 592745 | 482 | 501 | AGTGTGCGGCCAATGATGCA | n.d. | 7 | 8537 | 8556 | 704 |
| 592746 | 484 | 503 | CCAGTGTGCGGCCAATGATG | n.d. | 25 | 8539 | 8558 | 705 |
| 489511 | 486 | 505 | CACCAGTGTGCGGCCAATGA | n.d. | 28 | 8541 | 8560 | 706 |
| 150460 | 488 | 507 | ACCACCAGTGTGCGGCCAAT | n.d. | 52 | 8543 | 8562 | 77 |
| 592747 | 490 | 509 | GGACCACCAGTGTGCGGCCA | n.d. | 44 | n/a | n/a | 707 |
| 592748 | 492 | 511 | ATGGACCACCAGTGTGCGGC | n.d. | 40 | n/a | n/a | 708 |
| 150462 | 494 | 513 | TCATGGACCACCAGTGTGCG | n.d. | 39 | n/a | n/a | 78 |
| 592749 | 496 | 515 | TTTCATGGACCACCAGTGTG | n.d. | 35 | n/a | n/a | 709 |
| 592750 | 498 | 517 | TTTTTCATGGACCACCAGTG | n.d. | 23 | n/a | n/a | 710 |
| 592751 | 500 | 519 | GCTTTTTCATGGACCACCAG | n.d. | 63 | n/a | n/a | 711 |
| 333636 | 536 | 555 | GTACTTTCTTCATTTCCACC | n.d. | 65 | 9686 | 9705 | 79 |
| 333638 | 538 | 557 | TTGTACTTTCTTCATTTCCA | n.d. | 66 | 9688 | 9707 | 80 |
| 333640 | 540 | 559 | CTTTGTACTTTCTTCATTTC | n.d. | 37 | 9690 | 9709 | 81 |
| 592752 | 543 | 562 | TGTCTTTGTACTTTCTTCAT | n.d. | 63 | 9693 | 9712 | 712 |
| 592753 | 545 | 564 | CCTGTCTTTGTACTTTCTTC | n.d. | 74 | 9695 | 9714 | 713 |
| 592754 | 547 | 566 | TTCCTGTCTTTGTACTTTCT | n.d. | 72 | 9697 | 9716 | 714 |

TABLE 9-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | % inhibition with HTS90 | SEQ ID NO: 2 Start Site | SEQ ID NO: 2 Stop Site | SEQ ID NO |
|---|---|---|---|---|---|---|---|---|
| 592755 | 549 | 568 | GTTTCCTGTCTTTGTACTTT | n.d. | 57 | 9699 | 9718 | 715 |
| 592756 | 568 | 587 | AAGCCAAACGACTTCCAGCG | 72 | 66 | 9718 | 9737 | 716 |
| 592757 | 570 | 589 | ACAAGCCAAACGACTTCCAG | 72 | 74 | 9720 | 9739 | 717 |
| 489516 | 572 | 591 | CCACAAGCCAAACGACTTCC | 85 | 82 | 9722 | 9741 | 718 |
| 592758 | 574 | 593 | CACCACAAGCCAAACGACTT | 72 | 73 | 9724 | 9743 | 719 |
| 592759 | 576 | 595 | TACACCACAAGCCAAACGAC | 74 | 68 | 9726 | 9745 | 720 |
| 592760 | 578 | 597 | ATTACACCACAAGCCAAACG | 67 | 61 | 9728 | 9747 | 721 |
| 592761 | 580 | 599 | CAATTACACCACAAGCCAAA | 64 | 56 | 9730 | 9749 | 722 |
| 150466 | 640 | 659 | GATAACAGATGAGTTAAGGG | 66 | 65 | 9790 | 9809 | 82 |
| 489521 | 642 | 661 | AGGATAACAGATGAGTTAAG | 79 | 78 | 9792 | 9811 | 723 |
| 592762 | 663 | 682 | GGATACATTTCTACAGCTAG | 91 | 87 | 9813 | 9832 | 724 |
| 592763 | 665 | 684 | CAGGATACATTTCTACAGCT | 92 | 89 | 9815 | 9834 | 725 |
| 592764 | 667 | 686 | ATCAGGATACATTTCTACAG | 88 | 83 | 9817 | 9836 | 726 |
| 592765 | 669 | 688 | TTATCAGGATACATTTCTAC | 77 | 72 | 9819 | 9838 | 727 |
| 592766 | 671 | 690 | GTTTATCAGGATACATTTCT | 90 | 89 | 9821 | 9840 | 728 |
| 592767 | 673 | 692 | ATGTTTATCAGGATACATTT | 82 | 76 | 9823 | 9842 | 729 |
| 592768 | 675 | 694 | TAATGTTTATCAGGATACAT | 80 | 79 | 9825 | 9844 | 730 |
| 592769 | 677 | 696 | TTTAATGTTTATCAGGATAC | 82 | 78 | 9827 | 9846 | 731 |
| 592770 | 679 | 698 | TGTTTAATGTTTATCAGGAT | 79 | 75 | 9829 | 9848 | 732 |
| 592771 | 681 | 700 | AGTGTTTAATGTTTATCAGG | 84 | 81 | 9831 | 9850 | 733 |
| 489526 | 692 | 711 | TTTAAGATTACAGTGTTTAA | 36 | 38 | 9842 | 9861 | 734 |
| 592772 | 694 | 713 | CTTTTAAGATTACAGTGTTT | 46 | 47 | 9844 | 9863 | 735 |
| 592773 | 696 | 715 | CACTTTTAAGATTACAGTGT | 39 | 42 | 9846 | 9865 | 736 |
| 592774 | 698 | 717 | TACACTTTTAAGATTACAGT | 21 | 24 | 9848 | 9867 | 737 |
| 592775 | 700 | 719 | ATTACACTTTTAAGATTACA | 3 | 0 | 9850 | 9869 | 738 |
| 489527 | 702 | 721 | CAATTACACTTTTAAGATTA | 0 | 0 | 9852 | 9871 | 739 |
| 150467 | 704 | 723 | CACAATTACACTTTTAAGAT | 58 | 73 | 9854 | 9873 | 83 |
| 592776 | 706 | 725 | CACACAATTACACTTTTAAG | 29 | 5 | 9856 | 9875 | 740 |
| 592777 | 708 | 727 | GTCACACAATTACACTTTTA | 59 | 49 | 9858 | 9877 | 741 |
| 592778 | 710 | 729 | AAGTCACACAATTACACTTT | 40 | 34 | 9860 | 9879 | 742 |
| 489528 | 712 | 731 | AAAAGTCACACAATTACACT | 31 | 27 | 9862 | 9881 | 743 |
| 592779 | 714 | 733 | GAAAAGTCACACAATTACA | 21 | 7 | 9864 | 9883 | 744 |
| 592780 | 716 | 735 | CTGAAAAGTCACACAATTA | 18 | 13 | 9866 | 9885 | 745 |
| 592781 | 718 | 737 | CTCTGAAAAGTCACACAAT | 32 | 26 | 9868 | 9887 | 746 |
| 592782 | 720 | 739 | AACTCTGAAAAGTCACACA | 35 | 20 | 9870 | 9889 | 747 |

TABLE 10

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 333611 | 167 | 186 | CCGTCGCCCTTCAGCACGCA | 74 | 973 | 992 | 21 |
| 489529 | 722 | 741 | GCAACTCTGAAAAAGTCACA | 41 | 9872 | 9891 | 748 |
| 592783 | 724 | 743 | AAGCAACTCTGAAAAAGTCA | 34 | 9874 | 9893 | 749 |
| 592784 | 727 | 746 | TTAAAGCAACTCTGAAAAAG | 4 | 9877 | 9896 | 750 |
| 592785 | 729 | 748 | CTTTAAAGCAACTCTGAAAA | 36 | 9879 | 9898 | 751 |
| 592786 | 731 | 750 | TACTTTAAAGCAACTCTGAA | 28 | 9881 | 9900 | 752 |
| 592787 | 733 | 752 | GGTACTTTAAAGCAACTCTG | 48 | 9883 | 9902 | 753 |
| 592788 | 735 | 754 | CAGGTACTTTAAAGCAACTC | 38 | 9885 | 9904 | 754 |
| 592789 | 737 | 756 | TACAGGTACTTTAAAGCAAC | 20 | 9887 | 9906 | 755 |
| 592790 | 739 | 758 | ACTACAGGTACTTTAAAGCA | 26 | 9889 | 9908 | 756 |
| 592791 | 741 | 760 | TCACTACAGGTACTTTAAAG | 34 | 9891 | 9910 | 757 |
| 592792 | 743 | 762 | TCTCACTACAGGTACTTTAA | 50 | 9893 | 9912 | 758 |
| 592793 | 745 | 764 | TTTCTCACTACAGGTACTTT | 36 | 9895 | 9914 | 759 |
| 592794 | 747 | 766 | AGTTTCTCACTACAGGTACT | 53 | 9897 | 9916 | 760 |
| 592795 | 749 | 768 | TCAGTTTCTCACTACAGGTA | 37 | 9899 | 9918 | 761 |
| 150470 | 751 | 770 | AATCAGTTTCTCACTACAGG | 30 | 9901 | 9920 | 84 |
| 592796 | 753 | 772 | TAAATCAGTTTCTCACTACA | 21 | 9903 | 9922 | 762 |
| 150472 | 755 | 774 | CATAAATCAGTTTCTCACTA | 37 | 9905 | 9924 | 85 |
| 592797 | 757 | 776 | ATCATAAATCAGTTTCTCAC | 35 | 9907 | 9926 | 763 |
| 592798 | 759 | 778 | TGATCATAAATCAGTTTCTC | 35 | 9909 | 9928 | 764 |
| 592799 | 761 | 780 | AGTGATCATAAATCAGTTTC | 5 | 9911 | 9930 | 765 |
| 592800 | 763 | 782 | CAAGTGATCATAAATCAGTT | 21 | 9913 | 9932 | 766 |
| 592801 | 765 | 784 | TCCAAGTGATCATAAATCAG | 41 | 9915 | 9934 | 767 |
| 592802 | 767 | 786 | CTTCCAAGTGATCATAAATC | 44 | 9917 | 9936 | 768 |
| 592803 | 769 | 788 | ATCTTCCAAGTGATCATAAA | 30 | 9919 | 9938 | 769 |
| 592804 | 771 | 790 | AAATCTTCCAAGTGATCATA | 32 | 9921 | 9940 | 770 |
| 489534 | 792 | 811 | CTGAGTTTTATAAAACTATA | 4 | 9942 | 9961 | 771 |
| 150476 | 794 | 813 | AACTGAGTTTTATAAAACTA | 9 | 9944 | 9963 | 86 |
| 592805 | 796 | 815 | TTAACTGAGTTTTATAAAAC | 14 | 9946 | 9965 | 772 |
| 592806 | 798 | 817 | TTTTAACTGAGTTTTATAAA | 3 | 9948 | 9967 | 773 |
| 592807 | 800 | 819 | CATTTTAACTGAGTTTTATA | 13 | 9950 | 9969 | 774 |
| 489535 | 802 | 821 | GACATTTTAACTGAGTTTTA | 34 | 9952 | 9971 | 775 |
| 592808 | 804 | 823 | CAGACATTTTAACTGAGTTT | 40 | 9954 | 9973 | 776 |
| 592809 | 806 | 825 | AACAGACATTTTAACTGAGT | 36 | 9956 | 9975 | 777 |
| 592810 | 808 | 827 | GAAACAGACATTTTAACTGA | 25 | 9958 | 9977 | 778 |
| 592811 | 810 | 829 | TTGAAACAGACATTTTAACT | 24 | 9960 | 9979 | 779 |

TABLE 10-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 592812 | 835 | 854 | TTTAAGTCTGGCAAAATACA | 23 | 9985 | 10004 | 780 |
| 592813 | 837 | 856 | GATTTAAGTCTGGCAAAATA | 31 | 9987 | 10006 | 781 |
| 592814 | 839 | 858 | GTGATTTAAGTCTGGCAAAA | 41 | 9989 | 10008 | 782 |
| 592815 | 841 | 860 | CTGTGATTTAAGTCTGGCAA | 49 | 9991 | 10010 | 783 |
| 592816 | 843 | 862 | ATCTGTGATTTAAGTCTGGC | 53 | 9993 | 10012 | 784 |
| 150481 | 845 | 864 | CCATCTGTGATTTAAGTCTG | 51 | 9995 | 10014 | 87 |
| 592817 | 847 | 866 | ACCCATCTGTGATTTAAGTC | 51 | 9997 | 10016 | 785 |
| 592818 | 849 | 868 | ATACCCATCTGTGATTTAAG | 43 | 9999 | 10018 | 786 |
| 592819 | 851 | 870 | TAATACCCATCTGTGATTTA | 42 | 10001 | 10020 | 787 |
| 592820 | 870 | 889 | AAAGAAATTCTGACAAGTTT | 22 | 10020 | 10039 | 788 |
| 489542 | 872 | 891 | ACAAAGAAATTCTGACAAGT | 13 | 10022 | 10041 | 789 |
| 592821 | 874 | 893 | TGACAAAGAAATTCTGACAA | 24 | 10024 | 10043 | 790 |
| 592822 | 876 | 895 | AATGACAAAGAAATTCTGAC | 25 | 10026 | 10045 | 791 |
| 592823 | 878 | 897 | TGAATGACAAAGAAATTCTG | 6 | 10028 | 10047 | 792 |
| 592824 | 880 | 899 | CTTGAATGACAAAGAAATTC | 24 | 10030 | 10049 | 793 |
| 489543 | 882 | 901 | GGCTTGAATGACAAAGAAAT | 29 | 10032 | 10051 | 794 |
| 592825 | 884 | 903 | CAGGCTTGAATGACAAAGAA | 35 | 10034 | 10053 | 795 |
| 592826 | 886 | 905 | CACAGGCTTGAATGACAAAG | 32 | 10036 | 10055 | 796 |
| 592827 | 888 | 907 | TTCACAGGCTTGAATGACAA | 41 | 10038 | 10057 | 797 |
| 592828 | 890 | 909 | TATTCACAGGCTTGAATGAC | 30 | 10040 | 10059 | 798 |
| 150492 | 909 | 928 | AAGTGCCATACAGGGTTTTT | 32 | 10059 | 10078 | 88 |
| 592829 | 911 | 930 | ATAAGTGCCATACAGGGTTT | 0 | 10061 | 10080 | 799 |
| 150493 | 913 | 932 | TAATAAGTGCCATACAGGGT | 24 | 10063 | 10082 | 89 |
| 592830 | 915 | 934 | CATAATAAGTGCCATACAGG | 26 | 10065 | 10084 | 800 |
| 150495 | 917 | 936 | CTCATAATAAGTGCCATACA | 35 | 10067 | 10086 | 90 |
| 150496 | 919 | 938 | GCCTCATAATAAGTGCCATA | 37 | 10069 | 10088 | 91 |
| 592831 | 921 | 940 | TAGCCTCATAATAAGTGCCA | 19 | 10071 | 10090 | 801 |
| 592832 | 923 | 942 | AATAGCCTCATAATAAGTGC | 0 | 10073 | 10092 | 802 |
| 592833 | 925 | 944 | TTAATAGCCTCATAATAAGT | 19 | 10075 | 10094 | 803 |
| 150497 | 927 | 946 | TTTTAATAGCCTCATAATAA | 17 | 10077 | 10096 | 92 |
| 592834 | 929 | 948 | TCTTTTAATAGCCTCATAAT | 27 | 10079 | 10098 | 804 |
| 592835 | 931 | 950 | ATTCTTTTAATAGCCTCATA | 27 | 10081 | 10100 | 805 |
| 150498 | 933 | 952 | GGATTCTTTTAATAGCCTCA | 39 | 10083 | 10102 | 93 |
| 592836 | 935 | 954 | TTGGATTCTTTTAATAGCCT | 24 | 10085 | 10104 | 806 |
| 592837 | 937 | 956 | ATTTGGATTCTTTTAATAGC | 0 | 10087 | 10106 | 807 |

TABLE 10-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 592838 | 939 | 958 | GAATTTGGATTCTTTTAATA | 10 | 10089 | 10108 | 808 |
| 592839 | 941 | 960 | TTGAATTTGGATTCTTTTAA | 13 | 10091 | 10110 | 809 |
| 592840 | 943 | 962 | GTTTGAATTTGGATTCTTTT | 29 | 10093 | 10112 | 810 |
| 592841 | 945 | 964 | TAGTTTGAATTTGGATTCTT | 31 | 10095 | 10114 | 811 |
| 592842 | 947 | 966 | TTTAGTTTGAATTTGGATTC | 8 | 10097 | 10116 | 812 |
| 592843 | 949 | 968 | TTTTTAGTTTGAATTTGGAT | 10 | n/a | n/a | 813 |
| 592844 | 951 | 970 | TTTTTTTAGTTTGAATTTGG | 7 | n/a | n/a | 814 |

Example 2: Inhibition of Human SOD-1 in HepG2 Cells by MOE Gapmers

Modified oligonucleotides were designed targeting a superoxide dismutase 1, soluble (SOD-1) nucleic acid and were tested for their effects on SOD-1 mRNA in vitro. ISIS 146143, ISIS 150438-150440, ISIS 150442, ISIS 150450, ISIS 150455-150457, ISIS 150459, ISIS 150461, ISIS 150469, ISIS 150473, ISIS 150478, ISIS 150484, ISIS 150486, ISIS 150494, ISIS 150508-150510, ISIS 333607, ISIS 333608, ISIS 333611, ISIS 333618, previously disclosed in WO 2005/040180, were also included in this assay. The modified oligonucleotides were tested in a series of experiments that had similar culture conditions. The results for each experiment are presented in separate tables shown below. Cultured HepG2 cells at a density of 20,000 cells per well were transfected using electroporation with 5,000 nM modified oligonucleotide. After a treatment period of approximately 24 hours, RNA was isolated from the cells and SOD-1 mRNA levels were measured by quantitative real-time PCR.

Human primer probe set RTS3898 was used to measure mRNA levels. In cases where the oligonucleotide overlapped the amplicon of the primer probe set, an alternative primer probe set, HTS90, was used to measure mRNA levels. SOD-1 mRNA levels were adjusted according to total RNA content, as measured by RIBOGREEN®. Results are presented as percent inhibition of SOD-1, relative to untreated control cells. 'n.d.' indicates that inhibition levels were not measured using the particular primer probe set.

The newly designed modified oligonucleotides in the Tables below were designed as 5-10-5 MOE gapmers. The 5-10-5 MOE gapmers are 20 nucleosides in length, wherein the central gap segment is comprised of ten 2'-deoxyribonucleosides and is flanked by wing segments on the 5' direction and the 3' directions comprising five nucleosides each. Each nucleoside in the 5' wing segment and each nucleoside in the 3' wing segment has a 2'-MOE modification. The internucleoside linkages throughout each gapmer are phosphorothioate linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human SOD-1 mRNA, designated herein as SEQ ID NO: 1 (GENBANK Accession No. NM_000454.4) or the human SOD-1 genomic sequence, designated herein as SEQ ID NO: 2 (GENBANK Accession No. NT_011512.10 truncated from nucleotides 18693000 to Ser. No. 18/704,000). 'n/a' indicates that the modified oligonucleotide does not target that particular gene sequence with 100% complementarity.

TABLE 11

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 333611 | 167 | 186 | CCGTCGCCCTTCAGCACGCA | 64 | 973 | 992 | 21 |
| 596301 | 550 | 569 | CGTTTCCTGTCTTTGTACTT | n.d. | 9700 | 9719 | 815 |
| 596302 | 569 | 588 | CAAGCCAAACGACTTCCAGC | 54 | 9719 | 9738 | 816 |
| 596303 | 571 | 590 | CACAAGCCAAACGACTTCCA | 47 | 9721 | 9740 | 817 |
| 596304 | 573 | 592 | ACCACAAGCCAAACGACTTC | 28 | 9723 | 9742 | 818 |

TABLE 11-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 596305 | 575 | 594 | ACACCACAAGCCAAACGACT | 49 | 9725 | 9744 | 819 |
| 596306 | 577 | 596 | TTACACCACAAGCCAAACGA | 24 | 9727 | 9746 | 820 |
| 596307 | 641 | 660 | GGATAACAGATGAGTTAAGG | 48 | 9791 | 9810 | 821 |
| 596308 | 664 | 683 | AGGATACATTTCTACAGCTA | 79 | 9814 | 9833 | 822 |
| 596309 | 666 | 685 | TCAGGATACATTTCTACAGC | 70 | 9816 | 9835 | 823 |
| 596310 | 668 | 687 | TATCAGGATACATTTCTACA | 58 | 9818 | 9837 | 824 |
| 489524 | 672 | 691 | TGTTTATCAGGATACATTTC | 52 | 9822 | 9841 | 825 |
| 596311 | 674 | 693 | AATGTTTATCAGGATACATT | 54 | 9824 | 9843 | 826 |
| 596312 | 676 | 695 | TTAATGTTTATCAGGATACA | 34 | 9826 | 9845 | 827 |
| 596313 | 678 | 697 | GTTTAATGTTTATCAGGATA | 71 | 9828 | 9847 | 828 |
| 596314 | 680 | 699 | GTGTTTAATGTTTATCAGGA | 73 | 9830 | 9849 | 829 |
| 596315 | 693 | 712 | TTTTAAGATTACAGTGTTTA | 13 | 9843 | 9862 | 830 |
| 596316 | 695 | 714 | ACTTTTAAGATTACAGTGTT | 24 | 9845 | 9864 | 831 |
| 596317 | 697 | 716 | ACACTTTTAAGATTACAGTG | 15 | 9847 | 9866 | 832 |
| 596318 | 699 | 718 | TTACACTTTTAAGATTACAG | 0 | 9849 | 9868 | 833 |
| 596319 | 701 | 720 | AATTACACTTTTAAGATTAC | 1 | 9851 | 9870 | 834 |
| 596320 | 705 | 724 | ACACAATTACACTTTTAAGA | 0 | 9855 | 9874 | 835 |
| 596321 | 707 | 726 | TCACACAATTACACTTTTAA | 15 | 9857 | 9876 | 836 |
| 596322 | 711 | 730 | AAAGTCACACAATTACACTT | 15 | 9861 | 9880 | 837 |
| 596323 | 715 | 734 | TGAAAAGTCACACAATTAC | 0 | 9865 | 9884 | 838 |
| 596324 | 717 | 736 | TCTGAAAAGTCACACAATT | 5 | 9867 | 9886 | 839 |
| 596325 | 719 | 738 | ACTCTGAAAAGTCACACAA | 21 | 9869 | 9888 | 840 |
| 596326 | 723 | 742 | AGCAACTCTGAAAAGTCAC | 14 | 9873 | 9892 | 841 |
| 596327 | 730 | 749 | ACTTTAAAGCAACTCTGAAA | 0 | 9880 | 9899 | 842 |
| 489530 | 732 | 751 | GTACTTTAAAGCAACTCTGA | 22 | 9882 | 9901 | 843 |
| 596328 | 734 | 753 | AGGTACTTTAAAGCAACTCT | 36 | 9884 | 9903 | 844 |
| 596329 | 740 | 759 | CACTACAGGTACTTTAAAGC | 18 | 9890 | 9909 | 845 |
| 150469 | 742 | 761 | CTCACTACAGGTACTTTAAA | 25 | 9892 | 9911 | 94 |
| 596330 | 744 | 763 | TTCTCACTACAGGTACTTTA | 28 | 9894 | 9913 | 846 |
| 596331 | 746 | 765 | GTTTCTCACTACAGGTACTT | 30 | 9896 | 9915 | 847 |
| 596332 | 748 | 767 | CAGTTTCTCACTACAGGTAC | 25 | 9898 | 9917 | 848 |
| 596333 | 750 | 769 | ATCAGTTTCTCACTACAGGT | 22 | 9900 | 9919 | 849 |
| 489531 | 752 | 771 | AAATCAGTTTCTCACTACAG | 0 | 9902 | 9921 | 850 |
| 596334 | 756 | 775 | TCATAAATCAGTTTCTCACT | 21 | 9906 | 9925 | 851 |
| 596335 | 760 | 779 | GTGATCATAAATCAGTTTCT | 37 | 9910 | 9929 | 852 |
| 489532 | 762 | 781 | AAGTGATCATAAATCAGTTT | 8 | 9912 | 9931 | 853 |

TABLE 11-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 596336 | 764 | 783 | CCAAGTGATCATAAATCAGT | 39 | 9914 | 9933 | 854 |
| 436935 | 766 | 785 | TTCCAAGTGATCATAAATCA | 18 | 9916 | 9935 | 855 |
| 596337 | 768 | 787 | TCTTCCAAGTGATCATAAAT | 12 | 9918 | 9937 | 856 |
| 150473 | 770 | 789 | AATCTTCCAAGTGATCATAA | 4 | 9920 | 9939 | 95 |
| 596338 | 795 | 814 | TAACTGAGTTTTATAAAACT | 0 | 9945 | 9964 | 857 |
| 596339 | 807 | 826 | AAACAGACATTTTAACTGAG | 4 | 9957 | 9976 | 858 |
| 596340 | 809 | 828 | TGAAACAGACATTTTAACTG | 0 | 9959 | 9978 | 859 |
| 150478 | 811 | 830 | ATTGAAACAGACATTTTAAC | 0 | 9961 | 9980 | 96 |
| 596341 | 836 | 855 | ATTTAAGTCTGGCAAAATAC | 16 | 9986 | 10005 | 860 |
| 596342 | 840 | 859 | TGTGATTTAAGTCTGGCAAA | 34 | 9990 | 10009 | 861 |
| 489539 | 842 | 861 | TCTGTGATTTAAGTCTGGCA | 44 | 9992 | 10011 | 862 |
| 596343 | 844 | 863 | CATCTGTGATTTAAGTCTGG | 29 | 9994 | 10013 | 863 |
| 596344 | 846 | 865 | CCCATCTGTGATTTAAGTCT | 41 | 9996 | 10015 | 864 |
| 596345 | 848 | 867 | TACCCATCTGTGATTTAAGT | 50 | 9998 | 10017 | 865 |
| 596346 | 850 | 869 | AATACCCATCTGTGATTTAA | 0 | 10000 | 10019 | 866 |
| 489540 | 852 | 871 | TTAATACCCATCTGTGATTT | 11 | 10002 | 10021 | 867 |
| 150484 | 871 | 890 | CAAAGAAATTCTGACAAGTT | 7 | 10021 | 10040 | 97 |
| 596347 | 873 | 892 | GACAAAGAAATTCTGACAAG | 8 | 10023 | 10042 | 868 |
| 596348 | 877 | 896 | GAATGACAAAGAAATTCTGA | 0 | 10027 | 10046 | 869 |
| 596349 | 883 | 902 | AGGCTTGAATGACAAAGAAA | 27 | 10033 | 10052 | 870 |
| 150486 | 885 | 904 | ACAGGCTTGAATGACAAAGA | 19 | 10035 | 10054 | 98 |
| 596350 | 910 | 929 | TAAGTGCCATACAGGGTTTT | 13 | 10060 | 10079 | 871 |
| 596351 | 914 | 933 | ATAATAAGTGCCATACAGGG | 18 | 10064 | 10083 | 872 |
| 150494 | 916 | 935 | TCATAATAAGTGCCATACAG | 0 | 10066 | 10085 | 99 |
| 596352 | 918 | 937 | CCTCATAATAAGTGCCATAC | 23 | 10068 | 10087 | 873 |
| 596353 | 920 | 939 | AGCCTCATAATAAGTGCCAT | 6 | 10070 | 10089 | 874 |
| 596354 | 922 | 941 | ATAGCCTCATAATAAGTGCC | 19 | 10072 | 10091 | 875 |
| 596355 | 928 | 947 | CTTTTAATAGCCTCATAATA | 0 | 10078 | 10097 | 876 |
| 596356 | 930 | 949 | TTCTTTTAATAGCCTCATAA | 5 | 10080 | 10099 | 877 |
| 596357 | 932 | 951 | GATTCTTTTAATAGCCTCAT | 4 | 10082 | 10101 | 878 |
| 596358 | 934 | 953 | TGGATTCTTTTAATAGCCTC | 13 | 10084 | 10103 | 879 |
| 596359 | 936 | 955 | TTTGGATTCTTTTAATAGCC | 14 | 10086 | 10105 | 880 |
| 596360 | 938 | 957 | AATTTGGATTCTTTTAATAG | 14 | 10088 | 10107 | 881 |
| 596361 | 940 | 959 | TGAATTTGGATTCTTTTAAT | 0 | 10090 | 10109 | 882 |
| 596362 | 946 | 965 | TTAGTTTGAATTTGGATTCT | 0 | 10096 | 10115 | 883 |

TABLE 11-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | SEQ ID NO: 2 Start Site | SEQ ID NO: 2 Stop Site | SEQ ID NO |
|---|---|---|---|---|---|---|---|
| 596363 | 948 | 967 | TTTTAGTTTGAATTTGGATT | 0 | n/a | n/a | 884 |
| 596364 | 950 | 969 | TTTTTTAGTTTGAATTTGGA | 0 | n/a | n/a | 885 |

TABLE 12

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | % inhibition with HTS90 | SEQ ID NO: 2 Start Site | SEQ ID NO: 2 Stop Site | SEQ ID NO |
|---|---|---|---|---|---|---|---|---|
| 333611 | 167 | 186 | CCGTCGCCCTTCAGCACGCA | 66 | n.d. | 973 | 992 | 21 |
| 596230 | 246 | 265 | CAGTCCTTTAATGCTTCCCC | 51 | 40 | 5000 | 5019 | 886 |
| 596231 | 248 | 267 | GTCAGTCCTTTAATGCTTCC | 34 | 34 | 5002 | 5021 | 887 |
| 596232 | 250 | 269 | CAGTCAGTCCTTTAATGCTT | 35 | 29 | 5004 | 5023 | 888 |
| 596233 | 252 | 271 | TTCAGTCAGTCCTTTAATGC | 24 | 21 | 5006 | 5025 | 889 |
| 596234 | 256 | 275 | GGCCTTCAGTCAGTCCTTTA | 41 | 39 | 5010 | 5029 | 890 |
| 150450 | 258 | 277 | CAGGCCTTCAGTCAGTCCTT | 56 | 51 | 5012 | 5031 | 100 |
| 596235 | 260 | 279 | TGCAGGCCTTCAGTCAGTCC | 42 | 46 | 5014 | 5033 | 891 |
| 596236 | 262 | 281 | CATGCAGGCCTTCAGTCAGT | 37 | 33 | 5016 | 5035 | 892 |
| 596237 | 278 | 297 | TCATGAACATGGAATCCATG | 24 | 19 | 5032 | 5051 | 893 |
| 596238 | 280 | 299 | ACTCATGAACATGGAATCCA | 27 | 20 | 5034 | 5053 | 894 |
| 596239 | 295 | 314 | CTGTATTATCTCCAAACTCA | 32 | 28 | 5049 | 5068 | 895 |
| 596240 | 309 | 328 | ACTGGTACAGCCTGCTGTAT | 22 | 28 | n/a | n/a | 896 |
| 596241 | 311 | 330 | GCACTGGTACAGCCTGCTGT | 31 | 24 | n/a | n/a | 897 |
| 596242 | 313 | 332 | CTGCACTGGTACAGCCTGCT | 38 | 29 | n/a | n/a | 898 |
| 596243 | 315 | 334 | ACCTGCACTGGTACAGCCTG | 46 | 48 | n/a | n/a | 899 |
| 596244 | 341 | 360 | TTTCTGGATAGAGGATTAAA | 6 | 14 | 7657 | 7676 | 900 |
| 596245 | 343 | 362 | GTTTTCTGGATAGAGGATTA | 28 | 39 | 7659 | 7678 | 901 |
| 596246 | 347 | 366 | CCGTGTTTTCTGGATAGAGG | 44 | 37 | 7663 | 7682 | 902 |
| 596247 | 349 | 368 | CACCGTGTTTTCTGGATAGA | 24 | 11 | 7665 | 7684 | 903 |
| 596248 | 351 | 370 | CCCACCGTGTTTTCTGGATA | 46 | 40 | 7667 | 7686 | 904 |
| 596249 | 353 | 372 | GGCCCACCGTGTTTTCTGGA | 46 | 41 | 7669 | 7688 | 905 |
| 596250 | 355 | 374 | TTGGCCCACCGTGTTTTCTG | 35 | 26 | 7671 | 7690 | 906 |
| 596251 | 357 | 376 | CTTTGGCCCACCGTGTTTTC | 31 | 15 | 7673 | 7692 | 907 |
| 596252 | 359 | 378 | TCCTTTGGCCCACCGTGTTT | 30 | 23 | 7675 | 7694 | 908 |
| 596253 | 383 | 402 | AAGTCTCCAACATGCCTCTC | 20 | 6 | n/a | n/a | 909 |
| 596254 | 387 | 406 | GCCCAAGTCTCCAACATGCC | 61 | 53 | 8442 | 8461 | 910 |

TABLE 12-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | % inhibition with HTS90 | SEQ ID NO: 2 Start Site | SEQ ID NO: 2 Stop Site | SEQ ID NO |
|---|---|---|---|---|---|---|---|---|
| 596255 | 389 | 408 | TTGCCCAAGTCTCCAACATG | 41 | 33 | 8444 | 8463 | 911 |
| 596256 | 391 | 410 | CATTGCCCAAGTCTCCAACA | 39 | 25 | 8446 | 8465 | 912 |
| 150455 | 393 | 412 | CACATTGCCCAAGTCTCCAA | 36 | 19 | 8448 | 8467 | 101 |
| 596257 | 397 | 416 | CAGTCACATTGCCCAAGTCT | 40 | 27 | 8452 | 8471 | 913 |
| 596258 | 401 | 420 | TCAGCAGTCACATTGCCCAA | 52 | 42 | 8456 | 8475 | 914 |
| 596259 | 403 | 422 | TGTCAGCAGTCACATTGCCC | 55 | 49 | 8458 | 8477 | 915 |
| 596260 | 405 | 424 | TTTGTCAGCAGTCACATTGC | 26 | 16 | 8460 | 8479 | 916 |
| 596261 | 407 | 426 | TCTTTGTCAGCAGTCACATT | 20 | 11 | 8462 | 8481 | 917 |
| 596262 | 409 | 428 | CATCTTTGTCAGCAGTCACA | 34 | 13 | 8464 | 8483 | 918 |
| 596263 | 411 | 430 | ACCATCTTTGTCAGCAGTCA | 41 | 30 | 8466 | 8485 | 919 |
| 596264 | 415 | 434 | CCACACCATCTTTGTCAGCA | 39 | 20 | 8470 | 8489 | 920 |
| 596265 | 417 | 436 | GGCCACACCATCTTTGTCAG | 23 | 5 | 8472 | 8491 | 921 |
| 150456 | 419 | 438 | TCGGCCACACCATCTTTGTC | 32 | 28 | 8474 | 8493 | 102 |
| 150457 | 421 | 440 | CATCGGCCACACCATCTTTG | 34 | 38 | 8476 | 8495 | 103 |
| 596266 | 423 | 442 | CACATCGGCCACACCATCTT | 27 | 13 | 8478 | 8497 | 922 |
| 596267 | 425 | 444 | GACACATCGGCCACACCATC | 45 | 30 | 8480 | 8499 | 923 |
| 150459 | 427 | 446 | TAGACACATCGGCCACACCA | 46 | 36 | 8482 | 8501 | 104 |
| 596268 | 429 | 448 | AATAGACACATCGGCCACAC | 30 | 25 | 8484 | 8503 | 924 |
| 596269 | 431 | 450 | TCAATAGACACATCGGCCAC | 35 | 0 | 8486 | 8505 | 925 |
| 596270 | 433 | 452 | CTTCAATAGACACATCGGCC | 39 | 16 | 8488 | 8507 | 926 |
| 596271 | 435 | 454 | ATCTTCAATAGACACATCGG | 16 | 0 | 8490 | 8509 | 927 |
| 596272 | 437 | 456 | GAATCTTCAATAGACACATC | 22 | 11 | 8492 | 8511 | 928 |
| 596273 | 439 | 458 | CAGAATCTTCAATAGACACA | 17 | 0 | 8494 | 8513 | 929 |
| 596274 | 441 | 460 | CACAGAATCTTCAATAGACA | 10 | 14 | 8496 | 8515 | 930 |
| 596275 | 443 | 462 | ATCACAGAATCTTCAATAGA | 11 | 10 | 8498 | 8517 | 931 |
| 596276 | 445 | 464 | AGATCACAGAATCTTCAATA | 14 | 29 | 8500 | 8519 | 932 |
| 596277 | 447 | 466 | TGAGATCACAGAATCTTCAA | n.d. | 30 | 8502 | 8521 | 933 |
| 596278 | 449 | 468 | AGTGAGATCACAGAATCTTC | n.d. | 30 | 8504 | 8523 | 934 |
| 596279 | 453 | 472 | TGAGAGTGAGATCACAGAAT | n.d. | 18 | 8508 | 8527 | 935 |
| 333618 | 457 | 476 | CTCCTGAGAGTGAGATCACA | n.d. | 27 | 8512 | 8531 | 105 |
| 596281 | 459 | 478 | GTCTCCTGAGAGTGAGATCA | n.d. | 23 | 8514 | 8533 | 936 |
| 596282 | 461 | 480 | TGGTCTCCTGAGAGTGAGAT | n.d. | 24 | 8516 | 8535 | 937 |
| 596283 | 463 | 482 | AATGGTCTCCTGAGAGTGAG | n.d. | 22 | 8518 | 8537 | 938 |
| 596284 | 465 | 484 | GCAATGGTCTCCTGAGAGTG | n.d. | 57 | 8520 | 8539 | 939 |
| 596285 | 467 | 486 | ATGCAATGGTCTCCTGAGAG | n.d. | 0 | 8522 | 8541 | 940 |

TABLE 12-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition with RTS3898 | % inhibition with HTS90 | SEQ ID NO: 2 Start Site | SEQ ID NO: 2 Stop Site | SEQ ID NO |
|---|---|---|---|---|---|---|---|---|
| 596286 | 469 | 488 | TGATGCAATGGTCTCCTGAG | n.d. | 1 | 8524 | 8543 | 941 |
| 596287 | 471 | 490 | AATGATGCAATGGTCTCCTG | n.d. | 0 | 8526 | 8545 | 942 |
| 596288 | 473 | 492 | CCAATGATGCAATGGTCTCC | n.d. | 8 | 8528 | 8547 | 943 |
| 596289 | 475 | 494 | GGCCAATGATGCAATGGTCT | n.d. | 9 | 8530 | 8549 | 944 |
| 596290 | 477 | 496 | GCGGCCAATGATGCAATGGT | n.d. | 13 | 8532 | 8551 | 945 |
| 596291 | 479 | 498 | GTGCGGCCAATGATGCAATG | n.d. | 12 | 8534 | 8553 | 946 |
| 596292 | 481 | 500 | GTGTGCGGCCAATGATGCAA | n.d. | 15 | 8536 | 8555 | 947 |
| 596293 | 483 | 502 | CAGTGTGCGGCCAATGATGC | n.d. | 0 | 8538 | 8557 | 948 |
| 596294 | 485 | 504 | ACCAGTGTGCGGCCAATGAT | n.d. | 0 | 8540 | 8559 | 949 |
| 596295 | 487 | 506 | CCACCAGTGTGCGGCCAATG | n.d. | 22 | 8542 | 8561 | 950 |
| 596296 | 489 | 508 | GACCACCAGTGTGCGGCCAA | n.d. | 16 | n/a | n/a | 951 |
| 596297 | 491 | 510 | TGGACCACCAGTGTGCGGCC | n.d. | 28 | n/a | n/a | 952 |
| 150461 | 493 | 512 | CATGGACCACCAGTGTGCGG | n.d. | 25 | n/a | n/a | 106 |
| 596298 | 495 | 514 | TTCATGGACCACCAGTGTGC | n.d. | 21 | n/a | n/a | 953 |
| 596299 | 497 | 516 | TTTTCATGGACCACCAGTGT | n.d. | 17 | n/a | n/a | 954 |
| 596300 | 499 | 518 | CTTTTTCATGGACCACCAGT | n.d. | 9 | n/a | n/a | 955 |

Example 3: Inhibition of Human SOD-1 in HepG2 Cells by Deoxy, MOE and cEt Gapmers Modified oligonucleotides were designed targeting a superoxide dismutase 1, soluble (SOD-1) nucleic acid and were tested for their effects on SOD-1 mRNA in vitro. ISIS 333611, which was previously described in WO 2005/040180, was included as a benchmark. ISIS 590067, ISIS 590074, ISIS 590082, ISIS 590130, ISIS 590138, and ISIS 590146, which are 5-10-5 MOE gapmers as described above in Example 1, were also included in this assay. ISIS 590512, which has a similar sequence as ISIS 333611 but with deoxy, MOE, and cEt sugar modifications, was also included in this study.

The modified oligonucleotides were tested in a series of experiments that had similar culture conditions. The results for each experiment are presented in separate tables shown below. Cultured HepG2 cells at a density of 20,000 cells per well were transfected using electroporation with 3,000 nM modified oligonucleotide. After a treatment period of approximately 24 hours, RNA was isolated from the cells and SOD-1 mRNA levels were measured by quantitative real-time PCR.

Human primer probe set RTS3898 was used to measure mRNA levels. SOD-1 mRNA levels were adjusted according to total RNA content, as measured by RIBOGREEN®.

Results are presented as percent inhibition of SOD-1, relative to untreated control cells. 'n.d.' indicates that inhibition levels were not measured.

The newly designed modified oligonucleotides in the Tables below were designed as deoxy, MOE, and cEt gapmers. The gapmers are 17 nucleosides in length wherein each nucleoside has a MOE sugar modification, a cEt sugar modification, or a deoxy moiety. The sugar chemistry of each oligonucleotide is denoted as in the Chemistry column, where 'k' indicates a cEt modified sugar; 'd' indicates a 2'-deoxyribose; and 'e' indicates a 2'-MOE modified sugar. The internucleoside linkages throughout each gapmer are phosphorothioate linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human SOD-1 mRNA, designated herein as SEQ ID NO: 1 (GENBANK Accession No. NM_000454.4) or the human SOD-1 genomic sequence, designated herein as SEQ ID NO: 2 (GENBANK Accession No. NT_011512.10 truncated from nucleotides 18693000 to Ser. No. 18/704,000). 'n/a' indicates that the modified oligonucleotide does not target that particular gene sequence with 100% complementarity.

TABLE 13

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 590434 | 1 | 17 | CCACTCTGGCCCCAAAC | eeekkddddddddkkeee | 17 | 807 | 823 | 956 |
| 590435 | 2 | 18 | CCCACTCTGGCCCCAAA | eeekkddddddddkkeee | 15 | 808 | 824 | 957 |
| 590436 | 3 | 19 | GCCCACTCTGGCCCCAA | eeekkddddddddkkeee | 22 | 809 | 825 | 958 |
| 590437 | 4 | 20 | CGCCCACTCTGGCCCCA | eeekkddddddddkkeee | 14 | 810 | 826 | 959 |
| 590438 | 35 | 51 | CGACTACTTTATAGGCC | eeekkddddddddkkeee | 12 | 841 | 857 | 960 |
| 590439 | 36 | 52 | GCGACTACTTTATAGGC | eeekkddddddddkkeee | 12 | 842 | 858 | 961 |
| 590440 | 37 | 53 | CGCGACTACTTTATAGG | eeekkddddddddkkeee | 11 | 843 | 859 | 962 |
| 590441 | 38 | 54 | CCGCGACTACTTTATAG | eeekkddddddddkkeee | 5 | 844 | 860 | 963 |
| 590442 | 76 | 92 | CGCTGCAGGAGACTACG | eeekkddddddddkkeee | 0 | 882 | 898 | 964 |
| 590443 | 77 | 93 | ACGCTGCAGGAGACTAC | eeekkddddddddkkeee | 25 | 883 | 899 | 965 |
| 590444 | 167 | 183 | TCGCCCTTCAGCACGCA | eeekkddddddddkkeee | 31 | 973 | 989 | 966 |
| 590445 | 168 | 184 | GTCGCCCTTCAGCACGC | eeekkddddddddkkeee | 28 | 974 | 990 | 967 |
| 590512 | 169 | 185 | CGTCGCCCTTCAGCACG | eeekkddddddddkkeee | 8 | 975 | 991 | 968 |
| 590446 | 170 | 186 | CCGTCGCCCTTCAGCAC | eeekkddddddddkkeee | 27 | 976 | 992 | 969 |
| 590447 | 171 | 187 | GCCGTCGCCCTTCAGCA | eeekkddddddddkkeee | 33 | 977 | 993 | 970 |
| 590448 | 202 | 218 | TCTGCTCGAAATTGATG | eeekkddddddddkkeee | 34 | 1008 | 1024 | 971 |
| 590449 | 203 | 219 | TTCTGCTCGAAATTGAT | eeekkddddddddkkeee | 18 | 1009 | 1025 | 972 |
| 590450 | 204 | 220 | CTTCTGCTCGAAATTGA | eeekkddddddddkkeee | 13 | 1010 | 1026 | 973 |
| 590451 | 205 | 221 | CCTTCTGCTCGAAATTG | eeekkddddddddkkeee | 16 | 1011 | 1027 | 974 |
| 590452 | 206 | 222 | TCCTTCTGCTCGAAATT | eeekkddddddddkkeee | 14 | n/a | n/a | 975 |
| 590453 | 207 | 223 | TTCCTTCTGCTCGAAAT | eeekkddddddddkkeee | 13 | n/a | n/a | 976 |
| 590454 | 208 | 224 | TTTCCTTCTGCTCGAAA | eeekkddddddddkkeee | 6 | n/a | n/a | 977 |
| 590455 | 209 | 225 | CTTTCCTTCTGCTCGAA | eeekkddddddddkkeee | 0 | n/a | n/a | 978 |
| 590456 | 210 | 226 | ACTTTCCTTCTGCTCGA | eeekkddddddddkkeee | 0 | n/a | n/a | 979 |

TABLE 13-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 590457 | 211 | 227 | TACTTTCCTTCTGCTCG | eeekkddddddddkkeee | n.d. | n/a | n/a | 980 |
| 590458 | 212 | 228 | TTACTTTCCTTCTGCTC | eeekkddddddddkkeee | n.d. | n/a | n/a | 981 |
| 590459 | 213 | 229 | ATTACTTTCCTTCTGCT | eeekkddddddddkkeee | n.d. | n/a | n/a | 982 |
| 590461 | 214 | 230 | CATTACTTTCCTTCTGC | eeekkddddddddkkeee | n.d. | n/a | n/a | 983 |
| 590462 | 215 | 231 | CCATTACTTTCCTTCTG | eeekkddddddddkkeee | n.d. | n/a | n/a | 984 |
| 590463 | 216 | 232 | TCCATTACTTTCCTTCT | eeekkddddddddkkeee | n.d. | n/a | n/a | 985 |
| 590464 | 217 | 233 | GTCCATTACTTTCCTTC | eeekkddddddddkkeee | n.d. | n/a | n/a | 986 |
| 590465 | 218 | 234 | GGTCCATTACTTTCCTT | eeekkddddddddkkeee | n.d. | 4972 | 4988 | 987 |
| 590466 | 219 | 235 | TGGTCCATTACTTTCCT | eeekkddddddddkkeee | 5 | 4973 | 4989 | 988 |
| 590467 | 220 | 236 | CTGGTCCATTACTTTCC | eeekkddddddddkkeee | 11 | 4974 | 4990 | 989 |
| 590468 | 221 | 237 | ACTGGTCCATTACTTTC | eeekkddddddddkkeee | 14 | 4975 | 4991 | 990 |
| 590469 | 222 | 238 | CACTGGTCCATTACTTT | eeekkddddddddkkeee | 12 | 4976 | 4992 | 991 |
| 590470 | 223 | 239 | TCACTGGTCCATTACTT | eeekkddddddddkkeee | 15 | 4977 | 4993 | 992 |
| 590471 | 224 | 240 | TTCACTGGTCCATTACT | eeekkddddddddkkeee | 14 | 4978 | 4994 | 993 |
| 590472 | 225 | 241 | CTTCACTGGTCCATTAC | eeekkddddddddkkeee | 11 | 4979 | 4995 | 994 |
| 590473 | 226 | 242 | CCTTCACTGGTCCATTA | eeekkddddddddkkeee | 8 | 4980 | 4996 | 995 |
| 590474 | 227 | 243 | ACCTTCACTGGTCCATT | eeekkddddddddkkeee | 44 | 4981 | 4997 | 996 |
| 590475 | 228 | 244 | CACCTTCACTGGTCCAT | eeekkddddddddkkeee | 53 | 4982 | 4998 | 997 |
| 590476 | 229 | 245 | ACACCTTCACTGGTCCA | eeekkddddddddkkeee | 20 | 4983 | 4999 | 998 |
| 590477 | 230 | 246 | CACACCTTCACTGGTCC | eeekkddddddddkkeee | 12 | 4984 | 5000 | 999 |
| 590478 | 231 | 247 | CCACACCTTCACTGGTC | eeekkddddddddkkeee | 36 | 4985 | 5001 | 1000 |
| 590479 | 232 | 248 | CCCACACCTTCACTGGT | eeekkddddddddkkeee | 18 | 4986 | 5002 | 1001 |
| 590480 | 233 | 249 | CCCCACACCTTCACTGG | eeekkddddddddkkeee | 14 | 4987 | 5003 | 1002 |
| 590481 | 235 | 251 | TTCCCCACACCT | eeekkddddddddkkeee | 8 | 4989 | 5005 | 1003 |

TABLE 13-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| | | | TCACT | | | | | |
| 590482 | 236 | 252 | CTTCCCCACACCTTCAC | eeekkddddddddkkeee | 29 | 4990 | 5006 | 1004 |
| 590483 | 237 | 253 | GCTTCCCCACACCTTCA | eeekkddddddddkkeee | 36 | 4991 | 5007 | 1005 |
| 590484 | 238 | 254 | TGCTTCCCCACACCTTC | eeekkddddddddkkeee | 43 | 4992 | 5008 | 1006 |
| 590485 | 239 | 255 | ATGCTTCCCCACACCTT | eeekkddddddddkkeee | 41 | 4993 | 5009 | 1007 |
| 590486 | 240 | 256 | AATGCTTCCCCACACCT | eeekkddddddddkkeee | 35 | 4994 | 5010 | 1008 |
| 590487 | 241 | 257 | TAATGCTTCCCCACACC | eeekkddddddddkkeee | 52 | 4995 | 5011 | 1009 |
| 590488 | 264 | 280 | ATGCAGGCCTTCAGTCA | eeekkddddddddkkeee | 37 | 5018 | 5034 | 1010 |
| 590489 | 265 | 281 | CATGCAGGCCTTCAGTC | eeekkddddddddkkeee | 41 | 5019 | 5035 | 1011 |
| 590490 | 266 | 282 | CCATGCAGGCCTTCAGT | eeekkddddddddkkeee | 21 | 5020 | 5036 | 1012 |
| 590491 | 267 | 283 | TCCATGCAGGCCTTCAG | eeekkddddddddkkeee | 18 | 5021 | 5037 | 1013 |
| 590492 | 268 | 284 | ATCCATGCAGGCCTTCA | eeekkddddddddkkeee | 27 | 5022 | 5038 | 1014 |
| 590493 | 269 | 285 | AATCCATGCAGGCCTTC | eeekkddddddddkkeee | 13 | 5023 | 5039 | 1015 |
| 590494 | 270 | 286 | GAATCCATGCAGGCCTT | eeekkddddddddkkeee | 9 | 5024 | 5040 | 1016 |
| 590495 | 271 | 287 | GGAATCCATGCAGGCCT | eeekkddddddddkkeee | 7 | 5025 | 5041 | 1017 |
| 590496 | 272 | 288 | TGGAATCCATGCAGGCC | eeekkddddddddkkeee | 12 | 5026 | 5042 | 1018 |
| 590497 | 273 | 289 | ATGGAATCCATGCAGGC | eeekkddddddddkkeee | 9 | 5027 | 5043 | 1019 |
| 590498 | 274 | 290 | CATGGAATCCATGCAGG | eeekkddddddddkkeee | 14 | 5028 | 5044 | 1020 |
| 590499 | 275 | 291 | ACATGGAATCCATGCAG | eeekkddddddddkkeee | 0 | 5029 | 5045 | 1021 |
| 590500 | 276 | 292 | AACATGGAATCCATGCA | eeekkddddddddkkeee | 10 | 5030 | 5046 | 1022 |
| 590501 | 277 | 293 | GAACATGGAATCCATGC | eeekkddddddddkkeee | 9 | 5031 | 5047 | 1023 |
| 590502 | 278 | 294 | TGAACATGGAATCCATG | eeekkddddddddkkeee | 2 | 5032 | 5048 | 1024 |
| 590503 | 279 | 295 | ATGAACATGGAATCCAT | eeekkddddddddkkeee | 8 | 5033 | 5049 | 1025 |
| 590504 | 316 | 332 | CTGCACTGGTACAGCCT | eeekkddddddddkkeee | 3 | 7632 | 7648 | 1026 |

TABLE 13-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 590505 | 317 | 333 | CCTGCACTGGTACAGCC | eeekkddddddddkkeee | 17 | 7633 | 7649 | 1027 |
| 590506 | 318 | 334 | ACCTGCACTGGTACAGC | eeekkddddddddkkeee | 12 | 7634 | 7650 | 1028 |
| 590507 | 319 | 335 | GACCTGCACTGGTACAG | eeekkddddddddkkeee | 7 | 7635 | 7651 | 1029 |
| 590508 | 320 | 336 | GGACCTGCACTGGTACA | eeekkddddddddkkeee | 7 | 7636 | 7652 | 1030 |
| 590509 | 321 | 337 | AGGACCTGCACTGGTAC | eeekkddddddddkkeee | 4 | 7637 | 7653 | 1031 |
| 590510 | 322 | 338 | GAGGACCTGCACTGGTA | eeekkddddddddkkeee | 17 | 7638 | 7654 | 1032 |
| 590511 | 323 | 339 | TGAGGACCTGCACTGGT | eeekkddddddddkkeee | 8 | 7639 | 7655 | 1033 |

TABLE 14

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 590512 | 169 | 185 | CGTCGCCCTTCAGCACG | eeekkddddddddkkeee | 45 | 975 | 991 | 968 |
| 590513 | 324 | 340 | GTGAGGACCTGCACTGG | eeekkddddddddkkeee | 21 | 7640 | 7656 | 1034 |
| 590514 | 325 | 341 | AGTGAGGACCTGCACTG | eeekkddddddddkkeee | 21 | 7641 | 7657 | 1035 |
| 590515 | 326 | 342 | AAGTGAGGACCTGCACT | eeekkddddddddkkeee | 16 | 7642 | 7658 | 1036 |
| 590516 | 327 | 343 | AAAGTGAGGACCTGCAC | eeekkddddddddkkeee | 20 | 7643 | 7659 | 1037 |
| 590517 | 328 | 344 | TAAAGTGAGGACCTGCA | eeekkddddddddkkeee | 19 | 7644 | 7660 | 1038 |
| 590518 | 329 | 345 | TTAAAGTGAGGACCTGC | eeekkddddddddkkeee | 14 | 7645 | 7661 | 1039 |
| 590519 | 330 | 346 | ATTAAAGTGAGGACCTG | eeekkddddddddkkeee | 51 | 7646 | 7662 | 1040 |
| 590520 | 331 | 347 | GATTAAAGTGAGGACCT | eeekkddddddddkkeee | 8 | 7647 | 7663 | 1041 |
| 590521 | 332 | 348 | GGATTAAAGTGAGGACC | eeekkddddddddkkeee | 30 | 7648 | 7664 | 1042 |
| 590522 | 333 | 349 | AGGATTAAAGTGAGGAC | eeekkddddddddkkeee | 23 | 7649 | 7665 | 1043 |
| 590523 | 334 | 350 | GAGGATTAAAGTGAGGA | eeekkddddddddkkeee | 40 | 7650 | 7666 | 1044 |

TABLE 14-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 590524 | 335 | 351 | AGAGGATTAAAGTGAGG | eeekkddddddddkkeee | 16 | 7651 | 7667 | 1045 |
| 590525 | 336 | 352 | TAGAGGATTAAAGTGAG | eeekkddddddddkkeee | 21 | 7652 | 7668 | 1046 |
| 590526 | 337 | 353 | ATAGAGGATTAAAGTGA | eeekkddddddddkkeee | 9 | 7653 | 7669 | 1047 |
| 590527 | 338 | 354 | GATAGAGGATTAAAGTG | eeekkddddddddkkeee | 8 | 7654 | 7670 | 1048 |
| 590528 | 339 | 355 | GGATAGAGGATTAAAGT | eeekkddddddddkkeee | 14 | 7655 | 7671 | 1049 |
| 590530 | 340 | 356 | TGGATAGAGGATTAAAG | eeekkddddddddkkeee | 23 | 7656 | 7672 | 1050 |
| 590531 | 341 | 357 | CTGGATAGAGGATTAAA | eeekkddddddddkkeee | 26 | 7657 | 7673 | 1051 |
| 590532 | 342 | 358 | TCTGGATAGAGGATTAA | eeekkddddddddkkeee | 25 | 7658 | 7674 | 1052 |
| 590533 | 360 | 376 | CTTTGGCCCACCGTGTT | eeekkddddddddkkeee | 41 | 7676 | 7692 | 1053 |
| 590534 | 361 | 377 | CCTTTGGCCCACCGTGT | eeekkddddddddkkeee | 46 | 7677 | 7693 | 1054 |
| 590535 | 362 | 378 | TCCTTTGGCCCACCGTG | eeekkddddddddkkeee | 39 | 7678 | 7694 | 1055 |
| 590536 | 363 | 379 | ATCCTTTGGCCCACCGT | eeekkddddddddkkeee | n.d. | 7679 | 7695 | 1056 |
| 590537 | 364 | 380 | CATCCTTTGGCCCACCG | eeekkddddddddkkeee | n.d. | 7680 | 7696 | 1057 |
| 590538 | 365 | 381 | TCATCCTTTGGCCCACC | eeekkddddddddkkeee | n.d. | 7681 | 7697 | 1058 |
| 590539 | 366 | 382 | TTCATCCTTTGGCCCAC | eeekkddddddddkkeee | n.d. | 7682 | 7698 | 1059 |
| 590540 | 367 | 383 | CTTCATCCTTTGGCCCA | eeekkddddddddkkeee | n.d. | 7683 | 7699 | 1060 |
| 590541 | 368 | 384 | TCTTCATCCTTTGGCCC | eeekkddddddddkkeee | n.d. | 7684 | 7700 | 1061 |
| 590542 | 369 | 385 | CTCTTCATCCTTTGGCC | eeekkddddddddkkeee | n.d. | 7685 | 7701 | 1062 |
| 590543 | 370 | 386 | TCTCTTCATCCTTTGGC | eeekkddddddddkkeee | n.d. | 7686 | 7702 | 1063 |
| 590544 | 371 | 387 | CTCTCTTCATCCTTTGG | eeekkddddddddkkeee | 2 | 7687 | 7703 | 1064 |
| 590545 | 374 | 390 | TGCCTCTCTTCATCCTT | eeekkddddddddkkeee | 6 | n/a | n/a | 1065 |
| 590546 | 375 | 391 | ATGCCTCTCTTCATCCT | eeekkddddddddkkeee | 0 | n/a | n/a | 1066 |
| 590547 | 376 | 392 | CATGCCTCTCTTCATCC | eeekkddddddddkkeee | 14 | n/a | n/a | 1067 |
| 590548 | 377 | 393 | ACATGCCTCTCTTCATC | eeekkddddddddkkeee | 0 | n/a | n/a | 1068 |

TABLE 14-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 590549 | 378 | 394 | AACATGCCTCTCTTCAT | eeekkddddddddkkeee | 13 | n/a | n/a | 1069 |
| 590550 | 379 | 395 | CAACATGCCTCTCTTCA | eeekkddddddddkkeee | 3 | n/a | n/a | 1070 |
| 590551 | 380 | 396 | CCAACATGCCTCTCTTC | eeekkddddddddkkeee | 0 | n/a | n/a | 1071 |
| 590552 | 381 | 397 | TCCAACATGCCTCTCTT | eeekkddddddddkkeee | 0 | n/a | n/a | 1072 |
| 590553 | 382 | 398 | CTCCAACATGCCTCTCT | eeekkddddddddkkeee | 5 | n/a | n/a | 1073 |
| 590554 | 383 | 399 | TCTCCAACATGCCTCTC | eeekkddddddddkkeee | 10 | n/a | n/a | 1074 |
| 590555 | 384 | 400 | GTCTCCAACATGCCTCT | eeekkddddddddkkeee | 8 | n/a | n/a | 1075 |
| 590556 | 402 | 418 | AGCAGTCACATTGCCCA | eeekkddddddddkkeee | 18 | 8457 | 8473 | 1076 |
| 590557 | 403 | 419 | CAGCAGTCACATTGCCC | eeekkddddddddkkeee | 7 | 8458 | 8474 | 1077 |
| 590558 | 429 | 445 | AGACACATCGGCCACAC | eeekkddddddddkkeee | 21 | 8484 | 8500 | 1078 |
| 590559 | 436 | 452 | CTTCAATAGACACATCG | eeekkddddddddkkeee | 9 | 8491 | 8507 | 1079 |
| 590560 | 449 | 465 | GAGATCACAGAATCTTC | eeekkddddddddkkeee | 13 | 8504 | 8520 | 1080 |
| 590561 | 501 | 517 | TTTTTCATGGACCACCA | eeekkddddddddkkeee | 76 | n/a | n/a | 1081 |
| 590562 | 502 | 518 | CTTTTTCATGGACCACC | eeekkddddddddkkeee | 87 | n/a | n/a | 1082 |
| 590563 | 503 | 519 | GCTTTTTCATGGACCAC | eeekkddddddddkkeee | 71 | n/a | n/a | 1083 |
| 590564 | 504 | 520 | TGCTTTTTCATGGACCA | eeekkddddddddkkeee | 51 | n/a | n/a | 1084 |
| 590565 | 505 | 521 | CTGCTTTTTCATGGACC | eeekkddddddddkkeee | 65 | 9655 | 9671 | 1085 |
| 590566 | 506 | 522 | TCTGCTTTTTCATGGAC | eeekkddddddddkkeee | 55 | 9656 | 9672 | 1086 |
| 590567 | 507 | 523 | ATCTGCTTTTTCATGGA | eeekkddddddddkkeee | 42 | 9657 | 9673 | 1087 |
| 590568 | 508 | 524 | CATCTGCTTTTTCATGG | eeekkddddddddkkeee | 70 | 9658 | 9674 | 1088 |
| 590569 | 509 | 525 | TCATCTGCTTTTTCATG | eeekkddddddddkkeee | 71 | 9659 | 9675 | 1089 |
| 590570 | 510 | 526 | GTCATCTGCTTTTTCAT | eeekkddddddddkkeee | 74 | 9660 | 9676 | 1090 |
| 590571 | 511 | 527 | AGTCATCTGCTTTTTCA | eeekkddddddddkkeee | 76 | 9661 | 9677 | 1091 |
| 590572 | 512 | 528 | AAGTCATCTGCT | eeekkddddddddkkeee | 83 | 9662 | 9678 | 1092 |

TABLE 14-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| | | | TTTTC | | | | | |
| 590573 | 513 | 529 | CAAGTCATCTGC TTTTT | eeekkddddddddkkeee | 42 | 9663 | 9679 | 1093 |
| 590574 | 514 | 530 | CCAAGTCATCTG CTTTT | eeekkddddddddkkeee | 50 | 9664 | 9680 | 1094 |
| 590575 | 515 | 531 | CCCAAGTCATCT GCTTT | eeekkddddddddkkeee | 72 | 9665 | 9681 | 1095 |
| 590576 | 516 | 532 | GCCCAAGTCATC TGCTT | eeekkddddddddkkeee | 93 | 9666 | 9682 | 1096 |
| 590577 | 517 | 533 | TGCCCAAGTCAT CTGCT | eeekkddddddddkkeee | 90 | 9667 | 9683 | 1097 |
| 590578 | 518 | 534 | TTGCCCAAGTCA TCTGC | eeekkddddddddkkeee | 92 | 9668 | 9684 | 1098 |
| 590579 | 524 | 540 | CCACCTTTGCCC AAGTC | eeekkddddddddkkeee | 91 | 9674 | 9690 | 1099 |
| 590580 | 525 | 541 | TCCACCTTTGCC CAAGT | eeekkddddddddkkeee | 88 | 9675 | 9691 | 1100 |
| 590581 | 526 | 542 | TTCCACCTTTGC CCAAG | eeekkddddddddkkeee | 87 | 9676 | 9692 | 1101 |
| 590582 | 527 | 543 | TTTCCACCTTTG CCCAA | eeekkddddddddkkeee | 78 | 9677 | 9693 | 1102 |
| 590583 | 528 | 544 | ATTTCCACCTTT GCCCA | eeekkddddddddkkeee | 63 | 9678 | 9694 | 1103 |
| 590584 | 529 | 545 | CATTTCCACCTT TGCCC | eeekkddddddddkkeee | 73 | 9679 | 9695 | 1104 |
| 590585 | 530 | 546 | TCATTTCCACCT TTGCC | eeekkddddddddkkeee | 57 | 9680 | 9696 | 1105 |
| 590586 | 531 | 547 | TTCATTTCCACC TTTGC | eeekkddddddddkkeee | 33 | 9681 | 9697 | 1106 |
| 590587 | 533 | 549 | TCTTCATTTCCA CCTTT | eeekkddddddddkkeee | 31 | 9683 | 9699 | 1107 |
| 590588 | 536 | 552 | CTTTCTTCATTT CCACC | eeekkddddddddkkeee | 11 | 9686 | 9702 | 1108 |
| 590589 | 537 | 553 | ACTTTCTTCATT TCCAC | eeekkddddddddkkeee | 15 | 9687 | 9703 | 1109 |
| 590590 | 538 | 554 | TACTTTCTTCAT TTCCA | eeekkddddddddkkeee | 18 | 9688 | 9704 | 1110 |

TABLE 15

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 590512 | 169 | 185 | CGTCGCCCTTCAGCACG | eeekkddddddddkkeee | 21 | 975 | 991 | 968 |
| 590591 | 582 | 598 | AATTACACCACAAGCCA | eeekkddddddddkkeee | 21 | 9732 | 9748 | 1111 |
| 590592 | 583 | 599 | CAATTACACCACAAGCC | eeekkddddddddkkeee | 33 | 9733 | 9749 | 1112 |
| 590593 | 584 | 600 | CCAATTACACCACAAGC | eeekkddddddddkkeee | 29 | 9734 | 9750 | 1113 |
| 590594 | 585 | 601 | CCCAATTACACCACAAG | eeekkddddddddkkeee | 29 | 9735 | 9751 | 1114 |
| 590595 | 588 | 604 | GATCCCAATTACACCAC | eeekkddddddddkkeee | 3 | 9738 | 9754 | 1115 |
| 590596 | 589 | 605 | CGATCCCAATTACACCA | eeekkddddddddkkeee | 12 | 9739 | 9755 | 1116 |
| 590597 | 590 | 606 | GCGATCCCAATTACACC | eeekkddddddddkkeee | 19 | 9740 | 9756 | 1117 |
| 590598 | 591 | 607 | GGCGATCCCAATTACAC | eeekkddddddddkkeee | 9 | 9741 | 9757 | 1118 |
| 590599 | 592 | 608 | GGGCGATCCCAATTACA | eeekkddddddddkkeee | 18 | 9742 | 9758 | 1119 |
| 590600 | 593 | 609 | TGGGCGATCCCAATTAC | eeekkddddddddkkeee | 20 | 9743 | 9759 | 1120 |
| 590601 | 594 | 610 | TTGGGCGATCCCAATTA | eeekkddddddddkkeee | 26 | 9744 | 9760 | 1121 |
| 590602 | 595 | 611 | ATTGGGCGATCCCAATT | eeekkddddddddkkeee | 19 | 9745 | 9761 | 1122 |
| 590603 | 596 | 612 | TATTGGGCGATCCCAAT | eeekkddddddddkkeee | 3 | 9746 | 9762 | 1123 |
| 590604 | 597 | 613 | TTATTGGGCGATCCCAA | eeekkddddddddkkeee | 15 | 9747 | 9763 | 1124 |
| 590605 | 598 | 614 | TTTATTGGGCGATCCCA | eeekkddddddddkkeee | 20 | 9748 | 9764 | 1125 |
| 590606 | 599 | 615 | GTTTATTGGGCGATCCC | eeekkddddddddkkeee | 18 | 9749 | 9765 | 1126 |
| 590607 | 600 | 616 | TGTTTATTGGGCGATCC | eeekkddddddddkkeee | 21 | 9750 | 9766 | 1127 |
| 590608 | 601 | 617 | ATGTTTATTGGGCGATC | eeekkddddddddkkeee | 28 | 9751 | 9767 | 1128 |
| 590609 | 602 | 618 | AATGTTTATTGGGCGAT | eeekkddddddddkkeee | 30 | 9752 | 9768 | 1129 |
| 590610 | 603 | 619 | GAATGTTTATTGGGCGA | eeekkddddddddkkeee | 14 | 9753 | 9769 | 1130 |
| 590611 | 604 | 620 | GGAATGTTTATTGGGCG | eeekkddddddddkkeee | 15 | 9754 | 9770 | 1131 |
| 590612 | 607 | 623 | AAGGGAATGTTTATTGG | eeekkddddddddkkeee | 2 | 9757 | 9773 | 1132 |
| 590613 | 608 | 624 | CAAGGGAATGTTTATTG | eeekkddddddddkkeee | n.d. | 9758 | 9774 | 1133 |

TABLE 15-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 590614 | 609 | 625 | CCAAGGGAATGTTTATT | eeekkddddddddkkeee | n.d. | 9759 | 9775 | 1134 |
| 590615 | 610 | 626 | TCCAAGGGAATGTTTAT | eeekkddddddddkkeee | n.d. | 9760 | 9776 | 1135 |
| 590616 | 611 | 627 | ATCCAAGGGAATGTTTA | eeekkddddddddkkeee | n.d. | 9761 | 9777 | 1136 |
| 590617 | 612 | 628 | CATCCAAGGGAATGTTT | eeekkddddddddkkeee | n.d. | 9762 | 9778 | 1137 |
| 590618 | 613 | 629 | ACATCCAAGGGAATGTT | eeekkddddddddkkeee | n.d. | 9763 | 9779 | 1138 |
| 590619 | 614 | 630 | TACATCCAAGGGAATGT | eeekkddddddddkkeee | n.d. | 9764 | 9780 | 1139 |
| 590620 | 615 | 631 | CTACATCCAAGGGAATG | eeekkddddddddkkeee | n.d. | 9765 | 9781 | 1140 |
| 590621 | 616 | 632 | ACTACATCCAAGGGAAT | eeekkddddddddkkeee | 7 | 9766 | 9782 | 1141 |
| 590622 | 617 | 633 | GACTACATCCAAGGGAA | eeekkddddddddkkeee | 19 | 9767 | 9783 | 1142 |
| 590623 | 618 | 634 | AGACTACATCCAAGGGA | eeekkddddddddkkeee | 39 | 9768 | 9784 | 1143 |
| 590624 | 619 | 635 | CAGACTACATCCAAGGG | eeekkddddddddkkeee | 53 | 9769 | 9785 | 1144 |
| 590625 | 620 | 636 | TCAGACTACATCCAAGG | eeekkddddddddkkeee | 57 | 9770 | 9786 | 1145 |
| 590626 | 621 | 637 | CTCAGACTACATCCAAG | eeekkddddddddkkeee | 76 | 9771 | 9787 | 1146 |
| 590627 | 622 | 638 | CCTCAGACTACATCCAA | eeekkddddddddkkeee | 58 | 9772 | 9788 | 1147 |
| 590628 | 623 | 639 | GCCTCAGACTACATCCA | eeekkddddddddkkeee | 43 | 9773 | 9789 | 1148 |
| 590629 | 624 | 640 | GGCCTCAGACTACATCC | eeekkddddddddkkeee | 24 | 9774 | 9790 | 1149 |
| 590630 | 625 | 641 | GGGCCTCAGACTACATC | eeekkddddddddkkeee | 24 | 9775 | 9791 | 1150 |
| 590631 | 643 | 659 | GATAACAGATGAGTTAA | eeekkddddddddkkeee | 11 | 9793 | 9809 | 1151 |
| 590632 | 644 | 660 | GGATAACAGATGAGTTA | eeekkddddddddkkeee | 32 | 9794 | 9810 | 1152 |
| 590633 | 645 | 661 | AGGATAACAGATGAGTT | eeekkddddddddkkeee | 45 | 9795 | 9811 | 1153 |
| 590634 | 646 | 662 | CAGGATAACAGATGAGT | eeekkddddddddkkeee | 65 | 9796 | 9812 | 1154 |
| 590635 | 647 | 663 | GCAGGATAACAGATGAG | eeekkddddddddkkeee | 58 | 9797 | 9813 | 1155 |
| 590636 | 648 | 664 | AGCAGGATAACAGATGA | eeekkddddddddkkeee | 45 | 9798 | 9814 | 1156 |
| 590637 | 649 | 665 | TAGCAGGATAACAGATGAAC | eeekkddddddddkkeee | 34 | 9799 | 9815 | 1157 |

TABLE 15-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| | | | AGATG | | | | | |
| 590638 | 650 | 666 | CTAGCAGGATAACAGAT | eeekkddddddddkkeee | 39 | 9800 | 9816 | 1158 |
| 590639 | 651 | 667 | GCTAGCAGGATAACAGA | eeekkddddddddkkeee | 10 | 9801 | 9817 | 1159 |
| 590640 | 652 | 668 | AGCTAGCAGGATAACAG | eeekkddddddddkkeee | 15 | 9802 | 9818 | 1160 |
| 590641 | 653 | 669 | CAGCTAGCAGGATAACA | eeekkddddddddkkeee | 21 | 9803 | 9819 | 1161 |
| 590642 | 654 | 670 | ACAGCTAGCAGGATAAC | eeekkddddddddkkeee | 20 | 9804 | 9820 | 1162 |
| 590643 | 655 | 671 | TACAGCTAGCAGGATAA | eeekkddddddddkkeee | 40 | 9805 | 9821 | 1163 |
| 590644 | 656 | 672 | CTACAGCTAGCAGGATA | eeekkddddddddkkeee | 55 | 9806 | 9822 | 1164 |
| 590645 | 657 | 673 | TCTACAGCTAGCAGGAT | eeekkddddddddkkeee | 51 | 9807 | 9823 | 1165 |
| 590646 | 658 | 674 | TTCTACAGCTAGCAGGA | eeekkddddddddkkeee | 31 | 9808 | 9824 | 1166 |
| 590647 | 659 | 675 | TTTCTACAGCTAGCAGG | eeekkddddddddkkeee | 38 | 9809 | 9825 | 1167 |
| 590648 | 660 | 676 | ATTTCTACAGCTAGCAG | eeekkddddddddkkeee | 45 | 9810 | 9826 | 1168 |
| 590649 | 661 | 677 | CATTTCTACAGCTAGCA | eeekkddddddddkkeee | 34 | 9811 | 9827 | 1169 |
| 590650 | 664 | 680 | ATACATTTCTACAGCTA | eeekkddddddddkkeee | 57 | 9814 | 9830 | 1170 |
| 590651 | 665 | 681 | GATACATTTCTACAGCT | eeekkddddddddkkeee | 40 | 9815 | 9831 | 1171 |
| 590652 | 683 | 699 | GTGTTTAATGTTTATCA | eeekkddddddddkkeee | 37 | 9833 | 9849 | 1172 |
| 590653 | 684 | 700 | AGTGTTTAATGTTTATC | eeekkddddddddkkeee | 67 | 9834 | 9850 | 1173 |
| 590654 | 685 | 701 | CAGTGTTTAATGTTTAT | eeekkddddddddkkeee | 54 | 9835 | 9851 | 1174 |
| 590655 | 686 | 702 | ACAGTGTTTAATGTTTA | eeekkddddddddkkeee | 56 | 9836 | 9852 | 1175 |
| 590656 | 687 | 703 | TACAGTGTTTAATGTTT | eeekkddddddddkkeee | 30 | 9837 | 9853 | 1176 |
| 590657 | 688 | 704 | TTACAGTGTTTAATGTT | eeekkddddddddkkeee | 18 | 9838 | 9854 | 1177 |
| 590658 | 689 | 705 | ATTACAGTGTTTAATGT | eeekkddddddddkkeee | 24 | 9839 | 9855 | 1178 |
| 590659 | 690 | 706 | GATTACAGTGTTTAATG | eeekkddddddddkkeee | 10 | 9840 | 9856 | 1179 |
| 590660 | 691 | 707 | AGATTACAGTGTTTAAT | eeekkddddddddkkeee | 45 | 9841 | 9857 | 1180 |

TABLE 15-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 590661 | 692 | 708 | AAGATTACAGTGTTTAA | eeekkddddddddkkeee | 34 | 9842 | 9858 | 1181 |
| 590662 | 693 | 709 | TAAGATTACAGTGTTTA | eeekkddddddddkkeee | 54 | 9843 | 9859 | 1182 |
| 590663 | 694 | 710 | TTAAGATTACAGTGTTT | eeekkddddddddkkeee | 54 | 9844 | 9860 | 1183 |
| 590664 | 772 | 788 | ATCTTCCAAGTGATCAT | eeekkddddddddkkeee | 7 | 9922 | 9938 | 1184 |
| 590665 | 773 | 789 | AATCTTCCAAGTGATCA | eeekkddddddddkkeee | 23 | 9923 | 9939 | 1185 |
| 590666 | 774 | 790 | AAATCTTCCAAGTGATC | eeekkddddddddkkeee | 4 | 9924 | 9940 | 1186 |
| 590667 | 775 | 791 | CAAATCTTCCAAGTGAT | eeekkddddddddkkeee | 18 | 9925 | 9941 | 1187 |

TABLE 16

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 590512 | 169 | 185 | CGTCGCCCTTCAGCACG | eeekkddddddddkkeee | 16 | 975 | 991 | 968 |
| 590668 | 777 | 793 | TACAAATCTTCCAAGTG | eeekkddddddddkkeee | 17 | 9927 | 9943 | 1188 |
| 590669 | 778 | 794 | ATACAAATCTTCCAAGT | eeekkddddddddkkeee | 15 | 9928 | 9944 | 1189 |
| 590670 | 779 | 795 | TATACAAATCTTCCAAG | eeekkddddddddkkeee | 11 | 9929 | 9945 | 1190 |
| 590671 | 780 | 796 | CTATACAAATCTTCCAA | eeekkddddddddkkeee | 13 | 9930 | 9946 | 1191 |
| 590672 | 781 | 797 | ACTATACAAATCTTCCA | eeekkddddddddkkeee | 10 | 9931 | 9947 | 1192 |
| 590673 | 782 | 798 | AACTATACAAATCTTCC | eeekkddddddddkkeee | 28 | 9932 | 9948 | 1193 |
| 590674 | 783 | 799 | AAACTATACAAATCTTC | eeekkddddddddkkeee | 26 | 9933 | 9949 | 1194 |
| 590675 | 786 | 802 | ATAAAACTATACAAATC | eeekkddddddddkkeee | 14 | 9936 | 9952 | 1195 |
| 590676 | 791 | 807 | GTTTTATAAAACTATAC | eeekkddddddddkkeee | 22 | 9941 | 9957 | 1196 |
| 590677 | 793 | 809 | GAGTTTTATAAAACTAT | eeekkddddddddkkeee | 6 | 9943 | 9959 | 1197 |
| 590678 | 814 | 830 | ATTGAAACAGACATTTT | eeekkddddddddkkeee | 22 | 9964 | 9980 | 1198 |

TABLE 16-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 590679 | 815 | 831 | CATTGAAACAGACATTT | eeekkddddddddkkeee | 11 | 9965 | 9981 | 1199 |
| 590680 | 816 | 832 | TCATTGAAACAGACATT | eeekkddddddddkkeee | 10 | 9966 | 9982 | 1200 |
| 590681 | 817 | 833 | GTCATTGAAACAGACAT | eeekkddddddddkkeee | 23 | 9967 | 9983 | 1201 |
| 590682 | 818 | 834 | GGTCATTGAAACAGACA | eeekkddddddddkkeee | 11 | 9968 | 9984 | 1202 |
| 590683 | 819 | 835 | AGGTCATTGAAACAGAC | eeekkddddddddkkeee | 21 | 9969 | 9985 | 1203 |
| 590684 | 820 | 836 | CAGGTCATTGAAACAGA | eeekkddddddddkkeee | 14 | 9970 | 9986 | 1204 |
| 590685 | 821 | 837 | ACAGGTCATTGAAACAG | eeekkddddddddkkeee | 14 | 9971 | 9987 | 1205 |
| 590686 | 822 | 838 | TACAGGTCATTGAAACA | eeekkddddddddkkeee | 9 | 9972 | 9988 | 1206 |
| 590687 | 823 | 839 | ATACAGGTCATTGAAAC | eeekkddddddddkkeee | 14 | 9973 | 9989 | 1207 |
| 590688 | 824 | 840 | AATACAGGTCATTGAAA | eeekkddddddddkkeee | 6 | 9974 | 9990 | 1208 |
| 590689 | 825 | 841 | AAATACAGGTCATTGAA | eeekkddddddddkkeee | 2 | 9975 | 9991 | 1209 |
| 590690 | 826 | 842 | AAAATACAGGTCATTGA | eeekkddddddddkkeee | n.d. | 9976 | 9992 | 1210 |
| 590691 | 827 | 843 | CAAAATACAGGTCATTG | eeekkddddddddkkeee | n.d. | 9977 | 9993 | 1211 |
| 590692 | 828 | 844 | GCAAAATACAGGTCATT | eeekkddddddddkkeee | n.d. | 9978 | 9994 | 1212 |
| 590693 | 829 | 845 | GGCAAAATACAGGTCAT | eeekkddddddddkkeee | n.d. | 9979 | 9995 | 1213 |
| 590694 | 830 | 846 | TGGCAAAATACAGGTCA | eeekkddddddddkkeee | n.d. | 9980 | 9996 | 1214 |
| 590695 | 831 | 847 | CTGGCAAAATACAGGTC | eeekkddddddddkkeee | n.d. | 9981 | 9997 | 1215 |
| 590696 | 832 | 848 | TCTGGCAAAATACAGGT | eeekkddddddddkkeee | n.d. | 9982 | 9998 | 1216 |
| 590697 | 833 | 849 | GTCTGGCAAAATACAGG | eeekkddddddddkkeee | n.d. | 9983 | 9999 | 1217 |
| 590698 | 834 | 850 | AGTCTGGCAAAATACAG | eeekkddddddddkkeee | 1 | 9984 | 10000 | 1218 |
| 590699 | 835 | 851 | AAGTCTGGCAAAATACA | eeekkddddddddkkeee | 10 | 9985 | 10001 | 1219 |
| 590700 | 836 | 852 | TAAGTCTGGCAAAATAC | eeekkddddddddkkeee | 4 | 9986 | 10002 | 1220 |
| 590701 | 837 | 853 | TTAAGTCTGGCAAAATA | eeekkddddddddkkeee | 2 | 9987 | 10003 | 1221 |
| 590702 | 853 | 869 | AATACCCATCTGTGATT | eeekkddddddddkkeee | 7 | 10003 | 10019 | 1222 |

TABLE 16-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 590703 | 854 | 870 | TAATACCCATCTGTGAT | eeekkddddddddkkeee | 4 | 10004 | 10020 | 1223 |
| 590704 | 855 | 871 | TTAATACCCATCTGTGA | eeekkddddddddkkeee | 2 | 10005 | 10021 | 1224 |
| 590705 | 856 | 872 | TTTAATACCCATCTGTG | eeekkddddddddkkeee | 0 | 10006 | 10022 | 1225 |
| 590706 | 857 | 873 | GTTTAATACCCATCTGT | eeekkddddddddkkeee | 17 | 10007 | 10023 | 1226 |
| 590707 | 858 | 874 | AGTTTAATACCCATCTG | eeekkddddddddkkeee | 10 | 10008 | 10024 | 1227 |
| 590708 | 859 | 875 | AAGTTTAATACCCATCT | eeekkddddddddkkeee | 12 | 10009 | 10025 | 1228 |
| 590709 | 860 | 876 | CAAGTTTAATACCCATC | eeekkddddddddkkeee | 37 | 10010 | 10026 | 1229 |
| 590710 | 861 | 877 | ACAAGTTTAATACCCAT | eeekkddddddddkkeee | 23 | 10011 | 10027 | 1230 |
| 590711 | 862 | 878 | GACAAGTTTAATACCCA | eeekkddddddddkkeee | 24 | 10012 | 10028 | 1231 |
| 590712 | 863 | 879 | TGACAAGTTTAATACCC | eeekkddddddddkkeee | 27 | 10013 | 10029 | 1232 |
| 590713 | 864 | 880 | CTGACAAGTTTAATACC | eeekkddddddddkkeee | 10 | 10014 | 10030 | 1233 |
| 590714 | 865 | 881 | TCTGACAAGTTTAATAC | eeekkddddddddkkeee | 0 | 10015 | 10031 | 1234 |
| 590715 | 866 | 882 | TTCTGACAAGTTTAATA | eeekkddddddddkkeee | 6 | 10016 | 10032 | 1235 |
| 590716 | 867 | 883 | ATTCTGACAAGTTTAAT | eeekkddddddddkkeee | 9 | 10017 | 10033 | 1236 |
| 590717 | 868 | 884 | AATTCTGACAAGTTTAA | eeekkddddddddkkeee | 15 | 10018 | 10034 | 1237 |
| 590718 | 869 | 885 | AAATTCTGACAAGTTTA | eeekkddddddddkkeee | 21 | 10019 | 10035 | 1238 |
| 590719 | 870 | 886 | GAAATTCTGACAAGTTT | eeekkddddddddkkeee | 14 | 10020 | 10036 | 1239 |
| 590720 | 871 | 887 | AGAAATTCTGACAAGTT | eeekkddddddddkkeee | 8 | 10021 | 10037 | 1240 |
| 590721 | 872 | 888 | AAGAAATTCTGACAAGT | eeekkddddddddkkeee | 18 | 10022 | 10038 | 1241 |
| 590722 | 891 | 907 | TTCACAGGCTTGAATGA | eeekkddddddddkkeee | 9 | 10041 | 10057 | 1242 |
| 590723 | 892 | 908 | ATTCACAGGCTTGAATG | eeekkddddddddkkeee | 11 | 10042 | 10058 | 1243 |
| 590724 | 893 | 909 | TATTCACAGGCTTGAAT | eeekkddddddddkkeee | 0 | 10043 | 10059 | 1244 |
| 590725 | 894 | 910 | TTATTCACAGGCTTGAA | eeekkddddddddkkeee | 10 | 10044 | 10060 | 1245 |
| 590726 | 895 | 911 | TTTATTCACA | eeekkddddddddkkeee | 29 | 10045 | 10061 | 1246 |

TABLE 16-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| | | | GGCTTGA | | | | | |
| 590727 | 896 | 912 | TTTTATTCACAGGCTTG | eeekkddddddddkkeee | 28 | 10046 | 10062 | 1247 |
| 590728 | 897 | 913 | TTTTTATTCACAGGCTT | eeekkddddddddkkeee | 31 | 10047 | 10063 | 1248 |
| 590729 | 898 | 914 | GTTTTTATTCACAGGCT | eeekkddddddddkkeee | 10 | 10048 | 10064 | 1249 |
| 590731 | 899 | 915 | GGTTTTTATTCACAGGC | eeekkddddddddkkeee | 22 | 10049 | 10065 | 1250 |
| 590732 | 900 | 916 | GGGTTTTTATTCACAGG | eeekkddddddddkkeee | 17 | 10050 | 10066 | 1251 |
| 590733 | 901 | 917 | AGGGTTTTTATTCACAG | eeekkddddddddkkeee | 24 | 10051 | 10067 | 1252 |
| 590734 | 902 | 918 | CAGGGTTTTTATTCACA | eeekkddddddddkkeee | 17 | 10052 | 10068 | 1253 |
| 590735 | 903 | 919 | ACAGGGTTTTTATTCAC | eeekkddddddddkkeee | 10 | 10053 | 10069 | 1254 |
| 590736 | 904 | 920 | TACAGGGTTTTTATTCA | eeekkddddddddkkeee | 11 | 10054 | 10070 | 1255 |
| 590737 | 905 | 921 | ATACAGGGTTTTTATTC | eeekkddddddddkkeee | 3 | 10055 | 10071 | 1256 |
| 590738 | 906 | 922 | CATACAGGGTTTTTATT | eeekkddddddddkkeee | 0 | 10056 | 10072 | 1257 |
| 590739 | 907 | 923 | CCATACAGGGTTTTTAT | eeekkddddddddkkeee | 1 | 10057 | 10073 | 1258 |
| 590740 | 908 | 924 | GCCATACAGGGTTTTTA | eeekkddddddddkkeee | 11 | 10058 | 10074 | 1259 |
| 590741 | 909 | 925 | TGCCATACAGGGTTTTT | eeekkddddddddkkeee | 9 | 10059 | 10075 | 1260 |
| 590742 | 910 | 926 | GTGCCATACAGGGTTTT | eeekkddddddddkkeee | 7 | 10060 | 10076 | 1261 |
| 590743 | 911 | 927 | AGTGCCATACAGGGTTT | eeekkddddddddkkeee | 9 | 10061 | 10077 | 1262 |
| 590744 | 938 | 954 | TTGGATTCTTTTAATAG | eeekkddddddddkkeee | 8 | 10088 | 10104 | 1263 |
| 590745 | 951 | 967 | TTTTAGTTTGAATTTGG | eeekkddddddddkkeee | 12 | n/a | n/a | 1264 |

TABLE 17

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 333611 | 167 | 186 | CCGTCGCCCTTCAGCACGCA | eeeeddddddddddeeeee | 66 | 973 | 992 | 21 |
| 590067 | 202 | 221 | CCTTCTGCTCGAAATTGATG | eeeeddddddddddeeeee | 53 | 1008 | 1027 | 120 |
| 590074 | 209 | 228 | TTACTTTCCTTCTGCTCGAA | eeeeddddddddddeeeee | 30 | n/a | n/a | 127 |
| 590457 | 211 | 227 | TACTTTCCTTCTGCTCG | eeekddddddddkeee | 14 | n/a | n/a | 980 |
| 590458 | 212 | 228 | TTACTTTCCTTCTGCTC | eeekddddddddkeee | 22 | n/a | n/a | 981 |
| 590459 | 213 | 229 | ATTACTTTCCTTCTGCT | eeekddddddddkeee | 15 | n/a | n/a | 982 |
| 590461 | 214 | 230 | CATTACTTTCCTTCTGC | eeekddddddddkeee | 28 | n/a | n/a | 983 |
| 590462 | 215 | 231 | CCATTACTTTCCTTCTG | eeekddddddddkeee | 37 | n/a | n/a | 984 |
| 590463 | 216 | 232 | TCCATTACTTTCCTTCT | eeekddddddddkeee | 18 | n/a | n/a | 985 |
| 590082 | 217 | 236 | CTGGTCCATTACTTTCCTTC | eeeeddddddddddeeeee | 50 | n/a | n/a | 135 |
| 590464 | 217 | 233 | GTCCATTACTTTCCTTC | eeekddddddddkeee | 33 | n/a | n/a | 986 |
| 590465 | 218 | 234 | GGTCCATTACTTTCCTT | eeekddddddddkeee | 18 | 4972 | 4988 | 987 |
| 590130 | 363 | 382 | TTCATCCTTTGGCCCACCGT | eeeeddddddddddeeeee | 30 | 7679 | 7698 | 194 |
| 590536 | 363 | 379 | ATCCTTTGGCCCACCGT | eeekddddddddkeee | 51 | 7679 | 7695 | 1056 |
| 590537 | 364 | 380 | CATCCTTTGGCCCACCG | eeekddddddddkeee | 38 | 7680 | 7696 | 1057 |
| 590538 | 365 | 381 | TCATCCTTTGGCCCACC | eeekddddddddkeee | 27 | 7681 | 7697 | 1058 |
| 590539 | 366 | 382 | TTCATCCTTTGGCCCAC | eeekddddddddkeee | 26 | 7682 | 7698 | 1059 |
| 590540 | 367 | 383 | CTTCATCCTTTGGCCCA | eeekddddddddkeee | 35 | 7683 | 7699 | 1060 |
| 590541 | 368 | 384 | TCTTCATCCTTTGGCCC | eeekddddddddkeee | 15 | 7684 | 7700 | 1061 |
| 590542 | 369 | 385 | CTCTTCATCCTTTGGCC | eeekddddddddkeee | 26 | 7685 | 7701 | 1062 |
| 590543 | 370 | 386 | TCTCTTCATCCTTTGGC | eeekddddddddkeee | 14 | 7686 | 7702 | 1063 |
| 590138 | 371 | 390 | TGCCTCTCTTCATCCTTTGG | eeeeddddddddddeeeee | 32 | n/a | n/a | 202 |
| 590146 | 505 | 524 | CATCTGCTTTTTCATGGACC | eeeeddddddddddeeeee | 46 | 9655 | 9674 | 211 |
| 590613 | 608 | 624 | CAAGGGAATGTTTATTG | eeekddddddddkeee | 19 | 9758 | 9774 | 1133 |

TABLE 17-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 590614 | 609 | 625 | CCAAGGGAATGTTTATT | eeekkddddddddkkeee | 36 | 9759 | 9775 | 1134 |
| 590615 | 610 | 626 | TCCAAGGGAATGTTTAT | eeekkddddddddkkeee | 32 | 9760 | 9776 | 1135 |
| 590616 | 611 | 627 | ATCCAAGGGAATGTTTA | eeekkddddddddkkeee | 42 | 9761 | 9777 | 1136 |
| 590617 | 612 | 628 | CATCCAAGGGAATGTTT | eeekkddddddddkkeee | 16 | 9762 | 9778 | 1137 |
| 590618 | 613 | 629 | ACATCCAAGGGAATGTT | eeekkddddddddkkeee | 30 | 9763 | 9779 | 1138 |
| 590619 | 614 | 630 | TACATCCAAGGGAATGT | eeekkddddddddkkeee | 30 | 9764 | 9780 | 1139 |
| 590620 | 615 | 631 | CTACATCCAAGGGAATG | eeekkddddddddkkeee | 40 | 9765 | 9781 | 1140 |
| 590690 | 826 | 842 | AAAATACAGGTCATTGA | eeekkddddddddkkeee | 28 | 9976 | 9992 | 1210 |
| 590691 | 827 | 843 | CAAAATACAGGTCATTG | eeekkddddddddkkeee | 23 | 9977 | 9993 | 1211 |
| 590692 | 828 | 844 | GCAAAATACAGGTCATT | eeekkddddddddkkeee | 43 | 9978 | 9994 | 1212 |
| 590693 | 829 | 845 | GGCAAAATACAGGTCAT | eeekkddddddddkkeee | 39 | 9979 | 9995 | 1213 |
| 590694 | 830 | 846 | TGGCAAAATACAGGTCA | eeekkddddddddkkeee | 26 | 9980 | 9996 | 1214 |
| 590695 | 831 | 847 | CTGGCAAAATACAGGTC | eeekkddddddddkkeee | 18 | 9981 | 9997 | 1215 |
| 590696 | 832 | 848 | TCTGGCAAAATACAGGT | eeekkddddddddkkeee | 0 | 9982 | 9998 | 1216 |
| 590697 | 833 | 849 | GTCTGGCAAAATACAGG | eeekkddddddddkkeee | 24 | 9983 | 9999 | 1217 |

Example 4: Inhibition of Human SOD-1 in HepG2 Cells by Deoxy, MOE and cEt Gapmers Modified oligonucleotides were designed targeting a superoxide dismutase 1, soluble (SOD-1) nucleic acid and were tested for their effects on SOD-1 mRNA in vitro. ISIS 333611, a 5-10-5 MOE gapmer which was previously described in WO 2005/040180, was included as a benchmark.

The modified oligonucleotides were tested in a series of experiments that had similar culture conditions. The results for each experiment are presented in separate tables shown below. Cultured HepG2 cells at a density of 20,000 cells per well were transfected using electroporation with 4,000 nM modified oligonucleotide. After a treatment period of approximately 24 hours, RNA was isolated from the cells and SOD-1 mRNA levels were measured by quantitative real-time PCR.

Human primer probe set RTS3898 was used to measure mRNA levels. SOD-1 mRNA levels were adjusted according to total RNA content, as measured by RIBOGREEN®. Results are presented as percent inhibition of SOD-1, relative to untreated control cells. 'n.d.' indicates that inhibition levels were not measured.

The newly designed modified oligonucleotides in the Tables below were designed as deoxy, MOE, and cEt gapmers or 5-10-5 gapmers. The 5-10-5 MOE gapmers are 20 nucleosides in length, wherein the central gap segment is comprised of ten 2'-deoxyribonucleosides and is flanked by wing segments on the 5' direction and the 3' direction comprising five nucleosides each. Each nucleoside in the 5' wing segment and each nucleoside in the 3' wing segment has a 2'-MOE modification. The deoxy, MOE and cEt oligonucleotides are 17 nucleosides in length wherein the nucleoside has a MOE sugar modification, a cEt sugar modification, or a deoxy moiety. The sugar chemistry of each oligonucleotide is denoted as in the Chemistry column, where 'l' indicates a cEt modified sugar; 'd' indicates a 2'-deoxyribose; and 'e' indicates a 2'-MOE modified sugar.

The internucleoside linkages throughout each gapmer are phosphorothioate linkages. All cytosine residues throughout each gapmer are 5-methylcytosines. "Start site" indicates the 5'-most nucleoside to which the gapmer is targeted in the human gene sequence. Each gapmer listed in the Tables below is targeted to either the human SOD-1 mRNA, designated herein as SEQ ID NO: 1 (GENBANK Accession No. NM_000454.4) or the human SOD-1 genomic sequence, designated herein as SEQ ID NO: 2 (GENBANK Accession No. NT_011512.10 truncated from nucleotides 18693000 to Ser. No. 18/704,000). 'n/a' indicates that the modified oligonucleotide does not target that particular gene sequence with 100% complementarity.

TABLE 18

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 596168 | 3 | 22 | CTCGCCCACTCTGGCCCCAA | 45 | 809 | 828 | 1265 |
| 596169 | 5 | 24 | GCCTCGCCCACTCTGGCCCC | 37 | 811 | 830 | 1266 |
| 596170 | 7 | 26 | GCGCCTCGCCCACTCTGGCC | 33 | 813 | 832 | 1267 |
| 596171 | 9 | 28 | CCGCGCCTCGCCCACTCTGG | 27 | 815 | 834 | 1268 |
| 596172 | 11 | 30 | CTCCGCGCCTCGCCCACTCT | 40 | 817 | 836 | 1269 |
| 596173 | 13 | 32 | ACCTCCGCGCCTCGCCCACT | 77 | 819 | 838 | 1270 |
| 596174 | 15 | 34 | AGACCTCCGCGCCTCGCCCA | 72 | 821 | 840 | 1271 |
| 596175 | 17 | 36 | CCAGACCTCCGCGCCTCGCC | 46 | 823 | 842 | 1272 |
| 596176 | 19 | 38 | GGCCAGACCTCCGCGCCTCG | 49 | 825 | 844 | 1273 |
| 150508 | 21 | 40 | TAGGCCAGACCTCCGCGCCT | 33 | 827 | 846 | 107 |
| 596177 | 23 | 42 | TATAGGCCAGACCTCCGCGC | 40 | 829 | 848 | 1274 |
| 596178 | 25 | 44 | TTTATAGGCCAGACCTCCGC | 69 | 831 | 850 | 1275 |
| 150509 | 27 | 46 | ACTTTATAGGCCAGACCTCC | 64 | 833 | 852 | 108 |
| 596179 | 31 | 50 | GACTACTTTATAGGCCAGAC | 74 | 837 | 856 | 1276 |
| 596180 | 33 | 52 | GCGACTACTTTATAGGCCAG | 19 | 839 | 858 | 1277 |
| 596181 | 37 | 56 | CTCCGCGACTACTTTATAGG | 27 | 843 | 862 | 1278 |
| 596182 | 39 | 58 | GTCTCCGCGACTACTTTATA | 22 | 845 | 864 | 1279 |
| 596183 | 41 | 60 | CCGTCTCCGCGACTACTTTA | 20 | 847 | 866 | 1280 |
| 596184 | 43 | 62 | CCCCGTCTCCGCGACTACTT | 16 | 849 | 868 | 1281 |
| 596185 | 45 | 64 | CACCCCGTCTCCGCGACTAC | 13 | 851 | 870 | 1282 |
| 596186 | 47 | 66 | AGCACCCCGTCTCCGCGACT | 24 | 853 | 872 | 1283 |
| 596187 | 49 | 68 | CCAGCACCCCGTCTCCGCGA | 38 | 855 | 874 | 1284 |
| 596188 | 51 | 70 | AACCAGCACCCCGTCTCCGC | 11 | 857 | 876 | 1285 |
| 596189 | 53 | 72 | CAAACCAGCACCCCGTCTCC | 13 | 859 | 878 | 1286 |
| 596190 | 55 | 74 | CGCAAACCAGCACCCCGTCT | 21 | 861 | 880 | 1287 |
| 150510 | 57 | 76 | GACGCAAACCAGCACCCCGT | 45 | 863 | 882 | 109 |
| 596191 | 59 | 78 | ACGACGCAAACCAGCACCCC | 30 | 865 | 884 | 1288 |
| 596192 | 61 | 80 | CTACGACGCAAACCAGCACC | 19 | 867 | 886 | 1289 |
| 596193 | 63 | 82 | GACTACGACGCAAACCAGCA | 40 | 869 | 888 | 1290 |
| 596194 | 65 | 84 | GAGACTACGACGCAAACCAG | 23 | 871 | 890 | 1291 |
| 596195 | 67 | 86 | AGGAGACTACGACGCAAACC | 35 | 873 | 892 | 1292 |

TABLE 18-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 596196 | 69 | 88 | GCAGGAGACTACGACGCAAA | 33 | 875 | 894 | 1293 |
| 596197 | 71 | 90 | CTGCAGGAGACTACGACGCA | 36 | 877 | 896 | 1294 |
| 596198 | 73 | 92 | CGCTGCAGGAGACTACGACG | 23 | 879 | 898 | 1295 |
| 596199 | 91 | 110 | TGCAACGGAAACCCCAGACG | 21 | 897 | 916 | 1296 |
| 596200 | 93 | 112 | ACTGCAACGGAAACCCCAGA | 43 | 899 | 918 | 1297 |
| 596201 | 97 | 116 | GAGGACTGCAACGGAAACCC | 24 | 903 | 922 | 1298 |
| 596202 | 99 | 118 | CCGAGGACTGCAACGGAAAC | 29 | 905 | 924 | 1299 |
| 596203 | 101 | 120 | TTCCGAGGACTGCAACGGAA | 5 | 907 | 926 | 1300 |
| 150438 | 103 | 122 | GGTTCCGAGGACTGCAACGG | 35 | 909 | 928 | 110 |
| 345716 | 105 | 124 | CTGGTTCCGAGGACTGCAAC | 51 | 911 | 930 | 1301 |
| 150439 | 107 | 126 | TCCTGGTTCCGAGGACTGCA | 24 | 913 | 932 | 111 |
| 596204 | 109 | 128 | GGTCCTGGTTCCGAGGACTG | 14 | 915 | 934 | 1302 |
| 150440 | 111 | 130 | GAGGTCCTGGTTCCGAGGAC | 31 | 917 | 936 | 112 |
| 596205 | 113 | 132 | CCGAGGTCCTGGTTCCGAGG | 18 | 919 | 938 | 1303 |
| 345718 | 115 | 134 | CGCCGAGGTCCTGGTTCCGA | 24 | 921 | 940 | 1304 |
| 596206 | 117 | 136 | CACGCCGAGGTCCTGGTTCC | 23 | 923 | 942 | 1305 |
| 596207 | 119 | 138 | GCCACGCCGAGGTCCTGGTT | 38 | 925 | 944 | 1306 |
| 596208 | 123 | 142 | CTAGGCCACGCCGAGGTCCT | 39 | 929 | 948 | 1307 |
| 345720 | 125 | 144 | CGCTAGGCCACGCCGAGGTC | 52 | 931 | 950 | 1308 |
| 596209 | 127 | 146 | CTCGCTAGGCCACGCCGAGG | 46 | 933 | 952 | 1309 |
| 596210 | 129 | 148 | AACTCGCTAGGCCACGCCGA | 44 | 935 | 954 | 1310 |
| 596211 | 131 | 150 | ATAACTCGCTAGGCCACGCC | 12 | 937 | 956 | 1311 |
| 596212 | 133 | 152 | CCATAACTCGCTAGGCCACG | 22 | 939 | 958 | 1312 |
| 345722 | 135 | 154 | CGCCATAACTCGCTAGGCCA | 59 | 941 | 960 | 1313 |
| 150442 | 137 | 156 | GTCGCCATAACTCGCTAGGC | 40 | 943 | 962 | 113 |
| 146143 | 157 | 176 | TCAGCACGCACACGGCCTTC | 52 | 963 | 982 | 114 |
| 195753 | 159 | 178 | CTTCAGCACGCACACGGCCT | 57 | 965 | 984 | 115 |
| 333607 | 161 | 180 | CCCTTCAGCACGCACACGGC | 37 | 967 | 986 | 116 |
| 333608 | 163 | 182 | CGCCCTTCAGCACGCACACG | 23 | 969 | 988 | 117 |
| 333611 | 167 | 186 | CCGTCGCCCTTCAGCACGCA | 67 | 973 | 992 | 21 |
| 596213 | 171 | 190 | TGGGCCGTCGCCCTTCAGCA | 12 | 977 | 996 | 1314 |
| 596214 | 173 | 192 | ACTGGGCCGTCGCCCTTCAG | 26 | 979 | 998 | 1315 |
| 596215 | 175 | 194 | GCACTGGGCCGTCGCCCTTC | 14 | 981 | 1000 | 1316 |
| 596216 | 177 | 196 | CTGCACTGGGCCGTCGCCCT | 24 | 983 | 1002 | 1317 |
| 596217 | 181 | 200 | TGCCCTGCACTGGGCCGTCG | 38 | 987 | 1006 | 1318 |
| 596218 | 183 | 202 | GATGCCCTGCACTGGGCCGT | 15 | 989 | 1008 | 1319 |

TABLE 18-continued

Percent inhibition of SOD-1 mRNA by 5-10-5 MOE gapmers targeting SEQ ID NO: 1 and/or 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 596219 | 185 | 204 | ATGATGCCCTGCACTGGGCC | 20 | 991 | 1010 | 1320 |
| 596220 | 189 | 208 | ATTGATGATGCCCTGCACTG | 8 | 995 | 1014 | 1321 |
| 596221 | 191 | 210 | AAATTGATGATGCCCTGCAC | 14 | 997 | 1016 | 1322 |
| 596222 | 193 | 212 | CGAAATTGATGATGCCCTGC | 32 | 999 | 1018 | 1323 |
| 596223 | 195 | 214 | CTCGAAATTGATGATGCCCT | 31 | 1001 | 1020 | 1324 |
| 596224 | 197 | 216 | TGCTCGAAATTGATGATGCC | 20 | 1003 | 1022 | 1325 |
| 596225 | 199 | 218 | TCTGCTCGAAATTGATGATG | 14 | 1005 | 1024 | 1326 |
| 596226 | 201 | 220 | CTTCTGCTCGAAATTGATGA | 11 | 1007 | 1026 | 1327 |
| 596227 | 240 | 259 | TTTAATGCTTCCCCACACCT | 15 | 4994 | 5013 | 1328 |
| 596228 | 242 | 261 | CCTTTAATGCTTCCCCACAC | 1 | 4996 | 5015 | 1329 |
| 596229 | 244 | 263 | GTCCTTTAATGCTTCCCCAC | 9 | 4998 | 5017 | 1330 |

TABLE 19

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 596530 | 164 | 180 | CCCTTCAGCACGCACAC | eekkddddddddddkkeee | 74 | 970 | 986 | 1331 |
| 596721 | 164 | 180 | CCCTTCAGCACGCACAC | eekkddddddddddkkee | 81 | 970 | 986 | 1331 |
| 596531 | 165 | 181 | GCCCTTCAGCACGCACA | eekkddddddddddkkeee | 75 | 971 | 987 | 1332 |
| 596722 | 165 | 181 | GCCCTTCAGCACGCACA | eekkddddddddddkkee | 60 | 971 | 987 | 1332 |
| 596532 | 166 | 182 | CGCCCTTCAGCACGCAC | eekkddddddddddkkeee | 67 | 972 | 988 | 1333 |
| 596723 | 166 | 182 | CGCCCTTCAGCACGCAC | eekkddddddddddkkee | 73 | 972 | 988 | 1333 |
| 333611 | 167 | 186 | CCGTCGCCCTTCAGCACGCA | eeeeddddddddddeeeee | 73 | 973 | 992 | 21 |
| 596720 | 167 | 183 | TCGCCCTTCAGCACGCA | eekkddddddddddkkeee | 56 | 973 | 989 | 966 |
| 596911 | 167 | 183 | TCGCCCTTCAGCACGCA | eekkddddddddddkkee | 63 | 973 | 989 | 966 |
| 596533 | 168 | 184 | GTCGCCCTTCAGCACGC | eekkddddddddddkkeee | 60 | 974 | 990 | 967 |
| 596724 | 168 | 184 | GTCGCCCTTCAGCACGC | eekkddddddddddkkee | 72 | 974 | 990 | 967 |
| 596534 | 169 | 185 | CGTCGCCCTT | eekkddddddddddkkeee | 52 | 975 | 991 | 968 |

TABLE 19-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 596725 | 169 | 185 | CGTCGCCCTTCAGCACG | eekkddddddddddkkee | 43 | 975 | 991 | 968 |
| 596535 | 170 | 186 | CCGTCGCCCTTCAGCAC | eekkddddddddddkkeee | 71 | 976 | 992 | 969 |
| 596726 | 170 | 186 | CCGTCGCCCTTCAGCAC | eekkddddddddddkkee | 75 | 976 | 992 | 969 |
| 596536 | 171 | 187 | GCCGTCGCCCTTCAGCA | eekkddddddddddkkeee | 64 | 977 | 993 | 970 |
| 596727 | 171 | 187 | GCCGTCGCCCTTCAGCA | eekkddddddddddkkee | 57 | 977 | 993 | 970 |
| 596537 | 577 | 593 | CACCACAAGCCAAACGA | eekkddddddddddkkeee | 48 | 9727 | 9743 | 1334 |
| 596728 | 577 | 593 | CACCACAAGCCAAACGA | eekkddddddddddkkee | 46 | 9727 | 9743 | 1334 |
| 596538 | 578 | 594 | ACACCACAAGCCAAACG | eekkddddddddddkkeee | 27 | 9728 | 9744 | 1335 |
| 596729 | 578 | 594 | ACACCACAAGCCAAACG | eekkddddddddddkkee | 45 | 9728 | 9744 | 1335 |
| 596539 | 579 | 595 | TACACCACAAGCCAAAC | eekkddddddddddkkeee | 56 | 9729 | 9745 | 1336 |
| 596730 | 579 | 595 | TACACCACAAGCCAAAC | eekkddddddddddkkee | 63 | 9729 | 9745 | 1336 |
| 596540 | 580 | 596 | TTACACCACAAGCCAAA | eekkddddddddddkkeee | 60 | 9730 | 9746 | 1337 |
| 596731 | 580 | 596 | TTACACCACAAGCCAAA | eekkddddddddddkkee | 63 | 9730 | 9746 | 1337 |
| 596541 | 581 | 597 | ATTACACCACAAGCCAA | eekkddddddddddkkeee | 46 | 9731 | 9747 | 1338 |
| 596732 | 581 | 597 | ATTACACCACAAGCCAA | eekkddddddddddkkee | 63 | 9731 | 9747 | 1338 |
| 596542 | 582 | 598 | AATTACACCACAAGCCA | eekkddddddddddkkeee | 62 | 9732 | 9748 | 1111 |
| 596733 | 582 | 598 | AATTACACCACAAGCCA | eekkddddddddddkkee | 56 | 9732 | 9748 | 1111 |
| 596543 | 583 | 599 | CAATTACACCACAAGCC | eekkddddddddddkkeee | 58 | 9733 | 9749 | 1112 |
| 596734 | 583 | 599 | CAATTACACCACAAGCC | eekkddddddddddkkee | 61 | 9733 | 9749 | 1112 |
| 596544 | 584 | 600 | CCAATTACACCACAAGC | eekkddddddddddkkeee | 66 | 9734 | 9750 | 1113 |
| 596735 | 584 | 600 | CCAATTACACCACAAGC | eekkddddddddddkkee | 73 | 9734 | 9750 | 1113 |
| 596545 | 585 | 601 | CCCAATTACACCACAAG | eekkddddddddddkkeee | 63 | 9735 | 9751 | 1114 |
| 596736 | 585 | 601 | CCCAATTACACCACAAG | eekkddddddddddkkee | 74 | 9735 | 9751 | 1114 |

TABLE 19-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 596546 | 588 | 604 | GATCCCAATTACACCAC | eekkddddddddkkeee | 41 | 9738 | 9754 | 1115 |
| 596737 | 588 | 604 | GATCCCAATTACACCAC | eekkddddddddkkee | 58 | 9738 | 9754 | 1115 |
| 596547 | 589 | 605 | CGATCCCAATTACACCA | eekkddddddddkkeee | 57 | 9739 | 9755 | 1116 |
| 596738 | 589 | 605 | CGATCCCAATTACACCA | eekkddddddddkkee | 59 | 9739 | 9755 | 1116 |
| 596548 | 590 | 606 | GCGATCCCAATTACACC | eekkddddddddkkeee | 31 | 9740 | 9756 | 1117 |
| 596739 | 590 | 606 | GCGATCCCAATTACACC | eekkddddddddkkee | 58 | 9740 | 9756 | 1117 |
| 596549 | 591 | 607 | GGCGATCCCAATTACAC | eekkddddddddkkeee | 33 | 9741 | 9757 | 1118 |
| 596740 | 591 | 607 | GGCGATCCCAATTACAC | eekkddddddddkkee | 66 | 9741 | 9757 | 1118 |
| 596550 | 592 | 608 | GGGCGATCCCAATTACA | eekkddddddddkkeee | 30 | 9742 | 9758 | 1119 |
| 596741 | 592 | 608 | GGGCGATCCCAATTACA | eekkddddddddkkee | 30 | 9742 | 9758 | 1119 |
| 596551 | 593 | 609 | TGGGCGATCCCAATTAC | eekkddddddddkkeee | 19 | 9743 | 9759 | 1120 |
| 596742 | 593 | 609 | TGGGCGATCCCAATTAC | eekkddddddddkkee | 46 | 9743 | 9759 | 1120 |
| 596552 | 594 | 610 | TTGGGCGATCCCAATTA | eekkddddddddkkeee | 14 | 9744 | 9760 | 1121 |
| 596743 | 594 | 610 | TTGGGCGATCCCAATTA | eekkddddddddkkee | 5 | 9744 | 9760 | 1121 |
| 596553 | 595 | 611 | ATTGGGCGATCCCAATT | eekkddddddddkkeee | 2 | 9745 | 9761 | 1122 |
| 596744 | 595 | 611 | ATTGGGCGATCCCAATT | eekkddddddddkkee | 23 | 9745 | 9761 | 1122 |
| 596554 | 596 | 612 | TATTGGGCGATCCCAAT | eekkddddddddkkeee | 19 | 9746 | 9762 | 1123 |
| 596745 | 596 | 612 | TATTGGGCGATCCCAAT | eekkddddddddkkee | 6 | 9746 | 9762 | 1123 |
| 596555 | 597 | 613 | TTATTGGGCGATCCCAA | eekkddddddddkkeee | 41 | 9747 | 9763 | 1124 |
| 596746 | 597 | 613 | TTATTGGGCGATCCCAA | eekkddddddddkkee | 41 | 9747 | 9763 | 1124 |
| 596556 | 598 | 614 | TTTATTGGGCGATCCCA | eekkddddddddkkeee | 34 | 9748 | 9764 | 1125 |
| 596747 | 598 | 614 | TTTATTGGGCGATCCCA | eekkddddddddkkee | 46 | 9748 | 9764 | 1125 |
| 596557 | 599 | 615 | GTTTATTGGGCGATCCC | eekkddddddddkkeee | 54 | 9749 | 9765 | 1126 |
| 596748 | 599 | 615 | GTTTATTGGGCGATCCC | eekkddddddddkkee | 68 | 9749 | 9765 | 1126 |

TABLE 19-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
| --- | --- | --- | --- | --- | --- | --- | --- | --- |
| 596558 | 600 | 616 | TGTTTATTGGGCGATCC | eekkddddddddkkeee | 50 | 9750 | 9766 | 1127 |
| 596749 | 600 | 616 | TGTTTATTGGGCGATCC | eekkddddddddkkee | 47 | 9750 | 9766 | 1127 |
| 596559 | 601 | 617 | ATGTTTATTGGGCGATC | eekkddddddddkkeee | 76 | 9751 | 9767 | 1128 |
| 596750 | 601 | 617 | ATGTTTATTGGGCGATC | eekkddddddddkkee | 64 | 9751 | 9767 | 1128 |
| 596560 | 602 | 618 | AATGTTTATTGGGCGAT | eekkddddddddkkeee | 61 | 9752 | 9768 | 1129 |
| 596751 | 602 | 618 | AATGTTTATTGGGCGAT | eekkddddddddkkee | 64 | 9752 | 9768 | 1129 |
| 596561 | 603 | 619 | GAATGTTTATTGGGCGA | eekkddddddddkkeee | 47 | 9753 | 9769 | 1130 |
| 596752 | 603 | 619 | GAATGTTTATTGGGCGA | eekkddddddddkkee | 65 | 9753 | 9769 | 1130 |
| 596562 | 604 | 620 | GGAATGTTTATTGGGCG | eekkddddddddkkeee | 37 | 9754 | 9770 | 1131 |
| 596753 | 604 | 620 | GGAATGTTTATTGGGCG | eekkddddddddkkee | 58 | 9754 | 9770 | 1131 |
| 596563 | 608 | 624 | CAAGGGAATGTTTATTG | eekkddddddddkkeee | 43 | 9758 | 9774 | 1133 |
| 596754 | 608 | 624 | CAAGGGAATGTTTATTG | eekkddddddddkkee | 38 | 9758 | 9774 | 1133 |
| 596564 | 609 | 625 | CCAAGGGAATGTTTATT | eekkddddddddkkeee | 57 | 9759 | 9775 | 1134 |
| 596755 | 609 | 625 | CCAAGGGAATGTTTATT | eekkddddddddkkee | 52 | 9759 | 9775 | 1134 |
| 596565 | 610 | 626 | TCCAAGGGAATGTTTAT | eekkddddddddkkeee | 27 | 9760 | 9776 | 1135 |
| 596756 | 610 | 626 | TCCAAGGGAATGTTTAT | eekkddddddddkkee | 57 | 9760 | 9776 | 1135 |
| 596566 | 611 | 627 | ATCCAAGGGAATGTTTA | eekkddddddddkkeee | 35 | 9761 | 9777 | 1136 |
| 596757 | 611 | 627 | ATCCAAGGGAATGTTTA | eekkddddddddkkee | 39 | 9761 | 9777 | 1136 |
| 596567 | 616 | 632 | ACTACATCCAAGGGAAT | eekkddddddddkkeee | 42 | 9766 | 9782 | 1141 |
| 596758 | 616 | 632 | ACTACATCCAAGGGAAT | eekkddddddddkkee | 48 | 9766 | 9782 | 1141 |

TABLE 20

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 333611 | 167 | 186 | CCGTCGCCCTTCAGCACGCA | eeeeedddddddddeeeee | 64 | 973 | 992 | 21 |
| 596720 | 167 | 183 | TCGCCCTTCAGCACGCA | eekkddddddddkkeee | 56 | 973 | 989 | 966 |
| 596911 | 167 | 183 | TCGCCCTTCAGCACGCA | eekkddddddddkkee | 60 | 973 | 989 | 966 |
| 596568 | 617 | 633 | GACTACATCCAAGGGAA | eekkddddddddkkee | 50 | 9767 | 9783 | 1142 |
| 596759 | 617 | 633 | GACTACATCCAAGGGAA | eekkddddddddkkee | 57 | 9767 | 9783 | 1142 |
| 596569 | 618 | 634 | AGACTACATCCAAGGGA | eekkddddddddkkeee | 53 | 9768 | 9784 | 1143 |
| 596760 | 618 | 634 | AGACTACATCCAAGGGA | eekkddddddddkkee | 55 | 9768 | 9784 | 1143 |
| 596570 | 619 | 635 | CAGACTACATCCAAGGG | eekkddddddddkkeee | 81 | 9769 | 9785 | 1144 |
| 596761 | 619 | 635 | CAGACTACATCCAAGGG | eekkddddddddkkee | 78 | 9769 | 9785 | 1144 |
| 596571 | 620 | 636 | TCAGACTACATCCAAGG | eekkddddddddkkeee | 79 | 9770 | 9786 | 1145 |
| 596762 | 620 | 636 | TCAGACTACATCCAAGG | eekkddddddddkkee | 78 | 9770 | 9786 | 1145 |
| 596572 | 621 | 637 | CTCAGACTACATCCAAG | eekkddddddddkkeee | 85 | 9771 | 9787 | 1146 |
| 596763 | 621 | 637 | CTCAGACTACATCCAAG | eekkddddddddkkee | 76 | 9771 | 9787 | 1146 |
| 596573 | 622 | 638 | CCTCAGACTACATCCAA | eekkddddddddkkeee | 73 | 9772 | 9788 | 1147 |
| 596764 | 622 | 638 | CCTCAGACTACATCCAA | eekkddddddddkkee | 87 | 9772 | 9788 | 1147 |
| 596574 | 623 | 639 | GCCTCAGACTACATCCA | eekkddddddddkkeee | 69 | 9773 | 9789 | 1148 |
| 596765 | 623 | 639 | GCCTCAGACTACATCCA | eekkddddddddkkee | 82 | 9773 | 9789 | 1148 |
| 596575 | 624 | 640 | GGCCTCAGACTACATCC | eekkddddddddkkeee | 70 | 9774 | 9790 | 1149 |
| 596766 | 624 | 640 | GGCCTCAGACTACATCC | eekkddddddddkkee | 76 | 9774 | 9790 | 1149 |
| 596576 | 625 | 641 | GGGCCTCAGACTACATC | eekkddddddddkkeee | 55 | 9775 | 9791 | 1150 |
| 596767 | 625 | 641 | GGGCCTCAGACTACATC | eekkddddddddkkee | 58 | 9775 | 9791 | 1150 |
| 596577 | 640 | 656 | AACAGATGAGTTAAGGG | eekkddddddddkkeee | 73 | 9790 | 9806 | 1339 |
| 596768 | 640 | 656 | AACAGATGAGTTAAGGG | eekkddddddddkkee | 86 | 9790 | 9806 | 1339 |
| 596578 | 641 | 657 | TAACAGATGAGTTAAGG | eekkddddddddkkeee | 68 | 9791 | 9807 | 1340 |

TABLE 20-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 596769 | 641 | 657 | TAACAGATGAGTTAAGG | eekkddddddddddkkee | 80 | 9791 | 9807 | 1340 |
| 596579 | 642 | 658 | ATAACAGATGAGTTAAG | eekkddddddddddkkeee | 27 | 9792 | 9808 | 1341 |
| 596770 | 642 | 658 | ATAACAGATGAGTTAAG | eekkddddddddddkkee | 42 | 9792 | 9808 | 1341 |
| 596580 | 643 | 659 | GATAACAGATGAGTTAA | eekkddddddddddkkeee | 41 | 9793 | 9809 | 1151 |
| 596771 | 643 | 659 | GATAACAGATGAGTTAA | eekkddddddddddkkee | 28 | 9793 | 9809 | 1151 |
| 596581 | 644 | 660 | GGATAACAGATGAGTTA | eekkddddddddddkkeee | 63 | 9794 | 9810 | 1152 |
| 596772 | 644 | 660 | GGATAACAGATGAGTTA | eekkddddddddddkkee | 63 | 9794 | 9810 | 1152 |
| 596582 | 645 | 661 | AGGATAACAGATGAGTT | eekkddddddddddkkeee | 84 | 9795 | 9811 | 1153 |
| 596773 | 645 | 661 | AGGATAACAGATGAGTT | eekkddddddddddkkee | 86 | 9795 | 9811 | 1153 |
| 596583 | 646 | 662 | CAGGATAACAGATGAGT | eekkddddddddddkkeee | 95 | 9796 | 9812 | 1154 |
| 596774 | 646 | 662 | CAGGATAACAGATGAGT | eekkddddddddddkkee | 96 | 9796 | 9812 | 1154 |
| 596584 | 647 | 663 | GCAGGATAACAGATGAG | eekkddddddddddkkeee | 79 | 9797 | 9813 | 1155 |
| 596775 | 647 | 663 | GCAGGATAACAGATGAG | eekkddddddddddkkee | 86 | 9797 | 9813 | 1155 |
| 596585 | 651 | 667 | GCTAGCAGGATAACAGA | eekkddddddddddkkeee | 19 | 9801 | 9817 | 1159 |
| 596776 | 651 | 667 | GCTAGCAGGATAACAGA | eekkddddddddddkkee | 43 | 9801 | 9817 | 1159 |
| 596586 | 652 | 668 | AGCTAGCAGGATAACAG | eekkddddddddddkkeee | 57 | 9802 | 9818 | 1160 |
| 596777 | 652 | 668 | AGCTAGCAGGATAACAG | eekkddddddddddkkee | 54 | 9802 | 9818 | 1160 |
| 596587 | 653 | 669 | CAGCTAGCAGGATAACA | eekkddddddddddkkeee | 71 | 9803 | 9819 | 1161 |
| 596778 | 653 | 669 | CAGCTAGCAGGATAACA | eekkddddddddddkkee | 61 | 9803 | 9819 | 1161 |
| 596588 | 654 | 670 | ACAGCTAGCAGGATAAC | eekkddddddddddkkeee | 79 | 9804 | 9820 | 1162 |
| 596779 | 654 | 670 | ACAGCTAGCAGGATAAC | eekkddddddddddkkee | 83 | 9804 | 9820 | 1162 |
| 596589 | 655 | 671 | TACAGCTAGCAGGATAA | eekkddddddddddkkeee | 85 | 9805 | 9821 | 1163 |
| 596780 | 655 | 671 | TACAGCTAGCAGGATAA | eekkddddddddddkkee | 86 | 9805 | 9821 | 1163 |
| 596590 | 656 | 672 | CTACAGCTAG | eekkddddddddddkkeee | 87 | 9806 | 9822 | 1164 |

TABLE 20-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| | | | CAGGATA | | | | | |
| 596781 | 656 | 672 | CTACAGCTAGCAGGATA | eekkddddddddddkkee | 91 | 9806 | 9822 | 1164 |
| 596591 | 657 | 673 | TCTACAGCTAGCAGGAT | eekkddddddddddkkeee | 75 | 9807 | 9823 | 1165 |
| 596782 | 657 | 673 | TCTACAGCTAGCAGGAT | eekkddddddddddkkee | 83 | 9807 | 9823 | 1165 |
| 596592 | 658 | 674 | TTCTACAGCTAGCAGGA | eekkddddddddddkkeee | 74 | 9808 | 9824 | 1166 |
| 596783 | 658 | 674 | TTCTACAGCTAGCAGGA | eekkddddddddddkkee | 79 | 9808 | 9824 | 1166 |
| 596593 | 659 | 675 | TTTCTACAGCTAGCAGG | eekkddddddddddkkeee | 76 | 9809 | 9825 | 1167 |
| 596784 | 659 | 675 | TTTCTACAGCTAGCAGG | eekkddddddddddkkee | 84 | 9809 | 9825 | 1167 |
| 596594 | 660 | 676 | ATTTCTACAGCTAGCAG | eekkddddddddddkkeee | 66 | 9810 | 9826 | 1168 |
| 596785 | 660 | 676 | ATTTCTACAGCTAGCAG | eekkddddddddddkkee | 75 | 9810 | 9826 | 1168 |
| 596595 | 665 | 681 | GATACATTTCTACAGCT | eekkddddddddddkkeee | 64 | 9815 | 9831 | 1171 |
| 596786 | 665 | 681 | GATACATTTCTACAGCT | eekkddddddddddkkee | 77 | 9815 | 9831 | 1171 |
| 596596 | 666 | 682 | GGATACATTTCTACAGC | eekkddddddddddkkeee | 75 | 9816 | 9832 | 1342 |
| 596787 | 666 | 682 | GGATACATTTCTACAGC | eekkddddddddddkkee | 84 | 9816 | 9832 | 1342 |
| 596597 | 667 | 683 | AGGATACATTTCTACAG | eekkddddddddddkkeee | 60 | 9817 | 9833 | 1343 |
| 596788 | 667 | 683 | AGGATACATTTCTACAG | eekkddddddddddkkee | 77 | 9817 | 9833 | 1343 |
| 596598 | 668 | 684 | CAGGATACATTTCTACA | eekkddddddddddkkeee | 79 | 9818 | 9834 | 1344 |
| 596789 | 668 | 684 | CAGGATACATTTCTACA | eekkddddddddddkkee | 85 | 9818 | 9834 | 1344 |
| 596599 | 672 | 688 | TTATCAGGATACATTTC | eekkddddddddddkkeee | 57 | 9822 | 9838 | 1345 |
| 596790 | 672 | 688 | TTATCAGGATACATTTC | eekkddddddddddkkee | 67 | 9822 | 9838 | 1345 |
| 596600 | 674 | 690 | GTTTATCAGGATACATT | eekkddddddddddkkeee | 85 | 9824 | 9840 | 1346 |
| 596791 | 674 | 690 | GTTTATCAGGATACATT | eekkddddddddddkkee | 88 | 9824 | 9840 | 1346 |
| 596601 | 675 | 691 | TGTTTATCAGGATACAT | eekkddddddddddkkeee | 70 | 9825 | 9841 | 1347 |
| 596792 | 675 | 691 | TGTTTATCAGGATACAT | eekkddddddddddkkee | 83 | 9825 | 9841 | 1347 |

TABLE 20-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 596602 | 676 | 692 | ATGTTTATCAGGATACA | eekkddddddddkkeee | 85 | 9826 | 9842 | 1348 |
| 596793 | 676 | 692 | ATGTTTATCAGGATACA | eekkddddddddkkee | 81 | 9826 | 9842 | 1348 |
| 596603 | 677 | 693 | AATGTTTATCAGGATAC | eekkddddddddkkeee | 89 | 9827 | 9843 | 1349 |
| 596794 | 677 | 693 | AATGTTTATCAGGATAC | eekkddddddddkkee | 90 | 9827 | 9843 | 1349 |
| 596604 | 678 | 694 | TAATGTTTATCAGGATA | eekkddddddddkkeee | 90 | 9828 | 9844 | 1350 |
| 596795 | 678 | 694 | TAATGTTTATCAGGATA | eekkddddddddkkee | 85 | 9828 | 9844 | 1350 |
| 596605 | 679 | 695 | TTAATGTTTATCAGGAT | eekkddddddddkkeee | 90 | 9829 | 9845 | 1351 |
| 596796 | 679 | 695 | TTAATGTTTATCAGGAT | eekkddddddddkkee | 92 | 9829 | 9845 | 1351 |

Example 5: Inhibition of Human SOD-1 in HepG2 Cells by Deoxy, MOE and cEt Gapmers Modified oligonucleotides were designed targeting an SOD-1 nucleic acid and were tested for their effects on SOD-1 mRNA in vitro. ISIS 333611, a 5-10-5 MOE gapmer, which was previously described in WO 2005/040180, was included as a benchmark.

The modified oligonucleotides were tested in a series of experiments that had similar culture conditions. The results for each experiment are presented in separate tables shown below. Cultured HepG2 cells at a density of 20,000 cells per well were transfected using electroporation with 5,000 nM modified oligonucleotide. After a treatment period of approximately 24 hours, RNA was isolated from the cells and SOD-1 mRNA levels were measured by quantitative real-time PCR.

Human primer probe set RTS3898 was used to measure mRNA levels. SOD-1 mRNA levels were adjusted according to total RNA content, as measured by RIBOGREEN®. Results are presented as percent inhibition of SOD-1, relative to untreated control cells. 'n.d.' indicates that inhibition levels were not measured.

The newly designed modified oligonucleotides in the Tables below were designed as deoxy, MOE, and cEt gapmers. The gapmers are 17 nucleosides in length wherein each nucleoside has a MOE sugar modification, a cEt sugar modification, or a deoxy moiety. The sugar chemistry of each oligonucleotide is denoted as in the Chemistry column, where 'k' indicates a cEt modified sugar; 'd' indicates a 2'-deoxyribose; and 'e' indicates a 2'-MOE modified sugar. The internucleoside linkages throughout each gapmer are phosphorothioate linkages. All cytosine residues throughout each gapmer are 5-methylcytosines. "Start site" indicates the 5'-most nucleoside to which the gapmer is targeted in the human gene sequence. Each gapmer listed in the Tables below is targeted to either the human SOD-1 mRNA, designated herein as SEQ ID NO: 1 (GENBANK Accession No. NM_000454.4) or the human SOD-1 genomic sequence, designated herein as SEQ ID NO: 2 (GENBANK Accession No. NT_011512.10 truncated from nucleotides 18693000 to Ser. No. 18/704,000). 'n/a' indicates that the modified oligonucleotide does not target that particular gene sequence with 100% complementarity.

TABLE 21

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 333611 | 167 | 186 | CCGTCGCCCTTCAGCACGCA | eeeeddddddddddeeeee | 71 | 973 | 992 | 21 |
| 596720 | 167 | 183 | TCGCCCTTCAGCACGCA | eekkddddddddkkeee | 53 | 973 | 989 | 966 |

TABLE 21-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 596911 | 167 | 183 | TCGCCCTTCAGCACGCA | eekkddddddddddkkee | 61 | 973 | 989 | 966 |
| 596606 | 681 | 697 | GTTTAATGTTTATCAGG | eekkddddddddddkkeee | 87 | 9831 | 9847 | 1352 |
| 596797 | 681 | 697 | GTTTAATGTTTATCAGG | eekkddddddddddkkeee | 92 | 9831 | 9847 | 1352 |
| 596607 | 683 | 699 | GTGTTTAATGTTTATCA | eekkddddddddddkkeee | 86 | 9833 | 9849 | 1172 |
| 596798 | 683 | 699 | GTGTTTAATGTTTATCA | eekkddddddddddkkeee | 86 | 9833 | 9849 | 1172 |
| 596608 | 684 | 700 | AGTGTTTAATGTTTATC | eekkddddddddddkkeee | 88 | 9834 | 9850 | 1173 |
| 596799 | 684 | 700 | AGTGTTTAATGTTTATC | eekkddddddddddkkeee | 80 | 9834 | 9850 | 1173 |
| 596609 | 685 | 701 | CAGTGTTTAATGTTTAT | eekkddddddddddkkeee | 77 | 9835 | 9851 | 1174 |
| 596800 | 685 | 701 | CAGTGTTTAATGTTTAT | eekkddddddddddkkeee | 85 | 9835 | 9851 | 1174 |
| 596610 | 686 | 702 | ACAGTGTTTAATGTTTA | eekkddddddddddkkeee | 83 | 9836 | 9852 | 1175 |
| 596801 | 686 | 702 | ACAGTGTTTAATGTTTA | eekkddddddddddkkeee | 84 | 9836 | 9852 | 1175 |
| 596611 | 690 | 706 | GATTACAGTGTTTAATG | eekkddddddddddkkeee | 54 | 9840 | 9856 | 1179 |
| 596802 | 690 | 706 | GATTACAGTGTTTAATG | eekkddddddddddkkeee | 61 | 9840 | 9856 | 1179 |
| 596612 | 691 | 707 | AGATTACAGTGTTTAAT | eekkddddddddddkkeee | 68 | 9841 | 9857 | 1180 |
| 596803 | 691 | 707 | AGATTACAGTGTTTAAT | eekkddddddddddkkeee | 63 | 9841 | 9857 | 1180 |
| 596613 | 697 | 713 | CTTTTAAGATTACAGTG | eekkddddddddddkkeee | 62 | 9847 | 9863 | 1353 |
| 596804 | 697 | 713 | CTTTTAAGATTACAGTG | eekkddddddddddkkeee | 53 | 9847 | 9863 | 1353 |
| 596614 | 699 | 715 | CACTTTTAAGATTACAG | eekkddddddddddkkeee | 37 | 9849 | 9865 | 1354 |
| 596805 | 699 | 715 | CACTTTTAAGATTACAG | eekkddddddddddkkeee | 49 | 9849 | 9865 | 1354 |
| 596615 | 710 | 726 | TCACACAATTACACTTT | eekkddddddddddkkeee | 28 | 9860 | 9876 | 1355 |
| 596806 | 710 | 726 | TCACACAATTACACTTT | eekkddddddddddkkeee | 39 | 9860 | 9876 | 1355 |
| 596616 | 711 | 727 | GTCACACAATTACACTT | eekkddddddddddkkeee | 28 | 9861 | 9877 | 1356 |
| 596807 | 711 | 727 | GTCACACAATTACACTT | eekkddddddddddkkeee | 35 | 9861 | 9877 | 1356 |
| 596617 | 713 | 729 | AAGTCACACA | eekkddddddddddkkeee | 41 | 9863 | 9879 | 1357 |

TABLE 21-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| | | | ATTACAC | | | | | |
| 596808 | 713 | 729 | AAGTCACACAATTACAC | eekkddddddddddkkee | 37 | 9863 | 9879 | 1357 |
| 596618 | 737 | 753 | AGGTACTTTAAAGCAAC | eekkddddddddddkkeee | 35 | 9887 | 9903 | 1358 |
| 596809 | 737 | 753 | AGGTACTTTAAAGCAAC | eekkddddddddddkkee | 42 | 9887 | 9903 | 1358 |
| 596619 | 739 | 755 | ACAGGTACTTTAAAGCA | eekkddddddddddkkeee | 14 | 9889 | 9905 | 1359 |
| 596810 | 739 | 755 | ACAGGTACTTTAAAGCA | eekkddddddddddkkee | 20 | 9889 | 9905 | 1359 |
| 596620 | 740 | 756 | TACAGGTACTTTAAAGC | eekkddddddddddkkeee | 23 | 9890 | 9906 | 1360 |
| 596811 | 740 | 756 | TACAGGTACTTTAAAGC | eekkddddddddddkkee | 26 | 9890 | 9906 | 1360 |
| 596621 | 741 | 757 | CTACAGGTACTTTAAAG | eekkddddddddddkkeee | 2 | 9891 | 9907 | 1361 |
| 596812 | 741 | 757 | CTACAGGTACTTTAAAG | eekkddddddddddkkee | 16 | 9891 | 9907 | 1361 |
| 596622 | 743 | 759 | CACTACAGGTACTTTAA | eekkddddddddddkkeee | 27 | 9893 | 9909 | 1362 |
| 596813 | 743 | 759 | CACTACAGGTACTTTAA | eekkddddddddddkkee | 38 | 9893 | 9909 | 1362 |
| 596623 | 744 | 760 | TCACTACAGGTACTTTA | eekkddddddddddkkeee | 27 | 9894 | 9910 | 1363 |
| 596814 | 744 | 760 | TCACTACAGGTACTTTA | eekkddddddddddkkee | 35 | 9894 | 9910 | 1363 |
| 596624 | 745 | 761 | CTCACTACAGGTACTTT | eekkddddddddddkkeee | 40 | 9895 | 9911 | 1364 |
| 596815 | 745 | 761 | CTCACTACAGGTACTTT | eekkddddddddddkkee | 54 | 9895 | 9911 | 1364 |
| 596625 | 746 | 762 | TCTCACTACAGGTACTT | eekkddddddddddkkeee | 42 | 9896 | 9912 | 1365 |
| 596816 | 746 | 762 | TCTCACTACAGGTACTT | eekkddddddddddkkee | 46 | 9896 | 9912 | 1365 |
| 596626 | 747 | 763 | TTCTCACTACAGGTACT | eekkddddddddddkkeee | 26 | 9897 | 9913 | 1366 |
| 596817 | 747 | 763 | TTCTCACTACAGGTACT | eekkddddddddddkkee | 37 | 9897 | 9913 | 1366 |
| 596627 | 748 | 764 | TTTCTCACTACAGGTAC | eekkddddddddddkkeee | 35 | 9898 | 9914 | 1367 |
| 596818 | 748 | 764 | TTTCTCACTACAGGTAC | eekkddddddddddkkee | 45 | 9898 | 9914 | 1367 |
| 596628 | 749 | 765 | GTTTCTCACTACAGGTA | eekkddddddddddkkeee | 25 | 9899 | 9915 | 1368 |
| 596819 | 749 | 765 | GTTTCTCACTACAGGTA | eekkddddddddddkkee | 38 | 9899 | 9915 | 1368 |

TABLE 21-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 596629 | 750 | 766 | AGTTTCTCACTACAGGT | eekkddddddddkkeee | 33 | 9900 | 9916 | 1369 |
| 596820 | 750 | 766 | AGTTTCTCACTACAGGT | eekkddddddddddkkee | 50 | 9900 | 9916 | 1369 |
| 596630 | 751 | 767 | CAGTTTCTCACTACAGG | eekkddddddddkkeee | 38 | 9901 | 9917 | 1370 |
| 596821 | 751 | 767 | CAGTTTCTCACTACAGG | eekkddddddddddkkee | 38 | 9901 | 9917 | 1370 |
| 596631 | 752 | 768 | TCAGTTTCTCACTACAG | eekkddddddddkkeee | 25 | 9902 | 9918 | 1371 |
| 596822 | 752 | 768 | TCAGTTTCTCACTACAG | eekkddddddddddkkee | 43 | 9902 | 9918 | 1371 |
| 596632 | 753 | 769 | ATCAGTTTCTCACTACA | eekkddddddddkkeee | 31 | 9903 | 9919 | 1372 |
| 596823 | 753 | 769 | ATCAGTTTCTCACTACA | eekkddddddddddkkee | 44 | 9903 | 9919 | 1372 |
| 596633 | 754 | 770 | AATCAGTTTCTCACTAC | eekkddddddddkkeee | 34 | 9904 | 9920 | 1373 |
| 596824 | 754 | 770 | AATCAGTTTCTCACTAC | eekkddddddddddkkee | 53 | 9904 | 9920 | 1373 |
| 596634 | 761 | 777 | GATCATAAATCAGTTTC | eekkddddddddkkeee | 34 | 9911 | 9927 | 1374 |
| 596825 | 761 | 777 | GATCATAAATCAGTTTC | eekkddddddddddkkee | 38 | 9911 | 9927 | 1374 |
| 596635 | 762 | 778 | TGATCATAAATCAGTTT | eekkddddddddkkeee | 49 | 9912 | 9928 | 1375 |
| 596826 | 762 | 778 | TGATCATAAATCAGTTT | eekkddddddddddkkee | 38 | 9912 | 9928 | 1375 |
| 596636 | 763 | 779 | GTGATCATAAATCAGTT | eekkddddddddkkeee | 33 | 9913 | 9929 | 1376 |
| 596827 | 763 | 779 | GTGATCATAAATCAGTT | eekkddddddddddkkee | 48 | 9913 | 9929 | 1376 |
| 596637 | 764 | 780 | AGTGATCATAAATCAGT | eekkddddddddkkeee | 23 | 9914 | 9930 | 1377 |
| 596828 | 764 | 780 | AGTGATCATAAATCAGT | eekkddddddddddkkee | 32 | 9914 | 9930 | 1377 |
| 596638 | 766 | 782 | CAAGTGATCATAAATCA | eekkddddddddkkeee | 47 | 9916 | 9932 | 1378 |
| 596829 | 766 | 782 | CAAGTGATCATAAATCA | eekkddddddddddkkee | 29 | 9916 | 9932 | 1378 |
| 596639 | 767 | 783 | CCAAGTGATCATAAATC | eekkddddddddkkeee | 40 | 9917 | 9933 | 1379 |
| 596830 | 767 | 783 | CCAAGTGATCATAAATC | eekkddddddddddkkee | 48 | 9917 | 9933 | 1379 |
| 596640 | 768 | 784 | TCCAAGTGATCATAAAT | eekkddddddddkkeee | 42 | 9918 | 9934 | 1380 |
| 596831 | 768 | 784 | TCCAAGTGATCATAAAT | eekkddddddddddkkee | 39 | 9918 | 9934 | 1380 |

TABLE 21-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 596641 | 770 | 786 | CTTCCAAGTGATCATAA | eekkddddddddkkeeee | 40 | 9920 | 9936 | 1381 |
| 596832 | 770 | 786 | CTTCCAAGTGATCATAA | eekkddddddddkkee | 54 | 9920 | 9936 | 1381 |
| 596642 | 771 | 787 | TCTTCCAAGTGATCATA | eekkddddddddkkeeee | 33 | 9921 | 9937 | 1382 |
| 596833 | 771 | 787 | TCTTCCAAGTGATCATA | eekkddddddddkkee | 43 | 9921 | 9937 | 1382 |
| 596643 | 772 | 788 | ATCTTCCAAGTGATCAT | eekkddddddddkkeeee | 38 | 9922 | 9938 | 1184 |
| 596834 | 772 | 788 | ATCTTCCAAGTGATCAT | eekkddddddddkkee | 38 | 9922 | 9938 | 1184 |

TABLE 22

Percent inhibition of SOD-1 mRNA by deoxy, MOE and cEt argeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 333611 | 167 | 186 | CCGTCGCCCTTCAGCACGCA | eeeeddddddddddeeeee | 62 | 973 | 992 | 21 |
| 596720 | 167 | 183 | TCGCCCTTCAGCACGCA | eekkddddddddkkeeee | 53 | 973 | 989 | 966 |
| 596911 | 167 | 183 | TCGCCCTTCAGCACGCA | eekkddddddddkkee | 58 | 973 | 989 | 966 |
| 596644 | 773 | 789 | AATCTTCCAAGTGATCA | eekkddddddddkkeeee | 19 | 9923 | 9939 | 1185 |
| 596835 | 773 | 789 | AATCTTCCAAGTGATCA | eekkddddddddkkee | 38 | 9923 | 9939 | 1185 |
| 596645 | 774 | 790 | AAATCTTCCAAGTGATC | eekkddddddddkkeeee | 46 | 9924 | 9940 | 1186 |
| 596836 | 774 | 790 | AAATCTTCCAAGTGATC | eekkddddddddkkee | 48 | 9924 | 9940 | 1186 |
| 596646 | 782 | 798 | AACTATACAAATCTTCC | eekkddddddddkkeeee | 60 | 9932 | 9948 | 1193 |
| 596837 | 782 | 798 | AACTATACAAATCTTCC | eekkddddddddkkee | 63 | 9932 | 9948 | 1193 |
| 596647 | 783 | 799 | AAACTATACAAATCTTC | eekkddddddddkkeeee | 55 | 9933 | 9949 | 1194 |
| 596838 | 783 | 799 | AAACTATACAAATCTTC | eekkddddddddkkee | 55 | 9933 | 9949 | 1194 |
| 596648 | 806 | 822 | AGACATTTTAACTGAGT | eekkddddddddkkeeee | 46 | 9956 | 9972 | 1383 |
| 596839 | 806 | 822 | AGACATTTTAACTGAGT | eekkddddddddkkee | 53 | 9956 | 9972 | 1383 |

TABLE 22-continued

Percent inhibition of SOD-1 mRNA by deoxy, MOE and cEt argeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 596649 | 817 | 833 | GTCATTGAAACAGACAT | eekkddddddddkkeeee | 2 | 9967 | 9983 | 1201 |
| 596840 | 817 | 833 | GTCATTGAAACAGACAT | eekkddddddddkkee | 15 | 9967 | 9983 | 1201 |
| 596650 | 819 | 835 | AGGTCATTGAAACAGAC | eekkddddddddkkeeee | 40 | 9969 | 9985 | 1203 |
| 596841 | 819 | 835 | AGGTCATTGAAACAGAC | eekkddddddddkkee | 44 | 9969 | 9985 | 1203 |
| 596651 | 822 | 838 | TACAGGTCATTGAAACA | eekkddddddddkkeeee | 26 | 9972 | 9988 | 1206 |
| 596842 | 822 | 838 | TACAGGTCATTGAAACA | eekkddddddddkkee | 38 | 9972 | 9988 | 1206 |
| 596652 | 823 | 839 | ATACAGGTCATTGAAAC | eekkddddddddkkeeee | 33 | 9973 | 9989 | 1207 |
| 596843 | 823 | 839 | ATACAGGTCATTGAAAC | eekkddddddddkkee | 22 | 9973 | 9989 | 1207 |
| 596653 | 825 | 841 | AAATACAGGTCATTGAA | eekkddddddddkkeeee | 28 | 9975 | 9991 | 1209 |
| 596844 | 825 | 841 | AAATACAGGTCATTGAA | eekkddddddddkkee | 47 | 9975 | 9991 | 1209 |
| 596654 | 827 | 843 | CAAAATACAGGTCATTG | eekkddddddddkkeeee | 44 | 9977 | 9993 | 1211 |
| 596845 | 827 | 843 | CAAAATACAGGTCATTG | eekkddddddddkkee | 56 | 9977 | 9993 | 1211 |
| 596655 | 830 | 846 | TGGCAAAATACAGGTCA | eekkddddddddkkeeee | 33 | 9980 | 9996 | 1214 |
| 596846 | 830 | 846 | TGGCAAAATACAGGTCA | eekkddddddddkkee | 43 | 9980 | 9996 | 1214 |
| 596656 | 831 | 847 | CTGGCAAAATACAGGTC | eekkddddddddkkeeee | 25 | 9981 | 9997 | 1215 |
| 596847 | 831 | 847 | CTGGCAAAATACAGGTC | eekkddddddddkkee | 53 | 9981 | 9997 | 1215 |
| 596657 | 833 | 849 | GTCTGGCAAAATACAGG | eekkddddddddkkeeee | 30 | 9983 | 9999 | 1217 |
| 596848 | 833 | 849 | GTCTGGCAAAATACAGG | eekkddddddddkkee | 38 | 9983 | 9999 | 1217 |
| 596658 | 836 | 852 | TAAGTCTGGCAAAATAC | eekkddddddddkkeeee | 24 | 9986 | 10002 | 1220 |
| 596849 | 836 | 852 | TAAGTCTGGCAAAATAC | eekkddddddddkkee | 46 | 9986 | 10002 | 1220 |
| 596659 | 837 | 853 | TTAAGTCTGGCAAAATA | eekkddddddddkkeeee | 27 | 9987 | 10003 | 1221 |
| 596850 | 837 | 853 | TTAAGTCTGGCAAAATA | eekkddddddddkkee | 42 | 9987 | 10003 | 1221 |
| 596660 | 840 | 856 | GATTTAAGTCTGGCAAA | eekkddddddddkkeeee | 19 | 9990 | 10006 | 1384 |
| 596851 | 840 | 856 | GATTTAAGTCTGGCAAA | eekkddddddddkkee | 35 | 9990 | 10006 | 1384 |

TABLE 22-continued

Percent inhibition of SOD-1 mRNA by deoxy, MOE and cEt argeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| | | | TGGCAAA | | | | | |
| 596661 | 841 | 857 | TGATTTAAGTCTGGCAA | eekkddddddddkkeee | 52 | 9991 | 10007 | 1385 |
| 596852 | 841 | 857 | TGATTTAAGTCTGGCAA | eekkddddddddkkeee | 52 | 9991 | 10007 | 1385 |
| 596662 | 842 | 858 | GTGATTTAAGTCTGGCA | eekkddddddddkkeee | 54 | 9992 | 10008 | 1386 |
| 596853 | 842 | 858 | GTGATTTAAGTCTGGCA | eekkddddddddkkeee | 69 | 9992 | 10008 | 1386 |
| 596663 | 843 | 859 | TGTGATTTAAGTCTGGC | eekkddddddddkkeee | 45 | 9993 | 10009 | 1387 |
| 596854 | 843 | 859 | TGTGATTTAAGTCTGGC | eekkddddddddkkeee | 58 | 9993 | 10009 | 1387 |
| 596664 | 844 | 860 | CTGTGATTTAAGTCTGG | eekkddddddddkkeee | n.d. | 9994 | 10010 | 1388 |
| 596855 | 844 | 860 | CTGTGATTTAAGTCTGG | eekkddddddddkkeee | 61 | 9994 | 10010 | 1388 |
| 596665 | 845 | 861 | TCTGTGATTTAAGTCTG | eekkddddddddkkeee | 49 | 9995 | 10011 | 1389 |
| 596856 | 845 | 861 | TCTGTGATTTAAGTCTG | eekkddddddddkkeee | 49 | 9995 | 10011 | 1389 |
| 596666 | 846 | 862 | ATCTGTGATTTAAGTCT | eekkddddddddkkeee | 35 | 9996 | 10012 | 1390 |
| 596857 | 846 | 862 | ATCTGTGATTTAAGTCT | eekkddddddddkkeee | 37 | 9996 | 10012 | 1390 |
| 596667 | 847 | 863 | CATCTGTGATTTAAGTC | eekkddddddddkkeee | 42 | 9997 | 10013 | 1391 |
| 596858 | 847 | 863 | CATCTGTGATTTAAGTC | eekkddddddddkkeee | 48 | 9997 | 10013 | 1391 |
| 596668 | 848 | 864 | CCATCTGTGATTTAAGT | eekkddddddddkkeee | 46 | 9998 | 10014 | 1392 |
| 596859 | 848 | 864 | CCATCTGTGATTTAAGT | eekkddddddddkkeee | 47 | 9998 | 10014 | 1392 |
| 596669 | 849 | 865 | CCCATCTGTGATTTAAG | eekkddddddddkkeee | 49 | 9999 | 10015 | 1393 |
| 596860 | 849 | 865 | CCCATCTGTGATTTAAG | eekkddddddddkkeee | 49 | 9999 | 10015 | 1393 |
| 596670 | 850 | 866 | ACCCATCTGTGATTTAA | eekkddddddddkkeee | 33 | 10000 | 10016 | 1394 |
| 596861 | 850 | 866 | ACCCATCTGTGATTTAA | eekkddddddddkkeee | 44 | 10000 | 10016 | 1394 |
| 596671 | 851 | 867 | TACCCATCTGTGATTTA | eekkddddddddkkeee | 29 | 10001 | 10017 | 1395 |
| 596862 | 851 | 867 | TACCCATCTGTGATTTA | eekkddddddddkkeee | 45 | 10001 | 10017 | 1395 |
| 596672 | 854 | 870 | TAATACCCATCTGTGAT | eekkddddddddkkeee | 25 | 10004 | 10020 | 1223 |

TABLE 22-continued

Percent inhibition of SOD-1 mRNA by deoxy, MOE and cEt argeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 596863 | 854 | 870 | TAATACCCATCTGTGAT | eekkddddddddddkkee | 28 | 10004 | 10020 | 1223 |
| 596673 | 855 | 871 | TTAATACCCATCTGTGA | eekkddddddddddkkeee | 28 | 10005 | 10021 | 1224 |
| 596864 | 855 | 871 | TTAATACCCATCTGTGA | eekkddddddddddkkee | 26 | 10005 | 10021 | 1224 |
| 596674 | 858 | 874 | AGTTTAATACCCATCTG | eekkddddddddddkkeee | 29 | 10008 | 10024 | 1227 |
| 596865 | 858 | 874 | AGTTTAATACCCATCTG | eekkddddddddddkkee | 43 | 10008 | 10024 | 1227 |
| 596675 | 859 | 875 | AAGTTTAATACCCATCT | eekkddddddddddkkeee | 54 | 10009 | 10025 | 1228 |
| 596866 | 859 | 875 | AAGTTTAATACCCATCT | eekkddddddddddkkeee | 59 | 10009 | 10025 | 1228 |
| 596676 | 860 | 876 | CAAGTTTAATACCCATC | eekkddddddddddkkeee | 52 | 10010 | 10026 | 1229 |
| 596867 | 860 | 876 | CAAGTTTAATACCCATC | eekkddddddddddkkee | 62 | 10010 | 10026 | 1229 |
| 596677 | 861 | 877 | ACAAGTTTAATACCCAT | eekkddddddddddkkeee | 58 | 10011 | 10027 | 1230 |
| 596868 | 861 | 877 | ACAAGTTTAATACCCAT | eekkddddddddddkkee | 61 | 10011 | 10027 | 1230 |
| 596678 | 862 | 878 | GACAAGTTTAATACCCA | eekkddddddddddkkeee | 54 | 10012 | 10028 | 1231 |
| 596869 | 862 | 878 | GACAAGTTTAATACCCA | eekkddddddddddkkee | 59 | 10012 | 10028 | 1231 |
| 596679 | 863 | 879 | TGACAAGTTTAATACCC | eekkddddddddddkkeee | 43 | 10013 | 10029 | 1232 |
| 596870 | 863 | 879 | TGACAAGTTTAATACCC | eekkddddddddddkkee | 52 | 10013 | 10029 | 1232 |
| 596680 | 864 | 880 | CTGACAAGTTTAATACC | eekkddddddddddkkeee | 30 | 10014 | 10030 | 1233 |
| 596871 | 864 | 880 | CTGACAAGTTTAATACC | eekkddddddddddkkee | 36 | 10014 | 10030 | 1233 |
| 596681 | 865 | 881 | TCTGACAAGTTTAATAC | eekkddddddddddkkeee | 33 | 10015 | 10031 | 1234 |
| 596872 | 865 | 881 | TCTGACAAGTTTAATAC | eekkddddddddddkkee | 20 | 10015 | 10031 | 1234 |

TABLE 23

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 333611 | 167 | 186 | CCGTCGCCCTTCAGCACGCA | eeeeedddddddddddeeeee | 68 | 973 | 992 | 21 |
| 596720 | 167 | 183 | TCGCCCTTCAGCACGCA | eekkddddddddkkeee | 64 | 973 | 989 | 966 |
| 596911 | 167 | 183 | TCGCCCTTCAGCACGCA | eekkddddddddkkee | 71 | 973 | 989 | 966 |
| 596682 | 884 | 900 | GCTTGAATGACAAAGAA | eekkddddddddkkeee | 24 | 10034 | 10050 | 1396 |
| 596873 | 884 | 900 | GCTTGAATGACAAAGAA | eekkddddddddkkee | 32 | 10034 | 10050 | 1396 |
| 596683 | 885 | 901 | GGCTTGAATGACAAAGA | eekkddddddddkkeee | 54 | 10035 | 10051 | 1397 |
| 596874 | 885 | 901 | GGCTTGAATGACAAAGA | eekkddddddddkkee | 44 | 10035 | 10051 | 1397 |
| 596684 | 889 | 905 | CACAGGCTTGAATGACA | eekkddddddddkkeee | 34 | 10039 | 10055 | 1398 |
| 596875 | 889 | 905 | CACAGGCTTGAATGACA | eekkddddddddkkee | 47 | 10039 | 10055 | 1398 |
| 596685 | 890 | 906 | TCACAGGCTTGAATGAC | eekkddddddddkkeee | 28 | 10040 | 10056 | 1399 |
| 596876 | 890 | 906 | TCACAGGCTTGAATGAC | eekkddddddddkkee | 46 | 10040 | 10056 | 1399 |
| 596686 | 891 | 907 | TTCACAGGCTTGAATGA | eekkddddddddkkeee | 20 | 10041 | 10057 | 1242 |
| 596877 | 891 | 907 | TTCACAGGCTTGAATGA | eekkddddddddkkee | 16 | 10041 | 10057 | 1242 |
| 596687 | 892 | 908 | ATTCACAGGCTTGAATG | eekkddddddddkkeee | 19 | 10042 | 10058 | 1243 |
| 596878 | 892 | 908 | ATTCACAGGCTTGAATG | eekkddddddddkkee | 29 | 10042 | 10058 | 1243 |
| 596688 | 893 | 909 | TATTCACAGGCTTGAAT | eekkddddddddkkeee | 24 | 10043 | 10059 | 1244 |
| 596879 | 893 | 909 | TATTCACAGGCTTGAAT | eekkddddddddkkee | 11 | 10043 | 10059 | 1244 |
| 596689 | 894 | 910 | TTATTCACAGGCTTGAA | eekkddddddddkkeee | 26 | 10044 | 10060 | 1245 |
| 596880 | 894 | 910 | TTATTCACAGGCTTGAA | eekkddddddddkkee | 30 | 10044 | 10060 | 1245 |
| 596690 | 895 | 911 | TTTATTCACAGGCTTGA | eekkddddddddkkeee | 44 | 10045 | 10061 | 1246 |
| 596881 | 895 | 911 | TTTATTCACAGGCTTGA | eekkddddddddkkee | 55 | 10045 | 10061 | 1246 |
| 596691 | 896 | 912 | TTTTATTCACAGGCTTG | eekkddddddddkkeee | 43 | 10046 | 10062 | 1247 |
| 596882 | 896 | 912 | TTTTATTCACAGGCTTG | eekkddddddddkkee | 48 | 10046 | 10062 | 1247 |
| 596692 | 899 | 915 | GGTTTTTATTCACAGGC | eekkddddddddkkeee | 38 | 10049 | 10065 | 1250 |

TABLE 23-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 596883 | 899 | 915 | GGTTTTTATTCACAGGC | eekkdddddddddkkee | 57 | 10049 | 10065 | 1250 |
| 596693 | 903 | 919 | ACAGGGTTTTTATTCAC | eekkdddddddddkkeee | 29 | 10053 | 10069 | 1254 |
| 596884 | 903 | 919 | ACAGGGTTTTTATTCAC | eekkdddddddddkkee | 47 | 10053 | 10069 | 1254 |
| 596694 | 904 | 920 | TACAGGGTTTTTATTCA | eekkdddddddddkkeee | 13 | 10054 | 10070 | 1255 |
| 596885 | 904 | 920 | TACAGGGTTTTTATTCA | eekkdddddddddkkee | 31 | 10054 | 10070 | 1255 |
| 596695 | 907 | 923 | CCATACAGGGTTTTTAT | eekkdddddddddkkeee | 13 | 10057 | 10073 | 1258 |
| 596886 | 907 | 923 | CCATACAGGGTTTTTAT | eekkdddddddddkkee | 34 | 10057 | 10073 | 1258 |
| 596696 | 908 | 924 | GCCATACAGGGTTTTTA | eekkdddddddddkkeee | 13 | 10058 | 10074 | 1259 |
| 596887 | 908 | 924 | GCCATACAGGGTTTTTA | eekkdddddddddkkee | 26 | 10058 | 10074 | 1259 |
| 596697 | 909 | 925 | TGCCATACAGGGTTTTT | eekkdddddddddkkeee | 21 | 10059 | 10075 | 1260 |
| 596888 | 909 | 925 | TGCCATACAGGGTTTTT | eekkdddddddddkkee | 22 | 10059 | 10075 | 1260 |
| 596698 | 910 | 926 | GTGCCATACAGGGTTTT | eekkdddddddddkkeee | 20 | 10060 | 10076 | 1261 |
| 596889 | 910 | 926 | GTGCCATACAGGGTTTT | eekkdddddddddkkee | 28 | 10060 | 10076 | 1261 |
| 596699 | 911 | 927 | AGTGCCATACAGGGTTT | eekkdddddddddkkeee | 20 | 10061 | 10077 | 1262 |
| 596890 | 911 | 927 | AGTGCCATACAGGGTTT | eekkdddddddddkkee | 27 | 10061 | 10077 | 1262 |
| 596700 | 912 | 928 | AAGTGCCATACAGGGTT | eekkdddddddddkkeee | 15 | 10062 | 10078 | 1400 |
| 596891 | 912 | 928 | AAGTGCCATACAGGGTT | eekkdddddddddkkee | 21 | 10062 | 10078 | 1400 |
| 596701 | 913 | 929 | TAAGTGCCATACAGGGT | eekkdddddddddkkeee | 26 | 10063 | 10079 | 1401 |
| 596892 | 913 | 929 | TAAGTGCCATACAGGGT | eekkdddddddddkkee | 35 | 10063 | 10079 | 1401 |
| 596702 | 914 | 930 | ATAAGTGCCATACAGGG | eekkdddddddddkkeee | 36 | 10064 | 10080 | 1402 |
| 596893 | 914 | 930 | ATAAGTGCCATACAGGG | eekkdddddddddkkee | 46 | 10064 | 10080 | 1402 |
| 596703 | 915 | 931 | AATAAGTGCCATACAGG | eekkdddddddddkkeee | 40 | 10065 | 10081 | 1403 |
| 596894 | 915 | 931 | AATAAGTGCCATACAGG | eekkdddddddddkkee | 36 | 10065 | 10081 | 1403 |
| 596704 | 916 | 932 | TAATAAGTGC | eekkdddddddddkkeee | 22 | 10066 | 10082 | 1404 |

TABLE 23-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| | | | CATACAG | | | | | |
| 596895 | 916 | 932 | TAATAAGTGCCATACAG | eekkddddddddkkeee | 30 | 10066 | 10082 | 1404 |
| 596705 | 917 | 933 | ATAATAAGTGCCATACA | eekkddddddddkkeee | 27 | 10067 | 10083 | 1405 |
| 596896 | 917 | 933 | ATAATAAGTGCCATACA | eekkddddddddkkeee | 27 | 10067 | 10083 | 1405 |
| 596706 | 918 | 934 | CATAATAAGTGCCATAC | eekkddddddddkkeee | 32 | 10068 | 10084 | 1406 |
| 596897 | 918 | 934 | CATAATAAGTGCCATAC | eekkddddddddkkeee | 34 | 10068 | 10084 | 1406 |
| 596707 | 919 | 935 | TCATAATAAGTGCCATA | eekkddddddddkkeee | 28 | 10069 | 10085 | 1407 |
| 596898 | 919 | 935 | TCATAATAAGTGCCATA | eekkddddddddkkeee | 34 | 10069 | 10085 | 1407 |
| 596708 | 920 | 936 | CTCATAATAAGTGCCAT | eekkddddddddkkeee | 30 | 10070 | 10086 | 1408 |
| 596899 | 920 | 936 | CTCATAATAAGTGCCAT | eekkddddddddkkeee | 44 | 10070 | 10086 | 1408 |
| 596709 | 921 | 937 | CCTCATAATAAGTGCCA | eekkddddddddkkeee | 29 | 10071 | 10087 | 1409 |
| 596900 | 921 | 937 | CCTCATAATAAGTGCCA | eekkddddddddkkeee | 31 | 10071 | 10087 | 1409 |
| 596710 | 922 | 938 | GCCTCATAATAAGTGCC | eekkddddddddkkeee | 41 | 10072 | 10088 | 1410 |
| 596901 | 922 | 938 | GCCTCATAATAAGTGCC | eekkddddddddkkeee | 33 | 10072 | 10088 | 1410 |
| 596711 | 923 | 939 | AGCCTCATAATAAGTGC | eekkddddddddkkeee | 16 | 10073 | 10089 | 1411 |
| 596902 | 923 | 939 | AGCCTCATAATAAGTGC | eekkddddddddkkeee | 11 | 10073 | 10089 | 1411 |
| 596712 | 924 | 940 | TAGCCTCATAATAAGTG | eekkddddddddkkeee | 11 | 10074 | 10090 | 1412 |
| 596903 | 924 | 940 | TAGCCTCATAATAAGTG | eekkddddddddkkeee | 27 | 10074 | 10090 | 1412 |
| 596713 | 925 | 941 | ATAGCCTCATAATAAGT | eekkddddddddkkeee | 20 | 10075 | 10091 | 1413 |
| 596904 | 925 | 941 | ATAGCCTCATAATAAGT | eekkddddddddkkeee | 27 | 10075 | 10091 | 1413 |
| 596714 | 926 | 942 | AATAGCCTCATAATAAG | eekkddddddddkkeee | 20 | 10076 | 10092 | 1414 |
| 596905 | 926 | 942 | AATAGCCTCATAATAAG | eekkddddddddkkeee | 25 | 10076 | 10092 | 1414 |
| 596715 | 931 | 947 | CTTTTAATAGCCTCATA | eekkddddddddkkeee | 45 | 10081 | 10097 | 1415 |
| 596906 | 931 | 947 | CTTTTAATAGCCTCATA | eekkddddddddkkeee | 34 | 10081 | 10097 | 1415 |

TABLE 23-continued

Percent inhibition of SOD-1 mRNA by deoxy, MOE and cEt gapmers targeting SEQ ID NO: 1 and/or 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 596716 | 932 | 948 | TCTTTTAATAGCCTCAT | eekkddddddddkkeee | 52 | 10082 | 10098 | 1416 |
| 596907 | 932 | 948 | TCTTTTAATAGCCTCAT | eekkdddddddddkkee | 56 | 10082 | 10098 | 1416 |
| 596717 | 936 | 952 | GGATTCTTTTAATAGCC | eekkddddddddkkeee | 14 | 10086 | 10102 | 1417 |
| 596908 | 936 | 952 | GGATTCTTTTAATAGCC | eekkdddddddddkkee | 19 | 10086 | 10102 | 1417 |
| 596718 | 938 | 954 | TTGGATTCTTTTAATAG | eekkddddddddkkeee | 23 | 10088 | 10104 | 1263 |
| 596909 | 938 | 954 | TTGGATTCTTTTAATAG | eekkdddddddddkkee | 8 | 10088 | 10104 | 1263 |
| 596719 | 949 | 965 | TTAGTTTGAATTTGGAT | eekkddddddddkkeee | 31 | 10099 | 10115 | 1418 |
| 596910 | 949 | 965 | TTAGTTTGAATTTGGAT | eekkdddddddddkkee | 16 | 10099 | 10115 | 1418 |

Example 6: Dose-Dependent Inhibition of Human SOD-1 with Modified Oligonucleotides in HepG2 Cells Gapmers from the studies described above exhibiting significant in vitro inhibition of SOD-1 mRNA were selected and tested at various doses in HepG2 cells. Benchmark compound ISIS 333611 and other compounds previously disclosed in WO 2005/040180, including ISIS 146144, 146145, 150445, 150446, 150447, 150454, 150463, 150465, 333606, 333609, and 333611 were also tested.

The modified oligonucleotides were tested in a series of experiments that had similar culture conditions. The results for each experiment are presented in separate tables shown below. Cells were plated at a density of 20,000 cells per well and transfected using electroporation with 0.813 µM, 1.625 µM, 3.250 µM, 6.500 µM, and 13.000 µM concentrations of modified oligonucleotide, as specified in the Tables below. After a treatment period of approximately 16 hours, RNA was isolated from the cells and SOD-1 mRNA levels were measured by quantitative real-time PCR. Human primer probe set RTS3898 was used to measure mRNA levels. SOD-1 mRNA levels were adjusted according to total RNA content, as measured by RIBOGREEN®. Results are presented as percent inhibition of SOD-1, relative to untreated control cells.

The half maximal inhibitory concentration (IC$_{50}$) of each oligonucleotide is also presented. SOD-1 mRNA levels were significantly reduced in a dose-dependent manner in modified oligonucleotide treated cells.

TABLE 24

Dose-dependent inhibition of SOD-1 mRNA

| ISIS No | 0.813 µM | 1.625 µM | 3.250 µM | 6.500 µM | 13.000 µM | IC$_{50}$ (µM) |
|---|---|---|---|---|---|---|
| 150445 | 7 | 21 | 44 | 56 | 82 | 4.4 |
| 150446 | 15 | 32 | 47 | 71 | 87 | 3.2 |
| 150447 | 26 | 43 | 68 | 81 | 93 | 2.0 |
| 150463 | 16 | 38 | 51 | 66 | 85 | 3.1 |
| 333611 | 18 | 39 | 57 | 66 | 79 | 3.0 |
| 393336 | 18 | 34 | 53 | 69 | 83 | 3.1 |
| 393343 | 24 | 32 | 53 | 73 | 42 | 5.1 |
| 436863 | 18 | 42 | 58 | 72 | 89 | 2.6 |
| 590089 | 28 | 59 | 70 | 82 | 90 | 1.5 |
| 590090 | 34 | 56 | 76 | 82 | 51 | 1.1 |
| 590091 | 30 | 44 | 68 | 84 | 88 | 1.9 |
| 590094 | 16 | 35 | 57 | 73 | 76 | 3.0 |
| 590113 | 34 | 35 | 57 | 73 | 84 | 2.3 |

TABLE 25

Dose-dependent inhibition of SOD-1 mRNA

| ISIS No | 0.813 µM | 1.625 µM | 3.250 µM | 6.500 µM | 13.000 µM | IC$_{50}$ (µM) |
|---|---|---|---|---|---|---|
| 150465 | 42 | 59 | 77 | 82 | 87 | 1.0 |
| 333611 | 17 | 26 | 40 | 64 | 82 | 3.8 |
| 378879 | 14 | 35 | 63 | 72 | 86 | 2.8 |
| 393371 | 28 | 42 | 57 | 74 | 80 | 2.3 |
| 489520 | 28 | 44 | 64 | 72 | 84 | 2.2 |
| 590177 | 53 | 59 | 69 | 85 | 88 | 0.7 |
| 590178 | 40 | 53 | 71 | 73 | 87 | 1.3 |
| 590180 | 18 | 42 | 51 | 64 | 73 | 3.3 |
| 590187 | 34 | 51 | 68 | 80 | 92 | 1.6 |
| 590188 | 30 | 46 | 61 | 76 | 88 | 2.0 |
| 590189 | 37 | 49 | 68 | 78 | 88 | 1.6 |
| 590190 | 38 | 58 | 77 | 84 | 89 | 1.1 |

TABLE 25-continued

Dose-dependent inhibition of SOD-1 mRNA

| ISIS No | 0.813 µM | 1.625 µM | 3.250 µM | 6.500 µM | 13.000 µM | IC$_{50}$ (µM) |
|---|---|---|---|---|---|---|
| 590191 | 29 | 56 | 71 | 77 | 84 | 1.6 |
| 590192 | 37 | 59 | 72 | 80 | 87 | 1.2 |

TABLE 26

Dose-dependent inhibition of SOD-1 mRNA

| ISIS No | 0.813 µM | 1.625 µM | 3.250 µM | 6.500 µM | 13.000 µM | IC$_{50}$ (µM) |
|---|---|---|---|---|---|---|
| 146144 | 15 | 58 | 67 | 78 | 64 | 2.2 |
| 146145 | 31 | 53 | 67 | 81 | 90 | 1.6 |
| 333606 | 11 | 39 | 62 | 75 | 91 | 2.7 |
| 333609 | 13 | 37 | 57 | 71 | 85 | 2.9 |
| 333611 | 14 | 30 | 53 | 68 | 86 | 3.2 |
| 590250 | 8 | 19 | 47 | 64 | 84 | 3.9 |
| 590626 | 61 | 72 | 84 | 84 | 87 | 0.2 |
| 592630 | 24 | 33 | 58 | 70 | 85 | 2.7 |
| 592631 | 19 | 48 | 59 | 74 | 88 | 2.3 |
| 592645 | 20 | 31 | 53 | 74 | 89 | 2.8 |
| 592649 | 14 | 32 | 56 | 69 | 82 | 3.2 |

TABLE 27

Dose-dependent inhibition of SOD-1 mRNA

| ISIS No | 0.813 µM | 1.625 µM | 3.250 µM | 6.500 µM | 13.000 µM | IC$_{50}$ (µM) |
|---|---|---|---|---|---|---|
| 150454 | 13 | 24 | 49 | 69 | 83 | 3.5 |
| 333611 | 28 | 28 | 53 | 68 | 82 | 3.0 |
| 489505 | 13 | 24 | 38 | 56 | 81 | 4.5 |
| 489516 | 25 | 16 | 39 | 61 | 79 | 4.3 |
| 592652 | 11 | 31 | 52 | 74 | 46 | 5.1 |
| 592714 | 8 | 25 | 45 | 69 | 82 | 3.8 |
| 592715 | 18 | 35 | 50 | 70 | 83 | 3.1 |
| 592762 | 44 | 66 | 74 | 81 | 89 | 0.8 |
| 592763 | 50 | 68 | 74 | 86 | 95 | 0.7 |
| 592764 | 26 | 43 | 48 | 76 | 87 | 2.5 |
| 592766 | 36 | 53 | 66 | 77 | 89 | 1.5 |
| 592767 | 25 | 31 | 54 | 70 | 79 | 2.9 |
| 592769 | 35 | 31 | 56 | 73 | 80 | 2.5 |
| 592771 | 34 | 43 | 58 | 70 | 80 | 2.2 |

Example 7: Dose-Dependent Inhibition of Human SOD-1 with Modified Oligonucleotides in HepG2 Cells Gapmers from the studies described above exhibiting significant in vitro inhibition of SOD-1 mRNA were selected and tested at various doses in HepG2 cells. Benchmark compound, ISIS 333611, and ISIS 333625, both of which were previously disclosed in WO 2005/040180 were also tested.

The modified oligonucleotides were tested in a series of experiments that had similar culture conditions. The results for each experiment are presented in separate tables shown below. Cells were plated at a density of 20,000 cells per well and transfected using electroporation with 0.148 µM, 0.444 µM, 1.330 µM, 4.000 µM, and 12.000 µM concentrations of modified oligonucleotide, as specified in the Tables below. After a treatment period of approximately 16 hours, RNA was isolated from the cells and SOD-1 mRNA levels were measured by quantitative real-time PCR. Human primer probe sets RTS3898 or HTS90 was used to measure mRNA levels. SOD-1 mRNA levels were adjusted according to total RNA content, as measured by RIBOGREEN®. Results are presented as percent inhibition of SOD-1, relative to untreated control cells.

The half maximal inhibitory concentration (IC$_{50}$) of each oligonucleotide is also presented. SOD-1 mRNA levels were significantly reduced in a dose-dependent manner in modified oligonucleotide treated cells.

TABLE 28

Dose response assay with primer probe set RTS3898

| ISIS No | 0.148 µM | 0.444 µM | 1.330 µM | 4.000 µM | 12.000 µM | IC$_{50}$ (µM) |
|---|---|---|---|---|---|---|
| 333611 | 6 | 14 | 29 | 51 | 78 | 3.2 |
| 596911 | 8 | 12 | 23 | 54 | 74 | 3.6 |
| 596720 | 7 | 14 | 31 | 55 | 71 | 3.4 |
| 596800 | 44 | 60 | 75 | 84 | 82 | 0.2 |
| 596801 | 33 | 49 | 69 | 79 | 83 | 0.5 |
| 596610 | 16 | 44 | 65 | 78 | 84 | 0.8 |
| 596799 | 20 | 45 | 64 | 75 | 84 | 0.8 |
| 596609 | 17 | 54 | 65 | 75 | 81 | 0.7 |
| 596883 | 13 | 22 | 36 | 45 | 51 | 8.6 |
| 489523 | 16 | 40 | 62 | 78 | 90 | 0.9 |
| 590181 | 5 | 17 | 46 | 70 | 89 | 1.7 |
| 436868 | 10 | 35 | 47 | 69 | 82 | 1.4 |
| 596768 | 16 | 37 | 62 | 82 | 89 | 0.9 |
| 596775 | 36 | 50 | 66 | 83 | 89 | 0.4 |

TABLE 29

Dose response assay with primer probe set HTS90

| ISIS No | 0.148 µM | 0.444 µM | 1.330 µM | 4.000 µM | 12.000 µM | IC$_{50}$ (µM) |
|---|---|---|---|---|---|---|
| 333625 | 0 | 4 | 17 | 56 | 84 | 3.3 |
| 489532 | 54 | 70 | 78 | 86 | 96 | 0.1 |
| 590154 | 0 | 14 | 25 | 56 | 86 | 2.7 |
| 596173 | 0 | 5 | 25 | 63 | 92 | 2.4 |
| 596174 | 7 | 12 | 37 | 46 | 84 | 2.8 |
| 596178 | 2 | 16 | 40 | 68 | 82 | 2.1 |
| 596179 | 0 | 17 | 41 | 64 | 80 | 2.3 |
| 596308 | 0 | 5 | 22 | 56 | 80 | 3.3 |
| 596572 | 18 | 35 | 62 | 83 | 90 | 0.9 |
| 596589 | 10 | 45 | 61 | 77 | 91 | 0.9 |
| 596600 | 41 | 56 | 71 | 85 | 92 | 0.3 |
| 596602 | 14 | 51 | 74 | 86 | 95 | 0.6 |
| 596789 | 22 | 55 | 69 | 86 | 91 | 0.5 |
| 596795 | 16 | 43 | 64 | 82 | 93 | 0.8 |

Example 8: Dose-Dependent Inhibition of Human SOD-1 with Modified Oligonucleotides in HepG2 Cells Gapmers from the studies described above exhibiting significant in vitro inhibition of SOD-1 mRNA were selected and tested at various doses in HepG2 cells. Benchmark compound, ISIS 333611, and additional compounds including, ISIS 146143, 150442, 195753, 333607, and 333608, were previously disclosed in WO 2005/040180 were also tested.

The modified oligonucleotides were tested in a series of experiments that had similar culture conditions. The results for each experiment are presented in separate tables shown below. Cells were plated at a density of 20,000 cells per well and transfected using electroporation with 0.1875 µM, 0.7500 µM, 3.0000 µM, and 12.0000 µM concentrations of modified oligonucleotide, as specified in the Tables below.

After a treatment period of approximately 16 hours, RNA was isolated from the cells and SOD-1 mRNA levels were measured by quantitative real-time PCR. Human primer probe sets RTS3898 was used to measure mRNA levels. SOD-1 mRNA levels were adjusted according to total RNA content, as measured by RIBOGREEN®. Results are presented as percent inhibition of SOD-1, relative to untreated control cells.

The half maximal inhibitory concentration ($IC_{50}$) of each oligonucleotide is also presented. SOD-1 mRNA levels were significantly reduced in a dose-dependent manner in modified oligonucleotide treated cells.

TABLE 30

Dose-dependent inhibition of SOD-1 mRNA

| ISIS No | 0.1875 µM | 0.75 µM | 3.00 µM | 12.00 µM | $IC_{50}$ (µM) |
|---|---|---|---|---|---|
| 333611 | 0 | 27 | 60 | 91 | 2 |
| 596572 | 38 | 65 | 87 | 96 | 0.3 |
| 596583 | 62 | 89 | 95 | 95 | <0.1 |
| 596590 | 40 | 79 | 89 | 94 | 0.2 |
| 596602 | 40 | 75 | 92 | 98 | 0.2 |
| 596603 | 51 | 79 | 92 | 96 | 0.1 |
| 596604 | 48 | 78 | 91 | 95 | 0.1 |
| 596605 | 50 | 86 | 90 | 97 | 0.1 |
| 596764 | 11 | 67 | 89 | 94 | 0.7 |
| 596768 | 27 | 49 | 82 | 92 | 0.7 |
| 596773 | 32 | 62 | 89 | 98 | 0.4 |
| 596774 | 56 | 89 | 93 | 96 | <0.1 |
| 596775 | 31 | 75 | 90 | 97 | 0.3 |
| 596780 | 24 | 71 | 85 | 98 | 0.5 |
| 596781 | 30 | 80 | 93 | 97 | 0.3 |
| 596791 | 38 | 74 | 89 | 95 | 0.3 |
| 596794 | 43 | 75 | 91 | 97 | 0.2 |
| 596795 | 28 | 66 | 91 | 98 | 0.4 |
| 596796 | 43 | 78 | 93 | 98 | 0.2 |

TABLE 31

Dose-dependent inhibition of SOD-1 mRNA

| ISIS No | 0.1875 µM | 0.75 µM | 3.00 µM | 12.00 µM | $IC_{50}$ (µM) |
|---|---|---|---|---|---|
| 333611 | 0 | 15 | 68 | 95 | 2.1 |
| 596589 | 35 | 70 | 90 | 97 | 0.3 |
| 596789 | 38 | 71 | 89 | 97 | 0.3 |
| 596600 | 41 | 73 | 89 | 95 | 0.2 |
| 596582 | 30 | 71 | 87 | 95 | 0.4 |
| 596784 | 26 | 68 | 89 | 95 | 0.4 |
| 596787 | 44 | 67 | 89 | 94 | 0.2 |
| 596779 | 29 | 71 | 89 | 97 | 0.4 |
| 596792 | 37 | 63 | 83 | 95 | 0.4 |
| 596782 | 27 | 61 | 85 | 96 | 0.5 |
| 596765 | 34 | 59 | 87 | 95 | 0.4 |
| 596793 | 27 | 65 | 88 | 96 | 0.5 |
| 596570 | 25 | 60 | 84 | 91 | 0.6 |
| 596769 | 21 | 64 | 85 | 96 | 0.6 |
| 596783 | 10 | 57 | 84 | 94 | 0.9 |
| 596584 | 26 | 67 | 84 | 93 | 0.5 |
| 596571 | 37 | 71 | 81 | 92 | 0.3 |
| 596598 | 30 | 62 | 81 | 94 | 0.5 |
| 596588 | 11 | 64 | 87 | 95 | 0.7 |

TABLE 32

Dose-dependent inhibition of SOD-1 mRNA

| ISIS No | 0.1875 µM | 0.75 µM | 3.00 µM | 12.00 µM | $IC_{50}$ (µM) |
|---|---|---|---|---|---|
| 146143 | 6 | 12 | 51 | 88 | 2.5 |
| 150442 | 10 | 21 | 39 | 90 | 2.5 |

TABLE 32-continued

Dose-dependent inhibition of SOD-1 mRNA

| ISIS No | 0.1875 µM | 0.75 µM | 3.00 µM | 12.00 µM | $IC_{50}$ (µM) |
|---|---|---|---|---|---|
| 195753 | 13 | 23 | 48 | 77 | 2.8 |
| 333607 | 17 | 26 | 59 | 83 | 1.9 |
| 333608 | 0 | 2 | 28 | 92 | 3.7 |
| 333611 | 0 | 13 | 52 | 91 | 2.4 |
| 596573 | 26 | 51 | 77 | 91 | 0.8 |
| 596577 | 32 | 55 | 78 | 93 | 0.6 |
| 596591 | 23 | 51 | 74 | 91 | 0.8 |
| 596592 | 18 | 48 | 66 | 86 | 1.1 |
| 596593 | 16 | 58 | 78 | 87 | 0.8 |
| 596596 | 4 | 49 | 72 | 87 | 1.3 |
| 596761 | 28 | 55 | 74 | 91 | 0.7 |
| 596762 | 0 | 47 | 75 | 90 | 1.3 |
| 596763 | 0 | 40 | 78 | 92 | 1.5 |
| 596766 | 4 | 50 | 68 | 86 | 1.3 |
| 596785 | 10 | 47 | 77 | 91 | 1.1 |
| 596786 | 0 | 45 | 75 | 97 | 1.3 |
| 596788 | 9 | 52 | 81 | 95 | 1 |

TABLE 33

Dose-dependent inhibition of SOD-1 mRNA

| ISIS No | 0.1875 µM | 0.75 µM | 3.00 µM | 12.00 µM | $IC_{50}$ (µM) |
|---|---|---|---|---|---|
| 333611 | 3 | 22 | 60 | 92 | 2 |
| 596302 | 9 | 27 | 59 | 89 | 1.9 |
| 596308 | 29 | 47 | 82 | 96 | 0.7 |
| 596309 | 13 | 42 | 75 | 92 | 1.1 |
| 596310 | 13 | 16 | 48 | 81 | 2.8 |
| 596313 | 15 | 37 | 70 | 88 | 1.3 |
| 596314 | 18 | 45 | 74 | 92 | 1 |
| 596606 | 55 | 78 | 87 | 93 | 0.1 |
| 596607 | 44 | 71 | 83 | 84 | 0.2 |
| 596608 | 46 | 74 | 84 | 81 | 0.1 |
| 596609 | 30 | 61 | 79 | 87 | 0.5 |
| 596610 | 39 | 69 | 82 | 86 | 0.3 |
| 596612 | 16 | 50 | 62 | 77 | 1.4 |
| 596797 | 67 | 84 | 94 | 96 | <0.1 |
| 596798 | 42 | 68 | 86 | 89 | 0.2 |
| 596799 | 35 | 66 | 83 | 87 | 0.4 |
| 596800 | 45 | 73 | 84 | 87 | 0.2 |
| 596801 | 40 | 67 | 86 | 88 | 0.3 |
| 596803 | 28 | 41 | 63 | 71 | 1.4 |

TABLE 34

Dose-dependent inhibition of SOD-1 mRNA

| ISIS No | 0.1875 µM | 0.75 µM | 3.00 µM | 12.00 µM | $IC_{50}$ (µM) |
|---|---|---|---|---|---|
| 333611 | 0 | 30 | 56 | 69 | 3.1 |
| 590475 | 19 | 39 | 69 | 88 | 1.2 |
| 590625 | 19 | 51 | 74 | 85 | 1.0 |
| 590626 | 42 | 72 | 88 | 90 | 0.2 |
| 590627 | 16 | 42 | 70 | 84 | 1.0 |
| 590634 | 45 | 72 | 86 | 92 | 0.2 |
| 590635 | 39 | 60 | 80 | 90 | 0.4 |
| 590644 | 44 | 62 | 80 | 86 | 0.3 |
| 590650 | 34 | 56 | 82 | 93 | 0.5 |
| 590653 | 52 | 78 | 86 | 85 | 0.1 |
| 590655 | 35 | 71 | 79 | 82 | 0.3 |
| 596530 | 25 | 22 | 72 | 79 | 2.0 |
| 596531 | 8 | 38 | 74 | 96 | 1.2 |
| 596559 | 15 | 36 | 79 | 95 | 1.1 |
| 596721 | 14 | 47 | 82 | 97 | 0.9 |
| 596723 | 12 | 47 | 79 | 94 | 1.0 |

TABLE 34-continued

Dose-dependent inhibition of SOD-1 mRNA

| ISIS No | 0.1875 µM | 0.75 µM | 3.00 µM | 12.00 µM | IC$_{50}$ (µM) |
|---|---|---|---|---|---|
| 596726 | 24 | 42 | 80 | 94 | 0.9 |
| 596735 | 7 | 32 | 77 | 96 | 1.3 |
| 596736 | 25 | 52 | 82 | 97 | 0.7 |

Example 9: Dose-Dependent Inhibition of Human SOD-1 in HepG2 Cells by Gapmers with Mixed Backbone Chemistry Additional gapmers were designed based on the sequences of the oligonucleotides disclosed in studies described above. The oligonucleotides were designed as 5-10-5 MOE, 5-8-5 MOE, and deoxy, MOE and cEt oligonucleotides. The 5-10-5 MOE gapmers are 20 nucleosides in length, wherein the central gap segment is comprised of ten 2'-deoxyribonucleosides and is flanked by wing segments on the 5' direction and the 3' direction comprising five nucleosides each. The 5-8-5 MOE gapmers are 18 nucleosides in length, wherein the central gap segment is comprised of eight 2'-deoxyribonucleosides and is flanked by wing segments on the 5' direction and the 3' direction comprising five nucleosides each. Each nucleoside in the 5' wing segment and each nucleoside in the 3' wing segment has a 2'-MOE modification. The deoxy, MOE and cEt oligonucleotides are 16 or 17 nucleosides in length wherein each nucleoside has a MOE sugar modification, a cEt sugar modification, or a deoxy moiety. The sugar chemistry of each oligonucleotide is denoted as in the Chemistry column, where 'k' indicates a cEt modified sugar; 'd' indicates a 2'-deoxyribose; and 'e' indicates a 2'-MOE modified sugar. The internucleoside linkages throughout each gapmer are either phosphodiester or phosphorothioate linkages. The internucleoside linkages of each oligonucleotide are denoted in the Backbone Chemistry column, where 'o' indicates a phosphodiester linkage and 's' denotes a phosphorothioate linkage. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human SOD-1 mRNA, designated herein as SEQ ID NO: 1 (GENBANK Accession No. NM_000454.4) or the human SOD-1 genomic sequence, designated herein as SEQ ID NO: 2 (GENBANK Accession No. NT_011512.10 truncated from nucleotides 18693000 to Ser. No. 18/704,000).

TABLE 35

Modified oligonucleotides targeting human SOD-1 with mixed backbone chemistry

| ISIS NO | SEQ ID NO: 1 Start Site | SEQ ID NO: 1 Stop Site | Sequence | Sugar Modifications | Backbone Chemistry | SEQ ID NO: 2 Start Site | SEQ ID NO: 2 Stop Site | SEQ ID NO |
|---|---|---|---|---|---|---|---|---|
| 611458 | 226 | 245 | ACACCTTCACTGGTCCATTA | eeeeeddddddddddeeeee | sooosssssssssssooos | 4980 | 4999 | 23 |
| 654335 | 233 | 248 | CCCACACCTTCACTGG | ekdddddddddekekee | sossssssssooooss | 4987 | 5002 | 1420 |
| 611474 | 234 | 253 | GCTTCCCCACACCTTCACTG | eeeeeddddddddddeeeee | sooosssssssssssooos | 4988 | 5007 | 149 |
| 654301 | 234 | 251 | TTCCCCACACCTTCACTG | eeeeeddddddddeeeee | sooosssssssssooss | 4988 | 5005 | 1421 |
| 654336 | 234 | 249 | CCCCACACCTTCACTG | ekdddddddddekekee | sosssssssssooss | 4988 | 5003 | 1422 |
| 654302 | 235 | 252 | CTTCCCCACACCTTCACT | eeeeeddddddddeeeee | sooosssssssssooss | 4989 | 5006 | 1423 |
| 654319 | 235 | 250 | TCCCCACACCTTCACT | kekedddddddddekek | sooosssssssoss | 4989 | 5004 | 1424 |
| 654337 | 235 | 250 | TCCCCACACCTTCACT | ekdddddddddekekee | sosssssssooss | 4989 | 5004 | 1424 |
| 654303 | 236 | 253 | GCTTCCCCACACCTTCAC | eeeeeddddddddeeeee | sooosssssssssooss | 4990 | 5007 | 1425 |
| 654320 | 236 | 251 | TTCCCCACACCTTCAC | kekedddddddddekek | sooosssssssoss | 4990 | 5005 | 1426 |
| 654321 | 237 | 252 | CTTCCCCACACCTTCA | kekedddddddddekek | sooosssssssoss | 4991 | 5006 | 1427 |
| 611475 | 321 | 340 | GTGAGGACCTGCACTGGTAC | eeeeeddddddddddeeeee | sooosssssssssssooos | 7637 | 7656 | 172 |
| 611460 | 588 | 607 | GGCGATCCCAATTACACCAC | eeeeeddddddddddeeeee | sooosssssssssssooos | 9738 | 9757 | 47 |

TABLE 35-continued

Modified oligonucleotides targeting human SOD-1 with mixed backbone chemistry

| ISIS NO | SEQ ID NO: 1 Start Site | SEQ ID NO: 1 Stop Site | Sequence | Sugar Modifications | Backbone Chemistry | SEQ ID NO: 2 Start Site | SEQ ID NO: 2 Stop Site | SEQ ID NO |
|---|---|---|---|---|---|---|---|---|
| 654304 | 663 | 680 | ATACATTTCTACAGCTAG | eeeeedddddddddeeeee | sooossssssssssooss | 9813 | 9830 | 1429 |
| 654305 | 664 | 681 | GATACATTTCTACAGCTA | eeeeedddddddddeeeee | sooossssssssssooss | 9814 | 9831 | 1430 |
| 654340 | 664 | 679 | TACATTTCTACAGCTA | ekdddddddddekekee | sosssssssssooss | 9814 | 9829 | 1431 |
| 611492 | 665 | 684 | CAGGATACATTTCTACAGCT | eeeeeddddddddddeeeee | sooossssssssssssooos | 9815 | 9834 | 725 |
| 654306 | 665 | 682 | GGATACATTTCTACAGCT | eeeeedddddddddeeeee | sooossssssssssooss | 9815 | 9832 | 1432 |
| 654323 | 665 | 680 | ATACATTTCTACAGCT | kekeddddddddddekek | sooossssssssssoss | 9815 | 9830 | 1433 |
| 654341 | 665 | 680 | ATACATTTCTACAGCT | ekddddddddddekekee | sosssssssssooss | 9815 | 9830 | 1433 |
| 611500 | 666 | 685 | TCAGGATACATTTCTACAGC | eeeeeddddddddddeeeee | sooossssssssssssooos | 9816 | 9835 | 823 |
| 612941 | 666 | 682 | GGATACATTTCTACAGC | eekkdddddddddkkee | sooossssssssssoss | 9816 | 9832 | 1342 |
| 654307 | 666 | 683 | AGGATACATTTCTACAGC | eeeeedddddddddeeeee | sooossssssssssooss | 9816 | 9833 | 1434 |
| 654324 | 666 | 681 | GATACATTTCTACAGC | kekedddddddddekek | sooossssssssssoss | 9816 | 9831 | 1435 |
| 654342 | 666 | 681 | GATACATTTCTACAGC | ekdddddddddekekee | sosssssssssooss | 9816 | 9831 | 1435 |
| 654308 | 667 | 684 | CAGGATACATTTCTACAG | eeeeedddddddddeeeee | sooossssssssssooss | 9817 | 9834 | 1436 |
| 612925 | 676 | 692 | ATGTTTATCAGGATACA | eekkdddddddddkkeee | sooossssssssssooss | 9826 | 9842 | 1348 |
| 612944 | 676 | 692 | ATGTTTATCAGGATACA | eekkddddddddddkkee | sooossssssssssoss | 9826 | 9842 | 1348 |
| 654343 | 677 | 692 | ATGTTTATCAGGATAC | ekddddddddekekee | sosssssssssooss | 9827 | 9842 | 1437 |
| 612927 | 678 | 694 | TAATGTTTATCAGGATA | eekkdddddddddkkeee | sooossssssssssooss | 9828 | 9844 | 1350 |
| 654309 | 678 | 695 | TTAATGTTTATCAGGATA | eeeeedddddddddeeeee | sooossssssssssooss | 9828 | 9845 | 1438 |
| 612928 | 679 | 695 | TTAATGTTTATCAGGAT | eekkdddddddddkkeee | sooossssssssssooss | 9829 | 9845 | 1351 |
| 654310 | 679 | 696 | TTTAATGTTTATCAGGAT | eeeeedddddddddeeeee | sooossssssssssooss | 9829 | 9846 | 1439 |
| 654311 | 680 | 697 | GTTTAATGTTTATCAGGA | eeeeedddddddddeeeee | sooossssssssssooss | 9830 | 9847 | 1440 |
| 654327 | 680 | 695 | TTAATGTTTATCAGGA | kekedddddddddekek | sooossssssssssoss | 9830 | 9845 | 1441 |
| 654346 | 680 | 695 | TTAATGTTTATCAGGA | ekdddddddddekekee | sosssssssssooss | 9830 | 9845 | 1441 |
| 611497 | 681 | 700 | AGTGTTTAATGTTTATCAGG | eeeeeddddddddddeeeee | sooossssssssssssooos | 9831 | 9850 | 733 |

TABLE 35-continued

Modified oligonucleotides targeting human SOD-1 with mixed backbone chemistry

| ISIS NO | SEQ ID NO: 1 Start Site | SEQ ID NO: 1 Stop Site | Sequence | Sugar Modifications | Backbone Chemistry | SEQ ID NO: 2 Start Site | SEQ ID NO: 2 Stop Site | SEQ ID NO |
|---|---|---|---|---|---|---|---|---|
| 612948 | 681 | 697 | GTTTAATGTTTATCAGG | eekkddddddddddkkee | sooossssssssssoss | 9831 | 9847 | 1352 |
| 654312 | 681 | 698 | TGTTTAATGTTTATCAGG | eeeeeddddddddeeeee | sooossssssssssooss | 9831 | 9848 | 1442 |
| 654328 | 681 | 696 | TTTAATGTTTATCAGG | kekedddddddddekek | sooossssssssssoss | 9831 | 9846 | 1443 |
| 654347 | 681 | 696 | TTTAATGTTTATCAGG | ekddddddddekekee | sossssssssooooss | 9831 | 9846 | 1443 |
| 654313 | 682 | 699 | GTGTTTAATGTTTATCAG | eeeeeddddddddeeeee | sooossssssssssooss | 9832 | 9849 | 1444 |
| 654329 | 682 | 697 | GTTTAATGTTTATCAG | kekedddddddddekek | sooossssssssssoss | 9832 | 9847 | 1445 |
| 654348 | 682 | 697 | GTTTAATGTTTATCAG | ekddddddddekekee | sossssssssooooss | 9832 | 9847 | 1445 |
| 612949 | 683 | 699 | GTGTTTAATGTTTATCA | eekkddddddddddkkee | sooossssssssssoss | 9833 | 9849 | 1172 |
| 654314 | 683 | 700 | AGTGTTTAATGTTTATCA | eeeeeddddddddeeeee | sooossssssssssooss | 9833 | 9850 | 1446 |
| 654330 | 683 | 698 | TGTTTAATGTTTATCA | kekedddddddddekek | sooossssssssssoss | 9833 | 9848 | 1447 |
| 612931 | 684 | 700 | AGTGTTTAATGTTTATC | eekkddddddddddkkeee | sooossssssssssooss | 9834 | 9850 | 1173 |
| 654315 | 684 | 701 | CAGTGTTTAATGTTTATC | eeeeeddddddddeeeee | sooossssssssssooss | 9834 | 9851 | 1448 |
| 654331 | 684 | 699 | GTGTTTAATGTTTATC | kekedddddddddekek | sooossssssssssoss | 9834 | 9849 | 1449 |
| 654350 | 684 | 699 | GTGTTTAATGTTTATC | ekdddddddddekekee | sossssssssooooss | 9834 | 9849 | 1449 |
| 654316 | 685 | 702 | ACAGTGTTTAATGTTTAT | eeeeeddddddddeeeee | sooossssssssssooss | 9835 | 9852 | 1450 |
| 612918 | 686 | 702 | ACAGTGTTTAATGTTTA | eeekkddddddddkkeee | sooossssssssssooss | 9836 | 9852 | 1175 |
| 612932 | 686 | 702 | ACAGTGTTTAATGTTTA | eekkddddddddkkeee | sooossssssssssooss | 9836 | 9852 | 1175 |
| 654317 | 686 | 703 | TACAGTGTTTAATGTTTA | eeeeeddddddddeeeee | sooossssssssssooss | 9836 | 9853 | 1451 |
| 654333 | 686 | 701 | CAGTGTTTAATGTTTA | kekedddddddddekek | sooossssssssssoss | 9836 | 9851 | 1452 |
| 654352 | 686 | 701 | CAGTGTTTAATGTTTA | ekdddddddddekekee | sossssssssooooss | 9836 | 9851 | 1452 |
| 654318 | 687 | 704 | TTACAGTGTTTAATGTTT | eeeeeddddddddeeeee | sooossssssssssooss | 9837 | 9854 | 1453 |
| 654334 | 687 | 702 | ACAGTGTTTAATGTTT | kekedddddddddekek | sooossssssssssoss | 9837 | 9852 | 1454 |

The newly designed oligonucleotides were tested at various doses in HepG2 cells. The modified oligonucleotides were tested in a series of experiments that had similar culture conditions. The results for each experiment are presented in separate tables shown below. Cells were plated at a density of 20,000 cells per well and transfected using electroporation with 0.222 µM, 0.667 µM, 2.000 µM, and 6.000 µM concentrations of modified oligonucleotide, as specified in the Tables below. After a treatment period of approximately 16 hours, RNA was isolated from the cells and SOD-1 mRNA levels were measured by quantitative real-time PCR. Human primer probe sets RTS3898 was used to measure mRNA levels. SOD-1 mRNA levels were adjusted according to total RNA content, as measured by RIBOGREEN®. Results are presented as percent inhibition of SOD-1, relative to untreated control cells.

The half maximal inhibitory concentration ($IC_{50}$) of each oligonucleotide is also presented. SOD-1 mRNA levels were significantly reduced in a dose-dependent manner in modified oligonucleotide treated cells.

TABLE 36

Dose response assay

| ISIS No | 0.222 µM | 0.667 µM | 2.000 µM | 6.000 µM | $IC_{50}$ µM |
|---|---|---|---|---|---|
| 333611 | 0 | 28 | 53 | 77 | 1.9 |
| 611458 | 0 | 21 | 50 | 79 | 2.0 |
| 611460 | 24 | 34 | 55 | 79 | 1.3 |
| 611474 | 14 | 32 | 55 | 79 | 1.5 |
| 611475 | 0 | 16 | 35 | 70 | 3.0 |
| 611492 | 38 | 70 | 88 | 95 | 0.3 |
| 611497 | 28 | 55 | 80 | 89 | 0.6 |
| 611500 | 25 | 50 | 73 | 92 | 0.7 |
| 612918 | 51 | 70 | 74 | 80 | <0.2 |
| 612925 | 53 | 73 | 90 | 89 | <0.2 |
| 612927 | 64 | 89 | 92 | 94 | <0.2 |
| 612928 | 67 | 90 | 94 | 97 | <0.2 |
| 612931 | 68 | 76 | 84 | 86 | <0.2 |
| 612932 | 61 | 73 | 88 | 91 | <0.2 |
| 612941 | 62 | 78 | 91 | 95 | <0.2 |
| 612944 | 47 | 71 | 82 | 92 | 0.2 |
| 612948 | 76 | 90 | 93 | 94 | <0.2 |
| 612949 | 58 | 68 | 83 | 96 | <0.2 |
| 654301 | 7 | 4 | 17 | 42 | >6.0 |

TABLE 37

Dose response assay

| ISIS No | 0.222 µM | 0.667 µM | 2.000 µM | 6.000 µM | $IC_{50}$ µM |
|---|---|---|---|---|---|
| 333611 | 14 | 20 | 35 | 69 | 3.0 |
| 611458 | 11 | 27 | 36 | 68 | 2.9 |
| 654302 | 0 | 8 | 38 | 48 | 6.2 |
| 654303 | 8 | 29 | 46 | 76 | 1.9 |
| 654304 | 7 | 28 | 54 | 79 | 1.7 |
| 654305 | 28 | 59 | 73 | 85 | 0.6 |
| 654306 | 38 | 62 | 82 | 94 | 0.4 |
| 654307 | 9 | 43 | 65 | 86 | 1.1 |
| 654308 | 14 | 31 | 54 | 84 | 1.4 |
| 654309 | 0 | 17 | 47 | 72 | 2.4 |
| 654310 | 10 | 24 | 28 | 53 | 6.6 |
| 654311 | 45 | 73 | 78 | 87 | 0.2 |
| 654312 | 14 | 39 | 59 | 77 | 1.3 |
| 654313 | 20 | 43 | 56 | 81 | 1.2 |
| 654314 | 33 | 58 | 74 | 86 | 0.5 |
| 654315 | 21 | 47 | 64 | 84 | 0.9 |
| 654316 | 19 | 30 | 46 | 70 | 2.0 |
| 654317 | 13 | 46 | 57 | 70 | 1.4 |
| 654318 | 17 | 42 | 54 | 76 | 1.4 |

TABLE 38

Dose response assay

| ISIS No | 0.222 µM | 0.667 µM | 2.000 µM | 6.000 µM | $IC_{50}$ µM |
|---|---|---|---|---|---|
| 333611 | 14 | 19 | 50 | 73 | 2.1 |
| 611458 | 9 | 22 | 39 | 72 | 2.5 |
| 654319 | 19 | 9 | 31 | 61 | 5.1 |
| 654320 | 6 | 16 | 20 | 59 | 5.9 |
| 654321 | 8 | 14 | 51 | 76 | 2.1 |
| 654323 | 55 | 73 | 89 | 95 | <0.2 |
| 654324 | 54 | 78 | 89 | 96 | <0.2 |
| 654327 | 53 | 82 | 91 | 96 | <0.2 |
| 654328 | 73 | 90 | 93 | 97 | <0.2 |
| 654329 | 58 | 78 | 86 | 94 | <0.2 |
| 654330 | 42 | 54 | 69 | 86 | 0.4 |
| 654331 | 53 | 78 | 82 | 90 | <0.2 |
| 654333 | 50 | 67 | 81 | 86 | 0.2 |
| 654334 | 55 | 68 | 78 | 88 | <0.2 |
| 654335 | 15 | 31 | 58 | 81 | 1.4 |
| 654336 | 21 | 36 | 60 | 75 | 1.3 |
| 654337 | 16 | 34 | 58 | 80 | 1.4 |
| 654340 | 36 | 69 | 83 | 95 | 0.4 |
| 654341 | 43 | 58 | 79 | 91 | 0.3 |

TABLE 39

Dose response assay

| ISIS No | 0.222 µM | 0.667 µM | 2.00 µM | 6.00 µM | $IC_{50}$ µM |
|---|---|---|---|---|---|
| 333611 | 0 | 6 | 38 | 64 | 3.6 |
| 611458 | 3 | 14 | 36 | 63 | 3.6 |
| 654342 | 40 | 60 | 80 | 93 | 0.4 |
| 654343 | 64 | 81 | 90 | 94 | <0.2 |
| 654346 | 52 | 73 | 84 | 93 | <0.2 |
| 654347 | 21 | 38 | 58 | 81 | 1.2 |
| 654348 | 44 | 63 | 82 | 94 | 0.3 |
| 654350 | 40 | 63 | 76 | 86 | 0.3 |
| 654352 | 54 | 79 | 84 | 88 | <0.2 |

Example 10: Dose-Dependent Inhibition of Human SOD-1 by Gapmers with Mixed Backbone Chemistry Additional gapmers were designed based on the sequences of the oligonucleotides disclosed in studies described above. The oligonucleotides were designed as deoxy, MOE and cEt oligonucleotides. The deoxy, MOE and cEt oligonucleotides are 16 or 17 nucleosides in length wherein each nucleoside has a MOE sugar modification, a cEt sugar modification, or a deoxy moiety. The sugar chemistry of each oligonucleotide is denoted as in the Chemistry column, where 'k' indicates a cEt modified sugar; 'd' indicates a 2'-deoxyribose; and 'e' indicates a 2'-MOE modified sugar. The internucleoside linkages throughout each gapmer are either phosphodiester or phosphorothioate linkages. The internucleoside linkages of each oligonucleotide are denoted in the Backbone Chemistry column, where 'o' indicates a phosphodiester linkage and 's' indicates a phosphorothioate linkage. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human SOD-1 mRNA, designated herein as SEQ ID NO: 1 (GENBANK Accession No. NM_000454.4) or the human SOD-1 genomic sequence, designated herein as SEQ ID NO: 2 (GENBANK Accession No. NT_011512.10 truncated from nucleotides 18693000 to Ser. No. 18/704,000).

TABLE 40

Modified oligonucleotides targeting human SOD-1 with mixed backbone chemistry

| ISIS NO | SEQ ID NO: 1 Start Site | SEQ ID NO: 1 Stop Site | Sequence | Sugar Modifications | Backbone Chemistry | SEQ ID NO: 2 Start Site | SEQ ID NO: 2 Stop Site | SEQ ID NO |
|---|---|---|---|---|---|---|---|---|
| 612916 | 664 | 680 | ATACATTTCTACAGCTA | eeekkdddddddkkeee | soossssssssssooss | 9814 | 9830 | 1170 |
| 612947 | 679 | 695 | TTAATGTTTATCAGGAT | eekkdddddddddkkee | sooosssssssssoss | 9829 | 9845 | 1351 |
| 654322 | 664 | 679 | TACATTTCTACAGCTA | kekedddddddddekek | sooossssssssoss | 9814 | 9829 | 1431 |
| 654325 | 667 | 682 | GGATACATTTCTACAG | kekedddddddddekek | sooossssssssoss | 9817 | 9832 | 1455 |
| 654326 | 679 | 694 | TAATGTTTATCAGGAT | kekedddddddddekek | sooossssssssoss | 9829 | 9844 | 1456 |
| 654332 | 685 | 700 | AGTGTTTAATGTTTAT | kekedddddddddekek | sooossssssssoss | 9835 | 9850 | 1457 |
| 654338 | 662 | 677 | CATTTCTACAGCTAGC | ekddddddddekekee | sosssssssssooss | 9812 | 9827 | 1458 |
| 654339 | 663 | 678 | ACATTTCTACAGCTAG | ekddddddddekekee | sosssssssssooss | 9813 | 9828 | 1459 |
| 654344 | 678 | 693 | AATGTTTATCAGGATA | ekddddddddekekee | sosssssssssooss | 9828 | 9843 | 1460 |
| 654345 | 679 | 694 | TAATGTTTATCAGGAT | ekddddddddekekee | sosssssssssooss | 9829 | 9844 | 1456 |
| 654349 | 683 | 698 | TGTTTAATGTTTATCA | ekddddddddekekee | sosssssssssooss | 9833 | 9848 | 1447 |
| 654351 | 685 | 700 | AGTGTTTAATGTTTAT | ekddddddddekekee | sosssssssssooss | 9835 | 9850 | 1457 |

The newly designed oligonucleotides were tested at various doses in A431 cells. The modified oligonucleotides were tested in a series of experiments that had similar culture conditions. The results for each experiment are presented in separate tables shown below. Cells were plated at a density of 5,000 cells per well and modified oligonucleotides were added to the media at 0.12 µM, 0.60 µM, 3.00 µM, and 15.00 µM concentrations of modified oligonucleotide for free uptake by the cells, as specified in the Tables below. After a treatment period of approximately 16 hours, RNA was isolated from the cells and SOD-1 mRNA levels were measured by quantitative real-time PCR. Human primer probe sets RTS3898 was used to measure mRNA levels. SOD-1 mRNA levels were adjusted according to total RNA content, as measured by RIBOGREEN®. Results are presented as percent inhibition of SOD-1, relative to untreated control cells.

TABLE 41

| Dose response assay | | | | |
|---|---|---|---|---|
| ISIS No | 0.12 µM | 0.60 µM | 3.00 µM | 15.00 µM |
| 333611 | 0 | 7 | 17 | 31 |
| 611458 | 5 | 4 | 4 | 10 |
| 612916 | 4 | 13 | 26 | 37 |
| 612918 | 12 | 26 | 45 | 47 |
| 612944 | 1 | 4 | 21 | 29 |
| 612947 | 12 | 48 | 54 | 72 |
| 654305 | 7 | 15 | 39 | 52 |
| 654306 | 0 | 25 | 29 | 50 |
| 654313 | 1 | 15 | 36 | 50 |
| 654314 | 2 | 35 | 52 | 67 |
| 654321 | 0 | 8 | 8 | 18 |
| 654322 | 0 | 13 | 36 | 59 |
| 654329 | 7 | 7 | 41 | 66 |
| 654330 | 6 | 14 | 15 | 32 |
| 654337 | 0 | 0 | 7 | 21 |
| 654338 | 3 | 3 | 2 | 11 |
| 654345 | 1 | 9 | 22 | 46 |
| 654346 | 0 | 7 | 21 | 46 |

TABLE 42

Dose response assay

| ISIS No | 0.12 µM | 0.60 µM | 3.00 µM | 15.00 µM |
|---|---|---|---|---|
| 333611 | 0 | 0 | 0 | 2 |
| 611460 | 0 | 0 | 0 | 30 |
| 611474 | 0 | 0 | 11 | 0 |
| 612925 | 2 | 4 | 12 | 52 |
| 612927 | 0 | 38 | 54 | 68 |
| 612948 | 25 | 69 | 89 | 95 |
| 612949 | 22 | 57 | 73 | 84 |
| 654307 | 42 | 23 | 26 | 45 |
| 654308 | 2 | 31 | 9 | 18 |
| 654315 | 0 | 8 | 39 | 52 |
| 654316 | 0 | 18 | 26 | 45 |
| 654323 | 15 | 14 | 16 | 52 |
| 654324 | 12 | 22 | 21 | 34 |
| 654331 | 7 | 35 | 66 | 78 |
| 654332 | 2 | 31 | 47 | 61 |
| 654339 | 1 | 27 | 32 | 47 |
| 654340 | 37 | 0 | 22 | 12 |
| 654347 | 20 | 5 | 12 | 33 |
| 654348 | 2 | 19 | 33 | 62 |

TABLE 43

Dose response assay

| ISIS No | 0.12 µM | 0.60 µM | 3.00 µM | 15.00 µM |
|---|---|---|---|---|
| 333611 | 0 | 0 | 0 | 1 |
| 611475 | 0 | 17 | 0 | 16 |
| 611492 | 13 | 24 | 41 | 62 |
| 612928 | 12 | 36 | 49 | 72 |
| 612931 | 31 | 68 | 83 | 86 |
| 654301 | 2 | 0 | 0 | 9 |
| 654302 | 0 | 8 | 3 | 0 |
| 654309 | 18 | 7 | 11 | 9 |
| 654310 | 13 | 19 | 22 | 7 |
| 654317 | 3 | 0 | 1 | 20 |
| 654318 | 4 | 0 | 33 | 17 |
| 654325 | 0 | 0 | 0 | 14 |
| 654326 | 0 | 15 | 17 | 48 |
| 654333 | 19 | 18 | 36 | 55 |
| 654334 | 0 | 0 | 0 | 6 |
| 654341 | 0 | 9 | 0 | 25 |
| 654342 | 0 | 0 | 0 | 18 |
| 654349 | 0 | 13 | 31 | 49 |
| 654350 | 10 | 32 | 66 | 79 |

TABLE 44

Dose response assay

| ISIS No | 0.12 µM | 0.60 µM | 3.00 µM | 15.00 µM |
|---|---|---|---|---|
| 333611 | 5 | 0 | 7 | 3 |
| 611497 | 16 | 49 | 60 | 75 |
| 611500 | 9 | 8 | 21 | 49 |
| 612932 | 17 | 8 | 26 | 37 |
| 612941 | 4 | 12 | 36 | 51 |
| 654303 | 0 | 1 | 0 | 5 |
| 654304 | 9 | 10 | 27 | 43 |
| 654311 | 15 | 51 | 68 | 84 |
| 654312 | 6 | 26 | 29 | 33 |
| 654319 | 3 | 44 | 2 | 8 |
| 654320 | 4 | 12 | 5 | 12 |
| 654327 | 3 | 45 | 65 | 81 |
| 654328 | 15 | 44 | 73 | 85 |
| 654335 | 2 | 0 | 0 | 12 |
| 654336 | 0 | 0 | 0 | 0 |
| 654343 | 0 | 7 | 26 | 59 |
| 654344 | 10 | 30 | 51 | 72 |
| 654351 | 10 | 22 | 48 | 77 |
| 654352 | 8 | 26 | 57 | 76 |

Example 11: Dose-Dependent Inhibition of Human SOD-1 by Gapmers with Mixed Backbone Chemistry Additional gapmers were designed based on the sequences of the oligonucleotides disclosed in studies described above. The oligonucleotides were designed as 5-10-5 MOE gapmers, 4-8-5 MOE gapmers, 5-8-5 MOE gapmers, 5-8-7 MOE gapmers, 6-8-6 MOE gapmers, 6-9-5 MOE gapmers, or deoxy, MOE and cEt oligonucleotides.

The 5-10-5 MOE gapmers are 20 nucleosides in length, wherein the central gap segment is comprised of ten 2'-deoxynucleosides and is flanked by wing segments on the 5' direction and the 3' directions comprising five nucleosides each. The 4-8-5 MOE gapmers are 17 nucleosides in length, wherein the central gap segment is comprised of eight 2'-deoxyribonucleosides and is flanked by wing segments on the 5' direction and the 3' directions comprising four and five nucleosides respectively. The 5-8-5 MOE gapmers are 18 nucleosides in length, wherein the central gap segment is comprised of eight 2'-deoxynucleosides and is flanked by wing segments on the 5' direction and the 3' directions comprising five nucleosides each. The 5-8-7 MOE gapmers are 20 nucleosides in length, wherein the central gap segment is comprised of eight 2'-deoxynucleosides and is flanked by wing segments on the 5' direction and the 3' directions comprising five and seven nucleosides respectively. The 6-8-6 MOE gapmers are 20 nucleosides in length, wherein the central gap segment is comprised of eight 2'-deoxynucleosides and is flanked by wing segments on the 5' direction and the 3' directions comprising six nucleosides each. The 6-9-5 MOE gapmers are 20 nucleosides in length, wherein the central gap segment is comprised of nine 2'-deoxynucleosides and is flanked by wing segments on the 5' direction and the 3' directions comprising six and five nucleosides respectively. Each nucleoside in the 5' wing segment and each nucleoside in the 3' wing segment has a 2'-MOE modification.

The deoxy, MOE and cEt oligonucleotides are 17 nucleosides in length wherein each nucleoside has a MOE sugar modification, a cEt sugar modification, or a deoxy moiety. The sugar chemistry of each oligonucleotide is denoted as in the Chemistry column, where 'k' indicates a cEt modified sugar; 'd' indicates a 2'-deoxyribose; and 'e' indicates a 2'-MOE modified sugar.

The internucleoside linkages throughout each gapmer are either phosphodiester or phosphorothioate linkages. The internucleoside linkages of each oligonucleotide are denoted in the Backbone Chemistry column, where 'o' indicates a phosphodiester linkage and 's' indicates a phosphorothioate linkage. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human SOD-1 mRNA, designated herein as SEQ ID NO: 1 (GENBANK Accession No. NM_000454.4) or the human SOD-1 genomic sequence, designated herein as SEQ ID NO: 2 (GENBANK Accession No. NT 011512.10 truncated from nucleotides 18693000 to Ser. No. 18/704,000).

TABLE 45

Modified oligonucleotides targeting human SOD-1 with mixed backbone chemistry

| ISIS NO | SEQ ID NO: 1 Start Site | SEQ ID NO: 1 Stop Site | Sequence | Motif | Sugar Modifications | Backbone Chemistry | SEQ ID NO: 2 Start Site | SEQ ID NO: 2 Stop Site | SEQ ID NO |
|---|---|---|---|---|---|---|---|---|---|
| 666846 | 665 | 684 | CAGGATACATTTCTACAGCT | 5-10-5 MOE | eeeeedddddddddeeeee | sooosssssssssssooss | 9815 | 9834 | 725 |
| 666849 | 665 | 684 | CAGGATACATTTCTACAGCT | 5-10-5 MOE | eeeeedddddddddeeeee | sooosssssssssssooss | 9815 | 9834 | 725 |
| 666853 | 665 | 684 | CAGGATACATTTCTACAGCT | 5-10-5 MOE | eeeeedddddddddeeeee | sososssssssssososs | 9815 | 9834 | 725 |
| 666859 | 679 | 695 | TTAATGTTTATCAGGAT | Deoxy, MOE and cEt | eeeddddddddkeeee | sooosssssssssssooss | 9829 | 9845 | 1351 |
| 666861 | 679 | 695 | TTAATGTTTATCAGGAT | Deoxy, MOE and cEt | ekekdddddddeeeee | sooosssssssssssooss | 9829 | 9845 | 1351 |
| 666867 | 684 | 700 | AGTGTTTAATGTTTATC | Deoxy, MOE and cEt | eekkddddddddeeeee | sooossssssssssooss | 9834 | 9850 | 1173 |
| 666869 | 684 | 700 | AGTGTTTAATGTTTATC | Deoxy, MOE and cEt | ekekddddddddkekee | sooossssssssssooss | 9834 | 9850 | 1173 |
| 666870 | 684 | 700 | AGTGTTTAATGTTTATC | Deoxy, MOE and cEt | ekekddddddddeeeee | sooossssssssssooss | 9834 | 9850 | 1173 |
| 666919 | 666 | 682 | GGATACATTTCTACAGC | Deoxy, MOE and cEt | eeeddddddddkkee | soooossssssssssoss | 9816 | 9832 | 1342 |
| 666921 | 666 | 682 | GGATACATTTCTACAGC | Deoxy, MOE and cEt | eeeddddddddkkee | soooossssssssssoss | 9816 | 9832 | 1342 |
| 666922 | 666 | 682 | GGATACATTTCTACAGC | Deoxy, MOE and cEt | eeekdddddddddkeee | soooossssssssssoss | 9816 | 9832 | 1342 |
| 684059 | 676 | 692 | ATGTTTATCAGGATACA | Deoxy, MOE and cEt | eeekddddddddkeeee | sooossssssssssooss | 9826 | 9842 | 1348 |
| 684064 | 676 | 692 | ATGTTTATCAGGATACA | Deoxy, MOE and cEt | eeeddddddddkekee | sooossssssssssooss | 9826 | 9842 | 1348 |
| 684068 | 676 | 692 | ATGTTTATCAGGATACA | 4-8-5 MOE | eeeeddddddddeeeee | sooossssssssssooss | 9826 | 9842 | 1348 |
| 684087 | 590 | 607 | GGCGATCCCAATTACACC | 5-8-5 MOE | eeeeddddddddeeeee | sooossssssssssooss | 9740 | 9757 | 613 |
| 684088 | 167 | 184 | GTCGCCCTTCAGCACGCA | 5-8-5 MOE | eeeeddddddddeeeee | sooosssssssssooss | 973 | 990 | 1419 |
| 684095 | 167 | 186 | CCGTCGCCCTTCAGCACGCA | 5-10-5 MOE | eeeeedddddddddeeeee | sooosssssssssssooss | 973 | 992 | 21 |
| 684097 | 167 | 186 | CCGTCGCCCTTCAGCACGCA | 5-8-7 MOE | eeeeeddddddddeeeeeee | soooosssssssssoooss | 973 | 992 | 21 |
| 684101 | 588 | 607 | GGCGATCCCAATTACACCAC | 6-8-6 MOE | eeeeeeddddddddeeeeee | sooosssssssssssooss | 9738 | 9757 | 47 |
| 684102 | 588 | 607 | GGCGATCCCA | 5-8-7 | eeeeeddddddddeeeeeee | soooosssssssssoooss | 9738 | 9757 | 47 |

TABLE 45-continued

Modified oligonucleotides targeting human SOD-1 with mixed backbone chemistry

| ISIS NO | SEQ ID NO: 1 Start Site | SEQ ID NO: 1 Stop Site | Sequence | Motif | Sugar Modifications | Backbone Chemistry | SEQ ID NO: 2 Start Site | SEQ ID NO: 2 Stop Site | SEQ ID NO |
|---|---|---|---|---|---|---|---|---|---|
| 684104 | 588 | 607 | GGCGATCCCA ATTACACCAC | ATTACACCAC MOE 6-9-5 MOE | eeeeeedddddddddeeeee | soooosssssssssssooss | 9738 | 9757 | 47 |

The newly designed oligonucleotides were tested at various doses in A431 cells. The modified oligonucleotides were tested in a series of experiments that had similar culture conditions. The results for each experiment are presented in separate tables shown below. Cells were plated at a density of 5,000 cells per well and modified oligonucleotides were added to the media at 0.062 µM, 0.185 µM, 0.556 µM, 1.667 µM, 5.000 µM, and 15.000 µM concentrations of modified oligonucleotide for free uptake by the cells, as specified in the Tables below. After a treatment period of approximately 16 hours, RNA was isolated from the cells and SOD-1 mRNA levels were measured by quantitative real-time PCR. Human primer probe sets RTS3898 was used to measure mRNA levels. SOD-1 mRNA levels were adjusted according to total RNA content, as measured by RIBOGREEN®. Results are presented as percent inhibition of SOD-1, relative to untreated control cells.

TABLE 46

Dose response assay

| ISIS No | 0.062 µM | 0.185 µM | 0.556 µM | 1.667 µM | 5.000 µM | 15.000 µM | IC$_{50}$ (µM) |
|---|---|---|---|---|---|---|---|
| 666846 | 18 | 28 | 45 | 70 | 69 | 81 | 0.8 |
| 666919 | 0 | 1 | 13 | 28 | 42 | 55 | 11.0 |
| 666849 | 33 | 29 | 52 | 62 | 74 | 82 | 0.6 |
| 666921 | 2 | 4 | 15 | 19 | 37 | 44 | >15 |
| 666853 | 20 | 29 | 49 | 69 | 76 | 83 | 0.7 |
| 666922 | 8 | 7 | 30 | 33 | 66 | 59 | 4.1 |
| 666859 | 26 | 30 | 58 | 64 | 68 | 78 | 0.6 |
| 666861 | 6 | 21 | 44 | 76 | 68 | 77 | 1.1 |
| 666867 | 16 | 43 | 65 | 68 | 79 | 83 | 0.5 |
| 666869 | 52 | 68 | 79 | 88 | 89 | 91 | <0.06 |
| 666870 | 24 | 37 | 57 | 77 | 81 | 86 | 0.4 |

TABLE 47

Dose response assay

| ISIS No | 0.062 µM | 0.185 µM | 0.556 µM | 1.667 µM | 5.000 µM | 15.000 µM | IC$_{50}$ (µM) |
|---|---|---|---|---|---|---|---|
| 684059 | 7 | 18 | 38 | 53 | 68 | 79 | 1.5 |
| 684102 | 0 | 9 | 0 | 0 | 4 | 0 | >15 |
| 684064 | 12 | 19 | 29 | 38 | 51 | 61 | 5.0 |
| 684104 | 0 | 0 | 0 | 0 | 0 | 4 | >15 |
| 684068 | 0 | 4 | 10 | 33 | 50 | 56 | 8.0 |
| 684087 | 3 | 1 | 29 | 0 | 0 | 27 | >15 |
| 684088 | 10 | 11 | 11 | 3 | 4 | 18 | >15 |
| 684095 | 12 | 13 | 14 | 4 | 7 | 18 | >15 |
| 684097 | 8 | 4 | 5 | 4 | 3 | 9 | >15 |
| 684101 | 7 | 0 | 0 | 23 | 6 | 14 | >15 |

The newly designed oligonucleotides were also tested at various doses in SH-SY5Y cells. The modified oligonucleotides were tested in a series of experiments that had similar culture conditions. The results for each experiment are presented in separate tables shown below. Cells were plated at a density of 20,000 cells per well and modified oligonucleotides transfected using electroporation at 0.062 µM, 0.185 µM, 0.556 µM, 1.667 µM, 5.000 µM, and 15.000 µM concentrations of modified oligonucleotide, as specified in the Tables below. After a treatment period of approximately 16 hours, RNA was isolated from the cells and SOD-1 mRNA levels were measured by quantitative real-time PCR. Human primer probe set RTS3898 was used to measure mRNA levels. SOD-1 mRNA levels were adjusted according to total RNA content, as measured by RIBOGREEN®. Results are presented as percent inhibition of SOD-1, relative to untreated control cells.

wing segments on the 5' direction and the 3' directions comprising five nucleosides each. The 5-10-5 MOE gapmers are 20 nucleosides in length, wherein the central gap segment is comprised of ten 2'-deoxyribonucleosides and is flanked by wing segments on the 5' direction and the 3' directions comprising five nucleosides each. Each nucleoside in the 5' wing segment and each nucleoside in the 3' wing segment has a 2'-MOE modification. The deoxy, MOE and cEt oligonucleotides are 17 nucleosides in length wherein each nucleoside has a MOE sugar modification, a cEt sugar modification, or a deoxy moiety The sugar chemistry of each oligonucleotide is denoted as in the Chemistry column, where 'k' indicates a cEt modified sugar; 'd' indicates a 2'-deoxyribose; and 'e' indicates a 2'-MOE modified sugar. The internucleoside linkages throughout

TABLE 48

Dose response assay

| ISIS No | 0.062 µM | 0.185 µM | 0.556 µM | 1.667 µM | 5.000 µM | 15.000 µM | IC$_{50}$ (µM) |
|---|---|---|---|---|---|---|---|
| 666846 | 0 | 17 | 49 | 62 | 83 | 91 | 0.9 |
| 666919 | 10 | 3 | 23 | 35 | 77 | 78 | 2.2 |
| 666849 | 10 | 10 | 33 | 61 | 81 | 92 | 1.1 |
| 666921 | 0 | 0 | 12 | 30 | 56 | 68 | 4.8 |
| 666853 | 0 | 17 | 39 | 59 | 85 | 82 | 1.3 |
| 666922 | 9 | 0 | 12 | 33 | 65 | 76 | 3.2 |
| 666859 | 11 | 44 | 53 | 75 | 77 | 93 | 0.5 |
| 666861 | 0 | 0 | 34 | 61 | 81 | 90 | 1.4 |
| 666867 | 33 | 10 | 43 | 61 | 81 | 77 | 0.9 |
| 666869 | 38 | 49 | 61 | 83 | 81 | 84 | 0.2 |
| 666870 | 3 | 6 | 48 | 69 | 77 | 87 | 1.1 |

TABLE 49

Dose response assay

| ISIS No | 0.062 µM | 0.185 µM | 0.556 µM | 1.667 µM | 5.000 µM | 15.000 µM | IC$_{50}$ (µM) |
|---|---|---|---|---|---|---|---|
| 684059 | 4 | 30 | 51 | 68 | 88 | 92 | 0.7 |
| 684102 | 5 | 2 | 16 | 25 | 36 | 61 | 12.0 |
| 684064 | 15 | 27 | 52 | 63 | 79 | 92 | 0.7 |
| 684104 | 0 | 3 | 20 | 38 | 61 | 84 | 2.6 |
| 684068 | 0 | 4 | 32 | 37 | 61 | 83 | 2.3 |
| 684087 | 0 | 3 | 21 | 31 | 47 | 66 | 5.8 |
| 684088 | 13 | 4 | 5 | 40 | 52 | 77 | 3.9 |
| 684095 | 16 | 5 | 19 | 36 | 68 | 80 | 2.4 |
| 684097 | 11 | 15 | 9 | 30 | 59 | 76 | 3.6 |
| 684101 | 0 | 0 | 8 | 23 | 49 | 66 | 6.6 |

Example 12: Inhibition of Human SOD-1 in a Transgenic Rat Model

Gapmers from the studies described above, including benchmark compound ISIS 333611, which was previously disclosed in WO 2005/040180, were tested in an SOD-1 transgenic rat model (Taconic, Cat#2148-F and 2148-M). These hemizygous rats express mutant human SOD-1 in the spinal cord.

Additional gapmers were designed based on the sequences of the oligonucleotides disclosed in studies described above. The oligonucleotides were designed as 5-9-5 MOE gapmers, 5-10-5 MOE gapmers or deoxy, MOE and cEt oligonucleotides. The 5-9-5 MOE gapmers are 19 nucleosides in length, wherein the central gap segment is comprised of nine 2'-deoxyribonucleosides and is flanked by each gapmer are either phosphodiester or phosphorothioate linkages. The internucleoside linkages of each oligonucleotide is denoted in the Backbone Chemistry column, where 'o' indicates a phosphodiester linkage and 's' indicates a phosphorothioate linkage. All cytosine residues throughout each oligonucleotide are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Table below is targeted to either the human SOD-1 mRNA, designated herein as SEQ ID NO: 1 (GENBANK Accession No. NM_000454.4) or the human SOD-1 genomic sequence, designated herein as SEQ ID NO: 2 (GENBANK Accession No. NT_011512.10 truncated from nucleotides 18693000 to Ser. No. 18/704,000).

TABLE 50

Modified oligonucleotides targeting human SOD-1 with mixed backbone chemistry

| ISIS NO | SEQ ID NO: 1 Start Site | SEQ ID NO: 1 Stop Site | Sequence | Motif | Sugar Modifications | Backbone Chemistry | SEQ ID NO: 2 Start Site | SEQ ID NO: 2 Stop Site | SEQ ID NO |
|---|---|---|---|---|---|---|---|---|---|
| 383872 | 167 | 186 | CCGTCGCCCTTCAGCACGCA | 5-10-5 MOE | eeeeeddddddddddeeeee | sooossssssssssssooos | 973 | 992 | 21 |
| 611457 | 165 | 184 | GTCGCCCTTCAGCACGCACA | 5-10-5 MOE | eeeeeddddddddddeeeee | sooossssssssssssooos | 971 | 990 | 54 |
| 611464 | 164 | 183 | TCGCCCTTCAGCACGCACAC | 5-10-5 MOE | eeeeeddddddddddeeeee | sooossssssssssssooos | 970 | 989 | 67 |
| 611467 | 656 | 675 | TTTCTACAGCTAGCAGGATA | 5-10-5 MOE | eeeeeddddddddddeeeee | sooossssssssssssooos | 9806 | 9825 | 272 |
| 611468 | 583 | 602 | TCCCAATTACACCACAAGCC | 5-10-5 MOE | eeeeeddddddddddeeeee | sooossssssssssssooos | 9733 | 9752 | 227 |
| 611472 | 230 | 249 | CCCCACACCTTCACTGGTCC | 5-10-5 MOE | eeeeeddddddddddeeeee | sooossssssssssssooos | 4984 | 5003 | 145 |
| 611473 | 231 | 250 | TCCCCACACCTTCACTGGTC | 5-10-5 MOE | eeeeeddddddddddeeeee | sooossssssssssssooos | 4985 | 5004 | 146 |
| 611478 | 644 | 663 | GCAGGATAACAGATGAGTTA | 5-10-5 MOE | eeeeeddddddddddeeeee | sooossssssssssssooos | 9794 | 9813 | 260 |
| 611479 | 645 | 664 | AGCAGGATAACAGATGAGTT | 5-10-5 MOE | eeeeeddddddddddeeeee | sooossssssssssssooos | 9795 | 9814 | 261 |
| 611481 | 655 | 674 | TTCTACAGCTAGCAGGATAA | 5-10-5 MOE | eeeeeddddddddddeeeee | sooossssssssssssooos | 9805 | 9824 | 271 |
| 611484 | 660 | 679 | TACATTTCTACAGCTAGCAG | 5-10-5 MOE | eeeeeddddddddddeeeee | sooossssssssssssooos | 9810 | 9829 | 276 |
| 611485 | 661 | 680 | ATACATTTCTACAGCTAGCA | 5-10-5 MOE | eeeeeddddddddddeeeee | sooossssssssssssooos | 9811 | 9830 | 277 |
| 611488 | 124 | 143 | GCTAGGCCACGCCGAGGTCC | 5-10-5 MOE | eeeeeddddddddddeeeee | sooossssssssssssooos | 930 | 949 | 593 |
| 611490 | 402 | 421 | GTCAGCAGTCACATTGCCCA | 5-10-5 MOE | eeeeeddddddddddeeeee | sooossssssssssssooos | 8457 | 8476 | 666 |
| 611494 | 671 | 690 | GTTTATCAGGATACATTTCT | 5-10-5 MOE | eeeeeddddddddddeeeee | sooossssssssssssooos | 9821 | 9840 | 728 |
| 611495 | 673 | 692 | ATGTTTATCAGGATACATTT | 5-10-5 MOE | eeeeeddddddddddeeeee | sooossssssssssssooos | 9823 | 9842 | 729 |
| 611498 | 569 | 588 | CAAGCCAAACGACTTCCAGC | 5-10-5 MOE | eeeeeddddddddddeeeee | sooossssssssssssooos | 9719 | 9738 | 816 |
| 611499 | 664 | 683 | AGGATACATTTCTACAGCTA | 5-10-5 MOE | eeeeeddddddddddeeeee | sooossssssssssssooos | 9814 | 9833 | 822 |
| 612912 | 621 | 637 | CTCAGACTACATCCAAG | Deoxy, MOE, and cEt | eeekkddddddddkeee | sooossssssssssooss | 9771 | 9787 | 1146 |
| 612915 | 656 | 672 | CTACAGCTAGCAGGATA | Deoxy, MOE, and cEt | eeekkddddddddkeee | sooossssssssssooss | 9806 | 9822 | 1164 |
| 612917 | 684 | 700 | AGTGTTTAATGTTTATC | Deoxy, MOE, and cEt | eeekkddddddddkeee | sooossssssssssooss | 9834 | 9850 | 1173 |
| 612919 | 621 | 637 | CTCAGACTACATCCAAG | Deoxy, MOE, and cEt | eekkddddddddkkeee | sooossssssssssooss | 9771 | 9787 | 1146 |

TABLE 50-continued

Modified oligonucleotides targeting human SOD-1 with mixed backbone chemistry

| ISIS NO | SEQ ID NO: 1 Start Site | SEQ ID NO: 1 Stop Site | Sequence | Motif | Sugar Modifications | Backbone Chemistry | SEQ ID NO: 2 Start Site | SEQ ID NO: 2 Stop Site | SEQ ID NO |
|---|---|---|---|---|---|---|---|---|---|
| 612923 | 656 | 672 | CTACAGCTAGCAGGATA | Deoxy, MOE, and cEt | eekkddddddddkkeee | soosssssssssooss | 9806 | 9822 | 1164 |
| 612924 | 674 | 690 | GTTTATCAGGATACATT | Deoxy, MOE, and cEt | eekkddddddddkkeee | soosssssssssooss | 9824 | 9840 | 1346 |
| 612934 | 170 | 186 | CCGTCGCCCTTCAGCAC | Deoxy, MOE, and cEt | eekkddddddddkkee | sooossssssssoss | 976 | 992 | 969 |
| 612935 | 585 | 601 | CCCAATTACACCACAAG | Deoxy, MOE, and cEt | eekkddddddddkkee | sooossssssssssoss | 9735 | 9751 | 1114 |
| 612940 | 659 | 675 | TTTCTACAGCTAGCAGG | Deoxy, MOE, and cEt | eekkddddddddkkee | sooossssssssssoss | 9809 | 9825 | 1167 |
| 612942 | 668 | 684 | CAGGATACATTTCTACA | Deoxy, MOE, and cEt | eekkddddddddkkee | sooossssssssssoss | 9818 | 9834 | 1344 |
| 612943 | 674 | 690 | GTTTATCAGGATACATT | Deoxy, MOE, and cEt | eekkddddddddkkee | sooossssssssssoss | 9824 | 9840 | 1346 |
| 666854 | 665 | 681 | AGGATACATTTCTACAGCT | 5-9-5 MOE | eeeeddddddddddeeeee | soosssssssssssooss | 9815 | 9831 | 1428 |
| 666855 | 666 | 682 | CAGGATACATTTCTACAGC | 5-9-5 MOE | eeeeddddddddddeeeee | soosssssssssssooss | 9816 | 9832 | 1461 |
| 666857 | 679 | 695 | TTAATGTTTATCAGGAT | Deoxy, MOE, and cEt | eekkddddddddkeeee | soosssssssssooss | 9829 | 9845 | 1351 |
| 666858 | 679 | 695 | TTAATGTTTATCAGGAT | Deoxy, MOE, and cEt | eekkddddddddeeeee | soosssssssssooss | 9829 | 9845 | 1351 |
| 666864 | 679 | 695 | TTAATGTTTATCAGGAT | Deoxy, MOE, and cEt | kekeddddddddeeeee | soosssssssssooss | 9829 | 9845 | 1351 |
| 666865 | 679 | 695 | TTAATGTTTATCAGGAT | Deoxy, MOE, and cEt | eeeedddddddddekeke | soosssssssssooss | 9829 | 9845 | 1351 |
| 666866 | 684 | 700 | AGTGTTTAATGTTTATC | Deoxy, MOE, and cEt | eekkddddddddkeeee | soosssssssssooss | 9834 | 9850 | 1173 |
| 666908 | 686 | 702 | ACAGTGTTTAATGTTTA | Deoxy, MOE, and cEt | eeekddddddddkeeee | sooossssssssooss | 9836 | 9852 | 1175 |
| 666923 | 666 | 682 | GGATACATTTCTACAGC | Deoxy, MOE, and cEt | eekkddddddddkeeee | sooossssssssooss | 9816 | 9832 | 1342 |

The modified oligonucleotides were tested in a series of experiments that had similar conditions. The results for each experiment are presented in separate tables shown below. Rats were injected intrathecally with 30ℓ of a 16.67 mg/ml solution of modified oligonucleotide diluted in PBS (500 μg final dose). A control group of rats was injected intrathecally with PBS. Inhibition levels of SOD-1 in the lumbar spinal cord, thoracic spinal cord and cervical spinal cord were assessed. The data is presented below and indicate that several modified oligonucleotides inhibited human SOD-1 levels in this model.

TABLE 51

Percent inhibition of human SOD-1 in the spinal cord regions of transgenic rats

| ISIS No | Chemistry | Lumbar | Thoracic | Cervical | SEQ ID NO |
|---|---|---|---|---|---|
| 333611 | 5-10-5 MOE with phosphorothioate backbone chemistry | 51 | 51 | 47 | 21 |
| 383872 | 5-10-5 MOE with mixed backbone chemistry | 29 | 36 | 26 | 21 |
| 611460 | 5-10-5 MOE with mixed backbone chemistry | 55 | 53 | 25 | 1428 |
| 611464 | 5-10-5 MOE with mixed backbone chemistry | 52 | 54 | 26 | 67 |
| 611468 | 5-10-5 MOE with mixed backbone chemistry | 46 | 44 | 19 | 227 |
| 611481 | 5-10-5 MOE with mixed backbone chemistry | 39 | 44 | 33 | 271 |

TABLE 52

Percent inhibition of human SOD-1 in the spinal cord regions of transgenic rats

| ISIS No | Chemistry | Lumbar | Thoracic | Cervical | SEQ ID NO |
|---|---|---|---|---|---|
| 611473 | 5-10-5 MOE with mixed backbone chemistry | 47 | 42 | 5 | 146 |
| 611474 | 5-10-5 MOE with mixed backbone chemistry | 75 | 65 | 65 | 149 |
| 611479 | 5-10-5 MOE with mixed backbone chemistry | 24 | 13 | 20 | 261 |
| 611484 | 5-10-5 MOE with mixed backbone chemistry | 51 | 31 | 41 | 276 |
| 611485 | 5-10-5 MOE with mixed backbone chemistry | 52 | 40 | 35 | 277 |
| 611492 | 5-10-5 MOE with mixed backbone chemistry | 57 | 44 | 43 | 725 |

TABLE 53

Percent inhibition of human SOD-1 in the spinal cord regions of transgenic rats

| ISIS No | Chemistry | Lumbar | Thoracic | Cervical | SEQ ID NO |
|---|---|---|---|---|---|
| 611472 | 5-10-5 MOE with mixed backbone chemistry | 0 | 19 | 15 | 145 |
| 611478 | 5-10-5 MOE with mixed backbone chemistry | 16 | 33 | 24 | 260 |
| 611490 | 5-10-5 MOE with mixed backbone chemistry | 53 | 55 | 44 | 666 |

TABLE 53-continued

Percent inhibition of human SOD-1 in the spinal cord regions of transgenic rats

| ISIS No | Chemistry | Lumbar | Thoracic | Cervical | SEQ ID NO |
|---|---|---|---|---|---|
| 611494 | 5-10-5 MOE with mixed backbone chemistry | 34 | 39 | 38 | 728 |
| 611495 | 5-10-5 MOE with mixed backbone chemistry | 33 | 19 | 38 | 729 |
| 611498 | 5-10-5 MOE with mixed backbone chemistry | 30 | 43 | 27 | 816 |
| 611499 | 5-10-5 MOE with mixed backbone chemistry | 45 | 56 | 40 | 822 |
| 611500 | 5-10-5 MOE with mixed backbone chemistry | 56 | 58 | 52 | 823 |

TABLE 54

Percent inhibition of human SOD-1 in the spinal cord regions of transgenic rats

| ISIS No | Chemistry | Lumbar | Thoracic | Cervical | SEQ ID NO |
|---|---|---|---|---|---|
| 611457 | 5-10-5 MOE with mixed backbone chemistry | 56 | 46 | 43 | 54 |
| 611467 | 5-10-5 MOE with mixed backbone chemistry | 21 | 28 | 22 | 272 |
| 611488 | 5-10-5 MOE with mixed backbone chemistry | 14 | 23 | 4 | 593 |
| 612917 | Deoxy, MOE, and cEt with mixed backbone chemistry | 47 | 55 | 37 | 1173 |
| 612923 | Deoxy, MOE, and cEt with mixed backbone chemistry | 53 | 63 | 45 | 1164 |
| 612925 | Deoxy, MOE, and cEt with mixed backbone chemistry | 67 | 69 | 63 | 1348 |
| 612928 | Deoxy, MOE, and cEt with mixed backbone chemistry | 84 | 85 | 81 | 1351 |

TABLE 55

Percent inhibition of human SOD-1 in the spinal cord regions of transgenic rats

| ISIS No | Chemistry | Lumbar | Thoracic | Cervical | SEQ ID NO |
|---|---|---|---|---|---|
| 612912 | Deoxy, MOE, and cEt with mixed backbone chemistry | 59 | 60 | 48 | 1146 |
| 612919 | Deoxy, MOE, and cEt with mixed backbone chemistry | 60 | 60 | 58 | 1146 |
| 612916 | Deoxy, MOE, and cEt with mixed backbone chemistry | 72 | 69 | 69 | 1170 |
| 612931 | Deoxy, MOE, and cEt with mixed backbone chemistry | 81 | 79 | 72 | 1173 |

TABLE 55-continued

Percent inhibition of human SOD-1 in the spinal cord regions of transgenic rats

| ISIS No | Chemistry | Lumbar | Thoracic | Cervical | SEQ ID NO |
|---|---|---|---|---|---|
| 612932 | Deoxy, MOE, and cEt with mixed backbone chemistry | 21 | 26 | 24 | 1175 |

TABLE 56

Percent inhibition of human SOD-1 in the spinal cord regions of transgenic rats

| ISIS No | Chemistry | Lumbar | Thoracic | Cervical | SEQ ID NO |
|---|---|---|---|---|---|
| 612915 | Deoxy, MOE, and cEt with mixed backbone chemistry | 54 | 48 | 52 | 1164 |
| 612918 | Deoxy, MOE, and cEt with mixed backbone chemistry | 73 | 69 | 64 | 1175 |
| 612927 | Deoxy, MOE, and cEt with mixed backbone chemistry | 82 | 75 | 62 | 1350 |
| 612934 | Deoxy, MOE, and cEt with mixed backbone chemistry | 59 | 44 | 48 | 969 |
| 612935 | Deoxy, MOE, and cEt with mixed backbone chemistry | 64 | 54 | 62 | 1114 |
| 612940 | Deoxy, MOE, and cEt with mixed backbone chemistry | 11 | 26 | 17 | 1167 |
| 612941 | Deoxy, MOE, and cEt with mixed backbone chemistry | 81 | 75 | 71 | 1342 |
| 612942 | Deoxy, MOE, and cEt with mixed backbone chemistry | 40 | 42 | 41 | 1344 |
| 612943 | Deoxy, MOE, and cEt with mixed backbone chemistry | 61 | 54 | 51 | 1346 |
| 612944 | Deoxy, MOE, and cEt with mixed backbone chemistry | 59 | 52 | 51 | 1348 |

TABLE 57

Percent inhibition of human SOD-1 in the spinal cord regions of transgenic rats

| ISIS No | Chemistry | Lumbar | Thoracic | Cervical | SEQ ID NO |
|---|---|---|---|---|---|
| 612924 | Deoxy, MOE, and cEt with mixed backbone chemistry | 42 | 64 | 53 | 1346 |
| 612947 | Deoxy, MOE, and cEt with mixed backbone chemistry | 68 | 75 | 74 | 1351 |
| 612948 | Deoxy, MOE, and cEt with mixed backbone chemistry | 80 | 90 | 87 | 1352 |
| 612949 | Deoxy, MOE, and cEt with mixed backbone chemistry | 73 | 82 | 85 | 1172 |

TABLE 58

Percent inhibition of human SOD-1 in the spinal cord regions of transgenic rats

| ISIS No | Chemistry | Lumbar | Cervical | SEQ ID NO |
|---|---|---|---|---|
| 654304 | 5-8-5 MOE with mixed backbone chemistry | 28 | 6 | 1429 |
| 654305 | 5-8-5 MOE with mixed backbone chemistry | 14 | 0 | 1430 |
| 654306 | 5-8-5 MOE with mixed backbone chemistry | 36 | 0 | 1432 |
| 654307 | 5-8-5 MOE with mixed backbone chemistry | 17 | 0 | 1432 |

TABLE 59

Percent inhibition of human SOD-1 in the spinal cord regions of transgenic rats

| ISIS No | Chemistry | Lumbar | Cervical | SEQ ID NO |
|---|---|---|---|---|
| 654334 | Deoxy, MOE, and cEt with mixed backbone chemistry | 39 | 19 | 1454 |
| 666854 | 5-9-5 MOE with mixed backbone chemistry | 52 | 39 | 1428 |
| 666855 | 5-9-5 MOE with mixed backbone chemistry | 37 | 17 | 1461 |
| 666857 | Deoxy, MOE, and cEt with mixed backbone chemistry | 59 | 39 | 1351 |
| 666858 | Deoxy, MOE, and cEt with mixed backbone chemistry | 38 | 22 | 1351 |
| 666859 | Deoxy, MOE, and cEt with mixed backbone chemistry | 79 | 64 | 1351 |
| 666864 | Deoxy, MOE, and cEt with mixed backbone chemistry | 50 | 40 | 1351 |
| 666865 | Deoxy, MOE, and cEt with mixed backbone chemistry | 73 | 44 | 1351 |
| 666866 | Deoxy, MOE, and cEt with mixed backbone chemistry | 67 | 56 | 1173 |
| 666908 | Deoxy, MOE, and cEt with mixed backbone chemistry | 38 | 13 | 1175 |
| 666923 | Deoxy, MOE, and cEt with mixed backbone chemistry | 45 | 26 | 1342 |

TABLE 60

Percent inhibition of human SOD-1 in the spinal cord regions of transgenic rats

| ISIS No | Chemistry | Lumbar | Cervical | SEQ ID NO |
|---|---|---|---|---|
| 654323 | Deoxy, MOE, and cEt with mixed backbone chemistry | 53 | 35 | 1433 |
| 666846 | 5-10-5 MOE with mixed backbone chemistry | 64 | 50 | 725 |
| 666849 | 5-10-5 MOE with mixed backbone chemistry | 63 | 55 | 725 |
| 666853 | 5-10-5 MOE with mixed backbone chemistry | 81 | 74 | 725 |
| 666861 | Deoxy, MOE, and cEt with mixed backbone chemistry | 55 | 47 | 1351 |

TABLE 60-continued

Percent inhibition of human SOD-1 in the spinal cord regions of transgenic rats

| ISIS No | Chemistry | Lumbar | Cervical | SEQ ID NO |
|---|---|---|---|---|
| 666867 | Deoxy, MOE, and cEt with mixed backbone chemistry | 59 | 48 | 1173 |
| 666869 | Deoxy, MOE, and cEt with mixed backbone chemistry | 82 | 81 | 1173 |
| 666870 | Deoxy, MOE, and cEt with mixed backbone chemistry | 76 | 68 | 1173 |
| 666919 | Deoxy, MOE, and cEt with mixed backbone chemistry | 76 | 68 | 1342 |
| 666921 | Deoxy, MOE, and cEt with mixed backbone chemistry | 71 | 65 | 1342 |
| 666922 | Deoxy, MOE, and cEt with mixed backbone chemistry | 67 | 62 | 1342 |

TABLE 61

Percent inhibition of human SOD-1 in the spinal cord regions of transgenic rats

| ISIS No | Chemistry | Lumbar | SEQ ID NO |
|---|---|---|---|
| 684059 | Deoxy, MOE, and cEt with mixed backbone chemistry | 54 | 1348 |
| 684064 | Deoxy, MOE, and cEt with mixed backbone chemistry | 51 | 1348 |
| 684068 | 4-8-5 MOE with mixed backbone chemistry | 18 | 1348 |
| 684087 | 5-8-5 MOE with mixed backbone chemistry | 37 | 613 |
| 684088 | 5-8-5 MOE with mixed backbone chemistry | 31 | 1419 |
| 684095 | 5-10-5 MOE with mixed backbone chemistry | 34 | 21 |
| 684097 | 5-8-7 MOE with mixed backbone chemistry | 22 | 21 |
| 684101 | 6-8-6 MOE with mixed backbone chemistry | 22 | 47 |
| 684104 | 6-9-5 MOE with mixed backbone chemistry | 11 | 47 |

Example 13: Dose-Dependent Inhibition of Human SOD-1 with Modified Oligonucleotides in LLC-MK2 Cells Gapmers from the studies described above, including benchmark compound ISIS 333611, exhibiting significant in vitro inhibition of SOD-1 mRNA were selected and tested at various doses in LLC-MK2 cells. The cross-reactivity of the human modified oligonucleotides tested in this study with the rhesus monkey genomic sequence (the complement of GENBANK Accession No. NW_001114168.1 truncated from nucleotides 2258000 to 2271000, designated herein as SEQ ID NO: 3) is shown in the Table below.

TABLE 62

Cross-reactivity of antisense oligonucleotides targeting human SOD1 with SEQ ID NO: 3

| ISIS No | Start Site of SEQ ID NO: 3 | Mismatches |
|---|---|---|
| 333611 | 1572 | 2 |
| 436839 | 1564 | 0 |
| 436854 | 9049 | 0 |
| 436867 | 10347 | 0 |
| 666853 | 10375 | 1 |
| 666859 | 10389 | 1 |
| 666919 | 10376 | 1 |
| 666921 | 10376 | 1 |

Cells were plated at a density of 20,000 cells per well and transfected using electroporation with 0.078 µM, 0.156 µM, 0.313 µM, 0.625 µM, 1.25 µM, 2.50 µM, 5.00 µM, and 10.000 µM concentrations of modified oligonucleotide, as specified in the Tables below. After a treatment period of approximately 16 hours, RNA was isolated from the cells and SOD-1 mRNA levels were measured by quantitative real-time PCR Primer probe set RTS3121 (forward sequence TGGAGATAATACACAAGGCTGTACCA, designated herein as SEQ ID NO: 17; reverse sequence CAACATGC-CTCTCTTCATCCTTT, designated herein as SEQ ID NO: 18; probe sequence ATCCTCTATCCAGACAACACG-GTGGGC, designated herein as SEQ ID NO: 19) was used to measure mRNA levels. SOD-1 mRNA levels were adjusted according to total RNA content, as measured by RIBOGREEN®. Results are presented as percent inhibition of SOD-1, relative to untreated control cells. The half maximal inhibitory concentration ($IC_{50}$) of each oligonucleotide is also presented. As presented in the Table, several of the newly designed oligonucleotides were more potent than the benchmark, ISIS 336611.

TABLE 63

Dose-dependent inhibition of SOD-1 rhesus monkey mRNA

| ISIS No | 0.078 µM | 0.156 µM | 0.313 µM | 0.625 µM | 1.25 µM | 2.50 µM | 5.00 µM | 10.00 µM | $IC_{50}$ (µM) |
|---|---|---|---|---|---|---|---|---|---|
| 333611 | 3 | 2 | 0 | 0 | 17 | 15 | 19 | 40 | >10 |
| 436839 | 0 | 0 | 5 | 0 | 20 | 22 | 37 | 61 | 7.1 |
| 436854 | 34 | 34 | 40 | 39 | 52 | 65 | 69 | 84 | 1.2 |
| 436867 | 3 | 0 | 11 | 18 | 34 | 49 | 70 | 87 | 2.2 |
| 666853 | 7 | 34 | 20 | 39 | 60 | 80 | 79 | 92 | 1.0 |
| 666859 | 0 | 9 | 20 | 18 | 15 | 25 | 30 | 44 | >10 |
| 666919 | 11 | 15 | 16 | 36 | 51 | 65 | 73 | 84 | 1.4 |
| 666921 | 0 | 13 | 28 | 37 | 50 | 52 | 62 | 74 | 1.8 |

Example 14: Tolerability of SOD-1 Modified Oligonucleotides in a Rat Model

Gapmers from the studies described above, including benchmark compound ISIS 333611, which was previously disclosed in WO 2005/040180, were tested for tolerability in Sprague-Dawley rats.

The modified oligonucleotides were tested in a series of experiments that had similar conditions. Rats were injected intrathecally with 3 mg of a single dose of ISIS oligonucleotide. A control group of rats was injected intrathecally with PBS. Acute tolerability was assessed 3 hours post-dose using a functional observational battery (FOB). This score is used to evaluate the acute tolerability of a compound with lower scores denoting better tolerated compounds. Control animals usually have a score of '0' or '1'. At 3 hours post injection, the rats are observed by placing each rat on the cage top and evaluating certain functions, assigning a number of '0' or '1' depending on whether the rat exhibits normal function in the region of interest (0) or does not (1) for each function, and then adding the total scores. Seven regions are assessed, including tail, hind paws, hind legs, hind end, front posture, fore paws, and head. The results of the scoring are presented in the Table below. As presented in the Table, several newly designed oligonucleotides demonstrated more acute tolerability compared to the benchmark, ISIS 333611.

TABLE 64

FOB scores in Sprague-Dawley rats

| ISIS No | Target Start Site on SEQ ID NO: 1 | Chemistry | FOB score |
|---|---|---|---|
| 333611 | 167 | 5-10-5 MOE with phosphorothioate backbone | 4 |
| 684073 | 167 | Deoxy, MOE, and cEt with mixed backbone | 3 |
| 684081 | 167 | Deoxy, MOE, and cEt with mixed backbone | 1 |
| 684088 | 167 | 5-8-5 MOE with mixed backbone | 0 |
| 684093 | 167 | 5-9-5 MOE with mixed backbone | 0 |
| 684095 | 167 | 5-10-5 MOE with mixed backbone | 0 |
| 684096 | 167 | 6-8-6 MOE with mixed backbone | 0 |
| 684097 | 167 | 5-8-7 MOE with mixed backbone | 0 |
| 684098 | 167 | 7-8-5 MOE with mixed backbone | 0 |
| 684099 | 167 | 6-9-5 MOE with mixed backbone | 0 |
| 684074 | 168 | Deoxy, MOE, and cEt with mixed backbone | 0 |
| 684082 | 168 | Deoxy, MOE, and cEt with mixed backbone | 1 |
| 684089 | 168 | 5-8-5 MOE with mixed backbone | 0 |
| 684094 | 168 | 5-9-5 MOE with mixed backbone | 1 |
| 684075 | 169 | Deoxy, MOE, and cEt with mixed backbone | 3 |
| 684083 | 169 | Deoxy, MOE, and cEt with mixed backbone | 3 |
| 684090 | 169 | 5-8-5 MOE with mixed backbone | 2 |
| 684076 | 170 | Deoxy, MOE, and cEt with mixed backbone | 2 |
| 684084 | 170 | Deoxy, MOE, and cEt with mixed backbone | 4 |
| 611474 | 234 | 5-10-5 MOE with mixed backbone | 4 |
| 654301 | 234 | 5-8-5 MOE with mixed backbone | 3 |
| 654302 | 235 | 5-8-5 MOE with mixed backbone | 1 |
| 654303 | 236 | 5-8-5 MOE with mixed backbone | 0 |
| 684069 | 588 | Deoxy, MOE, and cEt with mixed backbone | 0 |
| 684077 | 588 | Deoxy, MOE, and cEt with mixed backbone | 1 |
| 684085 | 588 | 5-8-5 MOE with mixed backbone | 0 |
| 684091 | 588 | 5-9-5 MOE with mixed backbone | 0 |
| 684100 | 588 | 5-10-5 MOE with mixed backbone | 0 |
| 684101 | 588 | 6-8-6 MOE with mixed backbone | 0 |
| 684102 | 588 | 5-8-7 MOE with mixed backbone | 0 |
| 684103 | 588 | 7-8-5 MOE with mixed backbone | 0 |
| 684104 | 588 | 6-9-5 MOE with mixed backbone | 0 |
| 684070 | 589 | Deoxy, MOE, and cEt with mixed backbone | 0 |
| 684078 | 589 | Deoxy, MOE, and cEt with mixed backbone | 0 |
| 684086 | 589 | 5-8-5 MOE with mixed backbone | 0 |
| 684092 | 589 | 5-9-5 MOE with mixed backbone | 0 |
| 684071 | 590 | Deoxy, MOE, and cEt with mixed backbone | 0 |
| 684079 | 590 | Deoxy, MOE, and cEt with mixed backbone | 0 |
| 684087 | 590 | 5-8-5 MOE with mixed backbone | 0 |
| 684072 | 591 | Deoxy, MOE, and cEt with mixed backbone | 1 |
| 684080 | 591 | Deoxy, MOE, and cEt with mixed backbone | 1 |
| 654304 | 663 | 5-8-5 MOE with mixed backbone | 3 |
| 612916 | 664 | Deoxy, MOE, and cEt with mixed backbone | 0 |
| 654305 | 664 | 5-8-5 MOE with mixed backbone | 2 |
| 611492 | 665 | 5-10-5 MOE with mixed backbone | 0 |
| 654306 | 665 | 5-8-5 MOE with mixed backbone | 3 |
| 654323 | 665 | Deoxy, MOE, and cEt with mixed backbone | 0 |
| 654341 | 665 | Deoxy, MOE, and cEt with mixed backbone | 0 |
| 666846 | 665 | 5-10-5 MOE with mixed backbone | 0 |
| 666849 | 665 | 5-10-5 MOE with mixed backbone | 0 |
| 666851 | 665 | 5-10-5 MOE with mixed backbone | 1 |
| 666853 | 665 | 5-10-5 MOE with mixed backbone | 0 |
| 666854 | 665 | 5-9-5 MOE with mixed backbone | 1 |
| 611500 | 666 | 5-10-5 MOE with mixed backbone | 0 |
| 612941 | 666 | Deoxy, MOE, and cEt with mixed backbone | 3 |
| 654307 | 666 | 5-8-5 MOE with mixed backbone | 2 |
| 654342 | 666 | Deoxy, MOE, and cEt with mixed backbone | 2 |

TABLE 64-continued

FOB scores in Sprague-Dawley rats

| ISIS No | Target Start Site on SEQ ID NO: 1 | Chemistry | FOB score |
|---|---|---|---|
| 666845 | 666 | 5-10-5 MOE with mixed backbone | 0 |
| 666848 | 666 | 5-10-5 MOE with mixed backbone | 1 |
| 666850 | 666 | 5-10-5 MOE with mixed backbone | 0 |
| 666852 | 666 | 5-10-5 MOE with mixed backbone | 1 |
| 666855 | 666 | 5-9-5 MOE with mixed backbone | 1 |
| 666917 | 666 | Deoxy, MOE, and cEt with mixed backbone | 3 |
| 666918 | 666 | Deoxy, MOE, and cEt with mixed backbone | 3 |
| 666919 | 666 | Deoxy, MOE, and cEt with mixed backbone | 2 |
| 666920 | 666 | Deoxy, MOE, and cEt with mixed backbone | 1 |
| 666921 | 666 | Deoxy, MOE, and cEt with mixed backbone | 2 |
| 666922 | 666 | Deoxy, MOE, and cEt with mixed backbone | 3 |
| 666923 | 666 | Deoxy, MOE, and cEt with mixed backbone | 2 |
| 666856 | 667 | 5-9-5 MOE with mixed backbone | 3 |
| 612925 | 676 | Deoxy, MOE, and cEt with mixed backbone | 4 |
| 684059 | 676 | Deoxy, MOE, and cEt with mixed backbone | 4 |
| 684060 | 676 | Deoxy, MOE, and cEt with mixed backbone | 3 |
| 684061 | 676 | Deoxy, MOE, and cEt with mixed backbone | 4 |
| 684062 | 676 | Deoxy, MOE, and cEt with mixed backbone | 4 |
| 684063 | 676 | Deoxy, MOE, and cEt with mixed backbone | 5 |
| 684064 | 676 | Deoxy, MOE, and cEt with mixed backbone | 4 |
| 684065 | 676 | Deoxy, MOE, and cEt with mixed backbone | 4 |
| 684066 | 676 | Deoxy, MOE, and cEt with mixed backbone | 4 |
| 684067 | 676 | Deoxy, MOE, and cEt with mixed backbone | 5 |
| 684068 | 676 | 4-8-5 MOE with mixed backbone | 4 |
| 612927 | 678 | Deoxy, MOE, and cEt with mixed backbone | 4 |
| 654309 | 678 | 5-8-5 MOE with mixed backbone | 4 |
| 612928 | 679 | Deoxy, MOE, and cEt with mixed backbone | 2 |
| 612947 | 679 | Deoxy, MOE, and cEt with mixed backbone | 7 |
| 654310 | 679 | 5-8-5 MOE with mixed backbone | 3 |
| 666857 | 679 | Deoxy, MOE, and cEt with mixed backbone | 1 |
| 666858 | 679 | Deoxy, MOE, and cEt with mixed backbone | 1 |
| 666859 | 679 | Deoxy, MOE, and cEt with mixed backbone | 1 |
| 666860 | 679 | Deoxy, MOE, and cEt with mixed backbone | 0 |
| 666861 | 679 | Deoxy, MOE, and cEt with mixed backbone | 5 |
| 666862 | 679 | Deoxy, MOE, and cEt with mixed backbone | 1 |
| 666863 | 679 | Deoxy, MOE, and cEt with mixed backbone | 4 |
| 666864 | 679 | Deoxy, MOE, and cEt with mixed backbone | 4 |
| 666865 | 679 | Deoxy, MOE, and cEt with mixed backbone | 5 |
| 611497 | 681 | 5-10-5 MOE with mixed backbone | 5 |
| 612948 | 681 | Deoxy, MOE, and cEt with mixed backbone | 3 |
| 666847 | 681 | 5-10-5 MOE with mixed backbone | 7 |
| 612949 | 683 | Deoxy, MOE, and cEt with mixed backbone | 4 |
| 612931 | 684 | Deoxy, MOE, and cEt with mixed backbone | 4 |
| 666866 | 684 | Deoxy, MOE, and cEt with mixed backbone | 6 |
| 666867 | 684 | Deoxy, MOE, and cEt with mixed backbone | 6 |
| 666868 | 684 | Deoxy, MOE, and cEt with mixed backbone | 6 |
| 666869 | 684 | Deoxy, MOE, and cEt with mixed backbone | 6 |
| 666870 | 684 | Deoxy, MOE, and cEt with mixed backbone | 6 |
| 666871 | 684 | Deoxy, MOE, and cEt with mixed backbone | 6 |
| 666872 | 684 | Deoxy, MOE, and cEt with mixed backbone | 6 |
| 666873 | 684 | Deoxy, MOE, and cEt with mixed backbone | 6 |
| 666874 | 684 | Deoxy, MOE, and cEt with mixed backbone | 5 |
| 612918 | 686 | Deoxy, MOE, and cEt with mixed backbone | 4 |
| 612932 | 686 | Deoxy, MOE, and cEt with mixed backbone | 2 |
| 666906 | 686 | Deoxy, MOE, and cEt with mixed backbone | 2 |
| 666907 | 686 | Deoxy, MOE, and cEt with mixed backbone | 3 |
| 666908 | 686 | Deoxy, MOE, and cEt with mixed backbone | 1 |
| 666909 | 686 | Deoxy, MOE, and cEt with mixed backbone | 0 |
| 666910 | 686 | Deoxy, MOE, and cEt with mixed backbone | 2 |
| 666911 | 686 | Deoxy, MOE, and cEt with mixed backbone | 0 |
| 666912 | 686 | Deoxy, MOE, and cEt with mixed backbone | 0 |
| 666913 | 686 | Deoxy, MOE, and cEt with mixed backbone | 0 |
| 666914 | 686 | Deoxy, MOE, and cEt with mixed backbone | 0 |
| 666915 | 686 | Deoxy, MOE, and cEt with mixed backbone | 1 |
| 666916 | 686 | Deoxy, MOE, and cEt with mixed backbone | 1 |
| 654318 | 687 | 5-8-5 MOE with mixed backbone | 1 |
| 654334 | 687 | Deoxy, MOE, and cEt with mixed backbone | 3 |

Tolerability was also assessed 8 weeks post-dose by measuring the levels of IBA1, a microglial marker, and GFAP, an astrocytic marker, in the lumbar spinal cord region. Both IBA1 and GFAP are markers of CNS inflammation (Frank, M G, *Brain Behav. Immun.* 2007, 21, 47-59), hence the higher the level of either marker, the less tolerable the antisense oligonucleotide is deemed to be in this rat model.

IBA1 mRNA levels were measured with primer probe set rAIF1_LTS00219 (forward sequence AGGA-GAAAAACAAAGAACACCAGAA, designated herein as SEQ ID NO: 5; reverse sequence CAATTAGGGCAACTCAGAAATAGCT, designated herein as SEQ ID NO: 6; probe sequence CCAACTGGTCCCCCAGCCAAGA, designated herein as SEQ ID NO: 7). GFAP mRNA levels were measured with primer probe set mGFAP_LTS00370 (forward sequence GAAACCAGCCTGGACACCAA, designated herein as SEQ ID NO: 8; reverse sequence TCCACAGTCTTTACCACGATGTTC, designated herein as SEQ ID NO: 9; probe sequence TCCGTGTCAGAAGGCCACCTCAAGA, designated herein as SEQ ID NO: 10).

The results are presented in the Table below. As presented in the Table, several newly designed oligonucleotides were more tolerable compared to the benchmark, ISIS 333611.

TABLE 65

IBA1 and GFAP mRNA levels (% control) in the lumbar regions of Sprague-Dawley rats

| ISIS No. | IBA1 | GFAP |
|---|---|---|
| 333611 | 341 | 314 |
| 654301 | 149 | 137 |
| 654302 | 261 | 129 |
| 654303 | 110 | 80 |
| 654304 | 143 | 130 |
| 654305 | 185 | 158 |
| 654306 | 110 | 106 |
| 654307 | 152 | 144 |
| 654309 | 195 | 169 |
| 654310 | 119 | 141 |
| 654318 | 93 | 81 |
| 654323 | 125 | 113 |
| 654334 | 114 | 75 |
| 654341 | 209 | 224 |
| 654342 | 473 | 485 |
| 666845 | 389 | 416 |
| 666846 | 173 | 171 |
| 666847 | 271 | 297 |
| 666848 | 399 | 377 |
| 666849 | 140 | 150 |
| 666850 | 246 | 252 |
| 666851 | 246 | 199 |
| 666852 | 282 | 266 |
| 666853 | 168 | 147 |
| 666854 | 135 | 123 |
| 666855 | 238 | 221 |
| 666856 | 253 | 209 |
| 666857 | 242 | 182 |
| 666858 | 169 | 134 |
| 666859 | 185 | 162 |
| 666861 | 161 | 152 |
| 666862 | 254 | 285 |
| 666863 | 216 | 185 |
| 666864 | 174 | 154 |
| 666865 | 251 | 232 |
| 666866 | 281 | 135 |
| 666867 | 132 | 112 |
| 666868 | 199 | 211 |
| 666869 | 262 | 207 |
| 666870 | 201 | 189 |
| 666871 | 192 | 214 |
| 666872 | 441 | 136 |
| 666873 | 340 | 277 |
| 666874 | 204 | 199 |
| 666917 | 292 | 244 |
| 666919 | 115 | 85 |
| 666920 | 155 | 102 |
| 666921 | 108 | 82 |
| 666922 | 123 | 82 |
| 666923 | 118 | 93 |
| 684059 | 168 | 162 |
| 684060 | 158 | 141 |
| 684061 | 335 | 263 |
| 684062 | 218 | 265 |
| 684064 | 191 | 168 |

TABLE 65-continued

IBA1 and GFAP mRNA levels (% control) in the lumbar regions of Sprague-Dawley rats

| ISIS No. | IBA1 | GFAP |
|---|---|---|
| 684065 | 245 | 304 |
| 684066 | 313 | 376 |
| 684067 | 171 | 151 |
| 684068 | 157 | 135 |
| 684085 | 459 | 586 |
| 684086 | 187 | 227 |
| 684087 | 215 | 263 |
| 684088 | 151 | 183 |
| 684089 | 507 | 667 |
| 684090 | 130 | 170 |
| 684091 | 350 | 426 |
| 684092 | 366 | 333 |
| 684093 | 412 | 264 |
| 684094 | 294 | 373 |
| 684095 | 213 | 215 |
| 684096 | 404 | 335 |
| 684097 | 217 | 206 |
| 684098 | 378 | 438 |
| 684099 | 534 | 473 |
| 684100 | 276 | 259 |
| 684101 | 153 | 125 |
| 684102 | 237 | 242 |
| 684103 | 588 | 416 |
| 684104 | 221 | 193 |

Example 15: Dose Dependent Inhibition of Human SOD-1 in a Transgenic Rat Model

Gapmers from the studies described above, including benchmark compound ISIS 333611, were tested in an SOD-1 transgenic rat model (Taconic, Cat#2148-F and 2148-M). These hemizygous rats express mutant human SOD-1 in the spinal cord, many brain regions, and peripheral organs.

Rats were injected intrathecally with 10, 30, 100, 300, 1000, or 3000 μg of a gapmer listed in the table below or with only PBS. Two weeks later, the animals were sacrificed. Inhibition of SOD-1 mRNA in the lumbar spinal cord, cervical spinal cord, rostral cortex, and caudal cortex was assessed by RT-PCR using primer probe set RTS3898, described in Example 1. The data is presented below as $ED_{50}$ values, and indicates that the oligonucleotides inhibited SOD1 mRNA in multiple CNS tissues more potently than Isis 333611. Indeed, $ED_{50}$ values for Isis No. 333611 could not even be calculated, as indicated by an entry of "n/a," because even the highest concentration tested (3000 μg) did not inhibit SOD-1 mRNA greater than 55-65%. "n.d." indicates that there is no data available for the indicated sample.

TABLE 66

Inhibition of human SOD1 in transgenic rats

| Isis No. | $ED_{50}$ (μg) | | | | SEQ ID NO. |
|---|---|---|---|---|---|
| | Lumbar | Cervical | Rostral | Caudal | |
| 333611 | n/a | n/a | n.d. | n.d. | 21 |
| 666853 | 81.3 | 242.6 | 6434 | 931 | 725 |
| 666859 | 74.0 | 358.8 | 2360 | 1113 | 1351 |
| 666870 | 139.4 | 1111 | 5511 | 2105 | 1173 |
| 666919 | 104.1 | 613.5 | >6000 | 2655 | 1342 |

Example 16: Tolerability of SOD-1 Modified Oligonucleotides in Rats

Gapmers from the studies described above, including benchmark compound ISIS 333611, were tested for tolerability in Sprague-Dawley rats. Groups of 4 to 6 rats were injected intrathecally with 1 mg or 3 mg of a single dose of an ISIS oligonucleotide. A control group of rats was injected intrathecally with PBS. Acute tolerability was assessed 3 hours post-dose, as described in Example 14. The results for the 1 mg dose are the averages for each group following one experiment. The results for the 3 mg dose are the averages for each group across two replicate experiments. The results of the study, presented in the table below, indicate that several newly designed oligonucleotides were more tolerable than the benchmark, ISIS 333611.

TABLE 67

FOB values

| Isis No. | 3 hour FOB | | 8 week FOB | |
| --- | --- | --- | --- | --- |
| | 1 mg | 3 mg | 1 mg | 3mg |
| 333611 | 3.0 | 4.9 | 0.0 | 1.2 |
| 666853 | 0.0 | 0.5 | 0.0 | 0.0 |
| 666859 | 0.0 | 2.1 | 0.0 | 0.3 |
| 666870 | 2.3 | 5.8 | 0.0 | 0.8 |
| 666919 | 1.3 | 3.5 | 0.0 | 0.1 |

Example 17: Dose Dependent Inhibition of Human SOD-1 in a Transgenic Mouse Model In order to confirm the results obtained in transgenic rats in another species, gapmers from the studies described above were tested in an SOD-1 transgenic mouse model that expresses the same G93A human mutant SOD1 gene that the transgenic rat expresses (see Examples 12 and 15).

Mice received an intracerebral ventricular bolus (ICVB) of 10, 30, 100, 300, or 700 µg of a gapmer listed in the table below, or PBS. Two weeks later, the animals were sacrificed. Inhibition of SOD-1 mRNA in the lumbar spinal cord and cortex was assessed by RT-PCR using primer probe set RTS3898, described in Example 1. The data is presented below as $ED_{50}$ values, and indicates that the oligonucleotides inhibited SOD1 mRNA more potently than Isis 333611 in both rats and mice.

TABLE 68

Inhibition of human SOD1 in transgenic mice

| Isis No. | Lumbar $ED_{50}$ (µg) | Cortex $ED_{50}$ (µg) |
| --- | --- | --- |
| 333611 | 401 | 786 |
| 666853 | 136 | 188 |
| 666859 | 106 | 206 |
| 666870 | 148 | 409 |
| 666919 | 168 | 1211 |

Example 18: Tolerability of SOD-1 Modified Oligonucleotides in Mice

Gapmers from the studies described above, including benchmark compound ISIS 333611, were tested for tolerability in C57bl6 mice. Mice were injected stereotaxically into the cerebral ventricles with 700 ug of a single dose of ISIS oligonucleotide. A control group of mice was injected into the cerebral ventricle with PBS. Acute tolerability was assessed at 3 hours post injection using a functional observation battery (FOB) different from that used for the rats. Each mouse was evaluated according to 7 different criteria. The 7 criteria are (1) the mouse was bright, alert, and responsive; (2) the mouse was standing or hunched without stimuli; (3) the mouse shows any movement without stimuli (4) the mouse demonstrates forward movement after its lifted; (5) the mouse demonstrates any movement after its lifted; (6) the mouse responds to a tail pinch; (7) regular breathing. For each of the 7 different criteria, each mouse was given a sub-score of 0 if it met the criteria or 1 if it did not. After all of the 7 criteria were evaluated, the sub-scores were summed for each mouse and then averaged for each group. For example, if a mouse was bright, alert, and responsive 3 hours after the 700 µg ICV dose, and met all other criteria, it would get a summed score of 0. If another mouse was not bright, alert, and responsive 3 hours after the 700 µg ICV dose but met all other criteria, it would receive a score of 1. Saline treated mice generally receive a score of 0. A score at the top end of the range would be suggestive of acute toxicity.

Body weights were measured throughout the study and are reported below as percent change at 8 weeks relative to baseline. Long term tolerability was assessed 8 weeks post-dose by measuring the levels of IBA1 and GFAP, as described in Example 14. IBA1 and GFAP mRNA levels are reported relative to PBS treated animals. The results of the study, presented in the tables below, indicate that several newly designed oligonucleotides were more tolerable, in rats and mice, compared to the benchmark, ISIS 333611.

TABLE 69

FOB values and body weight change

| Isis No. | 3 hour FOB | Body weight (% change) |
| --- | --- | --- |
| 333611 | 6.5 | 3.8 |
| 666853 | 1.25 | 8.0 |
| 666859 | 1.75 | 14.0 |
| 666870 | 4.75 | 7.3 |
| 666919 | 0.0 | 5.2 |

TABLE 70

Inflammation markers

| Isis No. | IBA1 (% PBS) | | GFAP (% PBS) | |
| --- | --- | --- | --- | --- |
| | Lumbar | Cortex | Lumbar | Cortex |
| 333611 | 130.3 | 134.3 | 117.5 | 207.7 |
| 666853 | 102.8 | 109.3 | 103.3 | 103.7 |
| 666859 | 110.4 | 98.2 | 109.0 | 72.8 |
| 666870 | 158.8 | 117.8 | 106.7 | 128.6 |
| 666919 | 115.0 | 97.9 | 99.8 | 84.3 |

Example 19: Dose Dependent Inhibition of Monkey SOD-1 in Cynomolgus Monkey

Isis No. 666853 was tested in cynomolgus monkey. There is one mismatch between Isis No. 666853 and cynomolgus monkey SOD-1, and there are 17 contiguous bases in Isis No. 666853 that are 100% complementary to cynomolgus monkey SOD-1.

Groups of 6-10 male and female monkeys received an intrathecal lumbar bolus of PBS or 4, 12, or 35 mg of Isis No. 666853 on days 1, 14, 28, 56, and 84 of the study. Each group received the same dose on all five dosing days. On day 91, the animals were sacrificed. Inhibition of SOD-1 mRNA in the lumbar, thoracic, and cervical spinal cord and frontal cortex, motor cortex, hippocampus, pons, and cerebellum was assessed by RT-PCR using primer probe set RTS3898.

The data is presented below as the average percent inhibition for each treatment group, relative to the PBS treated group. The results indicate that Isis No. 666853 inhibited SOD-1 mRNA in multiple target tissues in cynomolgus monkey.

Treatment with 666853 was well tolerated for the duration of the 13 week study and there were no clinical observations of adverse reactions in monkeys.

TABLE 71

Inhibition of SOD-1 mRNA in monkeys

| Amount of 666853 per dose (mg) | Inhibition (%) | | | | | | | |
|---|---|---|---|---|---|---|---|---|
| | Lumbar | Thoracic | Cervical | Frontal cortex | Motor cortex | Hippocampus | Pons | Cerebellum |
| 4 | 44.4 | 27.1 | 20.1 | 21.5 | 21.6 | 32.0 | 6.8 | 15.4 |
| 12 | 75.4 | 69.0 | 42.1 | 56.7 | 55.7 | 31.8 | 13.2 | 33.3 |
| 35 | 87.0 | 74.8 | 72.1 | 80.5 | 82.6 | 80.1 | 48.6 | 48.4 |

What is claimed is:
1. A salt of an antisense compound, wherein the anion of the antisense compound has the following formula:
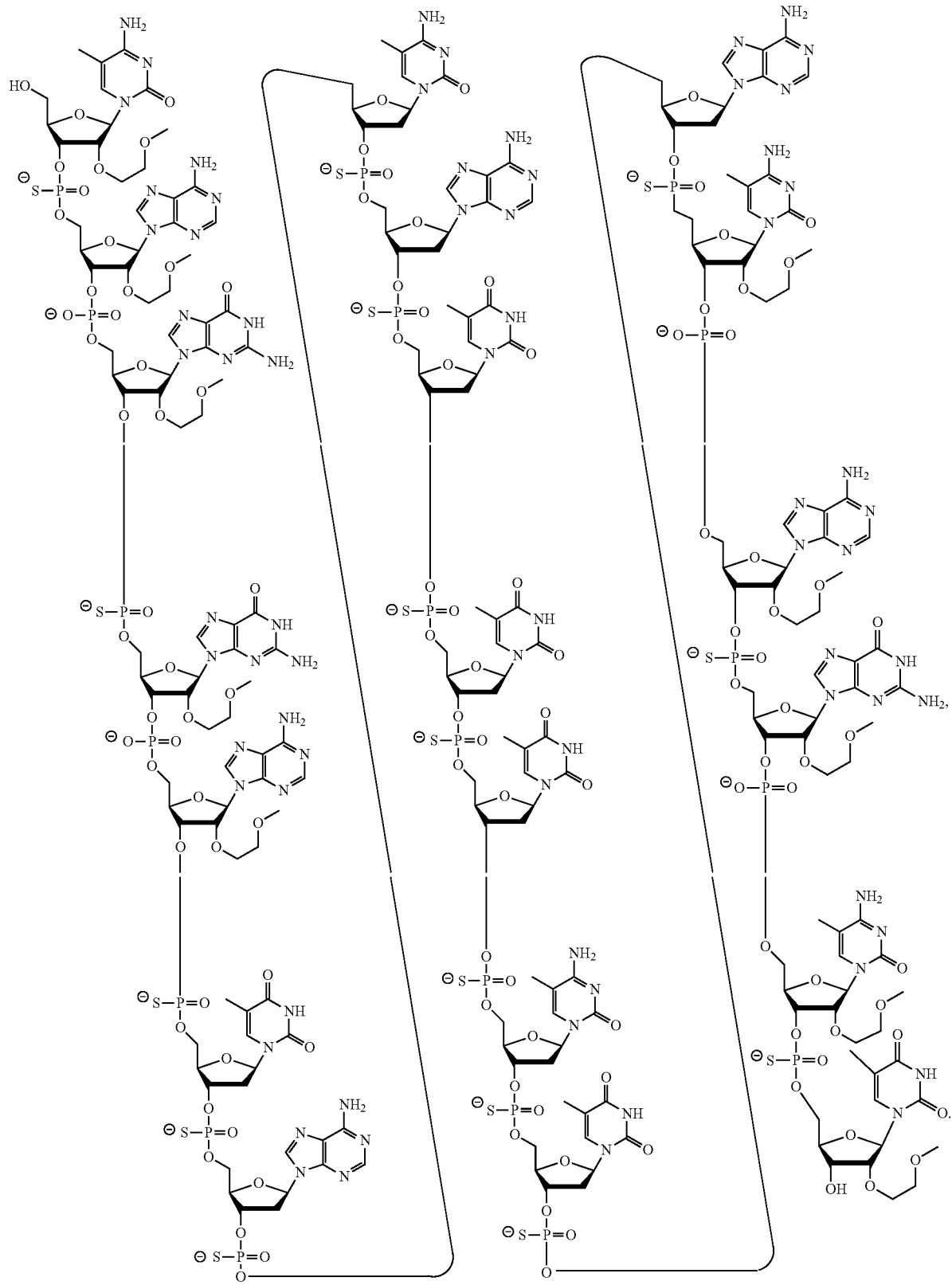

2. An antisense compound according to the following formula: mCes Aeo Ges Geo Aes Tds Ads mCds Ads Tds Tds Tds mCds Tds Aes mCeo Aes Geo mCes Te (nucleobase sequence of SEQ ID NO: 725); wherein A=an adenine,
mC=a 5-methylcytosine,
G=a guanine,
T=a thymine,
e=a 2'-O-methoxyethylribose modified sugar,
d=a 2'-deoxyribose sugar,
s=a phosphorothioate internucleoside linkage, and
o=a phosphodiester internucleoside linkage,
or a salt thereof.

3. A composition comprising the antisense compound or salt thereof of claim 2 and at least one of a pharmaceutically acceptable carrier or diluent.

4. A composition comprising the salt of the antisense compound of claim 1 and at least one of a pharmaceutically acceptable carrier or diluent.

5. The composition of claim 3, wherein the pharmaceutically acceptable carrier or diluent is phosphate-buffered saline (PBS).

6. The composition of claim 4, wherein the pharmaceutically acceptable carrier or diluent is PBS.

7. The composition of claim 3, which is formulated for intrathecal administration.

8. The composition of claim 4, which is formulated for intrathecal administation.

9. The antisense compound of claim 2.

10. The salt of the antisense compound of claim 2.

11. A composition comprising the antisense compound of claim 9 and at least one of a pharmaceutically acceptable carrier or diluent.

12. The composition of claim 11, wherein the pharmaceutically acceptable carrier or diluent is PBS.

13. The composition of claim 11, which is formulated for intrathecal administration.

14. A composition comprising the salt of the antisense compound of claim 10 and at least one of a pharmaceutically acceptable carrier or diluent.

15. The composition of claim 14, wherein the pharmaceutically acceptable carrier or diluent is PBS.

16. The composition of claim 14, which is formulated for intrathecal administration.

17. An antisense compound according to the following formula:

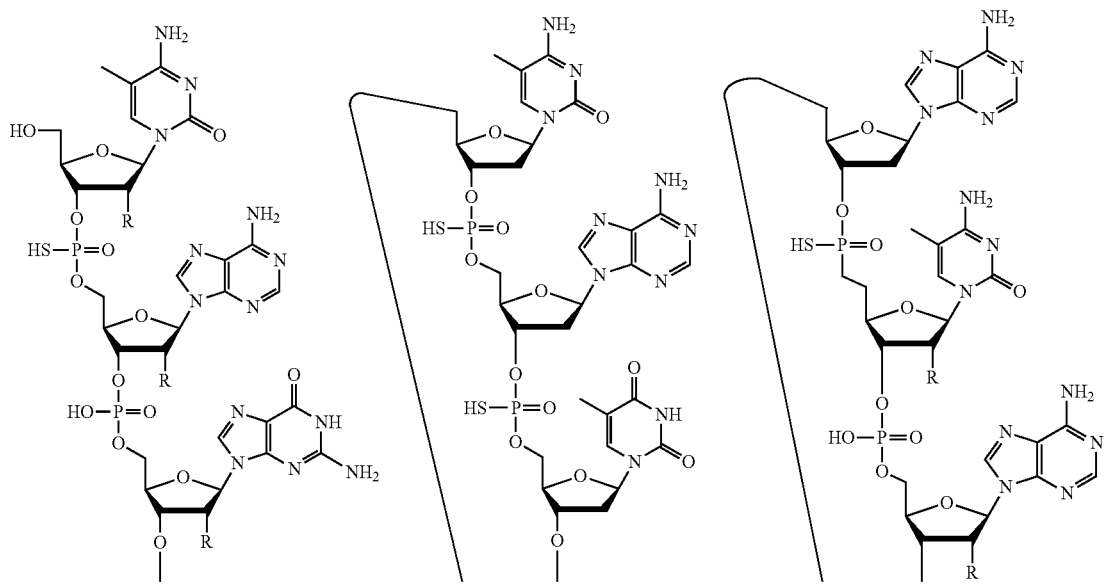

729

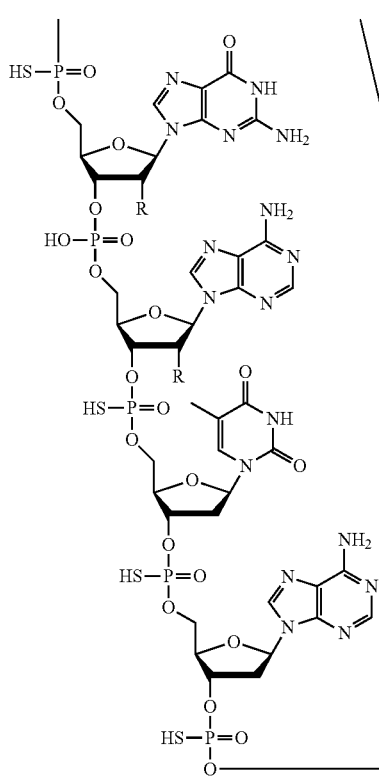

R = OCH₂CH₂OCH₃

-continued

730

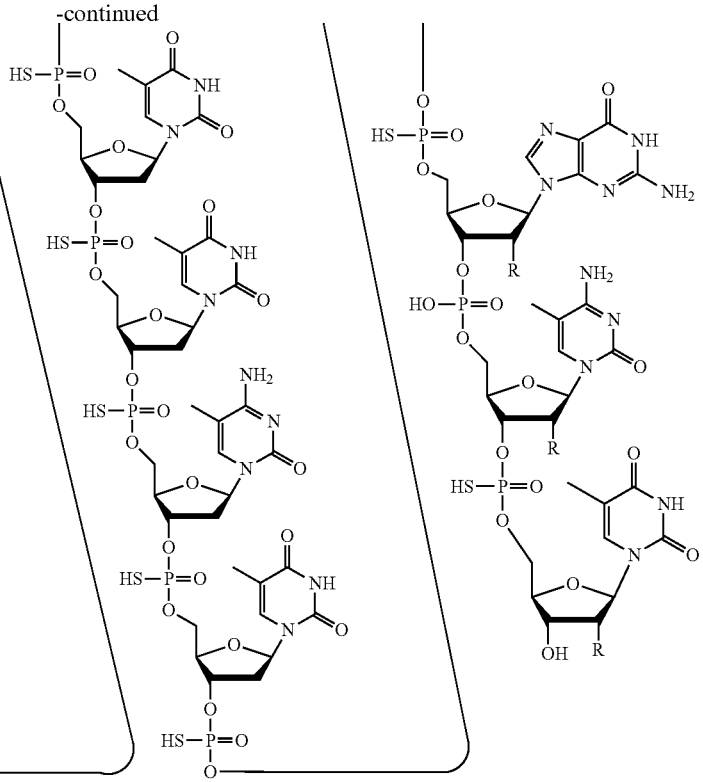

or a salt thereof.

18. A composition comprising the antisense compound or salt thereof of claim 17 and at least one of a pharmaceutically acceptable carrier or diluent.

19. The composition of claim 18, wherein the pharmaceutically acceptable carrier or diluent is PBS.

20. The composition of claim 18, which is formulated for intrathecal administration.

21. The antisense compound of claim 17.

22. A composition comprising the antisense compound of claim 21 and at least one of a pharmaceutically acceptable carrier or diluent.

23. The composition of claim 22, wherein the pharmaceutically acceptable carrier or diluent is PBS.

24. The composition of claim 22, which is formulated for intrathecal administration.

* * * * *

SEQUENCE LISTING

```
<160> NUMBER OF SEQ ID NOS: 1461

<210> SEQ ID NO 1
<211> LENGTH: 981
<212> TYPE: DNA
<213> ORGANISM: Homo sapiens

<400> SEQUENCE: 1
gtttggggcc agagtgggcg aggcgcggag gtctggccta taaagtagtc gcggagacgg      60
ggtgctggtt tgcgtcgtag tctcctgcag cgtctggggt ttccgttgca gtcctcggaa     120
ccaggacctc ggcgtggcct agcgagttat ggcgacgaag gccgtgtgcg tgctgaaggg     180
cgacggccca gtgcagggca tcatcaattt cgagcagaag gaaagtaatg gaccagtgaa     240
ggtgtgggga agcattaaag gactgactga aggcctgcat ggattccatg ttcatgagtt     300
tggagataat acagcaggct gtaccagtgc aggtcctcac tttaatcctc tatccagaaa     360
acacggtggg ccaaaggatg aagagaggca tgttggagac ttgggcaatg tgactgctga     420
caaagatggt gtggccgatg tgtctattga agattctgtg atctcactct caggagacca     480
ttgcatcatt ggccgcacac tggtggtcca tgaaaaagca gatgacttgg gcaaaggtgg     540
aaatgaagaa agtacaaaga caggaaacgc tggaagtcgt ttggcttgtg gtgtaattgg     600
gatcgcccaa taaacattcc cttggatgta gtctgaggcc ccttaactca tctgttatcc     660
tgctagctgt agaaatgtat cctgataaac attaaacact gtaatcttaa aagtgtaatt     720
gtgtgacttt ttcagagttg ctttaaagta cctgtagtga gaaactgatt tatgatcact     780
tggaagattt gtatagtttt ataaaactca gttaaaatgt ctgtttcaat gacctgtatt     840
ttgccagact taaatcacag atgggtatta aacttgtcag aatttctttg tcattcaagc     900
ctgtgaataa aaaccctgta tggcacttat tatgaggcta ttaaaagaat ccaaattcaa     960
actaaaaaaa aaaaaaaaa a                                                981

<210> SEQ ID NO 2
<211> LENGTH: 11001
<212> TYPE: DNA
<213> ORGANISM: Homo sapiens

<400> SEQUENCE: 2
```

```
cactgcactc cagcctgggt gacagagcga gaccctgtct caaaaatcaa acaaacaacc      60
ccctcgcccc ggacaaaagt agtttgcact attttctcat ttcacaatat gttttttgaaa    120
tatttcccttt gaaaggtaag tcatatttat cattcctgtt gtatggaggc atcataaatt    180
atttcaccat tctaccctcc ttgagtgttg tggcctttag ccagacaaa aacgcaggtg      240
atgcctagaa gccaactagt tgccgtttgg ttatctgtag ggttgtggcc ttgccaaaca     300
ggaaaaatat aaaagaata ccgaattctg ccaaccaaat aagaaactct atactaagga      360
ctaagaaaat tgcaggggaa gaaaaggtaa gtcccgggat tgaggtgtag cgactttcta    420
taccctcaga aaactaaaaa acaagacaaa aaatgaaaa ctacaaaagc atccatcttg      480
gggcgtccca attgctgagt aacaaatgag acgctgtggc caaactcagt cataactaat    540
gacatttcta gacaaagtga cttcagattt tcaaagcgta ccctgtttac atcattttgc    600
caatttcgcg tactgcaacc ggcgggccac gcccccgtga aaagaaggtt gttttctcca    660
catttcgggg ttctggacgt ttcccggctg cggggcgggg ggagtctccg gcgcacgcgg    720
cccccttggcc ccgcccccag tcattcccgg ccactcgcga cccgaggctg ccgcagggg    780
cgggctgagc gcgtgcgagg cgattggttt ggggccagag tgggcgaggc gcggaggtct   840
ggcctataaa gtagtcgcgg agacggggtg ctggtttgcg tcgtagtctc ctgcagcgtc    900
tggggtttcc gttgcagtcc tcggaaccag gacctcggcg tggcctagcg agttatggcg    960
acgaaggccg tgtgcgtgct gaagggcgac ggcccagtgc agggcatcat caatttcgag   1020
cagaaggcaa gggctgggac ggaggcttgt tgcgaggcc gctcccaccc gctcgtcccc    1080
ccgcgcacct ttgctaggag cgggtcgccc gccaggcctc ggggccgccc tggtccagcg   1140
cccggtcccg gccgtgccg cccgtcggt gccttcgccc ccagcggtgc ggtgcccaag    1200
tgctgagtca ccggcggc ccgggcgcgg ggcgtgggac cgaggccgcc gcggggctgg     1260
gcctgcgcgt ggcgggagcg cggggaggga ttgccgcggg ccggggaggg gcggggggcgg  1320
gcgtgctgcc ctctgtggtc cttgggccgc cgccgcgggt ctgtcgtggt gcctggagcg   1380
gctgtgctcg tcccttgctt ggccgtgttc tcgttcctga gggtcccgcg gacaccgagt   1440
ggcgcagtgc caggcccagc ccggggatgg cgactgcgcc tgggccogcc tggtgtcttc   1500
gcatccctct ccgctttccg gcttcagcgc tctaggtcag ggagtcttcg cttttgtaca   1560
gctctaaggc taggaatggt ttttatattt ttaaaaggct ttggaaaaca aaatacgca    1620
acagagaccg tttgtgtgac actttgcagg gaagtttgct ggcctctgtt ctaggtcatg   1680
attgggctgc aagggcagag aaggtagcct tgaacagagg tccttttcct cctcctaagc   1740
tccgggagcc agaggtttaa ctgacccttt tggggatttt tgagggcagt gatcttaact   1800
ttgggtgcac agttagctta tttgaagatc ttactaaaaa tacaccagag cccaacctcc   1860
gaccaattac atcaaaacct gtcctagtgc agggtgagta ttgctgtttt ttgaaagttt   1920
ccaaagtgaa ttttgatgtg cacctacgat tgagaactgt cgtttgagga cagtgggtgg   1980
agtttcgtat ttgaaattaa aagacctgg agtttccatt acaccgaatt ggcacttaat    2040
aactgttgtc ggagcatttc ttaagccaca ttttcgtaaa gtggctttaa aattgctctg   2100
ccagtaggca ggttgctaag atggtcagag acaaacttct gaacgactct tgtaaaatat   2160
acagaaatat tttcagaact tttatcagta aaattacaaa acgtgttgca aggaaggtgc   2220
ttgtgataac actgtcccca gaaccttagt gaagttacca actggtggaa aattttctct   2280
tgcactcggc ttaaaaatca tgagggaata tttactatac gaatgagatt cagtctttaa   2340
```

```
agggg tttac  agaaacgtga  gaggacagga  acagttagtc  tgtgtaaatg  tctgaaatat   2400
atgtgaggga  gataatgagt  ttagccttt   tctttaatag  gtctccagat  tttctggaaa   2460
aggttctttg  gcatttgact  ccatttgct   gtttcatttg  tcagacttct  ttttgtccct   2520
ctttacttct  ccccacataa  ttcaccagta  ctagtgtttt  gttttcaga   ccaagtctcg   2580 ctctgtcgcc  caggctggag  tgcagtggcg  cgatctcagc  tcactgcaac  ctccgcctcc   2640
caggttcaag  caattctcct  gcctcagcct  cccgggtagc  tgggactaca  ggcgcgcgcc   2700
gccacgcctg  gctaattttt  tatatttag   tagagacggc  gtttcaccat  gttggccagg   2760
atggtctcga  tctgttgacg  tcgtgatcca  cccgcctcgg  cctcccaaag  tgctgggatt   2820
acaggcgtga  gccaccccgc  ccggccacca  gtgctattct  taagacgcct  ctgaggaatc   2880
ccttctccct  ggccattgag  aatccatgca  tgaacccagg  ttttccacct  tccctgagca   2940
gcttgcatag  ttccttcttt  taagcgcctg  acttcgtttt  gtttggtgcc  cgttgtacct   3000
gagaatgagc  cttggatagt  ggagcattcc  agctttccag  atatgcagag  ataatacatt   3060
ggctatcagc  tacttggctt  ggcctattcc  gtgtttaaaa  tcttggactc  tttgctagtt   3120
tttacagatc  agaatttttc  acgtattaat  ccagttttcc  tagcttctct  tgaagaattt   3180
ttggagatct  cttcatactg  agccttcatt  agcccaggac  agtactgctg  tagcagttca   3240
tatatttttt  cgcttcccag  gcctgtgtta  ttcacttaag  ttcatagcct  ggtccctgca   3300
gggttgtacc  cgagcacagc  tacttagatg  tcctgaatgt  attaccggtt  aaatggaggt   3360
ttcaaagaac  ctgctgtttt  tggccctgtg  ctcttgataa  cagagtgttt  gagggacaac   3420
tttcacattt  gagttttcc   aaaattaaag  gttgtagaag  agtcacagta  tctattgtca   3480 aaagaaaag   aatttaaaaa  ggcagcaatt  gccaggatac  ttcatttgag  caatgatatt   3540
ttccagtgga  aagtcacatc  ttaagggtta  atgcccctta  actgttggcc  gtatttgaaa   3600
acaaaccaag  ctaaaaacaa  gagacactga  catgttgtat  gacggtgtgg  tgtggatgtt   3660
gtgtttattt  tagtcctgag  atctagttgt  aacttccttg  atttctgtat  gtagccacgg   3720
agcaccatta  cctgtcacca  ttacctgaat  ggctatactg  cttgctttca  ttttggtaga   3780
gtggaaaggt  tacctaggtt  tcagtgcttg  aaaagatttc  agaaagcagt  agtacgtctg   3840
gttagactag  aatcagtcct  ctcctggggg  cagtggaata  taatattttc  tgactgctaa   3900
ttaaaaatac  ctgtgatagc  cgggcgtggt  ggcttacgcc  tgtaatccca  gcactttggg   3960
aggccgagac  gggtggatca  cgaggtcagc  agatggagac  catcctggct  aacacggtga   4020
aaccccgtct  ctactaaaaa  tgcaaaaaaa  ttagccgggt  gtggtggtgg  gcgcctgtag   4080
tcccagctac  tcaggaggct  gaggcaggag  aatggcatga  acctgggagg  cggagcttgc   4140
agtgagccga  gatcatgtca  ctgcactcca  gcctgggcga  cagagcgaga  ctcgtctcaa   4200
aaaaaaaaag  aaaaaaactt  atgatggaca  cttaaaaaca  ctcactgagt  ggggagtgga   4260
gagcaggggt  cccagggtag  cctgttggac  atttccaggg  cgacttttc   ttttttttt   4320 tttaaagtca  agtgagtatg  ccatatggaa  aagggtgtgc  gtggagaaaa  agcaaggggc   4380
tccagagtgt  aggatgagac  atacacccttt  tgggttaaaa  aggctgaggc  aggagaatgg   4440
cgtgaacccg  ggaggcggag  cttgcagtga  gctgagatca  tgccactgca  ctccagcctg   4500
ggcgacagag  cgagactctt  gtctcaaaat  aaaaaacgtt  tacatgtaca  tgtatattca   4560
acatgtacaa  atataaccta  ttcaaaagta  tttactacat  aaataggtac  ttacattacc   4620
tatttactgt  aatagtcaaa  gcctatgaag  tatctaacac  tgatgtgtag  gtactcactt   4680
tgcttgccac  tctattaggt  gcttttatg   ttatttaatc  atgaagcctg  gccacagggt   4740
```

```
gcttgtgcat tgagtgtggg aacaagatta ccatctccct tttgaggaca caggcctaga      4800
gcagttaagc agcttgctgg aggttcactg gctagaaagt ggtcagcctg ggatttggac      4860 acagatttt  ccactcccaa gtctggctgc tttttacttc actgtgaggg gtaaaggtaa      4920
atcagctgtt ttctttgttc agaaactctc tccaactttg cacttttctt aaaggaaagt      4980
aatggaccag tgaaggtgtg gggaagcatt aaaggactga ctgaaggcct gcatggattc      5040
catgttcatg agtttggaga taatacagca ggtgggtgtt tgctgtgct ggtgacccat       5100 acttgttcac cctagttaga taaacagtag agtagcccct aaacgttaaa accctcaac       5160 ttgttttgt  ttttgagaaa gggtcttgct ctgtcgctca ggctggagtg cagtggcgct      5220
gtgcgatcat ggctgacctt agccttgacc tcccaggctc cattgatcct catgccttgg      5280
cccgtagctg ggactacagg tacacaccac cacgcctggc taattttgt  attttttct       5340 agaggtgggg tttcatcatg ttgcccaggc tggtcttgaa ctgctgggct caagtggtct      5400
atcctcctcg acctcccaaa gtgctgggat tacatgtgtg agccactgtg cctgggaaaa      5460
ccctcaactt ttctttaaa  aagaggtca  actttattgt atataagcac tgtgctaaaa      5520
ttgcaggaac tgggaccata tcctgatttt tgtaataatg ccagcagagt acacacaaga      5580
aaagtaactg cactagattg tgaagactgg ggtggacctg cttctgaagg tccagtgccc      5640
tttgtcttaa gatttggtgt agtgtgtctt tagaaaccaa aaaaagagaa gaagatcaac      5700
cttaagatta gccacaaaac tgggctttga tacctaggtg tggaaaagaa agggaaagag      5760
ttgatgtttt gtcttacagc atcattgtag aagagggtgt tttttgttt   gtttgtttt      5820 tgagacggag tcttactctg tgcccaggc  tggagtgcag tggcgcgatc tcggctcact      5880
gcaagctccg cctcccgggt tcatgccatt ctcctgcctc agcccctga  gtagctggga      5940 ctacaggtgc ccgccacccc gcctggctaa tttttgtat  tttagtaga  dacggggttt      6000 cactgtgtta gccaagatgg tctctctcct gacctcgtga tccgcctgtc tcagcctccc      6060
aaagtgctgg gattacaggc atgagccacc gcacccagcc agaagagggt gttttttaaa      6120
gaaggcaaat aggaaataaa aacttgggct cttaactttt gtaatgatcc caggtgtttg      6180 agctggggt  tgagggtggg tgcctcgagc aaaggggctg catttatttg cataatgcca      6240
tgtaagagta gctctacacc ccaaacacag gcttcttagt gggaccaaag tatgatacaa      6300
actgaagatg gaatgcagag gattattggt actttggaat atgcttaaaa aaaattttt      6360 taaagtattt ttaaaaaatc aggcaacccc tgaaccagag taggttcaga gaaactgcca      6420
aattttattt tcttaatttg ggattggaag caagttaaca gaagtttatg agttaagttg      6480
catttagtga tcttttgcca tatttgagta ataatctgat ttttttgttt atagatttct      6540
tcttaaatta actttattca tcttgctaat ttagtttcaa atagtgattt gtaatgatca      6600
gatttgatcc atttctgtaa ttgctgaaat tcccccgagt tgcttttgg  ctttaccgcc      6660 tctggtctgg gaggtgattg ctctgctgct tcctgtaact tgcctgcctt tctccctgtg      6720
tgggactcct gcgggtgaga gcgtggctga agacagccgt gttatgaaag ggcctcctgt      6780
gctgtcgagg ttgtgctctg tgaatgtcat cccctggtgc acagcagcac cttctacaca      6840
ggatacagtt ggaatgccgc cccctcgagt tgtgtaaggc agcagccttg gcccttgcac      6900
ataagatgct gttgaatatt ctgcctgcac caagtaaagg gcacagatag aactgcttgg      6960
catatgttgc tggggagatg agttttttgt aaagtatact acgttcttaa gaatttggat      7020
cataaccatg ggatttaat aatagaaaaa ctgttgaaga tcagtctggt cccttatttt       7080
```

```
tacagtgaag aagccaaagc ccagagaagg gtgttaactt tacaagtgtc agacagtagt    7140
tagaacttgg tggggttttt tttttttttt ttttgagatg gagtcttgct ctgttgccca    7200
ggctggagtg cagtggtgcg atctcagctc actgcaacct ctgcctccca ggttcaagcg    7260
attctcctgc ctcagcctac taagtagctg ggactatagg tgcgcaccac cacgcctagc    7320
taattttttgt atttttttcag tagagacagg gttttgctat gctggccagg ctggtctcaa    7380
actcctgacc tcagatgatc cagccacctc agcttcccaa agtgctgggg ttccaggtgt    7440
tagccaccat gcctggccat agacttgttt ctgttccctt ctcactgtgg ctgtaccaag    7500
gtgttgctta tcccagaagt cgtgatgcag gtcagcactt tctccatggg aagttttagc    7560
agtgtttctt tttagaatgt atttgggaac tttaattcat aatttagctt ttttttcttc    7620
ttcttataaa taggctgtac cagtgcaggt cctcacttta atcctctatc cagaaaacac    7680
ggtgggccaa aggatgaaga gaggtaacaa gatgcttaac tcttgtaata atggcgatag    7740
ctttctggag ttcatatggt atactacttg taaatatgtg ctaagataat tccgtgtttc    7800
ccccaccttt gcttttgaac ttgctgactc atctaaaccc ctgctcccaa atgctggaat    7860
gcttttactt cctgggctta aaggaattga caaatgggga cacttaaaac gatttggttt    7920
tgtagcattt attgaatata gaactaatac aagtgccaaa ggggaactaa tacaggaaat    7980
gtcatgaaca gtactgtcaa ccactagcaa atcaatcat cattgtgaaa cataggaagc    8040
ttctgtagat aaaaaaaaaa attgatactg aaaactagtc gagactccat ttatatgtgt    8100
atgttttctg aaagcctttc agaaaaatat taaatttaag gacaagattt ttatatcaga    8160
ggccttggga catagctttg ttagctatgc cagtaattaa caggcataac tcagtaactg    8220
agagtttacc ctttggtact tctgaaatca ggtgcagccc catctttctt cccagagcat    8280
tagtgtgtag acgtgaagcc ttgtttgaag agctgtattt agaatgccta gctacttgtt    8340
tgcaaatttg tgtctactca gtcaagtttt aatttagctc atgaactacc ttgatgttta    8400
gtggcatcag ccctaatcca tctgatgctt tttcattatt aggcatgttg gagacttggg    8460
caatgtgact gctgacaaag atggtgtggc cgatgtgtct attgaagatt ctgtgatctc    8520
actctcagga gaccattgca tcattggccg cacactggtg gtaagttttc ataaaaggat    8580
atgcataaaa cttcttctaa catacagtca tgtatctttt cactttgatt gttagtcgcg    8640
gtttctaaag atccagataa actgtacttg cagttcaaat taggaaaagc aattttattg    8700
gacaattacg gtgaaaatga attatttat ctaggtcagt taagaacact gttctgctaa    8760
gatgcagtaa aaagcaggtt acatttgacc atattagatc tgagtttgga aaacagaagt    8820
agtctttagt tttaaaatgg ccagattttc ttgccaggat tgggtttctc acttgttaaa    8880
cagaacattt tgttaagttt aaaacctggg atggacttaa gtattcatgt tcattcatgt    8940
tcattcagga ctgcaggtta tcatgacttg tttaacttgt gggaagctgt tgtcccaagt    9000
tatcctgggg aactgcatct ggttcttgca aaacaccaag tagacaggct ctcttttacc    9060
tccccttgag ggcattaaca ttcagtagtc acttccattc agttaaccct ttatttttat    9120
ggttttctt gagccatagt tgtaaagcag aaaaatcatt tataaaggtt tgttgaacaa    9180
aattcaaaat actgttgctt aaagtattaa gattttttag gattatacct tacttatagg    9240
cccgtcattc atttggcatg aaattttgag ttttattcac tttcactttc ctttttttcc    9300
aaagcaatta aaaaaactgc caaagtaaga gtgactgcgg aactaaggtt actgtaactt    9360
accatggagg attaagggta gcgtgtggtg gtctacaaca tagttatttg ggttttagta    9420
tttcatttag acagcaacac ttacctaatg tttaaaggta atgtctttgc aacaccaaga    9480
```

| | | | | |
|---|---|---|---|---|
| aaaagctttg | agtagtagtt | tctactttta | aactactaaa | tattagtata | tctctctact | 9540 |
| aggattaatg | ttatttttct | aatattatga | ggttcttaaa | catcttttgg | gtattgttgg | 9600 |
| gaggaggtag | tgattacttg | acagcccaaa | gttatcttct | taaaatttt | tacaggtcca | 9660 |
| tgaaaaagca | gatgacttgg | gcaaaggtgg | aaatgaagaa | agtacaaaga | caggaaacgc | 9720 |
| tggaagtcgt | ttggcttgtg | gtgtaattgg | gatcgcccaa | taaacattcc | cttggatgta | 9780 |
| gtctgaggcc | ccttaactca | tctgttatcc | tgctagctgt | agaaatgtat | cctgataaac | 9840 |
| attaaacact | gtaatcttaa | aagtgtaatt | gtgtgacttt | ttcagagttg | ctttaaagta | 9900 |
| cctgtagtga | gaaactgatt | tatgatcact | tggaagattt | gtatagtttt | ataaaactca | 9960 |
| gttaaaatgt | ctgtttcaat | gacctgtatt | ttgccagact | taaatcacag | atgggtatta | 10020 |
| aacttgtcag | aatttctttg | tcattcaagc | ctgtgaataa | aaaccctgta | tggcacttat | 10080 |
| tatgaggcta | ttaaaagaat | ccaaattcaa | actaaattag | ctctgatact | tatttatata | 10140 |
| aacagcttca | gtggaacaga | tttagtaata | ctaacagtga | tagcatttta | ttttgaaagt | 10200 |
| gttttgagac | catcaaaatg | catactttaa | aacagcaggt | cttttagcta | aaactaacac | 10260 |
| aactctgctt | agacaaatag | gctgtccttt | gaaagcttta | gggaaatgtt | cctgcttagt | 10320 |
| cattttagca | ttttgattca | taaagtacct | cctcatttta | aaaagacatt | atgatgtaag | 10380 |
| agagccattt | gataacttt | tagtgagctt | tgaaaggcaa | gttacagcct | cagctagcta | 10440 |
| gtaagattat | ctacctgcca | gaatggcaca | aattctacat | tcaagggtag | acgctggcac | 10500 |
| aacctactta | cagattagcc | ctttaaagca | atctgtagca | ttagaagatg | gaaccaagga | 10560 |
| aatgtttgac | tgtgggttct | ggctgttgag | aaataattta | cacaccgaat | tagtgaaatg | 10620 |
| agtcactttc | tcttaatgta | tttatgtacc | tgagagaatg | cttttcaatg | ttaacctaac | 10680 |
| tcaggtttga | ctaaattatt | caattggaaa | ttgtagaata | ttatttctga | taaaccagaa | 10740 |
| ataagtgaaa | tgctgtttgt | tcataaatat | gtactttatc | aaatgtagga | gagatcattt | 10800 |
| aggagaggaa | aagctaaatt | ggaagacaaa | tctgtagtgt | ttccaaagtt | ttaaaattat | 10860 |
| ggtaaacaac | agtatgttca | cagtaagtgg | ttaaaacaac | cattctttaa | atctcagtag | 10920 |
| agaatttta | aaaagcagta | tttaacacat | ttccctaatg | tagtttgttg | cctatgtgga | 10980 |
| ataactcaat | tagagactca | c | | | | 11001 |

<210> SEQ ID NO 3
<211> LENGTH: 13001
<212> TYPE: DNA
<213> ORGANISM: Macaca mulata

<400> SEQUENCE: 3

| | | | | | | |
|---|---|---|---|---|---|---|
| cctggaaccc | agagaaactt | cagccttggg | caaaggccgt | ttggccagca | tttgcactgt | 60 |
| ttatgcaacc | gtttagaata | tacgaattat | ctggaaacta | ctactaaata | caacacgcaa | 120 |
| aactgcaaat | atgtatactt | cctagaggat | gataaaaaaa | atgtgaattg | tgttttctct | 180 |
| gatagaggat | gcattagagt | ctgagggtct | aaataacata | aataataaat | aagtaaataa | 240 |
| atagatagta | gtgtactcca | aacgaggctg | gaatagcttc | tatcgttgtt | tcacgctgga | 300 |
| cttgaattaa | gtctgagtat | tttgccatgc | tcagtacgaa | atactaggct | ggacgtggtg | 360 |
| gcttatgtct | gtaatcccag | cactttggga | ggccgaggtg | ggcagactgg | cttgagctca | 420 |
| agagtttgaa | accagcctgg | gcaacatggt | aaaaccccat | ctctacccaa | aatacaaaaa | 480 |
| tcagccaggt | gtggtgccac | atgcctgtgg | tctcaggtac | ttgggaggct | gaggcagcag | 540 |

```
gatgactttt gaacccagga ggtcgaggct gcagtgagct atgatcgtgc cactgcactc    600
cagcctgggt gacagagcaa taccctgtct caaaaatcaa ataaacaacc ccttcgcccc    660
ggactaaagt agtttgtact attttctcat ttcatcaaag ttttttgaaat atttcccttg    720
aaaggtaagt catatttatc attcctgttg tatggagaca tcacaaatta tttcaccatt    780
ctaccctcct tgagtgttgt ggccttgggg ccaggcaaaa acgcaggaga tgcctagaag    840
ccaactagtt gccgttttgg ttatctgtgg ggctgtagcg ttgccaaaca ggaaaaatat    900
aaaaagaata ccgaattctg ccaaccaaat aagaaactat gtgctaagga ctaaaacaac    960
tgcaggggaa gaaaaggtga ggccagggat tgaggtgtag cgactttcta tgccctcaga   1020
aaattaaaaa acaagacaaa aaaaaaaaaa gaaaactaca aaagcatcca tcttgggccg   1080
tcctaatttc tgagtaacaa atgagatgct gtggcgaaag tcagtcataa ccaatgacat   1140
ttctagacaa agtgacttca gattttcaag gcgtaccttg tttacatcat tttgccaatt   1200
tcgcgtcctg caaccgtcgg gccacgcccc cgtgaaaaaa aggctgtgtt tttttccaca   1260
tttcggggtt ctggaccttt cccggctgcg gggcggggggg aagtctgagg cgcacgcggc   1320
cccttggccc cgcccccagt catttcctgc cactcgcgtc ccgaggctgc cgcagggggc   1380
gggctgagcg cgtgcgctgt gactggtttg gggccagagt gggcggggcg cggaggtccg   1440
gcctataaag tagtcgcggc gccgtggtac cgctttgcgg cgtagtctcc tgcagcgttt   1500
gcggtcagtc tcgcaatatt cggaagcagg accgcggcgt ggcctagcaa gtcatgcgga   1560
tgaaggccgt gtgcgtgttg aagggcgaca gcccagtgca gggcaccatc aatttcgagc   1620
agaaggcaag ggccggggcg gaggcttgtt tgcgaggccg ctcccgcccg cttgtcgccc   1680
cgagcacctg tgctaggagc gggtggccag ccaggcctcg ggaccgccct ggtcccgcgc   1740
ccggcctcgg cccgtgccgc ccggtcggtg cctttgcccc cagcggtgcg gtgccggcta   1800
agtgctgagt catcgggcgg gcccgggtgc ggggtgtggg accgaggccg ccgcggggct   1860
gggcctgcgc gtggcgggag cgcggggagg gattgccgcg ggggcgggcg tgggcgtgct   1920
gccctccggg gtccgtgggc ggccgccgcg ggctctgtcg tggtgcttgg agcagctgtg   1980
ctcctccctt gcttggctgt gttctcgttc ctgagggtcc cgcggacacc gagtggcgca   2040
gtgacaggcc cggcccgggg tggcgactgc gcctgggccc ggctggtgtc ttagcatccc   2100
tctccgcgtt ccggcttcag cgctctgggt cagggagtct ccgcttttgt acagctctaa   2160
ggctaagtat ggttttttata ttttttaaaag gctttggtaa acaaaaatac gcaacagaga   2220
ccgtttgtgt gacactttgc aggagttttgt tggcctctgt tctaggtcat ggttgggctg   2280
caagggcaga gaaggtagcc ttggatagag gtcctttttcc tcctcctaag ctccgagagc   2340
cagagtttta actgaccgtt tgggggactt tcgagggcaa tgattcttaa ctttgggtgc   2400
acaattagct tatttgaaga tcttactaaa aatacaccag agcccaacct cagaccaatt   2460
acatcaaaac ctgtcccagc gcaggtgatt attgctgttt tttaagtttc caaatgtgat   2520
tttgatgtgc acctacgatt gaggactgtt gtttgaggac agtgggtggg gtttggaatt   2580
tggaaattgg gaagacctga agtttccatt acacggaatt ggtacttagt aactcttgtc   2640
ggagcatttc ttaagccaca ttttctgtga agtggcttta aaattgctct gccagtaggc   2700
aggttgctaa gatggtcaga gacaaacttc tgaacgactc ttgtaaaatg tagtacagaa   2760
atattttcat aactattatc agtaaaattg caaacgtct gcaaggaag gtgcttgtga   2820
taacactgtc cccagagcct tagtgaagtt accaactggt ggaaaattgt ctggtactcg   2880
gcttaaaagt catgagagaa tatttatcat atgaatgaga ttcagtcttt aaagggggttt   2940
```

```
acagaaaggt gagaggacag gaacagttag tctgtgcaag tgtctgaaat gtgtatgagg    3000
gagatacgag tttagctttt ttctttaata cgtctccaga ttttctggaa aaggttcttt    3060
ggcatttgac tccatttgc tatttcattt gtcagacttc gttttgtccc tctttactta    3120
ttcccacata attcactagt actagtgctg tgttttgttt ctgagaccga gtcttgctct    3180
cttgcccagg ctggagtgca gtggcgcgat ctcggctcac tgcaacctcc gcttcctggg    3240
ttcaagcaat tctcctgcct caggctcccg ggtagctggg attacaggcg cgtgccacca    3300
cgcccagcta ttttttgta ttttagtagg gaccgggttt caccatgttg gccaggatgg    3360
tcacgatctc ttgacctggt gatccacccg cctcggcttc ccagagtggt gggattacag    3420
gcgtgagcca ccgcgcccgg ccaccagtac tagtcttaag acgcctctgt ggaattcctt    3480
ctccctggcc tttgagaatc catgcatgaa cccaggtttc tgtcattttc caccttccct    3540
gagcagcgag catagttcct tcttttaagc gcctgacttc gttttggttg tgccccttg     3600
tacctgagaa agagccttgg atagtggagc attccagctt tccagatatg cagagataat    3660
aaattggcta taaactacct ggcgtggcct attccgtgtt taaaatctta gactcgtggc    3720
tagttttac aaatcagaat cttcaccta atagtccagt tttcctagct tctcttgaag      3780
aattgttgga gatctcttca tactgagcct tcattagccc aggacagtac tgctggagct    3840
ttccaggcct gtgttactca cttgagttca cagcctggtc cctgtagggt tgtacctaag    3900
cacaactact tacatgttcc caatgtatta cccgttaaat ggaggtttga agaacctcc     3960
tcttttggc cctgtgctct tgataacaca gcatatttga gggacaactt tcacatttga    4020
gttttccaa aattagaggt tgtagaagag tcacagtgtc tattctgaaa aagaaaagaa     4080
tttttaaaag gccgcaattg ccagaatcct tcgtttgagc agtggtattt tccagtggaa    4140
agtcatgtct taagggttaa tgccccttaa ctgttgtccc tatttgaaaa ccaagctaaa    4200
aacaagagac acaaacatgt atgacggtgt ggtgtggatg atgtgtttat tttagtcctg    4260
agatctactc gtaacgtcct tgatttctgt atgtagccac ggagcaccat tacctgtcac    4320
cattgcctga atggcgatac tgcttgcttt cttttggta gagtggaaag gttatctagg    4380
tttcagtgct tgaaaagatt tcagaaaaca gtagtacctc tggttagact agaatcagtc    4440
ctctcctgag ggcagtgaaa taggatattt tctgactgct aattaaaaat acctatgata    4500
gccggacgtg gtggctcacg cctgtaatcc cagcagtttg ggaggcggaa ggggcggatc    4560
acgaggtcat gagatcgaga ccatcctggc taacacggtg aaaccccgtc tctgctaaaa    4620
atacaaaaaa ttaactgggc ttggtggtgg ttggcgcttg tagtcccagc tactcaggag    4680
gctgagggag gagaatggca tgaacctggg aggcggagct tgcagtgagc cgagatcatg    4740
ccactgctct tcagcctggg cgacagagct agactccatc tcaaaaaaaa aaaaaaaca    4800
aaaaactttt gatggaaact taaaaacaca cactgagtgg ggagtggaga gcagggtcc    4860
tagggtagcc tgttggacgt ctccagggtg cctttttctt tgttttaaag tgtgtatgct    4920
gtatggaaga gtgtctatat ggagaagcag caaggggcta aagagcatat gatgagacat    4980
acacctttg ggttaaaaag gctgaggcag gagaatggcg tgaacccggg aggtggagct     5040
tgcagtgagc cgagatcgcg ccactgccct ccagcctggg tgacagagcg agactctgtc    5100
tcaaaacaaa ccaaaaaggt ttacgtgtac atgtatattc aacatgtaca aatatgacct    5160
attcaagtgt ctactaaata ggtacttata ttacatattt actgtaatag tcaaacccta    5220
tgaagtatct aactctgatg tgtaggtact cactttgctt accactctat ttggtgcttt    5280
```

```
ttatgtttaa tcacgaagcc tggccacagg gcgcttgtgc attgagtgtg ggaacaagat    5340
taccatctcc cttttgagga cacaggccta gagcagttaa gcagcttgct ggaggtaccc    5400
tggctagaaa gtggtcggcc tgggatttgg acacagattt ttccactccc gagtctggct    5460
tcttttact ttactctgag gggtaaaggt aaatcagctg ttttctttgt tcagaaactc    5520
tctccaactt tgcactttc tttgattaaa ggaaagtaat ggaccagtga aggtgtgggg    5580
aagcattaca ggattgactg aaggcctgca tggattccat gttcatcagt ttggagataa    5640
tacacaaggt gggtgttgtg ctgtgctggt gacccatact tgttcaacct agttagataa    5700
acagtagagt agcccctaaa tgttaaaact cctcaacttg gttttgtttt tgagacaggg    5760
tcttgctctg tcacccaggc tggagtgcag tggtgctgtg cgatcatggc tcaccttagc    5820
ctcgacctcc caggctccag ttatcctcat gccttggcct gtagctggga ctacaggcat    5880
acgccaccac acctggctac tttctgtatt ttttctagc cgtggggttt catgttgtcc    5940
aggctagtct tgaactgctg ggctcaagtg gtttatcctc ctgcacctcc caaagtgctg    6000
ggattacagg tgtgagccac tgtgcctggc aaaaccctca acttttcttt taaaaaaaga    6060
ggtcaacttt attgtataaa cactgtgcta aaatggcaga aactaggacc atatcttggt    6120
ttttgtaata atgccagcag agtatacaca agaagaaaag taactgcact agattgtgaa    6180
gactggggtg gacctgcttc ttaatgccca gtgccctttg tcttaagatt tggtgtagta    6240
tatctttaga aaccaaaaaa aaaaaaaag tgaagttaaa ataactttga agatcaacct    6300
taagattagc cacaaaactg gttttgtca cctaggtgtg gaaagaaag ggaaagagtt    6360
gatgttttt gtcttatggc atcattgtag aagaggattt tttttttttt tttggagaca    6420
agtcttactc tgtcgcccag gctggagcgc agtggcgcca tcttggctcg ctgcaagctg    6480
tgcctcctgg gttcacgcca ttctcttgcc tcagcctcct gagtagctgg gactacaggc    6540
gccgccacca cgcctggtta atttttttgt ttttttagta gagatggggt ttcactgtgt    6600
tagccaagat ggtcttgatc tcctgacctc gtgatccacc catctcggcc tcccaaagtg    6660
ctgggattac aggcatgagc cactgtgccc agccagaaga aagtgttttt taaagaaggc    6720
aataggaaat aacttgggtt cttaacttt gtaatgatcc caggtgtttg agctgggggt    6780
tgagggtggg tgcctcaagc gaagggggctg cattcgtttg cataatgtca tgtaagagta    6840
gctccacacc gcaaacacag gctccttagt gggacaaaag taggatacaa cctggagatg    6900
gaatgcagag gatcactggt actttggaat atgcttaaaa aattttttta gtatttttaa    6960
aaaatcaggc agcccctgaa cctgagtagg ttcagagaaa ctgccaagtt ttatattctt    7020
aatttgggat tggaagcaag ttaacaaaag tttatgagtt aaattgcatt tagtggtctt    7080
ttgccatatt tgagttatct gaattttttg tttataggtt tcttcttaaa ttaacttcat    7140
tcatcttgct aatttagttt caaatagtga tttgtagtga tcagatttga tccatttctg    7200
taattgctga aattccccaa gttgcttttt ggcttcccgc ctctggtttg ggaggtgatt    7260
gcgctgctgc ttcctgtaac ttgcctgcct ttctccccgt gtgggactcc tgggggtgag    7320
aggacttgtt acgaaggcag ccgtgttacg aaagggcctc ctgtgccgtc gaggttgtgc    7380
tctgtgaatg tcatccctg gcccacagga gcaccttcta cacagggtac agtcggaatg    7440
ccgccccctg gagttgtgta aggcagcagc cttggccctt gcacataaga tgctgttgaa    7500
tattctgcct gcaccaagta aagggcacag gtagaactgc ttggcagtat gttgctgggg    7560
agatgagttt tttgtagtta aagtgtacta cattcttaca aatttggatc ttaaccatgg    7620
gattttaatg atagaaaaac tgttgaagat gagtctggtc ccttattgta cagtgaagca    7680
```

```
gcagaagccc cgaggaaggg tgttgacttt acgagtgtca gatagtagtt agaacttgct    7740
ttttttttg  agacgcagcc ttgctctgtt gcctaggctg gagtacagtg gtgcaatctc    7800
agcttactgc aatctctgcc tcccaggttc aagcgattct cctgcctctg cctatcaggt    7860
agctgggact acacgtgcac accaccatgc ctagctaatt tttgtatttt tcagtagaga    7920
cagggtttcg ccatgttggc caggctggtc tcaaactcct gacctcagat gattcaccca    7980
cctcagcttc ccaaagtgct gggattccag gtgttagcca ccatgcccgg ccatagactt    8040
gtttctgttc ccttctcacc atgcctggac caaggtgttg cttatcccag aagttgtgat    8100
gcaggtccct gctctctcca tgggaagttt tagcaatgtt tcttttttaga atgtatttgg   8160
gaactttaat tcataattta gcttttttttt tttttctttt tcttgtaaat aggctgtacc   8220
agtgcaggtc ctcactttaa tcctctatcc agacaacacg gtgggccaaa ggatgaagag    8280
aggtaacaag atgcttaact cttgtaataa tggcgatagc tttctggagt tcatatggta    8340
tactacttgt aaatatgtgc taagataatt ccgtgttctc ccccaccttt gttttttgaac   8400
ttgctgactc atctaaaccc ctgctcccaa atgctggaat gcttttactt cctgggctta    8460
aaggaattga caaatgggga cacttaaaac gatttggttt tgtagcattt attgaatata    8520
gaactaatac aggtgccaaa ggggaactta tacaggaaat gtcatgagta acagtactgt    8580
caaccactag cagaatcaat catcgtgaaa cataggaagc gtctgtagat aaaaaaaaaa    8640
ttgatattga aaactagtcg agactccatt tgtatgtgta tgttttctga aagcctttca    8700
ggaaaatact aaatctaagg acaagatttt tatatcagag gcctcgggac atagctttgt    8760
tagctatgcc aataattaac aggcataact cagtaactga gagtctaccc tttggtactt    8820
ctgaaatgag gtgcaccccc atctttcttc ccagagcatg agtttgtaga cttgaagcct    8880
tgtttgaaga gctgtgttta aatgcccag ctacttgttt gcaaatttgt gtttgctcag     8940
tcaagtttta atttagctca tgaactacct tgatgttcag tggagtcagc cctaatccat    9000
ctgatgcttt tccattatta ggcatgttgg agacctgggc aatgtgactg ctggcaaaga    9060
tggtgtggcc aaggtgtctt tcgaagattc tgtgatctcg ctctcaggag accattccat    9120
cattggccgc acattggtgg tgagttttca taaaaggatc tacataaaac ttcgtctaac    9180
atacagtcat gtatctcttc actttatgat tgttagtcgt ggtttctaaa gatccagata    9240
aattatactt gcagttcaaa ttaggaaaag caatttatt  ggacaattat ggtgaaaatc    9300
aattatttta tctgggtcag tcaagaacac tgttctgcta agatgcagta gaaagcaggt    9360
tacatttgac catattagat ctgagtttgg aaaacagagt agtctttagt tttaaaatgg    9420
ccagattttc ttgccaggat tgggtttctc acttgtgaaa cagaacatttt tgttaagttt   9480
aaaacctggg atggacttca gtattcatgt tcatccagga ctgcaggtta tcatgacttg    9540
tttaacttgt gggaagctgt tgccccaagt tattctgggg aatgcatctg gttcatgcaa    9600
aacaccaggt agactggctc tcttttacct cccttgagg  gcattaacat tcattagtca    9660
cttccactca gttaacccct ttatttttaa ggttttcttg agccatagtt gtaaagcaga    9720
aaaattgttt acaaaggttt gttgaacaaa attcaaaata ctgttgctaa agtattaagg    9780
tttttttagga ttatgtctta tttataggcc tgtcattcat ttggtatgaa attttgagcg   9840
ttactcactt tcactttcct tttttttccaa agcaattaaa ttgccaaaga gtgactgctg   9900
aactacagtt actgtaactt atcatggagg actaagggta gtgtgtggtg gtctacaaca    9960
tagttatttg ggttttttagt atttcattta gagatagcaa cacttaccta atgtttaaag  10020
```

```
gtaatgtctt tgcaacacca agaaaaagct ttgaatagta gttttacttt ttaaactact   10080
aagtattagt atatctacta ggattaatgt tattttcta atattatgag gttcttaaac   10140
tatcttttgg gtattgttgg gaggaggtag tgattacttg acagcccaaa gttatcttct   10200
tacaatttt tacaggtcca tgaaaaagca gatgacttgg gcaaaggtgg aaatgaagaa   10260
agtaaaaaga caggaaacgc tggaggtcgt ctggcttgtg gtgtaattgg gatcgcccaa   10320
taaacattcc cttggatgta gtctgaggcc cattaactca tctgttatcc tgctagctgt   10380
agaaatgtat cttgataaac attaaacact gtaatcttaa gagtgtaatt gtgtgacgtt   10440
tgcttagtac ctgtaatgag aaactggttg atgatcactt ggaagatttg tatagtttta   10500
taaaactcaa ttaaaatgtc tgtttcaatg acctgtattt tgccagactt aatcacagat   10560
gggtattaaa cttgtcagaa tttcttcaat tctcattcaa gcctgtgaat aaaaaccctg   10620
tatggcactc attttgagtc tattaaaaga atccaagttc aaactaaatt agctctgata   10680
cttatttata taaacagctt cagtggaaca gatttagtaa tgctaacagt gatagcattt   10740
tactttgaaa gtgttttgag atcatcaaaa tgcatacttt taaaacagca ggtctttag    10800
ctaatacgaa cacaactctg cttagacaac aggctgtcct ttgaaagctt tagggaaatg   10860
ttcttgctta gtcattttag cattttgatt cataaagtac ctcattttaa aaagacgtta   10920
tcgtgtaaga gagccatttg ataacttagt gagtttaaaa ggcaagttac agcctcagct   10980
agctaataag attatctacc tgccagaatg gcacaaattg tacattcaag ggtggacgtt   11040
ggcacaacct acttaacaga ttagccctt aaagaaatct atagcattgg aagatagaac    11100
caaggaaatg tttgactgtg ggtctggct gtttattaat ttcacaccg aattagtgaa     11160
atgagtcact ttcaatgtat ttacgtacct gagagagagt gcttttaaat gttattgact   11220
attcaattgg aaattgtaaa ttgtagaata tttctgataa accatgaata agtgacaatc   11280
tgttcataaa tacgtacttt atcaaatgta ggagaggaaa agctaaattg ggaagacaaa   11340
tctgtagtgt ttccaaagtt ttaaaattat gttaaagaac aatatgctta cagtaagtgg   11400
ttaaaaccac cattctttaa atctcggtaa tgtttaaaaa acactattta acccatttcc   11460
ctgatgtagt ttgttgccta tgtggaatta gagactcacg cctttcaaac ttcaaatata   11520
atcatgctac cagttaggag tagtcatttc atgtgcatat aggatgctct taagttggaa   11580
atacaggctg taagtccttc aagtctggat gttgagtaat cacgtttct tccagaagcc    11640
atttgttagg acttttttt gggccagtgt aaaattaagg acaagtttta taatttaaat    11700
ttacagatac aacaattttc tctcatttc taaaggcagg aatataagga cattgcccta    11760
gatatattct ccccatcaaa ccaaaggcct tgctgctgag tattatttaa aaaccagagt   11820
aataaagcag ctttgcctga ggatgacggc aaagacaaag ttaactgcta agcatactga   11880
aaccaagagt ttaaaaagt aattcaaaac aacttgaagg ccataaatat ttggatagtg    11940
tgacatcagg tcttggcact ggatttcctg caatttcaga taaaggcttg acttggcttt   12000
ggatgtcttc atgtaattct tggataacct acaacaattt ttcctagtta acccaccaac   12060
tttaagcaaa agaaaaaaag tgtatgtggg ggaaaagttc agtttacctc tgcccagcag   12120
gggaattaaa aaactggtaa agaaaggcaa taggcaaggc ttatataagg aaacaataat   12180
aggttgcact gaagtcctca acacaacaa aaagctttta gattgcaaat gttaaccttg    12240
attcttttac ccttttgaag aattcagtgg gatggttgga aaaaaaaaa caacacacac    12300
acacatgcaa ccttctaacg taatacccac gcagtcagat aatttatagt acaacatgta   12360
acactggaat taacttttcc cccagcaaaa tcttacaaat taattagggc aacatatacc   12420
```

-continued

```
acaaagccaa tgggaaaaa aaaaaacctc gattgaattg caaacacagc ttttcaattg    12480
acattaaaac aactaacctt taccttatga ctgaaacact aaaattcaaa agtattacat    12540
atgaaagtga gaataactac ataaaatgtc tattttcatc aaataagtct aatttagact    12600
ccaatacagt attaacagct caaactttga tggtgaacaa tccttttcca ccttaatgca    12660
gtgtaggaag aatagcacac attaaagttt gttacgaaaa tagagtttat taaaaacatc    12720
cctattgttt tgaggagctt tcaccgttac cttgtcttaa attaaaaaaa aaaaaaaata    12780
gagagcactt ctaattacga tttgtaaact ttttaaagtc aaaacttttta aaaagttaca    12840 gcaaaaaggg taatatttat tcatattttc agtattttt gttattttgt ggctattttt    12900
aaatagaagg gaagcaatca aattgcttac agttccccac cagctggcgc ggggctgcag    12960
tacagcggga gcggatataa tacagcatct gtacacctca a                        13001
```

<210> SEQ ID NO 4

<400> SEQUENCE: 4

000

<210> SEQ ID NO 5
<211> LENGTH: 25
<212> TYPE: DNA
<213> ORGANISM: Artificial sequence
<220> FEATURE:
<223> OTHER INFORMATION: Primer

<400> SEQUENCE: 5
aggagaaaaa caaagaacac cagaa                                          25

<210> SEQ ID NO 6
<211> LENGTH: 25
<212> TYPE: DNA
<213> ORGANISM: Artificial sequence
<220> FEATURE:
<223> OTHER INFORMATION: Primer

<400> SEQUENCE: 6
caattagggc aactcagaaa tagct                                          25

<210> SEQ ID NO 7
<211> LENGTH: 22
<212> TYPE: DNA
<213> ORGANISM: Artificial sequence
<220> FEATURE:
<223> OTHER INFORMATION: Probe

<400> SEQUENCE: 7
ccaactggtc ccccagccaa ga                                             22

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
gaaaccagcc tggacaccaa                                                20

<210> SEQ ID NO 9
<211> LENGTH: 24

```
<212> TYPE: DNA
<213> ORGANISM: Artificial sequence
<220> FEATURE:
<223> OTHER INFORMATION: Primer

<400> SEQUENCE: 9
tccacagtct ttaccacgat gttc                                           24

<210> SEQ ID NO 10
<211> LENGTH: 25
<212> TYPE: DNA
<213> ORGANISM: Artificial sequence
<220> FEATURE:
<223> OTHER INFORMATION: Probe

<400> SEQUENCE: 10
tccgtgtcag aaggccacct caaga                                          25

<210> SEQ ID NO 11
<211> LENGTH: 22
<212> TYPE: DNA
<213> ORGANISM: Artificial sequence
<220> FEATURE:
<223> OTHER INFORMATION: Primer

<400> SEQUENCE: 11
ctctcaggag accattgcat ca                                             22

<210> SEQ ID NO 12
<211> LENGTH: 27
<212> TYPE: DNA
<213> ORGANISM: Artificial sequence
<220> FEATURE:
<223> OTHER INFORMATION: Primer

<400> SEQUENCE: 12
tcctgtcttt gtactttctt catttcc                                        27

<210> SEQ ID NO 13
<211> LENGTH: 24
<212> TYPE: DNA
<213> ORGANISM: Artificial sequence
<220> FEATURE:
<223> OTHER INFORMATION: Probe

<400> SEQUENCE: 13
ccgcacactg gtggtccatg aaaa                                           24

<210> SEQ ID NO 14
<211> LENGTH: 20
<212> TYPE: DNA
<213> ORGANISM: Artificial sequence
<220> FEATURE:
<223> OTHER INFORMATION: Primer

<400> SEQUENCE: 14
cgtggcctag cgagttatgg                                                20

<210> SEQ ID NO 15
<211> LENGTH: 20
<212> TYPE: DNA
<213> ORGANISM: Artificial sequence
<220> FEATURE:
<223> OTHER INFORMATION: Primer

<400> SEQUENCE: 15
```

-continued gaaattgatg atgccctgca                                         20

<210> SEQ ID NO 16
<211> LENGTH: 21
<212> TYPE: DNA
<213> ORGANISM: Artificial sequence
<220> FEATURE:
<223> OTHER INFORMATION: Probe

<400> SEQUENCE: 16
acgaaggccg tgtgcgtgct g                                       21

<210> SEQ ID NO 17
<211> LENGTH: 26
<212> TYPE: DNA
<213> ORGANISM: Artificial sequence
<220> FEATURE:
<223> OTHER INFORMATION: Primer

<400> SEQUENCE: 17
tggagataat acacaaggct gtacca                                  26

<210> SEQ ID NO 18
<211> LENGTH: 23
<212> TYPE: DNA
<213> ORGANISM: Artificial sequence
<220> FEATURE:
<223> OTHER INFORMATION: Primer

<400> SEQUENCE: 18
caacatgcct ctcttcatcc ttt                                     23

<210> SEQ ID NO 19
<211> LENGTH: 27
<212> TYPE: DNA
<213> ORGANISM: Artificial sequence
<220> FEATURE:
<223> OTHER INFORMATION: Probe

<400> SEQUENCE: 19
atcctctatc cagacaacac ggtgggc                                 27

<210> SEQ ID NO 20

<400> SEQUENCE: 20

000

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
ccgtcgccct tcagcacgca                                         20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
cactggtcca ttactttcct                                                    20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
acaccttcac tggtccatta                                                    20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
ccacaccttc actggtccat                                                    20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
caacatgcct ctcttcatcc                                                    20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
ccaacatgcc tctcttcatc                                                    20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
tccaacatgc ctctcttcat                                                    20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
ctccaacatg cctctcttca                                                    20

<210> SEQ ID NO 29
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 29
tctccaacat gcctctcttc                                                    20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
gtctccaaca tgcctctctt                                                    20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
cacctttgcc caagtcatct                                                    20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
ccacctttgc ccaagtcatc                                                    20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
tccacctttg cccaagtcat                                                    20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
ttccaccttt gcccaagtca                                                    20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
tttccacctt tgcccaagtc                                                    20
```

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
atttccacct ttgcccaagt                                            20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
catttccacc tttgcccaag                                            20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
tcatttccac ctttgcccaa                                            20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
ttcatttcca cctttgccca                                            20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
cttcatttcc acctttgccc                                            20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
tcttcatttc cacctttgcc                                            20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 42
ttcttcattt ccacctttgc                                                    20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
tttcttcatt tccacctttg                                                    20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
ctttcttcat ttccaccttt                                                    20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
actttcttca tttccacctt                                                    20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
tactttcttc atttccacct                                                    20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
ggcgatccca attacaccac                                                    20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
ggaatgttta ttgggcgatc                                                    20

<210> SEQ ID NO 49
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
cctcagacta catccaaggg                                              20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
atacaaatct tccaagtgat                                              20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51 tgagtttat aaaactatac                                               20

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
tcattgaaac agacatttta                                              20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
atacaggtca ttgaaacaga                                              20

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
gtcgcccttc agcacgcaca                                              20

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
```
tttaataccc atctgtgatt                                                  20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
agtttaatac ccatctgtga                                                  20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
ggtttttatt cacaggcttg                                                  20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
agggttttta ttcacaggct                                                  20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
atacagggtt tttattcaca                                                  20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
ccatacaggg tttttattca                                                  20

<210> SEQ ID NO 61
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 61
acgctgcagg agactacgac                                                  20

<210> SEQ ID NO 62
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 62
cgaggactgc aacggaaacc                                                    20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
taggccacgc cgaggtcctg                                                    20

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
ttcagcacgc acacggcctt                                                    20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 65
ccttcagcac gcacacggcc                                                    20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
gcccttcagc acgcacacgg                                                    20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
tcgcccttca gcacgcacac                                                    20

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
cgtcgccctt cagcacgcac                                                    20
```

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
gccctgcact gggccgtcgc                                                    20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 70
aattgatgat gccctgcact                                                    20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
agtcctttaa tgcttcccca                                                    20

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72
aggccttcag tcagtccttt                                                    20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
gctgtattat ctccaaactc                                                    20

<210> SEQ ID NO 74
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 74
tgcccaagtc tccaacatgc                                                    20

<210> SEQ ID NO 75
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 75
acacatcggc cacaccatct                                           20

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76
tctcctgaga gtgagatcac                                           20

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 77
accaccagtg tgcggccaat                                           20

<210> SEQ ID NO 78
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 78
tcatggacca ccagtgtgcg                                           20

<210> SEQ ID NO 79
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 79
gtactttctt catttccacc                                           20

<210> SEQ ID NO 80
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 80
ttgtactttc ttcatttcca                                           20

<210> SEQ ID NO 81
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 81
ctttgtactt tcttcatttc                                           20

```
<210> SEQ ID NO 82
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 82
gataacagat gagttaaggg                                                   20

<210> SEQ ID NO 83
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 83
cacaattaca cttttaagat                                                   20

<210> SEQ ID NO 84
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 84
aatcagtttc tcactacagg                                                   20

<210> SEQ ID NO 85
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 85
cataaatcag tttctcacta                                                   20

<210> SEQ ID NO 86
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 86
aactgagttt tataaaacta                                                   20

<210> SEQ ID NO 87
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 87
ccatctgtga tttaagtctg                                                   20

<210> SEQ ID NO 88
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 88
aagtgccata cagggttttt                                                 20

<210> SEQ ID NO 89
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 89
taataagtgc catacagggt                                                 20

<210> SEQ ID NO 90
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 90
ctcataataa gtgccataca                                                 20

<210> SEQ ID NO 91
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 91
gcctcataat aagtgccata                                                 20

<210> SEQ ID NO 92
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 92
ttttaatagc ctcataataa                                                 20

<210> SEQ ID NO 93
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 93
ggattctttt aatagcctca                                                 20

<210> SEQ ID NO 94
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 94
ctcactacag gtactttaaa                                                 20

<210> SEQ ID NO 95
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 95
aatcttccaa gtgatcataa                                               20

<210> SEQ ID NO 96
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 96
attgaaacag acattttaac                                               20

<210> SEQ ID NO 97
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 97
caaagaaatt ctgacaagtt                                               20

<210> SEQ ID NO 98
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 98
acaggcttga atgacaaaga                                               20

<210> SEQ ID NO 99
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 99
tcataataag tgccatacag                                               20

<210> SEQ ID NO 100
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 100
caggccttca gtcagtcctt                                               20

<210> SEQ ID NO 101
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 101
```
cacattgccc aagtctccaa                                              20

<210> SEQ ID NO 102
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 102
tcggccacac catctttgtc                                              20

<210> SEQ ID NO 103
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 103
catcggccac accatctttg                                              20

<210> SEQ ID NO 104
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 104
tagacacatc ggccacacca                                              20

<210> SEQ ID NO 105
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 105
ctcctgagag tgagatcaca                                              20

<210> SEQ ID NO 106
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 106
catggaccac cagtgtgcgg                                              20

<210> SEQ ID NO 107
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 107
taggccagac ctccgcgcct                                              20

<210> SEQ ID NO 108
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 108
actttatagg ccagacctcc                                              20

<210> SEQ ID NO 109
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 109
gacgcaaacc agcaccccgt                                              20

<210> SEQ ID NO 110
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 110
ggttccgagg actgcaacgg                                              20

<210> SEQ ID NO 111
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 111
tcctggttcc gaggactgca                                              20

<210> SEQ ID NO 112
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 112
gaggtcctgg ttccgaggac                                              20

<210> SEQ ID NO 113
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 113
gtcgccataa ctcgctaggc                                              20

<210> SEQ ID NO 114
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 114
tcagcacgca cacggccttc                                              20

```
<210> SEQ ID NO 115
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 115
cttcagcacg cacacggcct                                                  20

<210> SEQ ID NO 116
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 116
cccttcagca cgcacacggc                                                  20

<210> SEQ ID NO 117
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 117
cgcccttcag cacgcacacg                                                  20

<210> SEQ ID NO 118
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 118
cgcccactct ggccccaaac                                                  20

<210> SEQ ID NO 119
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 119
ccgcgactac tttataggcc                                                  20

<210> SEQ ID NO 120
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 120
ccttctgctc gaaattgatg                                                  20

<210> SEQ ID NO 121
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 121
tccttctgct cgaaattgat                                           20

<210> SEQ ID NO 122
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 122
ttccttctgc tcgaaattga                                           20

<210> SEQ ID NO 123
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 123
tttccttctg ctcgaaattg                                           20

<210> SEQ ID NO 124
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 124
ctttccttct gctcgaaatt                                           20

<210> SEQ ID NO 125
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 125
actttccttc tgctcgaaat                                           20

<210> SEQ ID NO 126
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 126
tactttcctt ctgctcgaaa                                           20

<210> SEQ ID NO 127
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 127
ttactttcct tctgctcgaa                                           20

<210> SEQ ID NO 128

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 128
attactttcc ttctgctcga                                              20

<210> SEQ ID NO 129
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 129
cattactttc cttctgctcg                                              20

<210> SEQ ID NO 130
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 130
ccattacttt ccttctgctc                                              20

<210> SEQ ID NO 131
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 131
tccattactt tccttctgct                                              20

<210> SEQ ID NO 132
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 132
gtccattact ttccttctgc                                              20

<210> SEQ ID NO 133
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 133
ggtccattac tttccttctg                                              20

<210> SEQ ID NO 134
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 134
```
tggtccatta ctttccttct                                              20

<210> SEQ ID NO 135
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 135
ctggtccatt actttccttc                                              20

<210> SEQ ID NO 136
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 136
actggtccat tactttcctt                                              20

<210> SEQ ID NO 137
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 137
tcactggtcc attactttcc                                              20

<210> SEQ ID NO 138
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 138
ttcactggtc cattactttc                                              20

<210> SEQ ID NO 139
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 139
cttcactggt ccattacttt                                              20

<210> SEQ ID NO 140
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 140
ccttcactgg tccattactt                                              20

<210> SEQ ID NO 141
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 141
accttcactg gtccattact                                               20

<210> SEQ ID NO 142
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 142
caccttcact ggtccattac                                               20

<210> SEQ ID NO 143
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 143
cacaccttca ctggtccatt                                               20

<210> SEQ ID NO 144
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 144
cccacacctt cactggtcca                                               20

<210> SEQ ID NO 145
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 145
ccccacacct tcactggtcc                                               20

<210> SEQ ID NO 146
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 146
tccccacacc ttcactggtc                                               20

<210> SEQ ID NO 147
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 147
ttccccacac cttcactggt                                               20
```

```
<210> SEQ ID NO 148
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 148
cttccccaca ccttcactgg                                                    20

<210> SEQ ID NO 149
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 149
gcttccccac accttcactg                                                    20

<210> SEQ ID NO 150
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 150
tgcttcccca caccttcact                                                    20

<210> SEQ ID NO 151
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 151
atgcttcccc acaccttcac                                                    20

<210> SEQ ID NO 152
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 152
aatgcttccc cacaccttca                                                    20

<210> SEQ ID NO 153
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 153
taatgcttcc ccacaccttc                                                    20

<210> SEQ ID NO 154
<211> LENGTH: 20
<212> TYPE: DNA
<213> ORGANISM: Artificial sequence
<220> FEATURE:
```

<223> OTHER INFORMATION: Synthetic oligonucleotide

<400> SEQUENCE: 154
tccatgcagg ccttcagtca                                               20

<210> SEQ ID NO 155
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 155
atccatgcag gccttcagtc                                               20

<210> SEQ ID NO 156
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 156
aatccatgca ggccttcagt                                               20

<210> SEQ ID NO 157
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 157
gaatccatgc aggccttcag                                               20

<210> SEQ ID NO 158
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 158
ggaatccatg caggccttca                                               20

<210> SEQ ID NO 159
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 159
tggaatccat gcaggccttc                                               20

<210> SEQ ID NO 160
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 160
atggaatcca tgcaggcctt                                               20

```
<210> SEQ ID NO 161
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 161
catggaatcc atgcaggcct                                               20

<210> SEQ ID NO 162
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 162
acatggaatc catgcaggcc                                               20

<210> SEQ ID NO 163
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 163
aacatggaat ccatgcaggc                                               20

<210> SEQ ID NO 164
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 164
gaacatggaa tccatgcagg                                               20

<210> SEQ ID NO 165
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 165
tgaacatgga atccatgcag                                               20

<210> SEQ ID NO 166
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 166
atgaacatgg aatccatgca                                               20

<210> SEQ ID NO 167
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 167
gacctgcact ggtacagcct    20

<210> SEQ ID NO 168
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 168
ggacctgcac tggtacagcc    20

<210> SEQ ID NO 169
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 169
aggacctgca ctggtacagc    20

<210> SEQ ID NO 170
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 170
gaggacctgc actggtacag    20

<210> SEQ ID NO 171
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 171
tgaggacctg cactggtaca    20

<210> SEQ ID NO 172
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 172
gtgaggacct gcactggtac    20

<210> SEQ ID NO 173
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 173
agtgaggacc tgcactggta    20

<210> SEQ ID NO 174
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 174
aagtgaggac ctgcactggt                                                    20

<210> SEQ ID NO 175
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 175
aaagtgagga cctgcactgg                                                    20

<210> SEQ ID NO 176
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 176
taaagtgagg acctgcactg                                                    20

<210> SEQ ID NO 177
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 177
ttaaagtgag gacctgcact                                                    20

<210> SEQ ID NO 178
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 178
attaaagtga ggacctgcac                                                    20

<210> SEQ ID NO 179
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 179
gattaaagtg aggacctgca                                                    20

<210> SEQ ID NO 180
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 180
```

```
ggattaaagt gaggacctgc                                                20

<210> SEQ ID NO 181
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 181
aggattaaag tgaggacctg                                                20

<210> SEQ ID NO 182
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 182
gaggattaaa gtgaggacct                                                20

<210> SEQ ID NO 183
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 183
agaggattaa agtgaggacc                                                20

<210> SEQ ID NO 184
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 184
tagaggatta aagtgaggac                                                20

<210> SEQ ID NO 185
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 185
atagaggatt aaagtgagga                                                20

<210> SEQ ID NO 186
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 186
gatagaggat taaagtgagg                                                20

<210> SEQ ID NO 187
<211> LENGTH: 20
<212> TYPE: DNA
<213> ORGANISM: Artificial sequence
```

<220> FEATURE:
<223> OTHER INFORMATION: Synthetic oligonucleotide

<400> SEQUENCE: 187
ggatagagga ttaaagtgag                                               20

<210> SEQ ID NO 188
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 188
tggatagagg attaaagtga                                               20

<210> SEQ ID NO 189
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 189
ctggatagag gattaaagtg                                               20

<210> SEQ ID NO 190
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 190
tctggataga ggattaaagt                                               20

<210> SEQ ID NO 191
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 191
atcctttggc ccaccgtgtt                                               20

<210> SEQ ID NO 192
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 192
catcctttgg cccaccgtgt                                               20

<210> SEQ ID NO 193
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 193
tcatcctttg gcccaccgtg                                               20

<210> SEQ ID NO 194
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 194
ttcatccttt ggcccaccgt                                               20

<210> SEQ ID NO 195
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 195
cttcatcctt tggcccaccg                                               20

<210> SEQ ID NO 196
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 196
tcttcatcct ttggcccacc                                               20

<210> SEQ ID NO 197
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 197
ctcttcatcc tttggcccac                                               20

<210> SEQ ID NO 198
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 198
tctcttcatc ctttggccca                                               20

<210> SEQ ID NO 199
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 199
ctctcttcat cctttggccc                                               20

<210> SEQ ID NO 200
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 200
cctctcttca tcctttggcc                                               20

<210> SEQ ID NO 201
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 201
gcctctcttc atcctttggc                                               20

<210> SEQ ID NO 202
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 202
tgcctctctt catcctttgg                                               20

<210> SEQ ID NO 203
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 203
atgcctctct tcatcctttg                                               20

<210> SEQ ID NO 204
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 204
catgcctctc ttcatccttt                                               20

<210> SEQ ID NO 205
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 205
acatgcctct cttcatcctt                                               20

<210> SEQ ID NO 206
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 206
aacatgcctc tcttcatcct                                               20

<210> SEQ ID NO 207
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 207 tgcttttca tggaccacca                                                    20

<210> SEQ ID NO 208
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 208
ctgctttttc atggaccacc                                                   20

<210> SEQ ID NO 209
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 209 tctgctttt catggaccac                                                    20

<210> SEQ ID NO 210
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 210
atctgctttt tcatggacca                                                   20

<210> SEQ ID NO 211
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 211
catctgcttt ttcatggacc                                                   20

<210> SEQ ID NO 212
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 212
tcatctgctt tttcatggac                                                   20

<210> SEQ ID NO 213
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 213
```
gtcatctgct ttttcatgga                                          20

<210> SEQ ID NO 214
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 214
agtcatctgc tttttcatgg                                          20

<210> SEQ ID NO 215
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 215
aagtcatctg cttttcatg                                           20

<210> SEQ ID NO 216
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 216
caagtcatct gcttttcat                                           20

<210> SEQ ID NO 217
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 217
ccaagtcatc tgctttttca                                          20

<210> SEQ ID NO 218
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 218
cccaagtcat ctgcttttc                                           20

<210> SEQ ID NO 219
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 219
gcccaagtca tctgctttt                                           20

<210> SEQ ID NO 220
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 220
tgcccaagtc atctgctttt                                              20

<210> SEQ ID NO 221
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 221
ttgcccaagt catctgcttt                                              20

<210> SEQ ID NO 222
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 222
tttgcccaag tcatctgctt                                              20

<210> SEQ ID NO 223
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 223
ctttgcccaa gtcatctgct                                              20

<210> SEQ ID NO 224
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 224
cctttgccca agtcatctgc                                              20

<210> SEQ ID NO 225
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 225
acctttgccc aagtcatctg                                              20

<210> SEQ ID NO 226
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 226
cccaattaca ccacaagcca                                              20
```

<210> SEQ ID NO 227
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 227
tcccaattac accacaagcc                                                     20

<210> SEQ ID NO 228
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 228
atcccaatta caccacaagc                                                     20

<210> SEQ ID NO 229
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 229
gatcccaatt acaccacaag                                                     20

<210> SEQ ID NO 230
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 230
cgatcccaat tacaccacaa                                                     20

<210> SEQ ID NO 231
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 231
gcgatcccaa ttacaccaca                                                     20

<210> SEQ ID NO 232
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 232
gggcgatccc aattacacca                                                     20

<210> SEQ ID NO 233
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 233
tgggcgatcc caattacacc					20

<210> SEQ ID NO 234
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 234
ttgggcgatc ccaattacac					20

<210> SEQ ID NO 235
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 235
attgggcgat cccaattaca					20

<210> SEQ ID NO 236
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 236
tattgggcga tcccaattac					20

<210> SEQ ID NO 237
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 237
ttattgggcg atcccaatta					20

<210> SEQ ID NO 238
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 238
tttattgggc gatcccaatt					20

<210> SEQ ID NO 239
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 239
gtttattggg cgatcccaat					20

<210> SEQ ID NO 240
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 240
tgtttattgg gcgatcccaa            20

<210> SEQ ID NO 241
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 241
atgtttattg ggcgatccca            20

<210> SEQ ID NO 242
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 242
aatgtttatt gggcgatccc            20

<210> SEQ ID NO 243
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 243
gaatgtttat tgggcgatcc            20

<210> SEQ ID NO 244
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 244
tccaagggaa tgtttattgg            20

<210> SEQ ID NO 245
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 245
atccaaggga atgtttattg            20

<210> SEQ ID NO 246
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 246
catccaaggg aatgtttatt                                          20

<210> SEQ ID NO 247
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 247
acatccaagg gaatgtttat                                          20

<210> SEQ ID NO 248
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 248
tacatccaag ggaatgttta                                          20

<210> SEQ ID NO 249
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 249
ctacatccaa gggaatgttt                                          20

<210> SEQ ID NO 250
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 250
actacatcca agggaatgtt                                          20

<210> SEQ ID NO 251
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 251
gactacatcc aagggaatgt                                          20

<210> SEQ ID NO 252
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 252
agactacatc caagggaatg                                          20

<210> SEQ ID NO 253
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 253
cagactacat ccaagggaat                                          20

<210> SEQ ID NO 254
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 254
tcagactaca tccaagggaa                                          20

<210> SEQ ID NO 255
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 255
ctcagactac atccaaggga                                          20

<210> SEQ ID NO 256
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 256
gcctcagact acatccaagg                                          20

<210> SEQ ID NO 257
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 257
ggcctcagac tacatccaag                                          20

<210> SEQ ID NO 258
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 258
gggcctcaga ctacatccaa                                          20

<210> SEQ ID NO 259
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 259
```
caggataaca gatgagttaa 20

<210> SEQ ID NO 260
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 260
gcaggataac agatgagtta 20

<210> SEQ ID NO 261
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 261
agcaggataa cagatgagtt 20

<210> SEQ ID NO 262
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 262
tagcaggata acagatgagt 20

<210> SEQ ID NO 263
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 263
ctagcaggat aacagatgag 20

<210> SEQ ID NO 264
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 264
gctagcagga taacagatga 20

<210> SEQ ID NO 265
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 265
agctagcagg ataacagatg 20

<210> SEQ ID NO 266
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 266
cagctagcag gataacagat                                               20

<210> SEQ ID NO 267
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 267
acagctagca ggataacaga                                               20

<210> SEQ ID NO 268
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 268
tacagctagc aggataacag                                               20

<210> SEQ ID NO 269
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 269
ctacagctag caggataaca                                               20

<210> SEQ ID NO 270
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 270
tctacagcta gcaggataac                                               20

<210> SEQ ID NO 271
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 271
ttctacagct agcaggataa                                               20

<210> SEQ ID NO 272
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 272
tttctacagc tagcaggata                                               20
```

<210> SEQ ID NO 273
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 273
atttctacag ctagcaggat                                              20

<210> SEQ ID NO 274
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 274
catttctaca gctagcagga                                              20

<210> SEQ ID NO 275
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 275
acatttctac agctagcagg                                              20

<210> SEQ ID NO 276
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 276
tacatttcta cagctagcag                                              20

<210> SEQ ID NO 277
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 277
atacatttct acagctagca                                              20

<210> SEQ ID NO 278
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 278
gatacatttc tacagctagc                                              20

<210> SEQ ID NO 279
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 279
acagtgttta atgtttatca            20

<210> SEQ ID NO 280
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 280
tacagtgttt aatgtttatc            20

<210> SEQ ID NO 281
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 281
ttacagtgtt taatgtttat            20

<210> SEQ ID NO 282
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 282
attacagtgt ttaatgttta            20

<210> SEQ ID NO 283
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 283
gattacagtg tttaatgttt            20

<210> SEQ ID NO 284
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 284
agattacagt gtttaatgtt            20

<210> SEQ ID NO 285
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 285
aagattacag tgtttaatgt            20

<210> SEQ ID NO 286

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 286
taagattaca gtgtttaatg                                            20

<210> SEQ ID NO 287
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 287
ttaagattac agtgtttaat                                            20

<210> SEQ ID NO 288
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 288
caaatcttcc aagtgatcat                                            20

<210> SEQ ID NO 289
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 289
acaaatcttc caagtgatca                                            20

<210> SEQ ID NO 290
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 290
tacaaatctt ccaagtgatc                                            20

<210> SEQ ID NO 291
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 291
tatacaaatc ttccaagtga                                            20

<210> SEQ ID NO 292
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 292
```
ctatacaaat cttccaagtg                                               20

<210> SEQ ID NO 293
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 293
actatacaaa tcttccaagt                                               20

<210> SEQ ID NO 294
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 294
aactatacaa atcttccaag                                               20

<210> SEQ ID NO 295
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 295
aaactataca aatcttccaa                                               20

<210> SEQ ID NO 296
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 296
aaaactatac aaatcttcca                                               20

<210> SEQ ID NO 297
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 297
taaaactata caaatcttcc                                               20

<210> SEQ ID NO 298
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 298
ataaaactat acaaatcttc                                               20

<210> SEQ ID NO 299
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 299
tataaaacta tacaaatctt                                               20

<210> SEQ ID NO 300
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 300
ttataaaact atacaaatct                                               20

<210> SEQ ID NO 301
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 301
tttataaaac tatacaaatc                                               20

<210> SEQ ID NO 302
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 302
ttttataaaa ctatacaaat                                               20

<210> SEQ ID NO 303
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 303
gttttataaa actatacaaa                                               20

<210> SEQ ID NO 304
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 304
agttttataa aactatacaa                                               20

<210> SEQ ID NO 305
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 305
gagttttata aaactataca                                               20

<210> SEQ ID NO 306
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 306
cattgaaaca gacattttaa                                         20

<210> SEQ ID NO 307
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 307
gtcattgaaa cagacatttt                                         20

<210> SEQ ID NO 308
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 308
ggtcattgaa acagacattt                                         20

<210> SEQ ID NO 309
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 309
aggtcattga aacagacatt                                         20

<210> SEQ ID NO 310
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 310
caggtcattg aaacagacat                                         20

<210> SEQ ID NO 311
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 311
acaggtcatt gaaacagaca                                         20

<210> SEQ ID NO 312
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 312
tacaggtcat tgaaacagac                                            20

<210> SEQ ID NO 313
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 313
aatacaggtc attgaaacag                                            20

<210> SEQ ID NO 314
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 314
aaatacaggt cattgaaaca                                            20

<210> SEQ ID NO 315
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 315
aaaatacagg tcattgaaac                                            20

<210> SEQ ID NO 316
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 316
caaaatacag gtcattgaaa                                            20

<210> SEQ ID NO 317
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 317
ccttgccttc tgctcgaaat                                            20

<210> SEQ ID NO 318
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 318
aataaagttg acctcttttt                                            20

```
<210> SEQ ID NO 319
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 319
ctctgatata aaaatcttgt                                          20

<210> SEQ ID NO 320
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 320
gccccgcggc ggcctcggtc                                          20

<210> SEQ ID NO 321
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 321
gctatcgcca ttattacaag                                          20

<210> SEQ ID NO 322
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 322
ctcaaatgtg aaagttgtcc                                          20

<210> SEQ ID NO 323
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 323
gttctatatt caataaatgc                                          20

<210> SEQ ID NO 324
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 324
aattaaagtt cccaaataca                                          20

<210> SEQ ID NO 325
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 325
gatcattaca aaagttaaga					20

<210> SEQ ID NO 326
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 326
ccttctctgc ccttgcagcc					20

<210> SEQ ID NO 327
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 327
acccaaataa ctatgttgta					20

<210> SEQ ID NO 328
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 328
ccaggtttta aacttaacaa					20

<210> SEQ ID NO 329
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 329
atctcaggac taaaataaac					20

<210> SEQ ID NO 330
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 330
aaataactat gttgtagacc					20

<210> SEQ ID NO 331
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 331
aagaaccttt tccagaaaat					20

<210> SEQ ID NO 332
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 332
ggaacagaaa caagtctatg                                              20

<210> SEQ ID NO 333
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 333
agaaagctat cgccattatt                                              20

<210> SEQ ID NO 334
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 334
ttcccaaata cattctaaaa                                              20

<210> SEQ ID NO 335
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 335
aactgctcta ggcctgtgtc                                              20

<210> SEQ ID NO 336
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 336
aaatggatca aatctgatca                                              20

<210> SEQ ID NO 337
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 337
gtaggtgcac atcaaaatca                                              20

<210> SEQ ID NO 338
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 338
```
tctgatataa aaatcttgtc                          20

<210> SEQ ID NO 339
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 339
accatatgaa ctccagaaag                          20

<210> SEQ ID NO 340
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 340
aacatcaagg tagttcatga                          20

<210> SEQ ID NO 341
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 341
gcaattacag aaatggatca                          20

<210> SEQ ID NO 342
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 342
ttttaagcat attccaaagt                          20

<210> SEQ ID NO 343
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 343
tcaaccccca gctcaaacac                          20

<210> SEQ ID NO 344
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 344
agaaaaataa cattaatcct                          20

<210> SEQ ID NO 345
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 345
aagattttaa acacggaata                                                    20

<210> SEQ ID NO 346
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 346
agcagtcaca ttgcccaagt                                                    20

<210> SEQ ID NO 347
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 347
cagtgtttaa tgtttatcag                                                    20

<210> SEQ ID NO 348
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 348
gcaaaataca ggtcattgaa                                                    20

<210> SEQ ID NO 349
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 349
ggcaaaatac aggtcattga                                                    20

<210> SEQ ID NO 350
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 350
tggcaaaata caggtcattg                                                    20

<210> SEQ ID NO 351
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 351
ctggcaaaat acaggtcatt                                                    20

<210> SEQ ID NO 352
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 352
tctggcaaaa tacaggtcat                                              20

<210> SEQ ID NO 353
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 353
gtctggcaaa atacaggtca                                              20

<210> SEQ ID NO 354
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 354
agtctggcaa aatacaggtc                                              20

<210> SEQ ID NO 355
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 355
aagtctggca aaatacaggt                                              20

<210> SEQ ID NO 356
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 356
taagtctggc aaaatacagg                                              20

<210> SEQ ID NO 357
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 357
ttaagtctgg caaaatacag                                              20

<210> SEQ ID NO 358
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 358
gtttaatacc catctgtgat                                          20

<210> SEQ ID NO 359
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 359
aagtttaata cccatctgtg                                          20

<210> SEQ ID NO 360
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 360
caagtttaat acccatctgt                                          20

<210> SEQ ID NO 361
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 361
acaagtttaa tacccatctg                                          20

<210> SEQ ID NO 362
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 362
gacaagttta atacccatct                                          20

<210> SEQ ID NO 363
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 363
tgacaagttt aatacccatc                                          20

<210> SEQ ID NO 364
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 364
ctgacaagtt taatacccat                                          20

<210> SEQ ID NO 365

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 365
tctgacaagt ttaataccca                                               20

<210> SEQ ID NO 366
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 366
ttctgacaag tttaataccc                                               20

<210> SEQ ID NO 367
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 367
attctgacaa gtttaatacc                                               20

<210> SEQ ID NO 368
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 368
aattctgaca gtttaatac                                                20

<210> SEQ ID NO 369
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 369
aaattctgac aagtttaata                                               20

<210> SEQ ID NO 370
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 370
gaaattctga caagtttaat                                               20

<210> SEQ ID NO 371
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 371
```
agaaattctg acaagtttaa                                                20

<210> SEQ ID NO 372
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 372
aagaaattct gacaagttta                                                20

<210> SEQ ID NO 373
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 373
ttattcacag gcttgaatga                                                20

<210> SEQ ID NO 374
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 374
tttattcaca ggcttgaatg                                                20

<210> SEQ ID NO 375
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 375
ttttattcac aggcttgaat                                                20

<210> SEQ ID NO 376
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 376
tttttattca caggcttgaa                                                20

<210> SEQ ID NO 377
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 377
gtttttattc acaggcttga                                                20

<210> SEQ ID NO 378
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 378
gggtttttat tcacaggctt                                              20

<210> SEQ ID NO 379
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 379
cagggttttt attcacaggc                                              20

<210> SEQ ID NO 380
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 380
acagggtttt tattcacagg                                              20

<210> SEQ ID NO 381
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 381
tacagggttt ttattcacag                                              20

<210> SEQ ID NO 382
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 382
catacagggt ttttattcac                                              20

<210> SEQ ID NO 383
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 383
gccatacagg gttttattc                                               20

<210> SEQ ID NO 384
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 384
tgccatacag ggttttatt                                               20
```

<210> SEQ ID NO 385
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 385
gtgccataca gggtttttat                                              20

<210> SEQ ID NO 386
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 386
agtgccatac agggttttta                                              20

<210> SEQ ID NO 387
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 387
tggaaaaact caaatgtgaa                                              20

<210> SEQ ID NO 388
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 388
tttccctttc ttttccacac                                              20

<210> SEQ ID NO 389
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 389
tctttccctt tcttttccac                                              20

<210> SEQ ID NO 390
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 390
taccttctct gcccttgcag                                              20

<210> SEQ ID NO 391
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 391
gcaagggcca aggctgctgc                    20

<210> SEQ ID NO 392
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 392
aaagctaaat tatgaattaa                    20

<210> SEQ ID NO 393
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 393
ctaatgaagg ctcagtatga                    20

<210> SEQ ID NO 394
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 394
ggagtcaaat gccaaagaac                    20

<210> SEQ ID NO 395
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 395
tgaattaaag ttcccaaata                    20

<210> SEQ ID NO 396
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 396
acttggtgca ggcagaatat                    20

<210> SEQ ID NO 397
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 397
cctctgatat aaaaatcttg                    20

```
<210> SEQ ID NO 398
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 398
aaagttggag agagtttctg                                               20

<210> SEQ ID NO 399
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 399
tctctgccct tgcagcccaa                                               20

<210> SEQ ID NO 400
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 400
ttacttggtg caggcagaat                                               20

<210> SEQ ID NO 401
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 401
aatggagtca aatgccaaag                                               20

<210> SEQ ID NO 402
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 402
tatgaattaa agttcccaaa                                               20

<210> SEQ ID NO 403
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 403
agttctatat tcaataaatg                                               20

<210> SEQ ID NO 404
<211> LENGTH: 20
<212> TYPE: DNA
<213> ORGANISM: Artificial sequence
<220> FEATURE:
<223> OTHER INFORMATION: Synthetic oligonucleotide
```

-continued

```
<400> SEQUENCE: 404
tacaagtagt ataccatatg                                              20

<210> SEQ ID NO 405
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 405
tagccttaga gctgtacaaa                                              20

<210> SEQ ID NO 406
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 406
gtccccattt gtcaattcct                                              20

<210> SEQ ID NO 407
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 407
aacctgccta ctggcagagc                                              20

<210> SEQ ID NO 408
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 408
cttgttccca cactcaatgc                                              20

<210> SEQ ID NO 409
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 409
acaagtcatg ataacctgca                                              20

<210> SEQ ID NO 410
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 410
tgttttccaa actcagatct                                              20

<210> SEQ ID NO 411
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 411
agaacctcat aatattagaa                                                 20

<210> SEQ ID NO 412
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 412
ggttttaaac ttaacaaaat                                                 20

<210> SEQ ID NO 413
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 413
ctctggtgta tttttagtaa                                                 20

<210> SEQ ID NO 414
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 414
tatctctgca tatctggaaa                                                 20

<210> SEQ ID NO 415
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 415 cagcctttt aacccaaaag                                                  20

<210> SEQ ID NO 416
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 416
tggaatgctc cactatccaa                                                 20

<210> SEQ ID NO 417
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 417
```
cgttcagaag tttgtctctg                                           20

<210> SEQ ID NO 418
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 418
ctgctcaggg aaggtggaaa                                           20

<210> SEQ ID NO 419
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 419
tcaagagaag ctaggaaaac                                           20

<210> SEQ ID NO 420
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 420
tccctttctt ttccacacct                                           20

<210> SEQ ID NO 421
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 421
ttgttcccac actcaatgca                                           20

<210> SEQ ID NO 422
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 422
tcaccagcac agcacaacac                                           20

<210> SEQ ID NO 423
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 423
cctgggatca ttacaaaagt                                           20

<210> SEQ ID NO 424
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 424
agtagtatac catatgaact                                              20

<210> SEQ ID NO 425
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 425
tctaatatgg tcaaatgtaa                                              20

<210> SEQ ID NO 426
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 426
ggttgggctc tggtgtattt                                              20

<210> SEQ ID NO 427
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 427
tgccctttac ttggtgcagg                                              20

<210> SEQ ID NO 428
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 428
agagagtttc tgaacaaaga                                              20

<210> SEQ ID NO 429
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 429
gaatttcagc aattacagaa                                              20

<210> SEQ ID NO 430
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 430
acaagttaaa caagtcatga                                              20

```
<210> SEQ ID NO 431
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 431
tgtgcccttt acttggtgca                                               20

<210> SEQ ID NO 432
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 432
ttaggaggag gaaaaggacc                                               20

<210> SEQ ID NO 433
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 433
actggcagag caattttaaa                                               20

<210> SEQ ID NO 434
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 434
agtcaaatgc caaagaacct                                               20

<210> SEQ ID NO 435
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 435
aagcatcaga tggattaggg                                               20

<210> SEQ ID NO 436
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 436
gtccgcggga ccctcaggaa                                               20

<210> SEQ ID NO 437
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 437
caattacaga aatggatcaa                                          20

<210> SEQ ID NO 438
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 438
gctgtcaagt aatcactacc                                          20

<210> SEQ ID NO 439
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 439
agtgcaaagt tggagagagt                                          20

<210> SEQ ID NO 440
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 440
acttgcttcc aatcccaaat                                          20

<210> SEQ ID NO 441
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 441
aactcaaatg tgaaagttgt                                          20

<210> SEQ ID NO 442
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 442
ttttagtaag atcttcaaat                                          20

<210> SEQ ID NO 443
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 443
atttcagcaa ttacagaaat                                          20

<210> SEQ ID NO 444

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 444
ttaagtgtcc ccatttgtca                                          20

<210> SEQ ID NO 445
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 445
ttagcaacct gcctactggc                                          20

<210> SEQ ID NO 446
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 446
tattacaaga gttaagcatc                                          20

<210> SEQ ID NO 447
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 447
atgttgaata tacatgtaca                                          20

<210> SEQ ID NO 448
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 448
tttgtctctg accatcttag                                          20

<210> SEQ ID NO 449
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 449
ttttccacca gttggtaact                                          20

<210> SEQ ID NO 450
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 450
```
caacagcttc ccacaagtta                                              20

<210> SEQ ID NO 451
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 451
caaatgtgaa agttgtccct                                              20

<210> SEQ ID NO 452
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 452
gctaccttct ctgcccttgc                                              20

<210> SEQ ID NO 453
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 453
tcttagcaga acagtgttct                                              20

<210> SEQ ID NO 454
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 454
atacattcta aaagaaaaca                                              20

<210> SEQ ID NO 455
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 455
gcacatattt acaagtagta                                              20

<210> SEQ ID NO 456
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 456
gggtcaccag cacagcacaa                                              20

<210> SEQ ID NO 457
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 457
gtgcaagggc caaggctgct                                              20

<210> SEQ ID NO 458
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 458
acctgggttc atgcatggat                                              20

<210> SEQ ID NO 459
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 459
atcactattt gaaactaaat                                              20

<210> SEQ ID NO 460
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 460
atacaataaa gttgacctct                                              20

<210> SEQ ID NO 461
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 461
ttttaaactt aacaaaatgt                                              20

<210> SEQ ID NO 462
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 462
ctccccgcgc tcccgccacg                                              20

<210> SEQ ID NO 463
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 463
gaaggctcag tatgaagaga                                              20
```

<210> SEQ ID NO 464
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 464
agaaaacagc tgatttacct                                               20

<210> SEQ ID NO 465
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 465
ccacaagtta aacaagtcat                                               20

<210> SEQ ID NO 466
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 466
caaatttgca aacaagtagc                                               20

<210> SEQ ID NO 467
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 467
cctaatttga actgcaagta                                               20

<210> SEQ ID NO 468
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 468
aaaaaactca tctccccagc                                               20

<210> SEQ ID NO 469
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 469
aggctcagta tgaagagatc                                               20

<210> SEQ ID NO 470
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 470
tgttatcaag agcacagggc                                           20

<210> SEQ ID NO 471
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 471
cctcaaaagg gagatggtaa                                           20

<210> SEQ ID NO 472
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 472
agtatgggtc accagcacag                                           20

<210> SEQ ID NO 473
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 473
tcacaatcta gtgcagttac                                           20

<210> SEQ ID NO 474
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 474
caagtgagaa acccaatcct                                           20

<210> SEQ ID NO 475
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 475
agaaaatctg gccattttaa                                           20

<210> SEQ ID NO 476
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 476
acaggtaatg gtgctccgtg                                           20

```
<210> SEQ ID NO 477
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 477
tgaaaggctt tcagaaaaca                                            20

<210> SEQ ID NO 478
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 478
caggcaagtt acaggaagca                                            20

<210> SEQ ID NO 479
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 479
cagcaagctg cttaactgct                                            20

<210> SEQ ID NO 480
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 480
tgttgcaaag acattacctt                                            20

<210> SEQ ID NO 481
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 481
gaaactaaat tagcaagatg                                            20

<210> SEQ ID NO 482
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 482
tcaagagcac agggccaaaa                                            20

<210> SEQ ID NO 483
<211> LENGTH: 20
<212> TYPE: DNA
<213> ORGANISM: Artificial sequence
<220> FEATURE:
<223> OTHER INFORMATION: Synthetic oligonucleotide
```

-continued

<400> SEQUENCE: 483
aggaggagga aaaggacctc                                           20

<210> SEQ ID NO 484
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 484
cctcagcctt tttaacccaa                                           20

<210> SEQ ID NO 485
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 485
ctatgttgta gaccaccaca                                           20

<210> SEQ ID NO 486
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 486
ctccgtggct acatacagaa                                           20

<210> SEQ ID NO 487
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 487
tttatctgga tctttagaaa                                           20

<210> SEQ ID NO 488
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 488
aaaaaaagga aagtgaaagt                                           20

<210> SEQ ID NO 489
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 489
ggttcatgca tggattctca                                           20

<210> SEQ ID NO 490
<211> LENGTH: 20

<212> TYPE: DNA
<213> ORGANISM: Artificial sequence
<220> FEATURE:
<223> OTHER INFORMATION: Synthetic oligonucleotide

<400> SEQUENCE: 490
ctgcaaagtg tcacacaaac                                           20

<210> SEQ ID NO 491
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 491
ttcagaagta ccaaagggta                                           20

<210> SEQ ID NO 492
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 492
taaaagcatt ccagcatttg                                           20

<210> SEQ ID NO 493
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 493
tagtatacca tatgaactcc                                           20

<210> SEQ ID NO 494
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 494
tgcatatctg gaaagctgga                                           20

<210> SEQ ID NO 495
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 495
cttaactgct ctaggcctgt                                           20

<210> SEQ ID NO 496
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 496
aggcaccgac cgggcggcac                                        20

<210> SEQ ID NO 497
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 497
tgcaaagttg gagagagttt                                        20

<210> SEQ ID NO 498
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 498
tcctcaaaag ggagatggta                                        20

<210> SEQ ID NO 499
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 499
agtataccat atgaactcca                                        20

<210> SEQ ID NO 500
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 500
tatttgtaca tgttgaatat                                        20

<210> SEQ ID NO 501
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 501
acccaaaagg tgtatgtctc                                        20

<210> SEQ ID NO 502
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 502
ctttggaaaa aaaggaaagt                                        20

<210> SEQ ID NO 503
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 503
gggagaaagg caggcaagtt                                              20

<210> SEQ ID NO 504
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 504
ttaagcccag gaagtaaaag                                              20

<210> SEQ ID NO 505
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 505
agacattacc tttaaacatt                                              20

<210> SEQ ID NO 506
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 506
gtggcttaag aaatgctccg                                              20

<210> SEQ ID NO 507
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 507
gtgagaaggg aacagaaaca                                              20

<210> SEQ ID NO 508
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 508
aaaagcatca gatggattag                                              20

<210> SEQ ID NO 509
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 509
ttccaccagt tggtaacttc                                              20
```

<210> SEQ ID NO 510
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 510
tttttagtaa gatcttcaaa                                              20

<210> SEQ ID NO 511
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 511
atctgtgtcc aaatcccagg                                              20

<210> SEQ ID NO 512
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 512
taagatcttc aaataagcta                                              20

<210> SEQ ID NO 513
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 513
atcaactctt tccctttctt                                              20

<210> SEQ ID NO 514
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 514
tgtgtcctca aagggagat                                               20

<210> SEQ ID NO 515
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 515
tacctcctcc caacaatacc                                              20

<210> SEQ ID NO 516
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 516
ttctgcttta caactatggc                                              20

<210> SEQ ID NO 517
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 517
gtacatgttg aatatacatg                                              20

<210> SEQ ID NO 518
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 518
tttgtggcta atcttaaggt                                              20

<210> SEQ ID NO 519
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 519
tcctgcctca gcctttttaa                                              20

<210> SEQ ID NO 520
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 520
cggtgtccgc gggaccctca                                              20

<210> SEQ ID NO 521
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 521
gaaatggatc aaatctgatc                                              20

<210> SEQ ID NO 522
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 522
ggtagttcat gagctaaatt                                              20

<210> SEQ ID NO 523

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 523
aatggagtct cgactagttt                                              20

<210> SEQ ID NO 524
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 524
caagtatggg tcaccagcac                                              20

<210> SEQ ID NO 525
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 525
ggtgtccgcg ggaccctcag                                              20

<210> SEQ ID NO 526
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 526
cgccacgcgc aggcccagcc                                              20

<210> SEQ ID NO 527
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 527
tctaggcctg tgtcctcaaa                                              20

<210> SEQ ID NO 528
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 528
actgtcctgg gctaatgaag                                              20

<210> SEQ ID NO 529
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 529
```
aagcatcttg ttacctctct          20

<210> SEQ ID NO 530
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 530
gcccaggaag taaaagcatt          20

<210> SEQ ID NO 531
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 531
gtaagatctt caaataagct          20

<210> SEQ ID NO 532
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 532
aaagggagat ggtaatcttg          20

<210> SEQ ID NO 533
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 533
gccaaggctg ctgccttaca          20

<210> SEQ ID NO 534
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 534
cagactaact gttcctgtcc          20

<210> SEQ ID NO 535
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 535
tttgtcaatt cctttaagcc          20

<210> SEQ ID NO 536
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 536
actacctcct cccaacaata                                              20

<210> SEQ ID NO 537
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 537
tacctctctt catcctttgg                                              20

<210> SEQ ID NO 538
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 538
actgctctag gcctgtgtcc                                              20

<210> SEQ ID NO 539
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 539
cctcctccca acaataccca                                              20

<210> SEQ ID NO 540
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 540
ggcaggcaag ttacaggaag                                              20

<210> SEQ ID NO 541
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 541
tcgcccactc tggccccaaa                                              20

<210> SEQ ID NO 542
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 542
cctcgcccac tctggcccca                                              20
```

<210> SEQ ID NO 543
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 543
cgcctcgccc actctggccc                                                 20

<210> SEQ ID NO 544
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 544
cgcgcctcgc ccactctggc                                                 20

<210> SEQ ID NO 545
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 545
tccgcgcctc gcccactctg                                                 20

<210> SEQ ID NO 546
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 546
cctccgcgcc tcgcccactc                                                 20

<210> SEQ ID NO 547
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 547
gacctccgcg cctcgcccac                                                 20

<210> SEQ ID NO 548
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 548
cagacctccg cgcctcgccc                                                 20

<210> SEQ ID NO 549
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 549
gccagacctc cgcgcctcgc                                              20

<210> SEQ ID NO 550
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 550
aggccagacc tccgcgcctc                                              20

<210> SEQ ID NO 551
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 551
ataggccaga cctccgcgcc                                              20

<210> SEQ ID NO 552
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 552
ttataggcca gacctccgcg                                              20

<210> SEQ ID NO 553
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 553
ctttataggc cagacctccg                                              20

<210> SEQ ID NO 554
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 554
tactttatag gccagacctc                                              20

<210> SEQ ID NO 555
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 555
actactttat aggccagacc                                              20

```
<210> SEQ ID NO 556
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 556
cgactacttt ataggccaga                                          20

<210> SEQ ID NO 557
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 557
cgcgactact ttataggcca                                          20

<210> SEQ ID NO 558
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 558
tccgcgacta ctttataggc                                          20

<210> SEQ ID NO 559
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 559
tctccgcgac tactttatag                                          20

<210> SEQ ID NO 560
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 560
cgtctccgcg actactttat                                          20

<210> SEQ ID NO 561
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 561
cccgtctccg cgactacttt                                          20

<210> SEQ ID NO 562
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 562
accccgtctc cgcgactact                                               20

<210> SEQ ID NO 563
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 563
gcaccccgtc tccgcgacta                                               20

<210> SEQ ID NO 564
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 564
cagcaccccg tctccgcgac                                               20

<210> SEQ ID NO 565
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 565
accagcaccc cgtctccgcg                                               20

<210> SEQ ID NO 566
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 566
aaaccagcac cccgtctccg                                               20

<210> SEQ ID NO 567
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 567
gcaaaccagc accccgtctc                                               20

<210> SEQ ID NO 568
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 568
acgcaaacca gcaccccgtc                                               20

<210> SEQ ID NO 569
<211> LENGTH: 20
```

```
-continued

<212> TYPE: DNA
<213> ORGANISM: Artificial sequence
<220> FEATURE:
<223> OTHER INFORMATION: Synthetic oligonucleotide

<400> SEQUENCE: 569
cgacgcaaac cagcaccccg                                             20

<210> SEQ ID NO 570
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 570
tacgacgcaa accagcaccc                                             20

<210> SEQ ID NO 571
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 571
actacgacgc aaaccagcac                                             20

<210> SEQ ID NO 572
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 572
agactacgac gcaaaccagc                                             20

<210> SEQ ID NO 573
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 573
ggagactacg acgcaaacca                                             20

<210> SEQ ID NO 574
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 574
caggagacta cgacgcaaac                                             20

<210> SEQ ID NO 575
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 575
```
tgcaggagac tacgacgcaa                                               20

<210> SEQ ID NO 576
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 576
gctgcaggag actacgacgc                                               20

<210> SEQ ID NO 577
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 577
gcaacggaaa ccccagacgc                                               20

<210> SEQ ID NO 578
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 578
ctgcaacgga aacccagac                                                20

<210> SEQ ID NO 579
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 579
gactgcaacg gaaaccccag                                               20

<210> SEQ ID NO 580
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 580
ggactgcaac ggaaacccca                                               20

<210> SEQ ID NO 581
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 581
aggactgcaa cggaaacccc                                               20

<210> SEQ ID NO 582
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 582
tccgaggact gcaacggaaa                                              20

<210> SEQ ID NO 583
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 583
gttccgagga ctgcaacgga                                              20

<210> SEQ ID NO 584
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 584
tggttccgag gactgcaacg                                              20

<210> SEQ ID NO 585
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 585
cctggttccg aggactgcaa                                              20

<210> SEQ ID NO 586
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 586
gtcctggttc cgaggactgc                                              20

<210> SEQ ID NO 587
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 587
aggtcctggt tccgaggact                                              20

<210> SEQ ID NO 588
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 588
cgaggtcctg gttccgagga                                              20
```

<210> SEQ ID NO 589
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 589
gccgaggtcc tggttccgag                                               20

<210> SEQ ID NO 590
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 590
acgccgaggt cctggttccg                                               20

<210> SEQ ID NO 591
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 591
ccacgccgag gtcctggttc                                               20

<210> SEQ ID NO 592
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 592
ggccacgccg aggtcctggt                                               20

<210> SEQ ID NO 593
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 593
gctaggccac gccgaggtcc                                               20

<210> SEQ ID NO 594
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 594
tcgctaggcc acgccgaggt                                               20

<210> SEQ ID NO 595
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 595
actcgctagg ccacgccgag                                            20

<210> SEQ ID NO 596
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 596
taactcgcta ggccacgccg                                            20

<210> SEQ ID NO 597
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 597
cataactcgc taggccacgc                                            20

<210> SEQ ID NO 598
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 598
gccataactc gctaggccac                                            20

<210> SEQ ID NO 599
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 599
tcgccataac tcgctaggcc                                            20

<210> SEQ ID NO 600
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 600
cgtcgccata actcgctagg                                            20

<210> SEQ ID NO 601
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 601
cagcacgcac acggccttcg                                            20

<210> SEQ ID NO 602
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 602
gccgtcgccc ttcagcacgc                                               20

<210> SEQ ID NO 603
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 603
ggccgtcgcc cttcagcacg                                               20

<210> SEQ ID NO 604
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 604
gggccgtcgc ccttcagcac                                               20

<210> SEQ ID NO 605
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 605
ctgggccgtc gcccttcagc                                               20

<210> SEQ ID NO 606
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 606
cactgggccg tcgcccttca                                               20

<210> SEQ ID NO 607
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 607
tgcactgggc cgtcgccctt                                               20

<210> SEQ ID NO 608
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 608
```
cctgcactgg gccgtcgccc                                          20

<210> SEQ ID NO 609
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 609
atgccctgca ctgggccgtc                                          20

<210> SEQ ID NO 610
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 610
tgatgccctg cactgggccg                                          20

<210> SEQ ID NO 611
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 611
gatgatgccc tgcactgggc                                          20

<210> SEQ ID NO 612
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 612
ttgatgatgc cctgcactgg                                          20

<210> SEQ ID NO 613
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 613
ggcgatccca attacacc                                            18

<210> SEQ ID NO 614
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 614
tcgaaattga tgatgccctg                                          20

<210> SEQ ID NO 615
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 615
gctcgaaatt gatgatgccc                                              20

<210> SEQ ID NO 616
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 616
ctgctcgaaa ttgatgatgc                                              20

<210> SEQ ID NO 617
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 617
ttctgctcga aattgatgat                                              20

<210> SEQ ID NO 618
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 618
ttaatgcttc cccacacctt                                              20

<210> SEQ ID NO 619
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 619
ctttaatgct tccccacacc                                              20

<210> SEQ ID NO 620
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 620
tcctttaatg cttccccaca                                              20

<210> SEQ ID NO 621
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 621
tcagtccttt aatgcttccc                                              20

<210> SEQ ID NO 622
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 622
agtcagtcct ttaatgcttc                                              20

<210> SEQ ID NO 623
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 623
tcagtcagtc ctttaatgct                                              20

<210> SEQ ID NO 624
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 624
cttcagtcag tcctttaatg                                              20

<210> SEQ ID NO 625
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 625
gccttcagtc agtcctttaa                                              20

<210> SEQ ID NO 626
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 626
gcaggccttc agtcagtcct                                              20

<210> SEQ ID NO 627
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 627
atgcaggcct tcagtcagtc                                              20

<210> SEQ ID NO 628
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 628
ccatgcaggc cttcagtcag                                           20

<210> SEQ ID NO 629
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 629
catgaacatg gaatccatgc                                           20

<210> SEQ ID NO 630
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 630
ctcatgaaca tggaatccat                                           20

<210> SEQ ID NO 631
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 631
aactcatgaa catggaatcc                                           20

<210> SEQ ID NO 632
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 632
ccaaactcat gaacatggaa                                           20

<210> SEQ ID NO 633
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 633
ctccaaactc atgaacatgg                                           20

<210> SEQ ID NO 634
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 634
atctccaaac tcatgaacat                                           20

```
<210> SEQ ID NO 635
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 635
ttatctccaa actcatgaac                                               20

<210> SEQ ID NO 636
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 636
tattatctcc aaactcatga                                               20

<210> SEQ ID NO 637
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 637
tgtattatct ccaaactcat                                               20

<210> SEQ ID NO 638
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 638
ctgctgtatt atctccaaac                                               20

<210> SEQ ID NO 639
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 639
gcctgctgta ttatctccaa                                               20

<210> SEQ ID NO 640
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 640
cagcctgctg tattatctcc                                               20

<210> SEQ ID NO 641
<211> LENGTH: 20
<212> TYPE: DNA
<213> ORGANISM: Artificial sequence
<220> FEATURE:
<223> OTHER INFORMATION: Synthetic oligonucleotide
```

-continued

<400> SEQUENCE: 641
tacagcctgc tgtattatct    20

<210> SEQ ID NO 642
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 642
ggtacagcct gctgtattat    20

<210> SEQ ID NO 643
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 643
ctggtacagc ctgctgtatt    20

<210> SEQ ID NO 644
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 644
cactggtaca gcctgctgta    20

<210> SEQ ID NO 645
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 645
tgcactggta cagcctgctg    20

<210> SEQ ID NO 646
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 646
cctgcactgg tacagcctgc    20

<210> SEQ ID NO 647
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 647
ttctggatag aggattaaag    20

<210> SEQ ID NO 648
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 648
ttttctggat agaggattaa                                              20

<210> SEQ ID NO 649
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 649
tgttttctgg atagaggatt                                              20

<210> SEQ ID NO 650
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 650
cgtgttttct ggatagagga                                              20

<210> SEQ ID NO 651
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 651
accgtgtttt ctggatagag                                              20

<210> SEQ ID NO 652
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 652
ccaccgtgtt ttctggatag                                              20

<210> SEQ ID NO 653
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 653
gcccaccgtg ttttctggat                                              20

<210> SEQ ID NO 654
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 654
```
tggcccaccg tgttttctgg                                                  20

<210> SEQ ID NO 655
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 655
tttggcccac cgtgttttct                                                  20

<210> SEQ ID NO 656
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 656
cctttggccc accgtgtttt                                                  20

<210> SEQ ID NO 657
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 657
agtctccaac atgcctctct                                                  20

<210> SEQ ID NO 658
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 658
caagtctcca acatgcctct                                                  20

<210> SEQ ID NO 659
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 659
cccaagtctc caacatgcct                                                  20

<210> SEQ ID NO 660
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 660
attgcccaag tctccaacat                                                  20

<210> SEQ ID NO 661
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 661
acattgccca agtctccaac                                               20

<210> SEQ ID NO 662
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 662
tcacattgcc caagtctcca                                               20

<210> SEQ ID NO 663
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 663
agtcacattg cccaagtctc                                               20

<210> SEQ ID NO 664
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 664
gcagtcacat tgcccaagtc                                               20

<210> SEQ ID NO 665
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 665
cagcagtcac attgcccaag                                               20

<210> SEQ ID NO 666
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 666
gtcagcagtc acattgccca                                               20

<210> SEQ ID NO 667
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 667
ttgtcagcag tcacattgcc                                               20
```

<210> SEQ ID NO 668
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 668
ctttgtcagc agtcacattg                                                    20

<210> SEQ ID NO 669
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 669
atctttgtca gcagtcacat                                                    20

<210> SEQ ID NO 670
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 670
ccatctttgt cagcagtcac                                                    20

<210> SEQ ID NO 671
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 671
caccatcttt gtcagcagtc                                                    20

<210> SEQ ID NO 672
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 672
cacaccatct ttgtcagcag                                                    20

<210> SEQ ID NO 673
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 673
gccacaccat ctttgtcagc                                                    20

<210> SEQ ID NO 674
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 674
cggccacacc atctttgtca                                              20

<210> SEQ ID NO 675
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 675
atcggccaca ccatctttgt                                              20

<210> SEQ ID NO 676
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 676
acatcggcca caccatcttt                                              20

<210> SEQ ID NO 677
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 677
agacacatcg gccacaccat                                              20

<210> SEQ ID NO 678
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 678
atagacacat cggccacacc                                              20

<210> SEQ ID NO 679
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 679
caatagacac atcggccaca                                              20

<210> SEQ ID NO 680
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 680
ttcaatagac acatcggcca                                              20

<210> SEQ ID NO 681
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 681
tcttcaatag acacatcggc                                               20

<210> SEQ ID NO 682
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 682
aatcttcaat agacacatcg                                               20

<210> SEQ ID NO 683
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 683
agaatcttca atagacacat                                               20

<210> SEQ ID NO 684
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 684
acagaatctt caatagacac                                               20

<210> SEQ ID NO 685
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 685
tcacagaatc ttcaatagac                                               20

<210> SEQ ID NO 686
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 686
gatcacagaa tcttcaatag                                               20

<210> SEQ ID NO 687
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 687
```
gagatcacag aatcttcaat                                              20

<210> SEQ ID NO 688
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 688
gtgagatcac agaatcttca                                              20

<210> SEQ ID NO 689
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 689
gagtgagatc acagaatctt                                              20

<210> SEQ ID NO 690
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 690
gagagtgaga tcacagaatc                                              20

<210> SEQ ID NO 691
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 691
ctgagagtga gatcacagaa                                              20

<210> SEQ ID NO 692
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 692
tcctgagagt gagatcacag                                              20

<210> SEQ ID NO 693
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 693
ggtctcctga gagtgagatc                                              20

<210> SEQ ID NO 694
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 694
atggtctcct gagagtgaga                                             20

<210> SEQ ID NO 695
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 695
caatggtctc ctgagagtga                                             20

<210> SEQ ID NO 696
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 696
tgcaatggtc tcctgagagt                                             20

<210> SEQ ID NO 697
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 697
gatgcaatgg tctcctgaga                                             20

<210> SEQ ID NO 698
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 698
atgatgcaat ggtctcctga                                             20

<210> SEQ ID NO 699
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 699
caatgatgca atggtctcct                                             20

<210> SEQ ID NO 700
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 700
gccaatgatg caatggtctc                                             20
```

<210> SEQ ID NO 701
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 701
cggccaatga tgcaatggtc                                               20

<210> SEQ ID NO 702
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 702
tgcggccaat gatgcaatgg                                               20

<210> SEQ ID NO 703
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 703
tgtgcggcca atgatgcaat                                               20

<210> SEQ ID NO 704
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 704
agtgtgcggc caatgatgca                                               20

<210> SEQ ID NO 705
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 705
ccagtgtgcg gccaatgatg                                               20

<210> SEQ ID NO 706
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 706
caccagtgtg cggccaatga                                               20

<210> SEQ ID NO 707
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 707
ggaccaccag tgtgcggcca                                               20

<210> SEQ ID NO 708
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 708
atggaccacc agtgtgcggc                                               20

<210> SEQ ID NO 709
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 709
tttcatggac caccagtgtg                                               20

<210> SEQ ID NO 710
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 710
tttttcatgg accaccagtg                                               20

<210> SEQ ID NO 711
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 711 gcttttcat ggaccaccag                                                20

<210> SEQ ID NO 712
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 712
tgtctttgta ctttcttcat                                               20

<210> SEQ ID NO 713
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 713
cctgtctttg tactttcttc                                               20

```
<210> SEQ ID NO 714
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 714
ttcctgtctt tgtactttct                                               20

<210> SEQ ID NO 715
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 715
gtttcctgtc tttgtacttt                                               20

<210> SEQ ID NO 716
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 716
aagccaaacg acttccagcg                                               20

<210> SEQ ID NO 717
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 717
acaagccaaa cgacttccag                                               20

<210> SEQ ID NO 718
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 718
ccacaagcca aacgacttcc                                               20

<210> SEQ ID NO 719
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 719
caccacaagc caaacgactt                                               20

<210> SEQ ID NO 720
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 720
tacaccacaa gccaaacgac                                           20

<210> SEQ ID NO 721
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 721
attacaccac aagccaaacg                                           20

<210> SEQ ID NO 722
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 722
caattacacc acaagccaaa                                           20

<210> SEQ ID NO 723
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 723
aggataacag atgagttaag                                           20

<210> SEQ ID NO 724
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 724
ggatacattt ctacagctag                                           20

<210> SEQ ID NO 725
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 725
caggatacat ttctacagct                                           20

<210> SEQ ID NO 726
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 726
atcaggatac atttctacag                                           20

<210> SEQ ID NO 727
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 727
ttatcaggat acatttctac                                              20

<210> SEQ ID NO 728
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 728
gtttatcagg atacatttct                                              20

<210> SEQ ID NO 729
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 729
atgtttatca ggatacattt                                              20

<210> SEQ ID NO 730
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 730
taatgtttat caggatacat                                              20

<210> SEQ ID NO 731
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 731
tttaatgttt atcaggatac                                              20

<210> SEQ ID NO 732
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 732
tgtttaatgt ttatcaggat                                              20

<210> SEQ ID NO 733
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 733
```
agtgtttaat gtttatcagg 20

<210> SEQ ID NO 734
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 734
tttaagatta cagtgtttaa 20

<210> SEQ ID NO 735
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 735
cttttaagat tacagtgttt 20

<210> SEQ ID NO 736
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 736
cacttttaag attacagtgt 20

<210> SEQ ID NO 737
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 737 tacacttttta agattacagt 20

<210> SEQ ID NO 738
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 738
attacacttt taagattaca 20

<210> SEQ ID NO 739
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 739
caattacact tttaagatta 20

<210> SEQ ID NO 740
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 740
cacacaatta cacttttaag                                                    20

<210> SEQ ID NO 741
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 741
gtcacacaat tacacttttta                                                   20

<210> SEQ ID NO 742
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 742
aagtcacaca attacacttt                                                    20

<210> SEQ ID NO 743
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 743
aaaagtcaca caattacact                                                    20

<210> SEQ ID NO 744
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 744
gaaaaagtca cacaattaca                                                    20

<210> SEQ ID NO 745
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 745 ctgaaaagt cacacaatta                                                     20

<210> SEQ ID NO 746
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 746
ctctgaaaaa gtcacacaat                                                    20
```

<210> SEQ ID NO 747
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 747
aactctgaaa aagtcacaca                                              20

<210> SEQ ID NO 748
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 748
gcaactctga aaagtcaca                                               20

<210> SEQ ID NO 749
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 749
aagcaactct gaaaaagtca                                              20

<210> SEQ ID NO 750
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 750
ttaaagcaac tctgaaaaag                                              20

<210> SEQ ID NO 751
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 751
ctttaaagca actctgaaaa                                              20

<210> SEQ ID NO 752
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 752
tactttaaag caactctgaa                                              20

<210> SEQ ID NO 753
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 753
ggtactttaa agcaactctg                                               20

<210> SEQ ID NO 754
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 754
caggtacttt aaagcaactc                                               20

<210> SEQ ID NO 755
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 755
tacaggtact ttaaagcaac                                               20

<210> SEQ ID NO 756
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 756
actacaggta ctttaaagca                                               20

<210> SEQ ID NO 757
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 757
tcactacagg tactttaaag                                               20

<210> SEQ ID NO 758
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 758
tctcactaca ggtactttaa                                               20

<210> SEQ ID NO 759
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 759
tttctcacta caggtacttt                                               20

<210> SEQ ID NO 760
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 760
agtttctcac tacaggtact                                              20

<210> SEQ ID NO 761
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 761
tcagtttctc actacaggta                                              20

<210> SEQ ID NO 762
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 762
taaatcagtt tctcactaca                                              20

<210> SEQ ID NO 763
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 763
atcataaatc agtttctcac                                              20

<210> SEQ ID NO 764
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 764
tgatcataaa tcagtttctc                                              20

<210> SEQ ID NO 765
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 765
agtgatcata aatcagtttc                                              20

<210> SEQ ID NO 766
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 766
```
caagtgatca taaatcagtt 20

<210> SEQ ID NO 767
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 767
tccaagtgat cataaatcag 20

<210> SEQ ID NO 768
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 768
cttccaagtg atcataaatc 20

<210> SEQ ID NO 769
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 769
atcttccaag tgatcataaa 20

<210> SEQ ID NO 770
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 770
aaatcttcca agtgatcata 20

<210> SEQ ID NO 771
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 771
ctgagtttta taaaactata 20

<210> SEQ ID NO 772
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 772
ttaactgagt tttataaaac 20

<210> SEQ ID NO 773
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 773 tttaactga gttttataaa                                                    20

<210> SEQ ID NO 774
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 774
cattttaact gagttttata                                                   20

<210> SEQ ID NO 775
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 775
gacattttaa ctgagtttta                                                   20

<210> SEQ ID NO 776
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 776
cagacatttt aactgagttt                                                   20

<210> SEQ ID NO 777
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 777
aacagacatt ttaactgagt                                                   20

<210> SEQ ID NO 778
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 778
gaaacagaca ttttaactga                                                   20

<210> SEQ ID NO 779
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 779
ttgaaacaga cattttaact                                                   20
```

<210> SEQ ID NO 780
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 780
tttaagtctg gcaaataca                                          20

<210> SEQ ID NO 781
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 781
gatttaagtc tggcaaaata                                         20

<210> SEQ ID NO 782
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 782
gtgatttaag tctggcaaaa                                         20

<210> SEQ ID NO 783
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 783
ctgtgattta agtctggcaa                                         20

<210> SEQ ID NO 784
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 784
atctgtgatt taagtctggc                                         20

<210> SEQ ID NO 785
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 785
acccatctgt gatttaagtc                                         20

<210> SEQ ID NO 786
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 786
atacccatct gtgatttaag                                        20

<210> SEQ ID NO 787
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 787
taatacccat ctgtgattta                                        20

<210> SEQ ID NO 788
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 788
aaagaaattc tgacaagttt                                        20

<210> SEQ ID NO 789
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 789
acaaagaaat tctgacaagt                                        20

<210> SEQ ID NO 790
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 790
tgacaaagaa attctgacaa                                        20

<210> SEQ ID NO 791
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 791
aatgacaaag aaattctgac                                        20

<210> SEQ ID NO 792
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 792
tgaatgacaa agaaattctg                                        20

```
<210> SEQ ID NO 793
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 793
cttgaatgac aaagaaattc                                          20

<210> SEQ ID NO 794
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 794
ggcttgaatg acaaagaaat                                          20

<210> SEQ ID NO 795
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 795
caggcttgaa tgacaaagaa                                          20

<210> SEQ ID NO 796
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 796
cacaggcttg aatgacaaag                                          20

<210> SEQ ID NO 797
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 797
ttcacaggct tgaatgacaa                                          20

<210> SEQ ID NO 798
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 798
tattcacagg cttgaatgac                                          20

<210> SEQ ID NO 799
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 799
ataagtgcca tacagggttt                                              20

<210> SEQ ID NO 800
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 800
cataataagt gccatacagg                                              20

<210> SEQ ID NO 801
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 801
tagcctcata ataagtgcca                                              20

<210> SEQ ID NO 802
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 802
aatagcctca taataagtgc                                              20

<210> SEQ ID NO 803
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 803
ttaatagcct cataataagt                                              20

<210> SEQ ID NO 804
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 804
tcttttaata gcctcataat                                              20

<210> SEQ ID NO 805
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 805
attcttttaa tagcctcata                                              20

<210> SEQ ID NO 806
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 806
ttggattctt ttaatagcct                                               20

<210> SEQ ID NO 807
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 807
atttggattc ttttaatagc                                               20

<210> SEQ ID NO 808
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 808
gaatttggat tcttttaata                                               20

<210> SEQ ID NO 809
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 809
ttgaatttgg attcttttaa                                               20

<210> SEQ ID NO 810
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 810
gtttgaattt ggattctttt                                               20

<210> SEQ ID NO 811
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 811
tagtttgaat ttggattctt                                               20

<210> SEQ ID NO 812
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 812
```

```
tttagtttga atttggattc                                               20

<210> SEQ ID NO 813
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 813
tttttagttt gaatttggat                                               20

<210> SEQ ID NO 814
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 814 ttttttagt ttgaatttgg                                                20

<210> SEQ ID NO 815
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 815
cgtttcctgt ctttgtactt                                               20

<210> SEQ ID NO 816
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 816
caagccaaac gacttccagc                                               20

<210> SEQ ID NO 817
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 817
cacaagccaa acgacttcca                                               20

<210> SEQ ID NO 818
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 818
accacaagcc aaacgacttc                                               20

<210> SEQ ID NO 819
<211> LENGTH: 20
<212> TYPE: DNA
<213> ORGANISM: Artificial sequence
```

```
<220> FEATURE:
<223> OTHER INFORMATION: Synthetic oligonucleotide

<400> SEQUENCE: 819
acaccacaag ccaaacgact                                                 20

<210> SEQ ID NO 820
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 820
ttacaccaca agccaaacga                                                 20

<210> SEQ ID NO 821
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 821
ggataacaga tgagttaagg                                                 20

<210> SEQ ID NO 822
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 822
aggatacatt tctacagcta                                                 20

<210> SEQ ID NO 823
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 823
tcaggataca tttctacagc                                                 20

<210> SEQ ID NO 824
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 824
tatcaggata catttctaca                                                 20

<210> SEQ ID NO 825
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 825
tgtttatcag gatacatttc                                                 20
```

<210> SEQ ID NO 826
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 826
aatgtttatc aggatacatt                                               20

<210> SEQ ID NO 827
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 827
ttaatgttta tcaggataca                                               20

<210> SEQ ID NO 828
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 828
gtttaatgtt tatcaggata                                               20

<210> SEQ ID NO 829
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 829
gtgtttaatg tttatcagga                                               20

<210> SEQ ID NO 830
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 830
ttttaagatt acagtgttta                                               20

<210> SEQ ID NO 831
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 831
acttttaaga ttacagtgtt                                               20

<210> SEQ ID NO 832
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 832 acactttta a gattacagtg                      20

<210> SEQ ID NO 833
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 833
ttacactttt aagattacag                       20

<210> SEQ ID NO 834
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 834
aattacactt ttaagattac                       20

<210> SEQ ID NO 835
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 835
acacaattac acttttaaga                       20

<210> SEQ ID NO 836
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 836
tcacacaatt acactttttaa                      20

<210> SEQ ID NO 837
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 837
aaagtcacac aattacactt                       20

<210> SEQ ID NO 838
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 838
tgaaaaagtc acacaattac                       20

<210> SEQ ID NO 839

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 839
tctgaaaaag tcacacaatt                                              20

<210> SEQ ID NO 840
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 840
actctgaaaa agtcacacaa                                              20

<210> SEQ ID NO 841
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 841
agcaactctg aaaaagtcac                                              20

<210> SEQ ID NO 842
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 842
actttaaagc aactctgaaa                                              20

<210> SEQ ID NO 843
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 843
gtactttaaa gcaactctga                                              20

<210> SEQ ID NO 844
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 844
aggtacttta agcaactct                                               20

<210> SEQ ID NO 845
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 845
```
cactacaggt actttaaagc				20

<210> SEQ ID NO 846
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 846
ttctcactac aggtacttta				20

<210> SEQ ID NO 847
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 847
gtttctcact acaggtactt				20

<210> SEQ ID NO 848
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 848
cagtttctca ctacaggtac				20

<210> SEQ ID NO 849
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 849
atcagtttct cactacaggt				20

<210> SEQ ID NO 850
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 850
aaatcagttt ctcactacag				20

<210> SEQ ID NO 851
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 851
tcataaatca gtttctcact				20

<210> SEQ ID NO 852
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 852
gtgatcataa atcagtttct                                              20

<210> SEQ ID NO 853
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 853
aagtgatcat aaatcagttt                                              20

<210> SEQ ID NO 854
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 854
ccaagtgatc ataaatcagt                                              20

<210> SEQ ID NO 855
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 855
ttccaagtga tcataaatca                                              20

<210> SEQ ID NO 856
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 856
tcttccaagt gatcataaat                                              20

<210> SEQ ID NO 857
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 857
taactgagtt ttataaaact                                              20

<210> SEQ ID NO 858
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 858
aaacagacat tttaactgag                                              20
```

<210> SEQ ID NO 859
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 859
tgaaacagac attttaactg                                           20

<210> SEQ ID NO 860
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 860
atttaagtct ggcaaaatac                                           20

<210> SEQ ID NO 861
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 861
tgtgatttaa gtctggcaaa                                           20

<210> SEQ ID NO 862
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 862
tctgtgattt aagtctggca                                           20

<210> SEQ ID NO 863
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 863
catctgtgat ttaagtctgg                                           20

<210> SEQ ID NO 864
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 864
cccatctgtg atttaagtct                                           20

<210> SEQ ID NO 865
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 865
tacccatctg tgatttaagt                                            20

<210> SEQ ID NO 866
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 866
aatacccatc tgtgatttaa                                            20

<210> SEQ ID NO 867
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 867
ttaataccca tctgtgattt                                            20

<210> SEQ ID NO 868
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 868
gacaaagaaa ttctgacaag                                            20

<210> SEQ ID NO 869
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 869
gaatgacaaa gaaattctga                                            20

<210> SEQ ID NO 870
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 870
aggcttgaat gacaaagaaa                                            20

<210> SEQ ID NO 871
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 871
taagtgccat acagggtttt                                            20

```
<210> SEQ ID NO 872
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 872
ataataagtg ccatacaggg                                              20

<210> SEQ ID NO 873
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 873
cctcataata agtgccatac                                              20

<210> SEQ ID NO 874
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 874
agcctcataa taagtgccat                                              20

<210> SEQ ID NO 875
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 875
atagcctcat aataagtgcc                                              20

<210> SEQ ID NO 876
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 876
cttttaatag cctcataata                                              20

<210> SEQ ID NO 877
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 877
ttcttttaat agcctcataa                                              20

<210> SEQ ID NO 878
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 878 gattcttta atagcctcat                                               20

<210> SEQ ID NO 879
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 879
tggattcttt taatagcctc                                              20

<210> SEQ ID NO 880
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 880
tttggattct tttaatagcc                                              20

<210> SEQ ID NO 881
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 881
aatttggatt cttttaatag                                              20

<210> SEQ ID NO 882
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 882
tgaatttgga ttcttttaat                                              20

<210> SEQ ID NO 883
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 883
ttagtttgaa tttggattct                                              20

<210> SEQ ID NO 884
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 884
ttttagtttg aatttggatt                                              20

<210> SEQ ID NO 885
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 885 tttttagtt tgaatttgga                                                  20

<210> SEQ ID NO 886
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 886 cagtcctta atgcttcccc                                                  20

<210> SEQ ID NO 887
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 887
gtcagtcctt taatgcttcc                                                 20

<210> SEQ ID NO 888
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 888
cagtcagtcc tttaatgctt                                                 20

<210> SEQ ID NO 889
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 889
ttcagtcagt cctttaatgc                                                 20

<210> SEQ ID NO 890
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 890
ggccttcagt cagtccttta                                                 20

<210> SEQ ID NO 891
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 891
```
tgcaggcctt cagtcagtcc                                              20

<210> SEQ ID NO 892
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 892
catgcaggcc ttcagtcagt                                              20

<210> SEQ ID NO 893
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 893
tcatgaacat ggaatccatg                                              20

<210> SEQ ID NO 894
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 894
actcatgaac atggaatcca                                              20

<210> SEQ ID NO 895
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 895
ctgtattatc tccaaactca                                              20

<210> SEQ ID NO 896
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 896
actggtacag cctgctgtat                                              20

<210> SEQ ID NO 897
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 897
gcactggtac agcctgctgt                                              20

<210> SEQ ID NO 898
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 898
ctgcactggt acagcctgct                                              20

<210> SEQ ID NO 899
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 899
acctgcactg gtacagcctg                                              20

<210> SEQ ID NO 900
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 900
tttctggata gaggattaaa                                              20

<210> SEQ ID NO 901
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 901
gttttctgga tagaggatta                                              20

<210> SEQ ID NO 902
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 902
ccgtgttttc tggatagagg                                              20

<210> SEQ ID NO 903
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 903
caccgtgttt tctggataga                                              20

<210> SEQ ID NO 904
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 904
cccaccgtgt tttctggata                                              20
```

<210> SEQ ID NO 905
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 905
ggcccaccgt gttttctgga					20

<210> SEQ ID NO 906
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 906
ttggcccacc gtgttttctg					20

<210> SEQ ID NO 907
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 907
ctttggccca ccgtgttttc					20

<210> SEQ ID NO 908
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 908
tcctttggcc caccgtgttt					20

<210> SEQ ID NO 909
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 909
aagtctccaa catgcctctc					20

<210> SEQ ID NO 910
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 910
gcccaagtct ccaacatgcc					20

<210> SEQ ID NO 911
<211> LENGTH: 20
<212> TYPE: DNA
<213> ORGANISM: Artificial sequence
<220> FEATURE:
<223> OTHER INFORMATION: Synthetic oligonucleotide -continued

```
<400> SEQUENCE: 911
ttgcccaagt ctccaacatg                                              20

<210> SEQ ID NO 912
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 912
cattgcccaa gtctccaaca                                              20

<210> SEQ ID NO 913
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 913
cagtcacatt gcccaagtct                                              20

<210> SEQ ID NO 914
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 914
tcagcagtca cattgcccaa                                              20

<210> SEQ ID NO 915
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 915
tgtcagcagt cacattgccc                                              20

<210> SEQ ID NO 916
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 916
tttgtcagca gtcacattgc                                              20

<210> SEQ ID NO 917
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 917
tctttgtcag cagtcacatt                                              20

<210> SEQ ID NO 918
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 918
catctttgtc agcagtcaca                                               20

<210> SEQ ID NO 919
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 919
accatctttg tcagcagtca                                               20

<210> SEQ ID NO 920
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 920
ccacaccatc tttgtcagca                                               20

<210> SEQ ID NO 921
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 921
ggccacacca tctttgtcag                                               20

<210> SEQ ID NO 922
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 922
cacatcggcc acaccatctt                                               20

<210> SEQ ID NO 923
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 923
gacacatcgg ccacaccatc                                               20

<210> SEQ ID NO 924
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 924
```
aatagacaca tcggccacac                                       20

<210> SEQ ID NO 925
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 925
tcaatagaca catcggccac                                       20

<210> SEQ ID NO 926
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 926
cttcaataga cacatcggcc                                       20

<210> SEQ ID NO 927
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 927
atcttcaata gacacatcgg                                       20

<210> SEQ ID NO 928
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 928
gaatcttcaa tagacacatc                                       20

<210> SEQ ID NO 929
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 929
cagaatcttc aatagacaca                                       20

<210> SEQ ID NO 930
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 930
cacagaatct tcaatagaca                                       20

<210> SEQ ID NO 931
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 931
atcacagaat cttcaataga                                                 20

<210> SEQ ID NO 932
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 932
agatcacaga atcttcaata                                                 20

<210> SEQ ID NO 933
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 933
tgagatcaca gaatcttcaa                                                 20

<210> SEQ ID NO 934
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 934
agtgagatca cagaatcttc                                                 20

<210> SEQ ID NO 935
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 935
tgagagtgag atcacagaat                                                 20

<210> SEQ ID NO 936
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 936
gtctcctgag agtgagatca                                                 20

<210> SEQ ID NO 937
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 937
tggtctcctg agagtgagat                                                 20
```

-continued

<210> SEQ ID NO 938
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 938
aatggtctcc tgagagtgag                    20

<210> SEQ ID NO 939
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 939
gcaatggtct cctgagagtg                    20

<210> SEQ ID NO 940
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 940
atgcaatggt ctcctgagag                    20

<210> SEQ ID NO 941
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 941
tgatgcaatg gtctcctgag                    20

<210> SEQ ID NO 942
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 942
aatgatgcaa tggtctcctg                    20

<210> SEQ ID NO 943
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 943
ccaatgatgc aatggtctcc                    20

<210> SEQ ID NO 944
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 944
ggccaatgat gcaatggtct                                              20

<210> SEQ ID NO 945
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 945
gcggccaatg atgcaatggt                                              20

<210> SEQ ID NO 946
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 946
gtgcggccaa tgatgcaatg                                              20

<210> SEQ ID NO 947
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 947
gtgtgcggcc aatgatgcaa                                              20

<210> SEQ ID NO 948
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 948
cagtgtgcgg ccaatgatgc                                              20

<210> SEQ ID NO 949
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 949
accagtgtgc ggccaatgat                                              20

<210> SEQ ID NO 950
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 950
ccaccagtgt gcggccaatg                                              20

```
<210> SEQ ID NO 951
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 951
gaccaccagt gtgcggccaa                                               20

<210> SEQ ID NO 952
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 952
tggaccacca gtgtgcggcc                                               20

<210> SEQ ID NO 953
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 953
ttcatggacc accagtgtgc                                               20

<210> SEQ ID NO 954
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 954
ttttcatgga ccaccagtgt                                               20

<210> SEQ ID NO 955
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 955 cttttttcatg gaccaccagt                                              20

<210> SEQ ID NO 956
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 956
ccactctggc cccaaac                                                  17

<210> SEQ ID NO 957
<211> LENGTH: 17
<212> TYPE: DNA
<213> ORGANISM: Artificial sequence
<220> FEATURE:
<223> OTHER INFORMATION: Synthetic oligonucleotide
```

<400> SEQUENCE: 957
cccactctgg ccccaaa                                                     17

<210> SEQ ID NO 958
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 958
gcccactctg gccccaa                                                     17

<210> SEQ ID NO 959
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 959
cgcccactct ggccca                                                      17

<210> SEQ ID NO 960
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 960
cgactacttt ataggcc                                                     17

<210> SEQ ID NO 961
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 961
gcgactactt tataggc                                                     17

<210> SEQ ID NO 962
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 962
cgcgactact ttatagg                                                     17

<210> SEQ ID NO 963
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 963
ccgcgactac tttatag                                                     17

<210> SEQ ID NO 964
<211> LENGTH: 17

```
<212> TYPE: DNA
<213> ORGANISM: Artificial sequence
<220> FEATURE:
<223> OTHER INFORMATION: Synthetic oligonucleotide

<400> SEQUENCE: 964
cgctgcagga gactacg                                                    17

<210> SEQ ID NO 965
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 965
acgctgcagg agactac                                                    17

<210> SEQ ID NO 966
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 966
tcgcccttca gcacgca                                                    17

<210> SEQ ID NO 967
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 967
gtcgcccttc agcacgc                                                    17

<210> SEQ ID NO 968
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 968
cgtcgccctt cagcacg                                                    17

<210> SEQ ID NO 969
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 969
ccgtcgccct tcagcac                                                    17

<210> SEQ ID NO 970
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 970
```
gccgtcgccc ttcagca                                                    17

<210> SEQ ID NO 971
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 971
tctgctcgaa attgatg                                                    17

<210> SEQ ID NO 972
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 972
ttctgctcga aattgat                                                    17

<210> SEQ ID NO 973
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 973
cttctgctcg aaattga                                                    17

<210> SEQ ID NO 974
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 974
ccttctgctc gaaattg                                                    17

<210> SEQ ID NO 975
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 975
tccttctgct cgaaatt                                                    17

<210> SEQ ID NO 976
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 976
ttccttctgc tcgaaat                                                    17

<210> SEQ ID NO 977
<211> LENGTH: 17
<212> TYPE: DNA
<213> ORGANISM: Artificial sequence

```
<220> FEATURE:
<223> OTHER INFORMATION: Synthetic oligonucleotide

<400> SEQUENCE: 977
tttccttctg ctcgaaa                                                    17

<210> SEQ ID NO 978
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 978
ctttccttct gctcgaa                                                    17

<210> SEQ ID NO 979
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 979
actttccttc tgctcga                                                    17

<210> SEQ ID NO 980
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 980
tactttcctt ctgctcg                                                    17

<210> SEQ ID NO 981
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 981
ttactttcct tctgctc                                                    17

<210> SEQ ID NO 982
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 982
attactttcc ttctgct                                                    17

<210> SEQ ID NO 983
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 983
cattactttc cttctgc                                                    17
```

<210> SEQ ID NO 984
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 984
ccattacttt ccttctg                                                      17

<210> SEQ ID NO 985
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 985
tccattactt tccttct                                                      17

<210> SEQ ID NO 986
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 986
gtccattact ttccttc                                                      17

<210> SEQ ID NO 987
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 987
ggtccattac tttcctt                                                      17

<210> SEQ ID NO 988
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 988
tggtccatta ctttcct                                                      17

<210> SEQ ID NO 989
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 989
ctggtccatt actttcc                                                      17

<210> SEQ ID NO 990
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 990
actggtccat tactttc					17

<210> SEQ ID NO 991
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 991
cactggtcca ttacttt					17

<210> SEQ ID NO 992
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 992
tcactggtcc attactt					17

<210> SEQ ID NO 993
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 993
ttcactggtc cattact					17

<210> SEQ ID NO 994
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 994
cttcactggt ccattac					17

<210> SEQ ID NO 995
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 995
ccttcactgg tccatta					17

<210> SEQ ID NO 996
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 996
accttcactg gtccatt					17

<210> SEQ ID NO 997

```
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 997
caccttcact ggtccat                                                    17

<210> SEQ ID NO 998
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 998
acaccttcac tggtcca                                                    17

<210> SEQ ID NO 999
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 999
cacaccttca ctggtcc                                                    17

<210> SEQ ID NO 1000
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1000
ccacaccttc actggtc                                                    17

<210> SEQ ID NO 1001
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1001
cccacacctt cactggt                                                    17

<210> SEQ ID NO 1002
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1002
ccccacacct tcactgg                                                    17

<210> SEQ ID NO 1003
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1003
```
ttccccacac cttcact                                                    17

<210> SEQ ID NO 1004
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1004
cttccccaca ccttcac                                                    17

<210> SEQ ID NO 1005
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1005
gcttccccac accttca                                                    17

<210> SEQ ID NO 1006
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1006
tgcttcccca caccttc                                                    17

<210> SEQ ID NO 1007
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1007
atgcttcccc acacctt                                                    17

<210> SEQ ID NO 1008
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1008
aatgcttccc cacacct                                                    17

<210> SEQ ID NO 1009
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1009
taatgcttcc ccacacc                                                    17

<210> SEQ ID NO 1010
<211> LENGTH: 17
<212> TYPE: DNA

```
<213> ORGANISM: Artificial sequence
<220> FEATURE:
<223> OTHER INFORMATION: Synthetic oligonucleotide

<400> SEQUENCE: 1010
atgcaggcct tcagtca                                                17

<210> SEQ ID NO 1011
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1011
catgcaggcc ttcagtc                                                17

<210> SEQ ID NO 1012
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1012
ccatgcaggc cttcagt                                                17

<210> SEQ ID NO 1013
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1013
tccatgcagg ccttcag                                                17

<210> SEQ ID NO 1014
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1014
atccatgcag gccttca                                                17

<210> SEQ ID NO 1015
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1015
aatccatgca ggccttc                                                17

<210> SEQ ID NO 1016
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1016
gaatccatgc aggcctt                                                17
```

<210> SEQ ID NO 1017
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1017
ggaatccatg caggcct                                                17

<210> SEQ ID NO 1018
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1018
tggaatccat gcaggcc                                                17

<210> SEQ ID NO 1019
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1019
atggaatcca tgcaggc                                                17

<210> SEQ ID NO 1020
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1020
catggaatcc atgcagg                                                17

<210> SEQ ID NO 1021
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1021
acatggaatc catgcag                                                17

<210> SEQ ID NO 1022
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1022
aacatggaat ccatgca                                                17

<210> SEQ ID NO 1023
<211> LENGTH: 17
<212> TYPE: DNA
<213> ORGANISM: Artificial sequence
<220> FEATURE:

<223> OTHER INFORMATION: Synthetic oligonucleotide

<400> SEQUENCE: 1023
gaacatggaa tccatgc                                                    17

<210> SEQ ID NO 1024
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1024
tgaacatgga atccatg                                                    17

<210> SEQ ID NO 1025
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1025
atgaacatgg aatccat                                                    17

<210> SEQ ID NO 1026
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1026
ctgcactggt acagcct                                                    17

<210> SEQ ID NO 1027
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1027
cctgcactgg tacagcc                                                    17

<210> SEQ ID NO 1028
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1028
acctgcactg gtacagc                                                    17

<210> SEQ ID NO 1029
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1029
gacctgcact ggtacag                                                    17

```
<210> SEQ ID NO 1030
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1030
ggacctgcac tggtaca                                                        17

<210> SEQ ID NO 1031
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1031
aggacctgca ctggtac                                                        17

<210> SEQ ID NO 1032
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1032
gaggacctgc actggta                                                        17

<210> SEQ ID NO 1033
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1033
tgaggacctg cactggt                                                        17

<210> SEQ ID NO 1034
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1034
gtgaggacct gcactgg                                                        17

<210> SEQ ID NO 1035
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1035
agtgaggacc tgcactg                                                        17

<210> SEQ ID NO 1036
<211> LENGTH: 17
<212> TYPE: DNA
<213> ORGANISM: Artificial sequence
<220> FEATURE:
<223> OTHER INFORMATION: Synthetic oligonucleotide
```

```
<400> SEQUENCE: 1036
aagtgaggac ctgcact                                                     17

<210> SEQ ID NO 1037
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1037
aaagtgagga cctgcac                                                     17

<210> SEQ ID NO 1038
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1038
taaagtgagg acctgca                                                     17

<210> SEQ ID NO 1039
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1039
ttaaagtgag gacctgc                                                     17

<210> SEQ ID NO 1040
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1040
attaaagtga ggacctg                                                     17

<210> SEQ ID NO 1041
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1041
gattaaagtg aggacct                                                     17

<210> SEQ ID NO 1042
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1042
ggattaaagt gaggacc                                                     17

<210> SEQ ID NO 1043
<211> LENGTH: 17
```

```
<212> TYPE: DNA
<213> ORGANISM: Artificial sequence
<220> FEATURE:
<223> OTHER INFORMATION: Synthetic oligonucleotide

<400> SEQUENCE: 1043
aggattaaag tgaggac                                                    17

<210> SEQ ID NO 1044
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1044
gaggattaaa gtgagga                                                    17

<210> SEQ ID NO 1045
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1045
agaggattaa agtgagg                                                    17

<210> SEQ ID NO 1046
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1046
tagaggatta aagtgag                                                    17

<210> SEQ ID NO 1047
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1047
atagaggatt aaagtga                                                    17

<210> SEQ ID NO 1048
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1048
gatagaggat taaagtg                                                    17

<210> SEQ ID NO 1049
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1049
```
ggatagagga ttaaagt                                                  17

<210> SEQ ID NO 1050
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1050
tggatagagg attaaag                                                  17

<210> SEQ ID NO 1051
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1051
ctggatagag gattaaa                                                  17

<210> SEQ ID NO 1052
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1052
tctggataga ggattaa                                                  17

<210> SEQ ID NO 1053
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1053
ctttggccca ccgtgtt                                                  17

<210> SEQ ID NO 1054
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1054
cctttggccc accgtgt                                                  17

<210> SEQ ID NO 1055
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1055
tcctttggcc caccgtg                                                  17

<210> SEQ ID NO 1056
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1056
atcctttggc ccaccgt                                                   17

<210> SEQ ID NO 1057
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1057
catcctttgg cccaccg                                                   17

<210> SEQ ID NO 1058
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1058
tcatcctttg gcccacc                                                   17

<210> SEQ ID NO 1059
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1059
ttcatccttt ggcccac                                                   17

<210> SEQ ID NO 1060
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1060
cttcatcctt tggccca                                                   17

<210> SEQ ID NO 1061
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1061
tcttcatcct ttggccc                                                   17

<210> SEQ ID NO 1062
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1062
ctcttcatcc tttggcc                                                   17

-continued

```
<210> SEQ ID NO 1063
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1063
tctcttcatc ctttggc                                              17

<210> SEQ ID NO 1064
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1064
ctctcttcat cctttgg                                              17

<210> SEQ ID NO 1065
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1065
tgcctctctt catcctt                                              17

<210> SEQ ID NO 1066
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1066
atgcctctct tcatcct                                              17

<210> SEQ ID NO 1067
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1067
catgcctctc ttcatcc                                              17

<210> SEQ ID NO 1068
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1068
acatgcctct cttcatc                                              17

<210> SEQ ID NO 1069
<211> LENGTH: 17
<212> TYPE: DNA
<213> ORGANISM: Artificial sequence
<220> FEATURE:
<223> OTHER INFORMATION: Synthetic oligonucleotide
```

```
<400> SEQUENCE: 1069
aacatgcctc tcttcat                                                      17

<210> SEQ ID NO 1070
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1070
caacatgcct ctcttca                                                      17

<210> SEQ ID NO 1071
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1071
ccaacatgcc tctcttc                                                      17

<210> SEQ ID NO 1072
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1072
tccaacatgc ctctctt                                                      17

<210> SEQ ID NO 1073
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1073
ctccaacatg cctctct                                                      17

<210> SEQ ID NO 1074
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1074
tctccaacat gcctctc                                                      17

<210> SEQ ID NO 1075
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1075
gtctccaaca tgcctct                                                      17

<210> SEQ ID NO 1076
```

```
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1076
agcagtcaca ttgccca                                                   17

<210> SEQ ID NO 1077
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1077
cagcagtcac attgccc                                                   17

<210> SEQ ID NO 1078
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1078
agacacatcg gccacac                                                   17

<210> SEQ ID NO 1079
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1079
cttcaataga cacatcg                                                   17

<210> SEQ ID NO 1080
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1080
gagatcacag aatcttc                                                   17

<210> SEQ ID NO 1081
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1081
tttttcatgg accacca                                                   17

<210> SEQ ID NO 1082
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1082
``` cttttttcatg gaccacc　　　　　　　　　　　　　　　　　　　　　　　　　　　　17

<210> SEQ ID NO 1083
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1083 gcttttcat ggaccac　　　　　　　　　　　　　　　　　　　　　　　　　　　　17

<210> SEQ ID NO 1084
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1084
tgctttttca tggacca　　　　　　　　　　　　　　　　　　　　　　　　　　　　17

<210> SEQ ID NO 1085
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1085
ctgctttttc atggacc　　　　　　　　　　　　　　　　　　　　　　　　　　　　17

<210> SEQ ID NO 1086
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1086 tctgctttttt catggac　　　　　　　　　　　　　　　　　　　　　　　　　　　　17

<210> SEQ ID NO 1087
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1087
atctgctttt tcatgga　　　　　　　　　　　　　　　　　　　　　　　　　　　　17

<210> SEQ ID NO 1088
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1088
catctgcttt tcatgg　　　　　　　　　　　　　　　　　　　　　　　　　　　　17

<210> SEQ ID NO 1089
<211> LENGTH: 17
<212> TYPE: DNA

```
<213> ORGANISM: Artificial sequence
<220> FEATURE:
<223> OTHER INFORMATION: Synthetic oligonucleotide

<400> SEQUENCE: 1089
tcatctgctt tttcatg                                                    17

<210> SEQ ID NO 1090
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1090
gtcatctgct ttttcat                                                    17

<210> SEQ ID NO 1091
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1091
agtcatctgc tttttca                                                    17

<210> SEQ ID NO 1092
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1092
aagtcatctg ctttttc                                                    17

<210> SEQ ID NO 1093
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1093
caagtcatct gctttttt                                                   17

<210> SEQ ID NO 1094
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1094
ccaagtcatc tgctttt                                                    17

<210> SEQ ID NO 1095
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1095
cccaagtcat ctgcttt                                                    17
```

```
<210> SEQ ID NO 1096
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1096
gcccaagtca tctgctt                                                  17

<210> SEQ ID NO 1097
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1097
tgcccaagtc atctgct                                                  17

<210> SEQ ID NO 1098
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1098
ttgcccaagt catctgc                                                  17

<210> SEQ ID NO 1099
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1099
ccacctttgc ccaagtc                                                  17

<210> SEQ ID NO 1100
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1100
tccacctttg cccaagt                                                  17

<210> SEQ ID NO 1101
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1101
ttccaccttt gcccaag                                                  17

<210> SEQ ID NO 1102
<211> LENGTH: 17
<212> TYPE: DNA
<213> ORGANISM: Artificial sequence
<220> FEATURE:
```

<223> OTHER INFORMATION: Synthetic oligonucleotide

<400> SEQUENCE: 1102
tttccacctt tgcccaa                                                   17

<210> SEQ ID NO 1103
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1103
atttccacct ttgccca                                                   17

<210> SEQ ID NO 1104
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1104
catttccacc tttgccc                                                   17

<210> SEQ ID NO 1105
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1105
tcatttccac ctttgcc                                                   17

<210> SEQ ID NO 1106
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1106
ttcatttcca cctttgc                                                   17

<210> SEQ ID NO 1107
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1107
tcttcatttc caccttt                                                   17

<210> SEQ ID NO 1108
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1108
ctttcttcat ttccacc                                                   17

```
<210> SEQ ID NO 1109
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1109
actttcttca tttccac                                                    17

<210> SEQ ID NO 1110
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1110
tactttcttc atttcca                                                    17

<210> SEQ ID NO 1111
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1111
aattacacca caagcca                                                    17

<210> SEQ ID NO 1112
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1112
caattacacc acaagcc                                                    17

<210> SEQ ID NO 1113
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1113
ccaattacac cacaagc                                                    17

<210> SEQ ID NO 1114
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1114
cccaattaca ccacaag                                                    17

<210> SEQ ID NO 1115
<211> LENGTH: 17
<212> TYPE: DNA
<213> ORGANISM: Artificial sequence
<220> FEATURE:
<223> OTHER INFORMATION: Synthetic oligonucleotide
```

<400> SEQUENCE: 1115
gatcccaatt acaccac                                                  17

<210> SEQ ID NO 1116
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1116
cgatcccaat tacacca                                                  17

<210> SEQ ID NO 1117
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1117
gcgatcccaa ttacacc                                                  17

<210> SEQ ID NO 1118
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1118
ggcgatccca attacac                                                  17

<210> SEQ ID NO 1119
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1119
gggcgatccc aattaca                                                  17

<210> SEQ ID NO 1120
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1120
tgggcgatcc caattac                                                  17

<210> SEQ ID NO 1121
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1121
ttgggcgatc ccaatta                                                  17

<210> SEQ ID NO 1122
<211> LENGTH: 17

```
<212> TYPE: DNA
<213> ORGANISM: Artificial sequence
<220> FEATURE:
<223> OTHER INFORMATION: Synthetic oligonucleotide

<400> SEQUENCE: 1122
attgggcgat cccaatt                                                  17

<210> SEQ ID NO 1123
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1123
tattgggcga tcccaat                                                  17

<210> SEQ ID NO 1124
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1124
ttattgggcg atcccaa                                                  17

<210> SEQ ID NO 1125
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1125
tttattgggc gatccca                                                  17

<210> SEQ ID NO 1126
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1126
gtttattggg cgatccc                                                  17

<210> SEQ ID NO 1127
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1127
tgtttattgg gcgatcc                                                  17

<210> SEQ ID NO 1128
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1128
```

```
atgtttattg ggcgatc                                                  17

<210> SEQ ID NO 1129
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1129
aatgtttatt gggcgat                                                  17

<210> SEQ ID NO 1130
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1130
gaatgtttat tgggcga                                                  17

<210> SEQ ID NO 1131
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1131
ggaatgttta ttgggcg                                                  17

<210> SEQ ID NO 1132
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1132
aagggaatgt ttattgg                                                  17

<210> SEQ ID NO 1133
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1133
caagggaatg tttattg                                                  17

<210> SEQ ID NO 1134
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1134
ccaagggaat gtttatt                                                  17

<210> SEQ ID NO 1135
<211> LENGTH: 17
<212> TYPE: DNA
<213> ORGANISM: Artificial sequence
```

<220> FEATURE:
<223> OTHER INFORMATION: Synthetic oligonucleotide

<400> SEQUENCE: 1135
tccaagggaa tgtttat                                                    17

<210> SEQ ID NO 1136
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1136
atccaaggga atgttta                                                    17

<210> SEQ ID NO 1137
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1137
catccaaggg aatgttt                                                    17

<210> SEQ ID NO 1138
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1138
acatccaagg gaatgtt                                                    17

<210> SEQ ID NO 1139
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1139
tacatccaag ggaatgt                                                    17

<210> SEQ ID NO 1140
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1140
ctacatccaa gggaatg                                                    17

<210> SEQ ID NO 1141
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1141
actacatcca agggaat                                                    17

<210> SEQ ID NO 1142
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1142
gactacatcc aagggaa                                                      17

<210> SEQ ID NO 1143
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1143
agactacatc caaggga                                                      17

<210> SEQ ID NO 1144
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1144
cagactacat ccaaggg                                                      17

<210> SEQ ID NO 1145
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1145
tcagactaca tccaagg                                                      17

<210> SEQ ID NO 1146
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1146
ctcagactac atccaag                                                      17

<210> SEQ ID NO 1147
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1147
cctcagacta catccaa                                                      17

<210> SEQ ID NO 1148
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1148
gcctcagact acatcca					17

<210> SEQ ID NO 1149
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1149
ggcctcagac tacatcc					17

<210> SEQ ID NO 1150
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1150
gggcctcaga ctacatc					17

<210> SEQ ID NO 1151
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1151
gataacagat gagttaa					17

<210> SEQ ID NO 1152
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1152
ggataacaga tgagtta					17

<210> SEQ ID NO 1153
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1153
aggataacag atgagtt					17

<210> SEQ ID NO 1154
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1154
caggataaca gatgagt					17

<210> SEQ ID NO 1155

```
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1155
gcaggataac agatgag                                                    17

<210> SEQ ID NO 1156
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1156
agcaggataa cagatga                                                    17

<210> SEQ ID NO 1157
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1157
tagcaggata acagatg                                                    17

<210> SEQ ID NO 1158
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1158
ctagcaggat aacagat                                                    17

<210> SEQ ID NO 1159
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1159
gctagcagga taacaga                                                    17

<210> SEQ ID NO 1160
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1160
agctagcagg ataacag                                                    17

<210> SEQ ID NO 1161
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1161
```

-continued

| | |
|---|---|
| cagctagcag gataaca | 17 |

<210> SEQ ID NO 1162
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1162

| | |
|---|---|
| acagctagca ggataac | 17 |

<210> SEQ ID NO 1163
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1163

| | |
|---|---|
| tacagctagc aggataa | 17 |

<210> SEQ ID NO 1164
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1164

| | |
|---|---|
| ctacagctag caggata | 17 |

<210> SEQ ID NO 1165
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1165

| | |
|---|---|
| tctacagcta gcaggat | 17 |

<210> SEQ ID NO 1166
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1166

| | |
|---|---|
| ttctacagct agcagga | 17 |

<210> SEQ ID NO 1167
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1167

| | |
|---|---|
| tttctacagc tagcagg | 17 |

<210> SEQ ID NO 1168
<211> LENGTH: 17
<212> TYPE: DNA

```
<213> ORGANISM: Artificial sequence
<220> FEATURE:
<223> OTHER INFORMATION: Synthetic oligonucleotide

<400> SEQUENCE: 1168
atttctacag ctagcag                                                    17

<210> SEQ ID NO 1169
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1169
catttctaca gctagca                                                    17

<210> SEQ ID NO 1170
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1170
atacatttct acagcta                                                    17

<210> SEQ ID NO 1171
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1171
gatacatttc tacagct                                                    17

<210> SEQ ID NO 1172
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1172
gtgtttaatg tttatca                                                    17

<210> SEQ ID NO 1173
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1173
agtgtttaat gtttatc                                                    17

<210> SEQ ID NO 1174
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1174
cagtgtttaa tgtttat                                                    17
```

<210> SEQ ID NO 1175
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1175
acagtgttta atgttta                                                17

<210> SEQ ID NO 1176
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1176
tacagtgttt aatgttt                                                17

<210> SEQ ID NO 1177
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1177
ttacagtgtt taatgtt                                                17

<210> SEQ ID NO 1178
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1178
attacagtgt ttaatgt                                                17

<210> SEQ ID NO 1179
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1179
gattacagtg tttaatg                                                17

<210> SEQ ID NO 1180
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1180
agattacagt gtttaat                                                17

<210> SEQ ID NO 1181
<211> LENGTH: 17
<212> TYPE: DNA
<213> ORGANISM: Artificial sequence
<220> FEATURE:

<223> OTHER INFORMATION: Synthetic oligonucleotide

<400> SEQUENCE: 1181
aagattacag tgtttaa                                                  17

<210> SEQ ID NO 1182
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1182
taagattaca gtgttta                                                  17

<210> SEQ ID NO 1183
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1183
ttaagattac agtgttt                                                  17

<210> SEQ ID NO 1184
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1184
atcttccaag tgatcat                                                  17

<210> SEQ ID NO 1185
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1185
aatcttccaa gtgatca                                                  17

<210> SEQ ID NO 1186
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1186
aaatcttcca agtgatc                                                  17

<210> SEQ ID NO 1187
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1187
caaatcttcc aagtgat                                                  17

-continued

```
<210> SEQ ID NO 1188
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1188
tacaaatctt ccaagtg                                                17

<210> SEQ ID NO 1189
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1189
atacaaatct tccaagt                                                17

<210> SEQ ID NO 1190
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1190
tatacaaatc ttccaag                                                17

<210> SEQ ID NO 1191
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1191
ctatacaaat cttccaa                                                17

<210> SEQ ID NO 1192
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1192
actatacaaa tcttcca                                                17

<210> SEQ ID NO 1193
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1193
aactatacaa atcttcc                                                17

<210> SEQ ID NO 1194
<211> LENGTH: 17
<212> TYPE: DNA
<213> ORGANISM: Artificial sequence
<220> FEATURE:
<223> OTHER INFORMATION: Synthetic oligonucleotide
```

<400> SEQUENCE: 1194
aaactataca aatcttc                                                17

<210> SEQ ID NO 1195
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1195
ataaaactat acaaatc                                                17

<210> SEQ ID NO 1196
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1196
gttttataaa actatac                                                17

<210> SEQ ID NO 1197
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1197
gagttttata aaactat                                                17

<210> SEQ ID NO 1198
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1198
attgaaacag acatttt                                                17

<210> SEQ ID NO 1199
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1199
cattgaaaca gacattt                                                17

<210> SEQ ID NO 1200
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1200
tcattgaaac agacatt                                                17

<210> SEQ ID NO 1201
<211> LENGTH: 17

```
<212> TYPE: DNA
<213> ORGANISM: Artificial sequence
<220> FEATURE:
<223> OTHER INFORMATION: Synthetic oligonucleotide

<400> SEQUENCE: 1201
gtcattgaaa cagacat                                                    17

<210> SEQ ID NO 1202
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1202
ggtcattgaa acagaca                                                    17

<210> SEQ ID NO 1203
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1203
aggtcattga aacagac                                                    17

<210> SEQ ID NO 1204
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1204
caggtcattg aaacaga                                                    17

<210> SEQ ID NO 1205
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1205
acaggtcatt gaaacag                                                    17

<210> SEQ ID NO 1206
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1206
tacaggtcat tgaaaca                                                    17

<210> SEQ ID NO 1207
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1207
```

-continued atacaggtca ttgaaac					17

<210> SEQ ID NO 1208
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1208
aatacaggtc attgaaa					17

<210> SEQ ID NO 1209
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1209
aaatacaggt cattgaa					17

<210> SEQ ID NO 1210
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1210
aaaatacagg tcattga					17

<210> SEQ ID NO 1211
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1211
caaaatacag gtcattg					17

<210> SEQ ID NO 1212
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1212
gcaaaataca ggtcatt					17

<210> SEQ ID NO 1213
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1213
ggcaaaatac aggtcat					17

<210> SEQ ID NO 1214
<211> LENGTH: 17
<212> TYPE: DNA
<213> ORGANISM: Artificial sequence

```
<220> FEATURE:
<223> OTHER INFORMATION: Synthetic oligonucleotide

<400> SEQUENCE: 1214
tggcaaaata caggtca                                                    17

<210> SEQ ID NO 1215
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1215
ctggcaaaat acaggtc                                                    17

<210> SEQ ID NO 1216
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1216
tctggcaaaa tacaggt                                                    17

<210> SEQ ID NO 1217
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1217
gtctggcaaa atacagg                                                    17

<210> SEQ ID NO 1218
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1218
agtctggcaa aatacag                                                    17

<210> SEQ ID NO 1219
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1219
aagtctggca aaataca                                                    17

<210> SEQ ID NO 1220
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1220
taagtctggc aaaatac                                                    17
```

<210> SEQ ID NO 1221
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1221
ttaagtctgg caaaata                                                  17

<210> SEQ ID NO 1222
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1222
aatacccatc tgtgatt                                                  17

<210> SEQ ID NO 1223
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1223
taatacccat ctgtgat                                                  17

<210> SEQ ID NO 1224
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1224
ttaataccca tctgtga                                                  17

<210> SEQ ID NO 1225
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1225
tttaataccc atctgtg                                                  17

<210> SEQ ID NO 1226
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1226
gtttaatacc catctgt                                                  17

<210> SEQ ID NO 1227
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1227
agtttaatac ccatctg                                                  17

<210> SEQ ID NO 1228
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1228
aagtttaata cccatct                                                  17

<210> SEQ ID NO 1229
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1229
caagtttaat acccatc                                                  17

<210> SEQ ID NO 1230
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1230
acaagtttaa tacccat                                                  17

<210> SEQ ID NO 1231
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1231
gacaagttta ataccca                                                  17

<210> SEQ ID NO 1232
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1232
tgacaagttt aataccc                                                  17

<210> SEQ ID NO 1233
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1233
ctgacaagtt taatacc                                                  17

<210> SEQ ID NO 1234

-continued

<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1234
tctgacaagt ttaatac                                                    17

<210> SEQ ID NO 1235
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1235
ttctgacaag tttaata                                                    17

<210> SEQ ID NO 1236
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1236
attctgacaa gtttaat                                                    17

<210> SEQ ID NO 1237
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1237
aattctgaca agtttaa                                                    17

<210> SEQ ID NO 1238
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1238
aaattctgac aagttta                                                    17

<210> SEQ ID NO 1239
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1239
gaaattctga caagttt                                                    17

<210> SEQ ID NO 1240
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1240
agaaattctg acaagtt       17

<210> SEQ ID NO 1241
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1241
aagaaattct gacaagt       17

<210> SEQ ID NO 1242
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1242
ttcacaggct tgaatga       17

<210> SEQ ID NO 1243
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1243
attcacaggc ttgaatg       17

<210> SEQ ID NO 1244
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1244
tattcacagg cttgaat       17

<210> SEQ ID NO 1245
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1245
ttattcacag gcttgaa       17

<210> SEQ ID NO 1246
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1246
tttattcaca ggcttga       17

<210> SEQ ID NO 1247
<211> LENGTH: 17
<212> TYPE: DNA

```
<213> ORGANISM: Artificial sequence
<220> FEATURE:
<223> OTHER INFORMATION: Synthetic oligonucleotide

<400> SEQUENCE: 1247
ttttattcac aggcttg                                               17

<210> SEQ ID NO 1248
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1248
tttttattca caggctt                                               17

<210> SEQ ID NO 1249
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1249
gtttttattc acaggct                                               17

<210> SEQ ID NO 1250
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1250
ggtttttatt cacaggc                                               17

<210> SEQ ID NO 1251
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1251
gggtttttat tcacagg                                               17

<210> SEQ ID NO 1252
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1252
agggttttta ttcacag                                               17

<210> SEQ ID NO 1253
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1253
cagggttttt attcaca                                               17
```

<210> SEQ ID NO 1254
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1254
acagggtttt tattcac                                                    17

<210> SEQ ID NO 1255
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1255
tacagggttt ttattca                                                    17

<210> SEQ ID NO 1256
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1256
atacagggtt tttattc                                                    17

<210> SEQ ID NO 1257
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1257
catacagggt ttttatt                                                    17

<210> SEQ ID NO 1258
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1258
ccatacaggg tttttat                                                    17

<210> SEQ ID NO 1259
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1259
gccatacagg gttttta                                                    17

<210> SEQ ID NO 1260
<211> LENGTH: 17
<212> TYPE: DNA
<213> ORGANISM: Artificial sequence
<220> FEATURE:

<223> OTHER INFORMATION: Synthetic oligonucleotide

<400> SEQUENCE: 1260
tgccatacag ggttttt                17

<210> SEQ ID NO 1261
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1261
gtgccataca gggtttt                17

<210> SEQ ID NO 1262
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1262
agtgccatac agggttt                17

<210> SEQ ID NO 1263
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1263
ttggattctt ttaatag                17

<210> SEQ ID NO 1264
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1264
ttttagtttg aatttgg                17

<210> SEQ ID NO 1265
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1265
ctcgcccact ctggccccaa             20

<210> SEQ ID NO 1266
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1266
gcctcgccca ctctggcccc             20

```
<210> SEQ ID NO 1267
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1267
gcgcctcgcc cactctggcc                                              20

<210> SEQ ID NO 1268
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1268
ccgcgcctcg cccactctgg                                              20

<210> SEQ ID NO 1269
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1269
ctccgcgcct cgcccactct                                              20

<210> SEQ ID NO 1270
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1270
acctccgcgc ctcgcccact                                              20

<210> SEQ ID NO 1271
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1271
agacctccgc gcctcgccca                                              20

<210> SEQ ID NO 1272
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1272
ccagacctcc gcgcctcgcc                                              20

<210> SEQ ID NO 1273
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 1273
ggccagacct ccgcgcctcg                                        20

<210> SEQ ID NO 1274
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1274
tataggccag acctccgcgc                                        20

<210> SEQ ID NO 1275
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1275
tttataggcc agacctccgc                                        20

<210> SEQ ID NO 1276
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1276
gactacttta taggccagac                                        20

<210> SEQ ID NO 1277
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1277
gcgactactt tataggccag                                        20

<210> SEQ ID NO 1278
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1278
ctccgcgact actttatagg                                        20

<210> SEQ ID NO 1279
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1279
gtctccgcga ctactttata                                        20

<210> SEQ ID NO 1280
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 1280
ccgtctccgc gactacttta                                         20

<210> SEQ ID NO 1281
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1281
ccccgtctcc gcgactactt                                         20

<210> SEQ ID NO 1282
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1282
cacccCgtct ccgcgactac                                         20

<210> SEQ ID NO 1283
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1283
agcaccccgt ctccgcgact                                         20

<210> SEQ ID NO 1284
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1284
ccagcacccc gtctccgcga                                         20

<210> SEQ ID NO 1285
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1285
aaccagcacc ccgtctccgc                                         20

<210> SEQ ID NO 1286
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1286
```
caaaccagca ccccgtctcc                                              20

<210> SEQ ID NO 1287
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1287
cgcaaaccag cacccgtct                                               20

<210> SEQ ID NO 1288
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1288
acgacgcaaa ccagcacccc                                              20

<210> SEQ ID NO 1289
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1289
ctacgacgca aaccagcacc                                              20

<210> SEQ ID NO 1290
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1290
gactacgacg caaaccagca                                              20

<210> SEQ ID NO 1291
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1291
gagactacga cgcaaaccag                                              20

<210> SEQ ID NO 1292
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1292
aggagactac gacgcaaacc                                              20

<210> SEQ ID NO 1293
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 1293
gcaggagact acgacgcaaa                                              20

<210> SEQ ID NO 1294
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1294
ctgcaggaga ctacgacgca                                              20

<210> SEQ ID NO 1295
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1295
cgctgcagga gactacgacg                                              20

<210> SEQ ID NO 1296
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1296
tgcaacggaa accccagacg                                              20

<210> SEQ ID NO 1297
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1297
actgcaacgg aaaccccaga                                              20

<210> SEQ ID NO 1298
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1298
gaggactgca acggaaaccc                                              20

<210> SEQ ID NO 1299
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1299
ccgaggactg caacggaaac                                              20
```

```
<210> SEQ ID NO 1300
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1300
ttccgaggac tgcaacggaa                                              20

<210> SEQ ID NO 1301
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1301
ctggttccga ggactgcaac                                              20

<210> SEQ ID NO 1302
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1302
ggtcctggtt ccgaggactg                                              20

<210> SEQ ID NO 1303
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1303
ccgaggtcct ggttccgagg                                              20

<210> SEQ ID NO 1304
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1304
cgccgaggtc ctggttccga                                              20

<210> SEQ ID NO 1305
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1305
cacgccgagg tcctggttcc                                              20

<210> SEQ ID NO 1306
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 1306
gccacgccga ggtcctggtt					20

<210> SEQ ID NO 1307
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1307
ctaggccacg ccgaggtcct					20

<210> SEQ ID NO 1308
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1308
cgctaggcca cgccgaggtc					20

<210> SEQ ID NO 1309
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1309
ctcgctaggc cacgccgagg					20

<210> SEQ ID NO 1310
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1310
aactcgctag gccacgccga					20

<210> SEQ ID NO 1311
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1311
ataactcgct aggccacgcc					20

<210> SEQ ID NO 1312
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1312
ccataactcg ctaggccacg					20

<210> SEQ ID NO 1313

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1313
cgccataact cgctaggcca                                                       20

<210> SEQ ID NO 1314
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1314
tgggccgtcg cccttcagca                                                       20

<210> SEQ ID NO 1315
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1315
actgggccgt cgcccttcag                                                       20

<210> SEQ ID NO 1316
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1316
gcactgggcc gtcgcccttc                                                       20

<210> SEQ ID NO 1317
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1317
ctgcactggg ccgtcgccct                                                       20

<210> SEQ ID NO 1318
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1318
tgccctgcac tgggccgtcg                                                       20

<210> SEQ ID NO 1319
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1319
```
gatgccctgc actgggccgt 20

<210> SEQ ID NO 1320
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1320
atgatgccct gcactgggcc 20

<210> SEQ ID NO 1321
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1321
attgatgatg ccctgcactg 20

<210> SEQ ID NO 1322
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1322
aaattgatga tgccctgcac 20

<210> SEQ ID NO 1323
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1323
cgaaattgat gatgccctgc 20

<210> SEQ ID NO 1324
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1324
ctcgaaattg atgatgccct 20

<210> SEQ ID NO 1325
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1325
tgctcgaaat tgatgatgcc 20

<210> SEQ ID NO 1326
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 1326
tctgctcgaa attgatgatg                                               20

<210> SEQ ID NO 1327
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1327
cttctgctcg aaattgatga                                               20

<210> SEQ ID NO 1328
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1328
tttaatgctt ccccacacct                                               20

<210> SEQ ID NO 1329
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1329
cctttaatgc ttccccacac                                               20

<210> SEQ ID NO 1330
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1330
gtcctttaat gcttccccac                                               20

<210> SEQ ID NO 1331
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1331
cccttcagca cgcacac                                                  17

<210> SEQ ID NO 1332
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1332
gcccttcagc acgcaca                                                  17
```

<210> SEQ ID NO 1333
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1333
cgcccttcag cacgcac                                                  17

<210> SEQ ID NO 1334
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1334
caccacaagc caaacga                                                  17

<210> SEQ ID NO 1335
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1335
acaccacaag ccaaacg                                                  17

<210> SEQ ID NO 1336
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1336
tacaccacaa gccaaac                                                  17

<210> SEQ ID NO 1337
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1337
ttacaccaca agccaaa                                                  17

<210> SEQ ID NO 1338
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1338
attacaccac aagccaa                                                  17

<210> SEQ ID NO 1339
<211> LENGTH: 17
<212> TYPE: DNA
<213> ORGANISM: Artificial sequence
<220> FEATURE:

<223> OTHER INFORMATION: Synthetic oligonucleotide

<400> SEQUENCE: 1339
aacagatgag ttaaggg                                                    17

<210> SEQ ID NO 1340
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1340
taacagatga gttaagg                                                    17

<210> SEQ ID NO 1341
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1341
ataacagatg agttaag                                                    17

<210> SEQ ID NO 1342
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1342
ggatacattt ctacagc                                                    17

<210> SEQ ID NO 1343
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1343
aggatacatt tctacag                                                    17

<210> SEQ ID NO 1344
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1344
caggatacat ttctaca                                                    17

<210> SEQ ID NO 1345
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1345
ttatcaggat acatttc                                                    17

```
<210> SEQ ID NO 1346
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1346
gtttatcagg atacatt                                                  17

<210> SEQ ID NO 1347
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1347
tgtttatcag gatacat                                                  17

<210> SEQ ID NO 1348
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1348
atgtttatca ggataca                                                  17

<210> SEQ ID NO 1349
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1349
aatgtttatc aggatac                                                  17

<210> SEQ ID NO 1350
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1350
taatgtttat caggata                                                  17

<210> SEQ ID NO 1351
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1351
ttaatgttta tcaggat                                                  17

<210> SEQ ID NO 1352
<211> LENGTH: 17
<212> TYPE: DNA
<213> ORGANISM: Artificial sequence
<220> FEATURE:
<223> OTHER INFORMATION: Synthetic oligonucleotide
```

-continued

```
<400> SEQUENCE: 1352
gtttaatgtt tatcagg                                                    17

<210> SEQ ID NO 1353
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1353
cttttaagat tacagtg                                                    17

<210> SEQ ID NO 1354
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1354
cacttttaag attacag                                                    17

<210> SEQ ID NO 1355
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1355
tcacacaatt acacttt                                                    17

<210> SEQ ID NO 1356
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1356
gtcacacaat tacactt                                                    17

<210> SEQ ID NO 1357
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1357
aagtcacaca attacac                                                    17

<210> SEQ ID NO 1358
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1358
aggtacttta aagcaac                                                    17

<210> SEQ ID NO 1359
<211> LENGTH: 17
```

```
<212> TYPE: DNA
<213> ORGANISM: Artificial sequence
<220> FEATURE:
<223> OTHER INFORMATION: Synthetic oligonucleotide

<400> SEQUENCE: 1359
acaggtactt taaagca                                            17

<210> SEQ ID NO 1360
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1360
tacaggtact ttaaagc                                            17

<210> SEQ ID NO 1361
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1361
ctacaggtac tttaaag                                            17

<210> SEQ ID NO 1362
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1362
cactacaggt actttaa                                            17

<210> SEQ ID NO 1363
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1363
tcactacagg tacttta                                            17

<210> SEQ ID NO 1364
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1364
ctcactacag gtacttt                                            17

<210> SEQ ID NO 1365
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1365
```

-continued tctcactaca ggtactt 17

<210> SEQ ID NO 1366
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1366
ttctcactac aggtact 17

<210> SEQ ID NO 1367
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1367
tttctcacta caggtac 17

<210> SEQ ID NO 1368
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1368
gtttctcact acaggta 17

<210> SEQ ID NO 1369
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1369
agtttctcac tacaggt 17

<210> SEQ ID NO 1370
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1370
cagtttctca ctacagg 17

<210> SEQ ID NO 1371
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1371
tcagtttctc actacag 17

<210> SEQ ID NO 1372
<211> LENGTH: 17
<212> TYPE: DNA
<213> ORGANISM: Artificial sequence

```
<220> FEATURE:
<223> OTHER INFORMATION: Synthetic oligonucleotide

<400> SEQUENCE: 1372
atcagtttct cactaca                                                  17

<210> SEQ ID NO 1373
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1373
aatcagtttc tcactac                                                  17

<210> SEQ ID NO 1374
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1374
gatcataaat cagtttc                                                  17

<210> SEQ ID NO 1375
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1375
tgatcataaa tcagttt                                                  17

<210> SEQ ID NO 1376
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1376
gtgatcataa atcagtt                                                  17

<210> SEQ ID NO 1377
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1377
agtgatcata aatcagt                                                  17

<210> SEQ ID NO 1378
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1378
caagtgatca taaatca                                                  17
```

<210> SEQ ID NO 1379
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1379
ccaagtgatc ataaatc                                                  17

<210> SEQ ID NO 1380
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1380
tccaagtgat cataaat                                                  17

<210> SEQ ID NO 1381
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1381
cttccaagtg atcataa                                                  17

<210> SEQ ID NO 1382
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1382
tcttccaagt gatcata                                                  17

<210> SEQ ID NO 1383
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1383
agacatttta actgagt                                                  17

<210> SEQ ID NO 1384
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1384
gatttaagtc tggcaaa                                                  17

<210> SEQ ID NO 1385
<211> LENGTH: 17
<212> TYPE: DNA
<213> ORGANISM: Artificial sequence
<220> FEATURE:
<223> OTHER INFORMATION: Synthetic oligonucleotide

```
<400> SEQUENCE: 1385
tgatttaagt ctggcaa                                                        17

<210> SEQ ID NO 1386
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1386
gtgatttaag tctggca                                                        17

<210> SEQ ID NO 1387
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1387
tgtgatttaa gtctggc                                                        17

<210> SEQ ID NO 1388
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1388
ctgtgattta agtctgg                                                        17

<210> SEQ ID NO 1389
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1389
tctgtgattt aagtctg                                                        17

<210> SEQ ID NO 1390
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1390
atctgtgatt taagtct                                                        17

<210> SEQ ID NO 1391
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1391
catctgtgat ttaagtc                                                        17

<210> SEQ ID NO 1392
```

```
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1392
ccatctgtga tttaagt                                                    17

<210> SEQ ID NO 1393
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1393
cccatctgtg atttaag                                                    17

<210> SEQ ID NO 1394
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1394
acccatctgt gatttaa                                                    17

<210> SEQ ID NO 1395
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1395
tacccatctg tgattta                                                    17

<210> SEQ ID NO 1396
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1396
gcttgaatga caaagaa                                                    17

<210> SEQ ID NO 1397
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1397
ggcttgaatg acaaaga                                                    17

<210> SEQ ID NO 1398
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1398
```
cacaggcttg aatgaca                                            17

<210> SEQ ID NO 1399
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1399
tcacaggctt gaatgac                                            17

<210> SEQ ID NO 1400
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1400
aagtgccata cagggtt                                            17

<210> SEQ ID NO 1401
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1401
taagtgccat acagggt                                            17

<210> SEQ ID NO 1402
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1402
ataagtgcca tacaggg                                            17

<210> SEQ ID NO 1403
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1403
aataagtgcc atacagg                                            17

<210> SEQ ID NO 1404
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1404
taataagtgc catacag                                            17

<210> SEQ ID NO 1405
<211> LENGTH: 17
<212> TYPE: DNA

```
<213> ORGANISM: Artificial sequence
<220> FEATURE:
<223> OTHER INFORMATION: Synthetic oligonucleotide

<400> SEQUENCE: 1405
ataataagtg ccataca                                                  17

<210> SEQ ID NO 1406
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1406
cataataagt gccatac                                                  17

<210> SEQ ID NO 1407
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1407
tcataataag tgccata                                                  17

<210> SEQ ID NO 1408
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1408
ctcataataa gtgccat                                                  17

<210> SEQ ID NO 1409
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1409
cctcataata agtgcca                                                  17

<210> SEQ ID NO 1410
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1410
gcctcataat aagtgcc                                                  17

<210> SEQ ID NO 1411
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1411
agcctcataa taagtgc                                                  17
```

<210> SEQ ID NO 1412
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1412
tagcctcata ataagtg                                                  17

<210> SEQ ID NO 1413
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1413
atagcctcat aataagt                                                  17

<210> SEQ ID NO 1414
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1414
aatagcctca taataag                                                  17

<210> SEQ ID NO 1415
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1415
cttttaatag cctcata                                                  17

<210> SEQ ID NO 1416
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1416
tcttttaata gcctcat                                                  17

<210> SEQ ID NO 1417
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 1417
ggattctttt aatagcc                                                  17

<210> SEQ ID NO 1418
<211> LENGTH: 17
<212> TYPE: DNA
<213> ORGANISM: Artificial sequence
<220> FEATURE:

<223> OTHER INFORMATION: Synthetic oligonucleotide

<400> SEQUENCE: 1418
ttagtttgaa tttggat                                                          17

<210> SEQ ID NO 1419
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1419
gtcgcccttc agcacgca                                                         18

<210> SEQ ID NO 1420
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1420
cccacacctt cactgg                                                           16

<210> SEQ ID NO 1421
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1421
ttccccacac cttcactg                                                         18

<210> SEQ ID NO 1422
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1422
ccccacacct tcactg                                                           16

<210> SEQ ID NO 1423
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1423
cttccccaca ccttcact                                                         18

<210> SEQ ID NO 1424
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1424
tccccacacc ttcact                                                           16

```
<210> SEQ ID NO 1425
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1425
gcttccccac accttcac                                                 18

<210> SEQ ID NO 1426
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1426
ttccccacac cttcac                                                   16

<210> SEQ ID NO 1427
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1427
cttccccaca ccttca                                                   16

<210> SEQ ID NO 1428
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 1428
aggatacatt tctacagct                                                19

<210> SEQ ID NO 1429
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1429
atacatttct acagctag                                                 18

<210> SEQ ID NO 1430
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1430
gatacatttc tacagcta                                                 18

<210> SEQ ID NO 1431
<211> LENGTH: 16
<212> TYPE: DNA
<213> ORGANISM: Artificial sequence
<220> FEATURE:
<223> OTHER INFORMATION: Synthetic oligonucleotide
```

-continued

<400> SEQUENCE: 1431
tacatttcta cagcta						16

<210> SEQ ID NO 1432
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1432
ggatacattt ctacagct						18

<210> SEQ ID NO 1433
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1433
atacatttct acagct						16

<210> SEQ ID NO 1434
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1434
aggatacatt tctacagc						18

<210> SEQ ID NO 1435
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1435
gatacatttc tacagc						16

<210> SEQ ID NO 1436
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1436
caggatacat ttctacag						18

<210> SEQ ID NO 1437
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1437
atgtttatca ggatac						16

<210> SEQ ID NO 1438
<211> LENGTH: 18

```
<212> TYPE: DNA
<213> ORGANISM: Artificial sequence
<220> FEATURE:
<223> OTHER INFORMATION: Synthetic oligonucleotide

<400> SEQUENCE: 1438
ttaatgttta tcaggata                                                 18

<210> SEQ ID NO 1439
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1439
tttaatgttt atcaggat                                                 18

<210> SEQ ID NO 1440
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1440
gtttaatgtt tatcagga                                                 18

<210> SEQ ID NO 1441
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1441
ttaatgttta tcagga                                                   16

<210> SEQ ID NO 1442
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1442
tgtttaatgt ttatcagg                                                 18

<210> SEQ ID NO 1443
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1443
tttaatgttt atcagg                                                   16

<210> SEQ ID NO 1444
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1444
```
gtgtttaatg tttatcag                                              18

<210> SEQ ID NO 1445
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1445
gtttaatgtt tatcag                                                16

<210> SEQ ID NO 1446
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1446
agtgtttaat gtttatca                                              18

<210> SEQ ID NO 1447
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1447
tgtttaatgt ttatca                                                16

<210> SEQ ID NO 1448
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1448
cagtgtttaa tgtttatc                                              18

<210> SEQ ID NO 1449
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1449
gtgtttaatg tttatc                                                16

<210> SEQ ID NO 1450
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1450
acagtgttta atgtttat                                              18

<210> SEQ ID NO 1451
<211> LENGTH: 18
<212> TYPE: DNA
<213> ORGANISM: Artificial sequence -continued
<220> FEATURE:
<223> OTHER INFORMATION: Synthetic oligonucleotide

<400> SEQUENCE: 1451
tacagtgttt aatgttta                                          18

<210> SEQ ID NO 1452
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1452
cagtgtttaa tgttta                                            16

<210> SEQ ID NO 1453
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1453
ttacagtgtt taatgttt                                          18

<210> SEQ ID NO 1454
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1454
acagtgttta atgttt                                            16

<210> SEQ ID NO 1455
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1455
ggatacattt ctacag                                            16

<210> SEQ ID NO 1456
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1456
taatgtttat caggat                                            16

<210> SEQ ID NO 1457
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1457
agtgtttaat gtttat                                            16

```
<210> SEQ ID NO 1458
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1458
catttctaca gctagc                                                       16

<210> SEQ ID NO 1459
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1459
acatttctac agctag                                                       16

<210> SEQ ID NO 1460
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 1460
aatgtttatc aggata                                                       16

<210> SEQ ID NO 1461
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 1461
caggatacat ttctacagc                                                    19
```

UNITED STATES PATENT AND TRADEMARK OFFICE
CERTIFICATE OF CORRECTION

PATENT NO. : 10,385,341 B2
APPLICATION NO. : 15/301004
DATED : August 20, 2019
INVENTOR(S) : Eric E. Swayze Page 1 of 3

It is certified that error appears in the above-identified patent and that said Letters Patent is hereby corrected as shown below:

In the Claims

Column 725-726
Claim 1, delete:

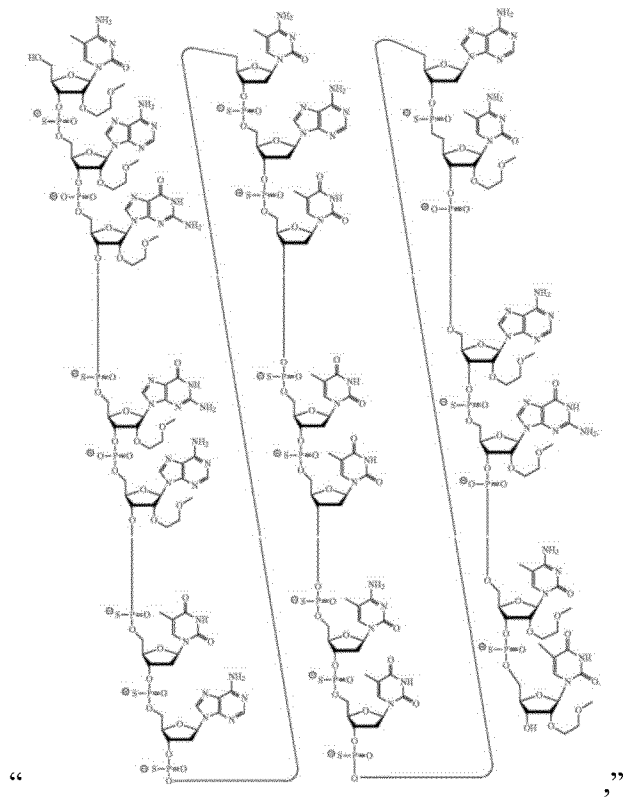

" ",

Signed and Sealed this
Twenty-sixth Day of May, 2020

Andrei Iancu
*Director of the United States Patent and Trademark Office*

And insert:
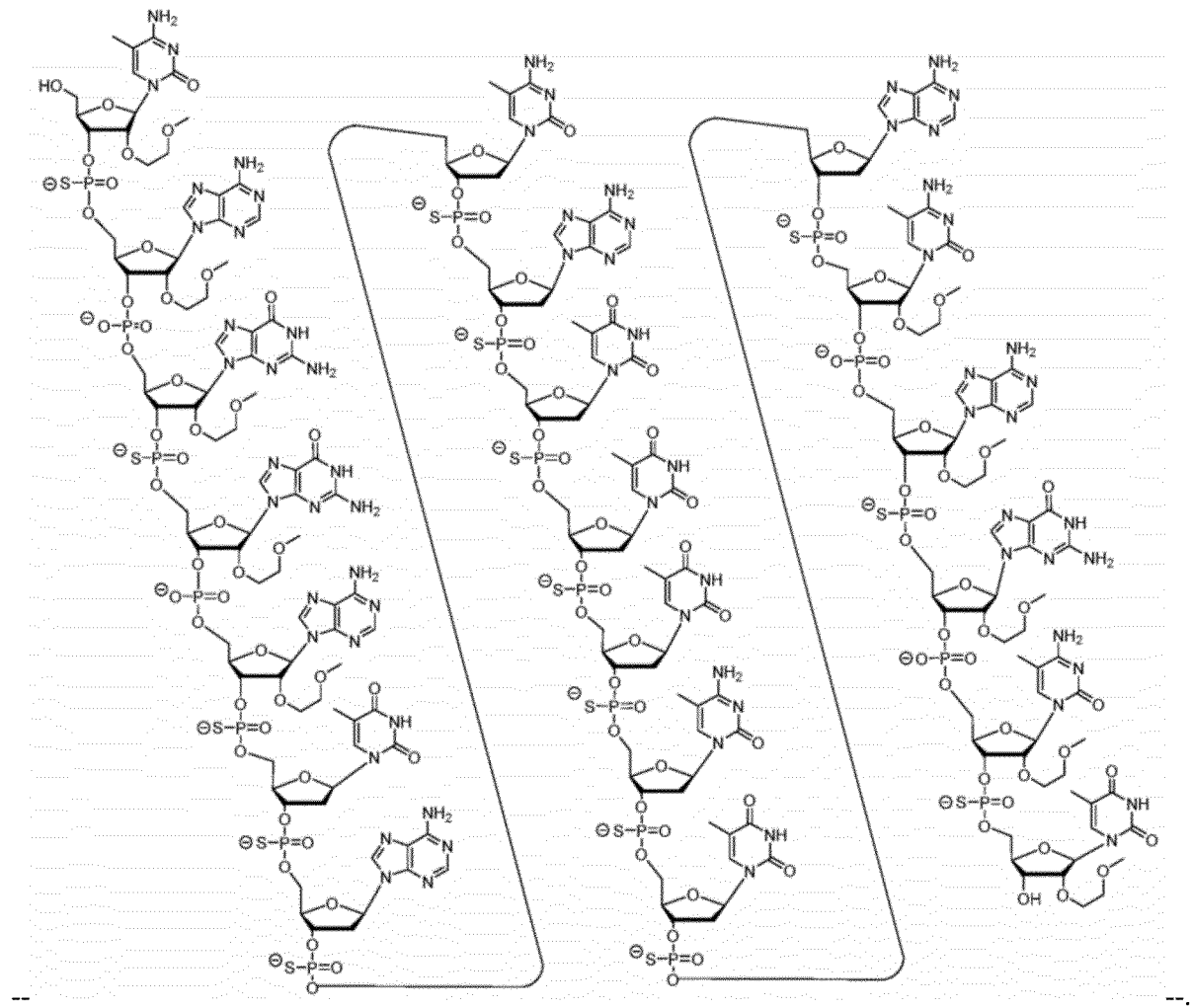
--          --.
Column 728
Claim 8, Line 5, delete:
"administation."
And insert:
-- administration. --.

CERTIFICATE OF CORRECTION (continued)
U.S. Pat. No. 10,385,341 B2

Columns 727-728
Claim 17, Line 29, delete:

"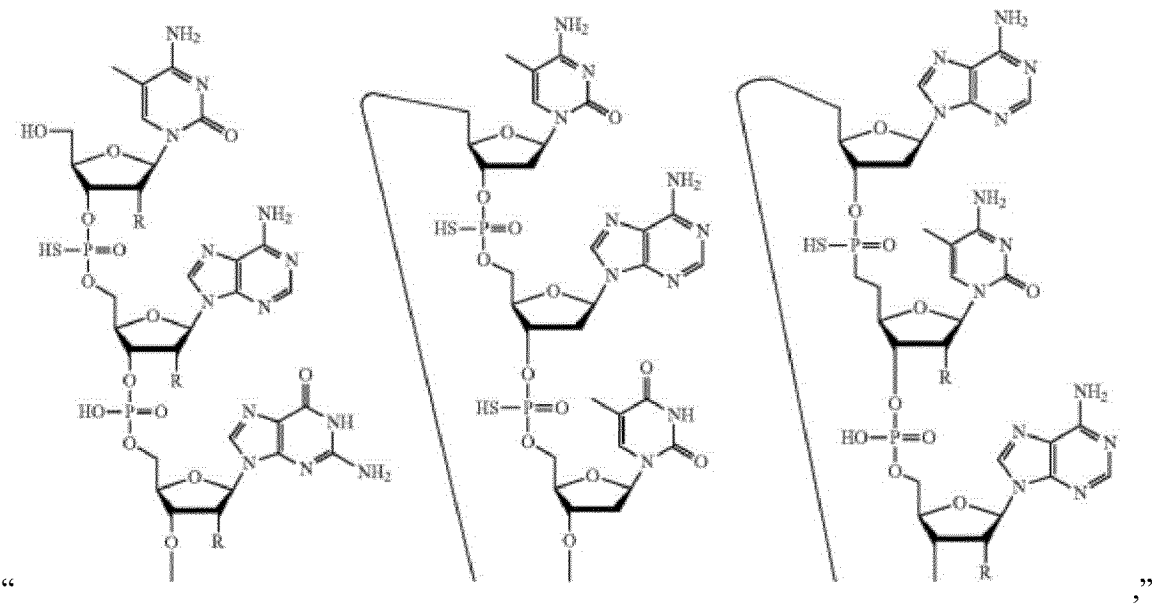"

And insert:

--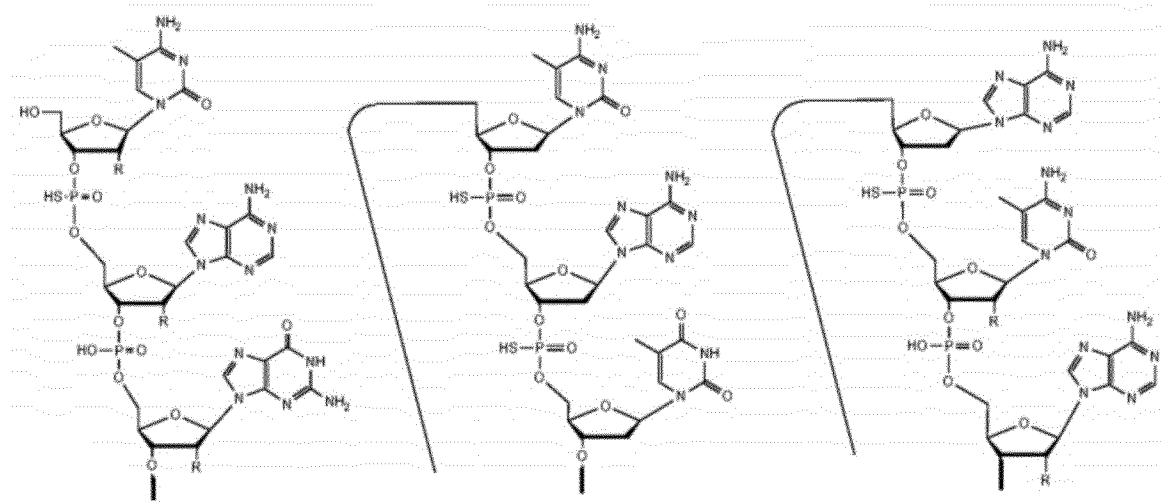--.